(12) United States Patent
Bamborough et al.

(10) Patent No.: US 6,602,877 B1
(45) Date of Patent: Aug. 5, 2003

(54) IMIDAZOLYL-CYCLIC ACETALS

(75) Inventors: Paul L. Bamborough, Dagenham (GB); Alan J. Collis, Dagenham (GB); Frank Halley, Dagenham (GB); Richard A. Lewis, Dagenham (GB); David J. Lythgoe, Dagenham (GB); Jeffrey M. McKenna, Dagenham (GB); Iain M. McLay, Dagenham (GB); Barry Porter, Dagenham (GB); Andrew J. Ratcliffe, Dagenham (GB); Paul A. Wallace, Dagenham (GB)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 09/456,360

(22) Filed: Dec. 8, 1999

Related U.S. Application Data

(63) Continuation of application No. PCT/GB98/01711, filed on Jun. 12, 1998.
(60) Provisional application No. 60/052,185, filed on Jul. 10, 1997, now abandoned, and provisional application No. 60/085,499, filed on May 14, 1998, now abandoned.

(30) Foreign Application Priority Data

Jun. 12, 1997 (GB) .............................. 9712270
Nov. 21, 1997 (GB) ............................. 9724678

(51) Int. Cl.$^7$ .................. C07D 233/54; A61K 31/4178; A61P 19/02
(52) U.S. Cl. ...................... 514/256; 544/333
(58) Field of Search ............................ 544/333; 514/256

(56) References Cited

U.S. PATENT DOCUMENTS

| | | | |
|---|---|---|---|
| 3,707,475 A | 12/1972 | Lombardino ................ | 260/309 |
| 3,940,486 A | 2/1976 | Fitzi ............................ | 424/273 |
| 4,175,127 A | 11/1979 | Bender et al. .............. | 546/271 |
| 4,503,065 A | 3/1985 | Wilkerson ................... | 548/337 |
| 5,179,117 A | 1/1993 | Maduskuie, Jr. ............ | 548/333 |
| 5,593,991 A | 1/1997 | Adams et al. ............... | 544/128 |
| 5,593,992 A | 1/1997 | Adams et al. ............... | 544/122 |
| 5,656,644 A | 8/1997 | Adams et al. ............... | 546/278 |
| 5,663,334 A | 9/1997 | Sheldrake et al. .......... | 544/122 |
| 5,670,527 A | 9/1997 | Adams et al. ............... | 546/274.1 |
| 5,686,455 A | 11/1997 | Adams et al. ............... | 546/278 |

FOREIGN PATENT DOCUMENTS

EP 0229496 7/1987

(List continued on next page.)

OTHER PUBLICATIONS

Asltes et al., "Acyl–COA: cholesterol O–acyltransferase (ACAT) Inhibitors. 2–(1,3–D Ioxan–2–yl)–4, 5–diphenyl–1H–imidazoles as potent inhibitors of ACAT." Journal of Medicinal Chemistry, 39(7):1423–1432 (1996).

Schmidt et al. "Die Gallussaureester des Glycerin." Chemische Beritchte, 89(2):283–290 (1956).

(List continued on next page.)

Primary Examiner—Richard L. Raymond
Assistant Examiner—Venkataraman Balasubramanian
(74) Attorney, Agent, or Firm—Paul R. Darkes; Irving Newman

(57) ABSTRACT

Compounds of formula (I) are described in which $R^1$ is optionally substituted heteroaryl; $R^2$ is optionally substituted aryl or optionally substituted heteroaryl; $R^3$ is a group —$L^1$—$R^7$ or —$L^2$—$R^8$ [where $L^1$ is an optionally substituted alkylene linkage; $R^7$ is hydrogen, aryl, cyano, cycloalkyl, heteroaryl, heterocycloalkyl, nitro, —$S(O)_nR^9$, —$NHSO_2R^9$, —$C(=Z)OR^{10}$, —$C(=Z)R^{10}$, —$OR^{10}$, —$N(R^{11})$—$C(=Z)R^9$, —$NY^1Y^2$, —$SO_2NY^1Y^2$, —$C(=Z)$—$NY^1Y^2$, —$N(R^{11})$—$C(=Z)$—$NY^1Y^2$, —$N(OR^{10})$—$C(=Z)$—$NY^1Y^2$, —$N(OR^{10})$—$C(=Z)R^{10}$, —$C(=NOR^{10})R^{10}$, —$C(=Z)NR^{10}OR^{12}$, —$N(R^{11})$—$C(=NR^{13})$—$NY^1Y^2$ or —$N(R^{11})$—$C(=Z)OR^{11}$; $L^2$ is a direct bond or a straight- or branched-carbon chain comprising from 2 to about 6 carbon atoms and contains a double or triple carbon-carbon bond; and $R^8$ is hydrogen, aryl, cycloalkenyl, cycloalkyl, heteroaryl or heterocycloalkyl]; $R^4$ is a group —$L^3$—$R^{14}$ [where $L^3$ is a direct bond or an optionally substituted alkylene linkage and $R^{14}$ is hydrogen, alkyl, azido, hydroxy, alkoxy, aryl, arylalkyloxy, aryloxy, carboxy (or an acid bioisostere), cycloalkyloxy, heteroaryl, heteroarylalkyloxy, heteroaryloxy, heterocycloalkyl, heterocycloalkyloxy, nitro, —$NY^4Y^5$, —$N(R^{10})$—$C(=Z)$—$R^{15}$; —$N(R^{10})$—$C(=Z)$—$L^4$—$R^{16}$, —$NH$—$C(=Z)$—$NH$—$R^{15}$, —$NH$—$C(=Z)$—$NH$—$L^4$—$R^{16}$, —$N(R^{10})$—$SO_2$—$R^{15}$, —$N(R^{10})$—$SO_2$—$L^4$—$R^{16}$, —$S(O)_n R^9$, —$C(=Z)$—$NY^4Y^5$ or —$C(=Z)$—$OR^9$]; $R^5$ is hydrogen, alkyl or hydroxyalkyl; or $R^4$ and $R^5$, when attached to the same carbon atom, may form with the said carbon atom a cycloalkyl, cycloalkenyl or heterocycloalkyl ring or a group $C=CH_2$; $R^6$ is hydrogen or alkyl; and m is zero or an integer 1 or 2; and N-oxides thereof, and their prodrugs; and pharmaceutically acceptable salts and solvates (e.g. hydrates) of compounds of formula (I) and N-oxides thereof, and their prodrugs.

The compounds are TNF inhibitors and are useful as pharmaceuticals.

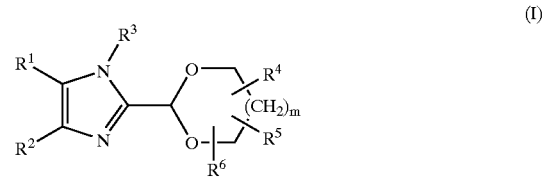

(I)

36 Claims, No Drawings

FOREIGN PATENT DOCUMENTS

| EP | 0236628 | 9/1987 |
|---|---|---|
| EP | 0275820 | 11/1987 |
| EP | 0264883 | 4/1988 |
| EP | 0274353 | 7/1988 |
| EP | 0424195 | 4/1991 |
| EP | 0506437 | 9/1992 |
| EP | 0653421 | 5/1995 |
| EP | 0790238 | 8/1997 |
| GB | 2306108 | 4/1997 |
| JP | 7053546 | 2/1995 |
| JP | 9124640 | 5/1997 |
| WO | 8302611 | 8/1983 |
| WO | 9103243 | 3/1991 |
| WO | 9205148 | 4/1992 |
| WO | 9314081 | 7/1993 |
| WO | 9314082 | 7/1993 |
| WO | 9323392 | 11/1993 |
| WO | 9419350 | 9/1994 |
| WO | 9503297 | 2/1995 |
| WO | 9513067 | 5/1995 |
| WO | 9616040 | 5/1996 |
| WO | 9621452 | 7/1996 |
| WO | 9705877 | 2/1997 |
| WO | 9705878 | 2/1997 |
| WO | 9712876 | 4/1997 |
| WO | 9716426 | 5/1997 |
| WO | 9716441 | 5/1997 |
| WO | 9716442 | 5/1997 |
| WO | 9735855 | 10/1997 |

OTHER PUBLICATIONS

Searles et al. "Oxetanes IX. Structural and solvent effects in the reaction of gamma–bromoalcohols with base." Journal of Organic Chemistry, 24(12):1839–1844 (1960).

Nys et al. "The chemistry of the delta2–dihydrazoles." Bulletin Des Societies Chimique Belges. 65:37–402 (1956).

Czech et al. "Synthesis of Benzo–13–crown–4 derivatives." Journal of Heterocyclic Chemistry. 28:1387–1394 (1991).

Shiuh–Tzung et al., "Synthesis of amino–containing phosphines. The use of iminophosphorane as a protecting for primary amines." Journal of Organic Chemistry 57:6079–6080 (1992).

Mozingo et al. Hydrogenolysis of beta–oxygenated esters to glycoles. JACS 70:227–229 (1948).

Cherbuliez et al. , "Recherches sur la formation et al tranformation des esters." Helvetica Chimica Acta 50(8):2563–2569 (1967).

Broadbent et al., "Novel Heteroyclic Systems." J. Hetero. Chem. 13:337–348(1976).

Gallagher et al. "2,4,5–triarylimidazole inhibitors of IL–1 biosynthesis." Bioorganic and Medicinal Chemistry Letters, 5(11):1171–1176 (1995).

Gallagher et al. "Regulation of stress–induced cytokine production by pyridinylimidazoles; inhibition of CSBP kinase." Bioorganic & Medicinal Chemistry 5(1):49–64 (1997).

Boehm et al. 1–substituted 4–aryl–5–pyridinylimidazoles: A new class of cytokine suppressive drugs with low 5–lipoxygene and cyclooxygenasse inhibitory potency. J. Med. Chem. 39(20):3929–3937 (1996).

Hadri et al. A convenient synthesis of cis–4–(sulfomethyl) piperidine–2–carboxylic acid. J. Hetero. Chem. 30(3):631–635 (1993).

Procopiou et al. "A novel oxidative rearrangement of a pentasubstituted pyrrole to an unsaturated hydroxy gamma––lactam." J. Chem. Soc., Perkin Trans. 1(3):245–247 (1994).

Gilligan, et al. "Novel piperidine sigma–receptor ligands as potential antipsychotic drugs." J. Med. Chem. 35(23):4344–4361 (1992).

Senderoff, et al. "Synthesis of carbon–14–labeled 6–(4–fluorophenyl)–5–(4–pyridyl)–2,3–dihydroimidazo [2,1–b] thiazole." J. Labelled Compd. Radiopharm. 24(8):971–978 (1987).

Lantos, et al. "Antiinflammatory activity of 5,6–diaryl–2, 3–dihydroimidazo [2,1–b] tiazoles. Isomeric 4–pyridyl and 4–substituted–phenyl derivatives." J. Med. Chem. 27(1):72–75 (1984).

Procopiou et al. "Inhibitors of cholesterol biosynthesis. 2 3,5–dihydroxy–7–(N–pyrrolyl)–6–heptenoates, a novel series of HMG–CoA Reductase Inhibitors." J. Med. Chem. 36:3658–3662 (1993).

IMIDAZOLYL-CYCLIC ACETALS

This application is a continuation of international application No. PCT/GB98/01711, filed Jun. 12, 1998, which is a continuation-in-part application of U.S. provisional application No. 60/052,185, filed Jul. 10, 1997, now abandoned, and U.S. provisional application No. 60/085,499, filed May 14, 1998, now abandoned.

This invention is directed to imidazolyl-cyclic acetals, their preparation, pharmaceutical compositions containing these compounds, and their pharmaceutical use in the treatment of disease states capable of being modulated by the inhibition of TNF.

Tumour necrosis factor (TNF) is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and adult respiratory distress syndrome, and its role in many other immunologic processes, this factor is regarded as an important mediator of general inflammation.

TNF primes or activates neutrophils, eosinophils, and endothelial cells to release tissue damaging mediators and increase the expression of adhesion molecules. In fibroblasts, TNF stimulates the production of collagenase, an enzyme implicated in the joint destruction in rheumatoid arthritis. TNF also activates monocytes, macrophages and T-lymphocytes to cause the production of colony stimulating factors and other pro-inflammatory cytokines such IL-1, IL-6, IL-8 and GM-CSF, which in some cases mediate the end effects of TNF. The ability of TNF to activate T-lymphocytes, monocytes, macrophages and related cells has been implicated in the progression of Human Immuno-deficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF. The cachexia associated with certain disease states is mediated through indirect effects on protein catabolism. TNF also promotes bone resorption and acute phase protein synthesis.

TNF-alpha inhibits surfactant protein C gene transcription, which may contribute to abnormalities of surfactant homeostasis associated with pulmonary injury and infection, induces mucin hypersecretion and mediates the recruitment of neutrophils and eosinophils during airway inflammation. Although TNF-alpha inhibits collagen synthesis in fibroblasts, a number of studies point to it being pro-fibrotic in vivo. Thus, by inhibiting TNF-alpha production, the compounds of the invention have potential in suppressing the inflammation and airways remodelling that occurs in asthma.

TNF-alpha inhibits the ability of insulin to stimulate glucose uptake in adipose tissue. In obesity the overproduction of TNF is thought to cause an insulin-resistant state. Thus, by blocking TNF release the compounds of the invention have anti-diabetic potential.

TNF-alpha can induce angiogenesis in normally avascular tissue, possibly through upregulation of other pro-inflammatory cytokines, upregulation of adhesion molecules, stimulation of matrix mettalloproteinase expression and increased prostaglandin production. Thus, inhibition of TNF-alpha release by compounds of the invention will have benefit in angiogenesis dependent diseases including arthritis, diabetic retinopathies and ischemia induced diseases (myocardial infarction) and cancer.

The discussion herein relates to disease states associated with TNF including those disease states related to the production of TNF itself, and disease states associated with other cytokines, such as, but not limited to IL-1 or IL-6, that are modulated by association with TNF. For example, a IL-1 associated disease state, where IL-1 production or action is exacerbated or secreted in response to TNF, would therefore be considered a disease state associated with TNF. TNF-alpha and TNF-beta are also herein referred to collectively as "TNF" unless specifically delineated otherwise, since there is a close structural homology between TNF-alpha (cachectin) and TNF-beta (lymphotoxin) and each of them has a capacity to induce similar biological responses and bind to the same cellular receptor.

We have now found a novel group of imidazolyl-cyclic acetals which have valuable pharmaceutical properties, in particular the ability to regulate proteins that mediate cellular activity, for example TNF.

Thus, in one aspect, the present invention is directed to compounds of general formula (I):

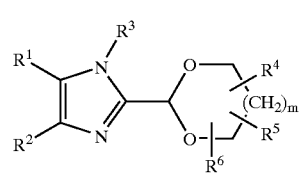

wherein:

$R^1$ is optionally substituted heteroaryl;

$R^2$ is optionally substituted aryl or optionally substituted heteroaryl;

$R^3$ represents a group —$L^1$—$R^7$ or —$L^2$—$R^8$

[where $L^1$ represents a straight- or branched-chain alkylene linkage containing from 1 to about 6 carbon atoms optionally substituted by halogen or oxo; $R^7$ is hydrogen, aryl, cyano, cycloalkyl, heteroaryl, heterocycloalkyl, nitro, —S(O)$_n$R$^9$, (where R$^9$ is alkyl, aryl, arylalkyl, cycloalkyl, heteroaryl, heteroarylalkyl, or heterocycloalkyl and n is zero or an integer 1 or 2), —NHSO$_2$R$^9$, —C(=Z)OR$^{10}$ (where Z is an oxygen or sulphur atom and R$^{10}$ is hydrogen or R$^9$), —C(=Z)R$^{10}$, —OR$^{10}$, —N(R$^{11}$)—C(=Z)R$^9$ (where R$^{11}$ is hydrogen or alkyl), —NY$^1$Y$^2$ {where Y$^1$ and Y$^2$ are independently hydrogen, alkenyl, alkyl, alkynyl, aryl, arylalkyl, cycloalkenyl, cycloalkyl, heteroaryl or heteroarylalkyl, or the group —NY$^1$Y$^2$ may form a 5–7 membered cyclic amine which may optionally contain a further heteroatom selected from O, S, or NY$^3$ (where Y$^3$ is hydrogen, alkyl, aryl, arylalkyl, —CHO, —C(=Z)R$^9$ or —SO$_2$R$^9$), or which may also be fused to additional aryl, heteroaryl, heterocycloalkyl or cycloalkyl rings to form a bicyclic or tricyclic ring system}, —SO$_2$—NY$^1$Y$^2$, —C(=Z)—NY$^1$Y$^2$, —N(R$^{11}$)—C(=Z)—NY$^1$Y$^2$, —N(OR$^{10}$)—C(=Z)—NY$^1$Y$^2$, —N(OR$^{10}$)—C(=Z)R$^{10}$, —C(=NOR$^{10}$)R$^{10}$, —C(=Z)NR$^{10}$OR$^{12}$ (where R$^{12}$ is hydrogen, alkyl, aryl or arylalkyl), —N(R$^{11}$)—C(=NR$^{13}$)—NY$^1$Y$^2$ (where R$^{13}$ is hydrogen, cyano, alkyl, cycloalkyl or aryl), or —N(R$^{11}$)—C(=Z)OR$^{11}$; L$^2$ represents a direct bond or a straight- or branched-carbon chain comprising from 2 to about 6 carbon atoms and contains a double or triple carbon-carbon bond; and R$^8$ is hydrogen, aryl, cycloalkenyl, cycloalkyl, heteroaryl or heterocycloalkyl];

R$^4$ represents a group —L$^3$—R$^{14}$

[where L$^3$ represents a direct bond or a straight- or branched-chain alkylene linkage containing from 1 to about 6 carbon atoms (optionally substituted by halogen, hydroxy, alkoxy or oxo); and R$^{14}$ is hydrogen, alkyl, azido, hydroxy, alkoxy, aryl, arylalkyloxy, aryloxy, carboxy (or an acid bioisostere), cycloalkyloxy, heteroaryl, heteroarylalkyloxy, heteroaryloxy, heterocycloalkyl, heterocycloalkyloxy, nitro, —NY$^4$Y$^5$, {where Y$^4$ and Y$^5$ are independently hydrogen, aryl, cycloalkyl, heterocycloalkyl, heteroaryl or alkyl optionally substituted by alkoxy, aryl, cyano, cycloalkyl, heteroaryl, heterocycloalkyl, hydroxy, oxo, —CO$_2$R$^{10}$, —CONY$^1$Y$^2$ or —NY$^1$Y$^2$, or the group —NY$^4$Y$^5$ may form a 5–7 membered cyclic amine which (i) may be optionally substituted with one or more substituents selected from alkoxy, carboxamido, carboxy, hydroxy, oxo (or a 5, 6,or 7 membered cyclic acetal derivative thereof), R$^9$ or alkyl substituted by carboxy, carboxamido or hydroxy (ii) may also contain a further heteroatom selected from O, S, SO$_2$ or NY$^6$ (where Y$^6$ is hydrogen, alkyl, aryl, arylalkyl, —C(=Z)R$^9$, —C(=Z)OR$^9$ or —SO$_2$R$^9$) and (iii) may also be fused to additional aryl, heteroaryl, heterocycloalkyl or cycloalkyl rings to form a bicyclic or tricyclic ring system}, —N(R$^{10}$)—C(=Z)—R$^{15}$ (where R$^{15}$ is alkyl, alkoxy, aryl, arylalkyloxy, cycloalkyl, heteroaryl, heteroarylalkoxy or heterocycloalkyl); —N(R$^{10}$)—C(=Z)—L$^4$—R$^{16}$ (where R$^{16}$ is alkoxy, aryl, arylalkyl arylalkyloxy carbonylamino, carboxy (or an acid bioisostere), cycloalkyl, cyano, halo, heteroaryl, heteroarylalkoxy, heterocycloalkyl, hydroxy or —NY$^1$Y$^2$, and L$^4$ is a straight- or branched-chain alkylene linkage containing from 1 to about 6 carbon atoms), —NH—C(=Z)—NH—R$^{15}$, —NH—C(=Z)—NH—L$^4$—R$^{16}$, —N(R$^{10}$)—SO$_2$—R$^{15}$, —N(R$^{10}$)—SO$_2$—L$^4$—R$^{16}$, —S(O)$_n$R$^9$, —C(=Z)—NY$^4$Y$^5$ or —C(=Z)—OR$^9$];

R$^5$ represents hydrogen, alkyl or hydroxyalkyl; or

R$^4$ and R$^5$, when attached to the same carbon atom, may form with the said carbon atom a cycloalkyl, cycloalkenyl or heterocycloalkyl ring or a group C=CH$_2$;

R$^6$ represents hydrogen or alkyl; and m is zero or an integer 1 or 2;

and N-oxides thereof, and their prodrugs; and pharmaceutically acceptable salts and solvates (e.g. hydrates) of compounds of formula (I) and N-oxides thereof, and their prodrugs.

In the present specification, the term "compounds of the invention", and equivalent expressions, are meant to embrace compounds of general formula (I) as hereinbefore described, which expression includes the N-oxides, the prodrugs, the pharmaceutically acceptable salts, and the solvates, e.g. hydrates, where the context so permits. Similarly, reference to intermediates, whether or not they themselves are claimed, is meant to embrace their N-oxides, salts, and solvates, where the context so permits. For the sake of clarity, particular instances when the context so permits are sometimes indicated in the text, but these instances are purely illustrative and it is not intended to exclude other instances when the context so permits.

It will be appreciated that when m is zero the cyclic acetal system in formula (I) represents a 1,3-dioxolane ring; when m is 1 the cyclic acetal system in formula (I) represents a 1,3-dioxane; and when m is 2 the cyclic acetal system in formula (I) represents a 1,3-dioxepane.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, page 283 "Bioisosterism In Drug Design"; Yun, Hwahak Sekye, 1993, 33, pages 576–579 "Application Of Bioisosterism To New Drug Design"; Zhao, Huaxue Tongbao, 1995, pages 34–38 "Bioisosteric Replacement And Development Of Lead Compounds In Drug Design"; Graham, Theochem, 1995, 343, pages 105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxymethyl" means an alkyl-O—CH$_2$— group in which the alkyl group is as described herein. Exemplary alkoxymethyl groups include methoxymethyl and ethoxymethyl.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain, optionally substituted by one or more halogen atoms. Particular alkyl groups have from 1 to about 6 carbon atoms. Exemplary alkyl groups for $R^5$, $R^6$ and within $R^4$ include $C_{1-4}$alkyl groups such as methyl, ethyl, n-propyl and i-propyl.

"Alkylene" means a straight or branched bivalent hydrocarbon chain having from 1 to about 15 carbon atoms. Particular alkylene groups are the lower alkylene groups having from 1 to about 6 carbon atoms. Exemplary groups include methylene and ethylene.

"Alkylsulphinyl" means an alkyl-SO— group in which the alkyl group is as previously described. Preferred groups are those in which the alkyl group is $C_{1-4}$alkyl.

"Alkylsulphonyl" means an alkyl-$SO_2$— group in which the alkyl group is as previously described. Preferred groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^7Y^8N$—, $Y^7Y^8NCO$—, $Y^7Y^8NSO_2$—(where $Y^7$ and $Y^8$ are independently hydrogen, alkyl, aryl, arylalkyl, heteroaryl and heteroarylalkyl), $Y^7Y^8N$—$C_{2-6}$alkylene-$Z^2$— (where $Z^2$ is O, $NR^5$ or $S(O)_n$), alkylC(=O)—$Y^7N$—, alkyl$SO_2$—$Y^7N$— or alkyl optionally substituted with aryl, heteroaryl, hydroxy, or $Y^7Y^8N$—. Preferred aryl group substituents within $R^2$ include halogen, alkoxy, trifluoromethyl, alkylthio, alkylsulphinyl, $Y^7Y^8N$—, alkylC(=O)—$Y^7N$— or alkyl$SO_2$—$Y^7N$—, more preferably fluoro.

"Arylalkyl" means an aryl-alkyl— group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include optionally substituted phenoxy and naphthoxy.

"Aryloxycarbonyl" means an aryl-O—CO— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of optionally substituted azaheteroaryl groups include pyridyl, pyrimidinyl, quinolinyl, isoquinolinyl, quinazolinyl, imidazolyl, and benzimidazolyl, optionally substituted with one or more "heteroaryl group substituents". Preferred azaheteroaryl groups within $R^1$ include optionally substituted pyridyl and pyrimidinyl. Preferred heteroaryl group substituents when $R^1$ is pyrimidinyl include $R^{17}Z^3$— [where $R^{17}$ is alkyl, aryl, cycloalkyl, heteroaryl, heterocycloalkyl, or alkyl substituted by alkoxy, aryl, cyano, cycloalkyl, heteroaryl, heterocycloalkyl, hydroxy, oxo, —$CO_2R^{10}$, —$CONY^1Y^2$ or—$NY^4Y^5$ and $Z^3$ is O or $S(O)_n$] and $Y^4Y^5N$—.

"Cycloalkenyl" means an optionally substituted non-aromatic monocyclic or multicyclic ring system containing at least one carbon-carbon double bond and having about 5 to about 10 carbon atoms. Exemplary monocyclic cycloalkenyl rings include cyclopentenyl, cyclohexenyl and cyclopentenyl. Exemplary multicyclic cycloalkenyl ring include norbornenyl. The cycloalkenyl group may be substituted by one or more substituents chosen from, for example, halo, or alkyl.

"Cycloalkoxymethyl" means a cycloalkyl-O—$CH_2$- group in which the cycloalkyl group is as described hereinafter. Exemplary cycloalkoxymethyl groups include cyclopropyloxymethyl and cyclopentyloxymethyl.

"Cycloalkyl" means an optionally substituted non-aromatic monocyclic or multicyclic ring system of about 3 to about 10 carbon atoms. Exemplary monocyclic cycloalkyl rings include cyclopropyl, cyclopentyl, cyclohexyl and cycloheptyl. Exemplary multicyclic cycloalkyl rings include perhydronaphthyl, adamant-(1- or 2-)yl and norbornyl and spirocyclic groups e.g. spiro[4,4]non-2yl. When $R^3$ is, or contains, a cycloalkyl ring this may particularly represent a 3 to 7 membered monocyclic ring, especially cyclohexyl. The cycloalkyl group may be substituted by one or more (e.g. 1, 2, or 3) substituents chosen from, for example, alkyl, aryl, arylalkyl, halo, halo substituted alkyl (such as trifluoromethyl), hydroxyalkyl, hydroxy, alkoxy, —S(O)$_n$-alkyl, —NY$^1$Y$^2$ or —CO$_2$R$^{12}$.

"Cycloalkylalkyl" means a cycloalkyl-alkyl— group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkyloxy" means a cycloalkyl-O— group in which the cycloalkyl group is as described herein. Exemplary cycloalkyloxy groups include cyclopropyloxy, cyclopentyloxy, cyclohexyloxy and cycloheptyloxy.

"Halo" or "halogen" means fluoro, chloro, bromo, or iodo. Preferred are fluoro or chloro.

"Heteroaroyl" means a heteroaryl-CO— group in which the heteroaryl group is as described herein. Exemplary groups include pyridylcarbonyl.

"Heteroaroylamino" means a heteroaroyl-NH— group in which the heteroaroyl moiety is as previously described.

"Heteroaryl" as a group or part of a group denotes an optionally substituted aromatic monocyclic or multicyclic organic moiety of about 5 to about 10 ring members in which one or more of the ring members is/are element(s) other than carbon, for example nitrogen, oxygen or sulphur. Examples of suitable optionally substituted heteroaryl groups include benzimidazolyl, furyl, imidazolyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups. When $R^1$ is an optionally substituted heteroaryl group this may particularly represent an optionally substituted "azaheteroaryl" group. Heteroaryl groups may be substituted with one or more heteroaryl group substituents which may be the same or different, where "heteroaryl group substituent" includes, for example acyl, acylamino, alkoxycarbonyl, alkylenedioxy, aroyl, aroylamino, aryl, arylalkyloxycarbonyl, aryloxycarbonyl, carboxy, cyano, halo, heteroaroyl, heteroaryl, heteroaroylamino, hydroxy, nitro, trifluoromethyl, $R^{17}Z^3$—, $Y^4Y^5N$—, $Y^4Y^5N$—CO—, $Y^4Y^5NSO_2$—, alkylSO$_2$—Y$^4$N— or alkyl optionally substituted with aryl, heteroaryl, hydroxy, oxo, —CO$_2$R$^{10}$, —CONY$^1$Y$^2$ or Y$^4$Y$^5$N—.

"Heteroarylalkyl" means a heteroaryl-alkyl— group in which the heteroaryl and alkyl moieties are as previously described. Preferred heteroarylalkyl groups contain a C$_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-SO$_2$—NH—C(=O)— group in which the heteroaryl group is as previously described.

"Heterocycloalkyl" means a cycloalkyl group of about 3 to 7 ring members which contains one or more heteroatoms selected from O, S or NY$^3$. Exemplary heterocycloalkyl groups include 5–7 membered cyclic ethers such as tetrahydrofuran and perhydropyran.

"Heterocycloalkylalkyl" means a heterocycloalkylalkyl— group in which the heterocycloalkyl and alkyl moieties are as previously described.

"Heterocycloalkyloxy" means a heterocycloalkyl-O— group in which the heterocycloalkyl is as previously defined.

"Hydroxyalkyl" means a HO-alkyl— group in which alkyl is as previously defined. Preferred hydroxyalkyl groups contain C$_{1-4}$alkyl. Exemplary hydroxyalkyl groups include hydroxymethyl and 2-hydroxyethyl.

"Y$^7$Y$^8$N—" means a substituted or unsubstituted amino group, wherein Y$^7$ and Y$^8$ are as previously described. Exemplary groups include amino (H$_2$N—), methylamino, ethylmethylamino, dimethylamino and diethylamino.

"Y$^7$Y$^8$NCO—" means a substituted or unsubstituted carbamoyl group, wherein Y$^7$ and Y$^8$ are as previously described. Exemplary groups are carbamoyl (H$_2$NCO—) and dimethylcarbamoyl (Me$_2$NCO—).

"Y$^7$Y$^8$NSO$_2$—" means a substituted or unsubstituted sulphamoyl group, wherein Y$^7$ and Y$^8$ are as previously described. Exemplary groups are sulphamoyl (H$_2$NSO$_2$—) and dimethylsulphamoyl (Me$_2$NSO$_2$—).

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates, methanolates, and the like.

Suitable esters of compounds of formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, iseth ionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, omithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent optionally substituted azaheteroaryl such as optionally substituted pyridyl, pyrimidinyl, quinolinyl, isoquinolinyl, quinazolinyl, imidazolyl or benzimidazolyl (for example optionally substituted 4-pyridyl, 4-pyrimidinyl, 4-quinolinyl, 6-isoquinolinyl, 4-quinazolinyl, 1-imidazolyl or 1-benzimidazolyl). $R^1$ is preferably optionally substituted 4-pyridyl or 4-pyrimidinyl, especially unsubstituted 4-pyridyl or 2-substituted 4-pyrimidinyl. Preferred substituents include $C_{1-4}$alkyl, especially methyl, —$NY^4Y^5$ (especially where at least one of $Y^4$ and $Y^5$ is hydrogen) or —$OR^{17}$ (especially where $R^{17}$ is cycloalkyl).

$R^2$ is preferably optionally substituted phenyl, particularly when substituted by halogen, especially fluoro and chloro, or an alkylthio or alkylsulphinyl group, especially methylthio or methysulphinyl, or a trifluoromethyl group. $R^2$ is more preferably phenyl substituted by a halogen (e.g. fluorine) atom, especially in the 4-position.

$R^3$ may particularly represent hydrogen or $C_{1-4}$alkyl, preferably hydrogen.

$R^4$ may particularly represent a group —$L^3$—$R^{14}$ where $L^3$ is a direct bond and $R^{14}$ is —$NY^4Y^5$, where $Y^4$ and $Y^5$ are as defined hereinbefore, especially where $Y^4$ and $Y^5$ are hydrogen.

$R^4$ may also particularly represent a group —$L^3$—$R^{14}$ where $L^3$ is a direct bond and $R^{14}$ is —$N(R^{10})$—$C(=Z)$—$R^{15}$, in which Z, $R^{10}$ and $R^{15}$ are as defined hereinbefore, especially where Z is oxygen, $R^{10}$ is hydrogen and $R^{15}$ is alkyl (especially methyl), aryl (e.g. substituted or more preferably, unsubstituted phenyl) or heteroaryl.

$R^4$ may also particularly represent a group —$L^3$—$R^{14}$ where $L^3$ is a direct bond and $R^{14}$ is —$N(R^{10})$—$C(=Z)$—$L^4$—$R^{16}$, in which Z, $L^4$, $R^{10}$ and $R^{16}$ are as defined hereinbefore, especially where Z is oxygen, $L^4$ is methylene, $R^{10}$ is hydrogen, and $R^{16}$ is aryl (e.g. substituted or more preferably, unsubstituted phenyl) or heteroaryl.

$R^4$ may also particularly represent a group —$L^3$—$R^{14}$ where $L^3$ is a direct bond and $R^{14}$ is —$C(=Z)$—$NY^4Y^5$, in which Z is as defined hereinbefore, especially oxygen, and $Y^4$ and $Y^5$ are as defined hereinbefore, especially where $Y^4$ and $Y^5$ are hydrogen or where $Y^4$ is hydrogen and $Y^5$ is aryl, arylalkyl, heteroaryl or heteroarylalkyl.

$R^4$ may also particularly represent a group —$L^3$—$R^{14}$ where $L^3$ is a direct bond and $R^{14}$ is —$C(=Z)$—$NY^4Y^5$, in which Z is as defined hereinbefore, especially oxygen, and the group —$NY^4Y^5$ forms a 5–7 membered cyclic amine [which may optionally contain a further heteroatom selected from O, S or $NY^6$ (where $Y^6$ is as defined hereinbefore)], preferably a 5–7 membered cyclic amine optionally containing oxygen, especially a morpholine ring.

$R^4$ may also particularly represent a group —$L^3$—$R^{14}$ where $L^3$ is a direct bond and $R^{14}$ is —$C(=Z)$—$OR^9$, in which Z and $R^9$ are as defined hereinbefore, especially where Z is oxygen and $R^9$ is $C_{1-4}$alkyl, preferably methyl.

$R^4$ may also particularly represent a group —$L^3$—$R^{14}$ where $L^3$ is a direct bond, especially methylene or ethylene, and $R^{14}$ is alkyl, especially methyl.

$R^4$ may also particularly represent a group —$L^3$—$R^{14}$ where $L^3$ is $C_{1-6}$alkylene, especially methylene, and $R^{14}$ is hydroxy.

$R^4$ may also particularly represent a group —$L^3$—$R^{14}$ where $L^3$ is $C_{1-6}$alkylene, especially methylene, and $R^{14}$ is —$N(R^{10})$—$C(=Z)$—$R^{15}$, in which Z, $R^{10}$ and $R^{15}$ are as defined hereinbefore, especially where Z is oxygen, $R^{10}$ is hydrogen and $R^{15}$ is alkyl, aryl or heteroaryl.

$R^4$ may also particularly represent a group —$L^3$—$R^{14}$ where $L^3$ is $C_{1-6}$alkylene, especially methylene, and $R^{14}$ is —$N(R^{10})$—$C(=Z)$—$L^4$—$R^{16}$, in which Z, $L^4$, $R^{10}$ and $R^{15}$ are as defined hereinbefore, especially where Z is oxygen, $L^4$ is $C_{1-6}$alkylene, especially methylene, $R^{10}$ is hydrogen and $R^{16}$ is aryl or heteroaryl.

$R^4$ may also particularly represent a group —$L^3$—$R^{14}$ where $L^3$ is $C_{1-6}$alkylene, especially methylene, and $R^{14}$ is —$NHC(=Z)$—$NH$—$R^{15}$, in which Z and $R^{15}$ are as defined hereinbefore, especially where $R^{15}$ is alkyl, aryl or heteroaryl.

$R^4$ may also particularly represent a group —$L^3$—$R^{14}$ where $L^3$ is $C_{1-6}$alkylene, especially methylene, and $R^{14}$ is —NH—C(=Z)—NH—$L^4$—$R^{16}$, in which Z, $L^4$ and $R^{16}$ are as defined hereinbefore, especially where $L^4$ is methylene and $R^{15}$ is aryl or heteroaryl.

$R^4$ may also particularly represent a group —$L^3$—$R^{14}$ where $L^3$ is $C_{1-6}$alkylene, especially $C_{1-3}$alkylene, preferably methylene, and $R^{14}$ is —$NY^4Y^5$, where $Y^4$ and $Y^5$ are as defined hereinbefore, especially where $Y^4$ and $Y^5$ are hydrogen.

$R^4$ may also particularly represent a group —$L^3$—$R^{14}$ where $L^3$ is $C_{1-6}$alkylene, especially methylene or ethylene, and $R^{14}$ is aryl or heteroaryl.

$R^4$ may also particularly represent a group —$L^3$—$R^{14}$ where $L^3$ is $C_{1-6}$alkylene, especially methylene, and $R^{14}$ is —N($R^{10}$)—$SO_2$—$R^{15}$, in which $R^{10}$ and $R^{15}$ are as defined hereinbefore, especially where $R^{10}$ is hydrogen and $R^{15}$ is alkyl, aryl or heteroaryl.

$R^4$ may also particularly represent a group —$L^3$—$R^{14}$ where $L^3$ is $C_{1-6}$alkylene, especially methylene, and $R^{14}$ is —N($R^{10}$)—$SO_2$—$L^4$—$R^{15}$, in which $L^4$, $R^{10}$ and $R^{15}$ are as defined hereinbefore, especially where $L^4$ is methylene, $R^{10}$ is hydrogen and $R^{15}$ is alkyl, aryl or heteroaryl.

$R^5$ may particularly represent hydrogen or $C_{1-4}$alkyl, especially methyl.

$R^5$ may also particularly represent hydroxyalkyl, especially hydroxymethyl.

$R^4$ and $R^5$ together with the carbon atom to which they are attached may particularly represent a group C=$CH_2$ or a 5–7 membered cyclic ether such as tetrahydrofuran-2-yl or perhydropyran-2-yl.

$R^6$ may particularly represent hydrogen or $C_{1-4}$alkyl, especially hydrogen.

m is preferably an integer 1.

It is to be understood that this invention covers all appropriate combinations of the particular and preferred groupings referred to herein.

A particular group of compounds of the invention are compounds of formula (Ia):

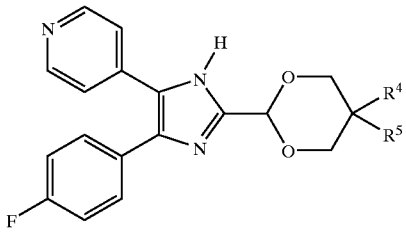

(Ia)

in which $R^4$ and $R^5$ are as hereinbefore defined, and N-oxides thereof, and their prodrugs; and pharmaceutically acceptable salts and solvates (e.g. hydrates) of compounds of formula (Ia) and N-oxides thereof, and their prodrugs.

Compounds of formula (Ia) in which $R^4$ represents a group —$L^3$—$R^{14}$ where $L^3$ is a direct bond and $R^{14}$ is —$NY^4Y^5$, where $Y^4$ and $Y^5$ are as defined hereinbefore, especially where $Y^4$ and $Y^5$ are hydrogen, are preferred.

Compounds of formula (Ia) in which $R^4$ represents a group —$L^3$—$R^{14}$ where $L^3$ is a direct bond and $R^{14}$ is —N($R^{10}$)—C(=Z)—$R^{15}$, in which Z, $R^{10}$ and $R^{15}$ are as defined hereinbefore, especially where Z is oxygen, $R^{10}$ is hydrogen and $R^{15}$ is alkyl (especially methyl), aryl (e.g. substituted or more preferably, unsubstituted phenyl) or heteroaryl, are also preferred.

Compounds of formula (Ia) in which $R^4$ represents a group —$L^3$—$R^{14}$ where $L^3$ is a direct bond and $R^{14}$ is —N($R^{10}$)—C(=Z)—$L^4$—$R^{16}$, in which Z, $L^4$, $R^{10}$ and $R^{16}$ are as defined hereinbefore, especially where Z is oxygen, $L^4$ is methylene, $R^{10}$ is hydrogen, and $R^{16}$ is aryl (e.g. substituted or more preferably, unsubstituted phenyl) or heteroaryl, are also preferred.

Compounds of formula (Ia) in which $R^4$ represents a group —$L^3$—$R^{14}$ where $L^3$ is a direct bond and $R^{14}$ is —C(=Z)—$NY^4Y^5$, in which Z is as defined hereinbefore, especially oxygen, and $Y^4$ and $Y^5$ are as defined hereinbefore, especially where $Y^4$ and $Y^5$ are hydrogen or where $Y^4$ is hydrogen and $Y^5$ is aryl, heteroaryl or heteroarylalkyl, are also preferred.

Compounds of formula (Ia) in which $R^4$ represents a group —$L^3$—$R^{14}$ where $L^3$ is a direct bond and $R^{14}$ is —C(=Z)—$NY^4Y^5$, in which Z is as defined hereinbefore, especially oxygen, and the group —$NY^4Y^5$ forms a 5–7 membered cyclic amine [which may optionally contain a further heteroatom selected from O, S or $NY^6$ (where $Y^6$ is as defined hereinbefore)], preferably a 5–7 membered cyclic amine optionally containing oxygen, especially a morpholine ring, are also preferred.

Compounds of formula (Ia) in which $R^4$ represents a group —$L^3$—$R^{14}$ where $L^3$ is a direct bond and $R^{14}$ is —C(=Z)—$OR^9$, in which Z and $R^9$ are as defined hereinbefore, especially where Z is oxygen and $R^9$ is $C_{1-4}$alkyl, preferably methyl, are also preferred.

Compounds of formula (Ia) in which $R^4$ represents a group —$L^3$—$R^{14}$ where $L^3$ is a direct bond, especially methylene or ethylene, and $R^{14}$ is alkyl, especially methyl, are also preferred.

Compounds of formula (Ia) in which $R^4$ represents a group —$L^3$—$R^{14}$ where $L^3$ is $C_{1-6}$alkylene, especially methylene, and $R^{14}$ is hydroxy, are also preferred.

Compounds of formula (Ia) in which $R^4$ represents a group —$L^3$—$R^{14}$ where $L^3$ is $C_{1-6}$alkylene, especially methylene, and $R^{14}$ is —N($R^{10}$)—C(=Z)—$R^{15}$, in which Z, $R^{10}$ and $R^{15}$ are as defined hereinbefore, especially where Z is oxygen, $R^{10}$ is hydrogen and $R^{15}$ is alkyl, aryl or heteroaryl, are also preferred.

Compounds of formula (Ia) in which $R^4$ represents a group —$L^3$—$R^{14}$ where $L^3$ is $C_{1-6}$alkylene, especially methylene, and $R^{14}$ is —N($R^{10}$)—C(=Z)—$L^4$—$R^{16}$, in which Z, $L^4$, $R^{10}$ and $R^{15}$ are as defined hereinbefore, especially where Z is oxygen, $L^4$ is $C_{1-6}$alkylene, especially methylene, $R^{10}$ is hydrogen and $R^{16}$ is aryl or heteroaryl, are also preferred.

Compounds of formula (Ia) in which $R^4$ represents a group —$L^3$—$R^{14}$ where $L^3$ is $C_{1-6}$alkylene, especially methylene, and $R^{14}$ is —NH—C(=Z)—NH—$R^{15}$, in which Z and $R^{15}$ are as defined hereinbefore, especially where $R^{15}$ is alkyl, aryl or heteroaryl, are also preferred.

Compounds of formula (Ia) in which $R^4$ represents a group —$L^3$—$R^{14}$ where $L^3$ is $C_{1-6}$alkylene, especially methylene, and $R^{14}$ is —NH—C(=Z)—NH—$L^4$—$R^{16}$, in which Z, $L^4$ and $R^{16}$ are as defined hereinbefore, especially where $L^4$ is methylene and $R^{15}$ is aryl or heteroaryl, are also preferred.

Compounds of formula (Ia) in which $R^4$ represents a group —$L^3$—$R^{14}$ where $L^3$ is $C_{1-6}$alkylene, especially $C_{1-3}$alkylene, preferably methylene, and $R^{14}$ is —$NY^4Y^5$, where $Y^4$ and $Y^5$ are as defined hereinbefore, especially where $Y^4$ and $Y^5$ are hydrogen, are also preferred.

Compounds of formula (Ia) in which $R^4$ represents a group —$L^3$—$R^{14}$ where $L^3$ is $C_{1-6}$alkylene, especially methylene or ethylene, and $R^{14}$ is aryl or heteroaryl, are also preferred.

Compounds of formula (Ia) in which $R^4$ represents a group —$L^3$—$R^{14}$ where $L^3$ is $C_{1-6}$alkylene, especially methylene, and $R^{14}$ is —N($R^{10}$)—SO$_2$—$R^{15}$, in which $R^{10}$ and $R^{15}$ are as defined hereinbefore, especially where $R^{10}$ is hydrogen and $R^{15}$ is alkyl, aryl or heteroaryl, are also preferred.

Compounds of formula (Ia) in which $R^4$ represents a group —$L^3$—$R^{14}$ where $L^3$ is $C_{1-6}$alkylene, especially methylene, and $R^{14}$ is —N($R^{10}$)—SO$_2$—$L^4$—$R^{15}$, in which $L^4$, $R^{10}$ and $R^{15}$ are as defined hereinbefore, especially where $L^4$ is methylene, $R^{10}$ is hydrogen and $R^{15}$ is alkyl, aryl or heteroaryl, are also preferred.

Compounds of formula (Ia) in which $R^5$ represents hydrogen, $C_{1-4}$alkyl (e.g. methyl) or hydroxy$C_{1-4}$alkyl (e.g. hydroxymethyl), especially methyl, are preferred.

Compounds of formula (Ia) in which $R^4$ and $R^5$ together with the carbon atom to which they are attached represent a group C=CH$_2$ or a 5–7 membered cyclic ether such as tetrahydrofuran-2-yl or perhydropyran-2-yl are also preferred.

A preferred group of compounds of the invention are compounds of formula (Ia) in which $R^4$ is a group —$L^3$—$R^{14}$ {where $L^3$ is a direct bond and $R^{14}$ is (i) —NY$^4$Y$^5$, preferably —NH$_2$; (ii) —N($R^{10}$)—C(=Z)—$R^{15}$, preferably —NH—C(=O)-alkyl, —NH—C(=O)-aryl or —NH—C(=O)-heteroaryl, especially —NH—C(=O)-aryl, particularly where aryl is substituted, or more preferably, unsubstituted phenyl; (iii) —N($R^{10}$)—C(=Z)—$L^4$—$R^{16}$, preferably —NH—C(=O)—CH$_2$-aryl or —NH—C(=O)—CH$_2$-heteroaryl, particularly where aryl is substituted, or more preferably, unsubstituted phenyl; (iv) —C(=Z)—NY$^4$Y$^5$, preferably —C(=O)—NH$_2$; (v) —C(=Z)—NY$^4$Y$^5$, preferably —C(=O)—NY$^4$Y$^5$ where the group —NY$^4$Y$^5$ forms a 5–7 membered cyclic amine [which may optionally contain a further heteroatom selected from O, S or NY$^6$ (where Y$^6$ is as defined hereinbefore), preferably a 5–7 membered cyclic amine optionally containing oxygen, especially a morpholine ring]; (vi) —C(=Z)OR$^9$, particularly —CO$_2$Me; or (vii) alkyl, especially methyl} and $R^5$ represents hydrogen, $C_{1-4}$alkyl (e.g. methyl) or hydroxy$C_{1-4}$alkyl (e.g. hydroxymethyl), especially methyl; and N-oxides thereof, and their prodrugs; and pharmaceutically acceptable salts and solvates (e.g. hydrates) of compounds of formula (Ia) herein and N-oxides thereof, and their prodrugs.

A further preferred group of compounds of formula (Ia) are compounds in which $R^4$ is a group —$L^3$—$R^{14}$ {where $L^3$ is a methylene linkage and $R^{14}$ is (i) hydroxy; (ii) —N($R^{10}$)—C(=Z)—$R^{15}$, preferably —NH—C(=O-alkyl, —NH—C(=O)-aryl or —NH—C(=O)-heteroaryl; (iii) —N($R^{10}$)—C(=Z)—$L^4$—$R^{16}$, preferably —NH—C(=O)—CH$_2$-aryl or —NH—C(=O)—CH$_2$-heteroaryl; (iv) —NH—C(=Z)—NH—$R^{15}$ preferably —NH—C(=O)—NH—alkyl, —NH—C(=O)—NH-aryl or —NH—C(=O)—NH-heteroaryl;(v) NH—C(=Z)—NH—$L^4$—$R^{16}$ preferably —NH—C(=O)—NH—CH$_2$-alkyl, —NH—C(=O)—NH—CH$_2$-aryl or —NH—C(=O)—NH—CH$_2$-heteroaryl; (vi) —NY$^4$Y$^5$, preferably —NH$_2$; (vii) aryl; (viii) heteroaryl; (ix) —N($R^{10}$)—SO$_2$—$R^{15}$, preferably —NH—SO$_2$-alkyl, NH—SO$_2$-aryl or —NH—SO$_2$-heteroaryl} and $R^5$ represents hydrogen, $C_{1-4}$alkyl (e.g. methyl) or hydroxy$C_{1-4}$alkyl (e.g. hydroxymethyl), especially methyl; and N-oxides thereof, and their prodrugs; and pharmaceutically acceptable salts and solvates (e.g. hydrates) of compounds of formula (Ia) herein and N-oxides thereof, and their prodrugs.

A further particular group of compounds of the invention are compounds of formula (Ib):

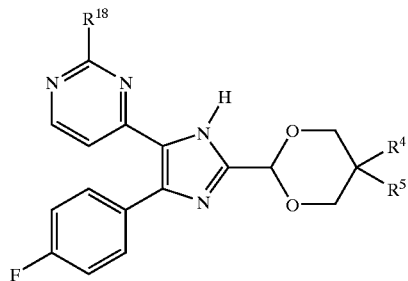

(Ib)

in which $R^4$ and $R^5$ are as hereinbefore defined, and $R^{18}$ is $R^{17}Z^3$— or $Y^4Y^5$N— (in which $R^{17}$, $Y^4$, $Y^5$ and $Z^3$ are as hereinbefore defined), and N-oxides thereof, and their prodrugs; and pharmaceutically acceptable salts and solvates (e.g. hydrates) of compounds of formula (Ib) and N-oxides thereof, and their prodrugs.

Compounds of formula (Ib) in which $R^4$ represents a group —$L^3$—$R^{14}$ where $L^3$ is a direct bond and $R^{14}$ is —NY$^4$Y$^5$, where Y$^4$ and Y$^5$ are as defined hereinbefore, especially where Y$^4$ and Y$^5$ are hydrogen, are preferred.

Compounds of formula (Ib) in which $R^4$ represents a group —$L^3$—$R^{14}$ where $L^3$ is a direct bond and $R^{14}$ is —N($R^{10}$)—C(=Z)—$R^{15}$, in which Z, $R^{10}$ and $R^{15}$ are as defined hereinbefore, especially where Z is oxygen, $R^{10}$ is hydrogen and $R^{15}$ is alkyl (especially methyl), aryl (e.g. substituted or more preferably, unsubstituted phenyl) or heteroaryl, are also preferred.

Compounds, of formula (Ib) in which $R^4$ represents a group —$L^3$—$R^{14}$ where $L^3$ is a direct bond and $R^{14}$ is —N($R^{10}$)—C(=Z)—$L^4$—$R^{16}$, in which Z, $L^4$, $R^{10}$ and $R^{16}$ are as defined hereinbefore, especially where Z is oxygen, $L^4$ is methylene, $R^{10}$ is hydrogen, and $R^{16}$ is aryl (e.g. substituted or more preferably, unsubstituted phenyl) or heteroaryl, are also preferred.

Compounds of formula (Ib) in which $R^4$ represents a group —$L^3$—$R^{14}$ where $L^3$ is a direct bond and $R^{14}$ is —C(=Z)—NY$^4$Y$^5$, in which Z is as defined hereinbefore, especially oxygen, and Y$^4$ and Y$^5$ are as defined hereinbefore, especially where Y$^4$ and Y$^5$ are hydrogen or where Y$^4$ is hydrogen and Y$^5$ is aryl, heteroaryl or heteroarylalkyl, are also preferred.

Compounds of formula (Ib) in which $R^4$ represents a group —$L^3$—$R^{14}$ where $L^3$ is a direct bond and $R^{14}$ is —C(=Z)—NY$^4$Y$^5$, in which Z is as defined hereinbefore, especially oxygen, and the group —NY$^4$Y$^5$ forms a 5–7 membered cyclic amine [which may optionally contain a further heteroatom selected from O, S or NY$^6$ (where Y$^6$ is as defined hereinbefore)], preferably a 5–7 membered cyclic amine optionally containing oxygen, especially a morpholine ring, are also preferred.

Compounds of formula (Ib) in which $R^4$ represents a group —$L^3$—$R^{14}$ where $L^3$ is a direct bond and $R^{14}$ is —C(=Z)—OR$^9$, in which Z and $R^9$ are as defined hereinbefore, especially where Z is oxygen and $R^9$ is $C_{1-4}$alkyl, preferably methyl, are also preferred.

Compounds of formula (Ib) in which $R^4$ represents a group —$L^3$—$R^{14}$ where $L^3$ is a direct bond, especially methylene or ethylene, and $R^{14}$ is alkyl, especially methyl, are also preferred.

Compounds of formula (Ib) in which $R^4$ represents a group —$L^3$—$R^{14}$ where $L^3$ is $C_{1-6}$alkylene, especially methylene, and $R^{14}$ is hydroxy, are also preferred.

Compounds of formula (Ib) in which $R^4$ represents a group —$L^3$—$R^{14}$ where $L^3$ is $C_{1-6}$alkylene, especially methylene, and $R^{14}$ is —N($R^{10}$)—C(=Z)—$R^{15}$, in which Z, $R^{10}$ and $R^{15}$ are as defined hereinbefore, especially where Z is oxygen, $R^{10}$ is hydrogen and $R^{15}$ is alkyl, aryl or heteroaryl, are also preferred.

Compounds of formula (Ib) in which $R^4$ represents a group —$L^3$—$R^{14}$ where $L^3$ is $C_{1-6}$alkylene, especially methylene, and $R^{14}$ is —N($R^{10}$)—C(=Z)—$L^4$—$R^{16}$, in which Z, $L^4$, $R^{10}$ and $R^{15}$ are as defined hereinbefore, especially where Z is oxygen, $L^4$ is $C_{1-6}$alkylene, especially methylene, $R^{10}$ is hydrogen and $R^{16}$ is aryl or heteroaryl, are also preferred.

Compounds of formula (Ib) in which $R^4$ represents a group —$L^3$—$R^{14}$ where $L^3$ is $C_{1-6}$alkylene, especially methylene, and $R^{14}$ is —NH—C(=Z)—NH—$R^{15}$, in which Z and $R^{15}$ are as defined hereinbefore, especially where $R^{15}$ is alkyl, aryl or heteroaryl, are also preferred.

Compounds of formula (Ib) in which $R^4$ represents a group —$L^3$—$R^{14}$ where $L^3$ is $C_{1-6}$alkylene, especially methylene, and $R^{14}$ is —NH—C(=Z)—NH—$L^4$—$R^{16}$, in which Z, $L^4$ and $R^{16}$ are as defined hereinbefore, especially where $L^4$ is methylene and $R^{15}$ is aryl or heteroaryl, are also preferred.

Compounds of formula (Ib) in which $R^4$ represents a group —$L^3$—$R^{14}$ where $L^3$ is $C_{1-6}$alkylene, especially $C_{1-3}$alkylene, preferably methylene, and $R^{14}$ is —N$Y^4Y^5$, where $Y^4$ and $Y^5$ are as defined hereinbefore, especially where $Y^4$ and $Y^5$ are hydrogen, are also preferred.

Compounds of formula (Ib) in which $R^4$ represents a group —$L^3$—$R^{14}$ where $L^3$ is $C_{1-6}$alkylene, especially methylene or ethylene, and $R^{14}$ is aryl or heteroaryl, are also preferred.

Compounds of formula (Ib) in which $R^4$ represents a group —$L^3$—$R^{14}$ where $L^3$ is $C_{1-6}$alkylene, especially methylene, and $R^{14}$ is —N($R^{10}$)—$SO_2$—$R^{15}$, in which $R^{10}$ and $R^{15}$ are as defined hereinbefore, especially where $R^{10}$ is hydrogen and $R^{15}$ is alkyl, aryl or heteroaryl, are also preferred.

Compounds of formula (Ib) in which $R^4$ represents a group —$L^3$—$R^{14}$ where $L^3$ is $C_{1-6}$alkylene, especially methylene, and $R^{14}$ is —N($R^{10}$)—$SO_2$—$L^4$—$R^{15}$, in which $L^4$, $R^{10}$ and $R^{15}$ are as defined hereinbefore, especially where $L^4$ is methylene, $R^{10}$ is hydrogen and $R^{15}$ is alkyl, aryl or heteroaryl, are also preferred.

Compounds of formula (Ib) in which $R^5$ represents hydrogen, $C_{1-4}$alkyl (e.g. methyl) or hydroxy$C_{1-4}$alkyl (e.g. hydroxymethyl), especially methyl, are preferred.

Compounds of formula (Ib) in which $R^4$ and $R^5$ together with the carbon atom to which they are attached represent a group C=$CH_2$ or a 5–7 membered cyclic ether such as tetrahydrofuran-2-yl or perhydropyran-2-yl are also preferred.

Compounds of formula (Ib) in which $R^{18}$ is —N$Y^4Y^5$, where $Y^4$ and $Y^5$ are as hereinbefore defined, especially where $Y^4$ is hydrogen and $Y^5$ is (i) arylalkyl, particularly optionally substituted benzyl or optionally substituted α-methylbenzyl (in which the phenyl group may be optionally substituted by one or more aryl group substituents, especially halo, methoxy, trifluoromethyl, methyl and methylenedioxy); (ii) heteroarylalkyl, particularly azaheteroaryl-alkyl, more particularly azaheteroaryl-$CH_2$—; (iii) $C_{2-6}$alkyl substituted by alkoxy, particularly $C_{2-6}$alkyl substituted by methoxy; (iv) $C_{2-6}$alkyl substituted by —N$Y^1Y^2$, particularly $C_{2-6}$alkyl substituted by —$NMe_2$; (v) $C_{2-6}$alkyl substituted by hydroxy; (vi) cycloalkyl or (vii) aryl, especially phenyl optionally substituted by one or more aryl group substituents, especially halo, methoxy, trifluoromethyl, methyl or methylenedioxy; are preferred.

Compounds of formula (Ib) in which $R^{18}$ is —O$R^{17}$, where $R^{17}$ is as hereinbefore defined, especially where $R^{17}$ is alkyl, aryl (especially phenyl optionally substituted by one or more aryl group substituents, especially halo, methoxy, trifluoromethyl, methyl or methylenedioxy) or cycloalkyl, are also preferred.

A preferred group of compounds of the invention are compounds of formula (Ib) in which $R^4$ is a group —$L^3$—$R^{14}$ {where $L^3$ is a direct bond and $R^{14}$ is (i) —N$Y^4Y^5$, preferably —$NH_2$; (ii) —N($R^{10}$)—C(=Z)—$R^{15}$, preferably —NH—C(=O)-alkyl, —NH—C(=O)-aryl or —NH—C(=O)-heteroaryl, especially —NH—C(=O)-aryl, particularly where aryl is substituted, or more preferably, unsubstituted phenyl; (iii) —N($R^{10}$)—C(=Z)—$L^4$—$R^{16}$, preferably —NH—C(=O)—$CH_2$-aryl or —NH—C(=O)—$CH_2$-heteroaryl, particularly where aryl is substituted, or more preferably, unsubstituted phenyl; (iv) —C(=Z)—N$Y^4Y^5$, preferably —C(=O)—$NH_2$; (v) —C(=Z)—N$Y^4Y^5$, preferably —C(=O)—N$Y^4Y^5$ where the group —N$Y^4Y^5$ forms a 5–7 membered cyclic amine [which may optionally contain a further heteroatom selected from O, S or N$Y^6$ (where $Y^6$ is as defined hereinbefore), preferably a 5–7 membered cyclic amine optionally containing oxygen, especially a morpholine ring]; (vi) —C(=Z)O$R^9$, particularly —$CO_2$Me; or (vii) alkyl, especially methyl} $R^5$ represents hydrogen, $C_{1-4}$alkyl (e.g. methyl) or hydroxy$C_{1-4}$alkyl (e.g. hydroxymethyl), especially methyl and $R^{18}$ represents —N$Y^4Y^5$ {where $Y^4$ and $Y^5$ are as hereinbefore defined, especially where $Y^4$ is hydrogen and $Y^5$ is (i) arylalkyl, particularly benzyl or α-methylbenzyl; (ii) heteroarylalkyl, particularly azaheteroaryl-alkyl, more particularly azaheteroaryl-$CH_2$—; (iii) $C_{2-6}$alkyl substituted by alkoxy, particularly $C_{2-6}$alkyl substituted by methoxy; (iv) $C_{2-6}$alkyl substituted by —N$Y^1Y^2$, particularly $C_{2-6}$alkyl substituted by —$NMe_2$; (v) $C_{2-6}$alkyl substituted by hydroxy; (vi) cycloalkyl or (vii) aryl, especially phenyl optionally substituted by one or more aryl group substituents, especially halo, methoxy, trifluoromethyl, methyl or methylenedioxy} or —O$R^{17}$, where $R^{17}$ is alkyl or cycloalkyl; and N-oxides thereof, and their prodrugs; and pharmaceutically acceptable salts and solvates (e.g. hydrates) of compounds of formula (Ia) herein and N-oxides thereof, and their prodrugs.

A further preferred group of compounds of formula (Ib) are compounds in which $R^4$ is a group —$L^3$—$R^{14}$ {where $L^3$ is a methylene linkage and $R^{14}$ is (i) hydroxy; (ii) —N($R^{10}$)—C(=Z)—$R^{15}$, preferably —NH—C(=O)-alkyl, —NH—C(=O)-aryl or —NH—C(=O)-heteroaryl; (iii) —N($R^{10}$)—C(=Z)—$L^4$-$R^{16}$, preferably —NH—C(=O)—$CH_2$-aryl or —NH—C(=O)—$CH_2$-heteroaryl; (iv) —NH—C(=Z)—NH—$R^{15}$ preferably —NH—C(=O)—NH—alkyl, —NH—C(=O)—NH-aryl or —NH—C(=O)—NH-heteroaryl;(v) NH—C(=Z)—NH—$L^4$—$R^{16}$ preferably —NH—C(=O)—NH—$CH_2$-alkyl, —NH—C(=O)—NH—$CH_2$-aryl or —NH—C(=O)—NH—$CH_2$-heteroaryl; (vi) —N$Y^4Y^5$, preferably —$NH_2$; (vii) aryl; (viii) heteroaryl; (ix) —N($R^{10}$)—$SO_2$—$R^{15}$, preferably —NH—$SO_2$-alkyl, NH—$SO_2$-aryl or —NH—$SO_2$-heteroaryl} and $R^5$ represents hydrogen, $C_{1-4}$alkyl (e.g. methyl) or hydroxy$C_{1-4}$alkyl (e.g. hydroxymethyl), especially methyl and $R^{18}$ represents —N$Y^4Y^5$ {where $Y^4$ and $Y^5$ are as hereinbefore defined, especially where $Y^4$ is hydrogen and $Y^5$ is (i) arylalkyl, particularly benzyl or α-methylbenzyl; (ii) heteroarylalkyl, particularly azaheteroarylalkyl, more particularly azaheteroaryl-$CH_2$—; (iii) $C_{2-6}$alkyl substituted by alkoxy, particularly $C_{2-6}$alkyl substituted by methoxy; (iv) $C_{2-6}$alkyl substituted by —NY¹Y², particularly $C_{2-6}$alkyl substituted by —NMe₂; (v) $C_{2-6}$alkyl substituted by hydroxy; or (vi) cycloalkyl} or —OR¹⁷, where R¹⁷ is alkyl or cycloalkyl; and N-oxides thereof, and their prodrugs; and pharmaceutically acceptable salts and solvates (e.g. hydrates) of compounds of formula (Ia) herein and N-oxides thereof, and their prodrugs.

A particular group of compounds of the invention are those selected from the following:

{2-[5-(4-fluoro-phenyl)-4-pyridin-4-yl-1H-imidazol-2-yl]-5-methyl-[1,3]dioxan-5-yl}-methanol, cis-isomer, (Compound A);

{2-[5-(4-fluoro-phenyl)-4-pyridin-4-yl-1H-imidazol-2-yl]-5-methyl-[1,3]dioxan-5-yl}-methanol, trans-isomer, (Compound B);

4-[2-(5,5-dimethyl-[1,3]dioxan-2-yl)-5-(4-fluoro-phenyl)-1H-imidazol-4-yl]-pyridine, (Compound C);

C-[5-methyl-2-{5-(4-fluoro-phenyl)-4-pyridin-4-yl-1H-imidazol-2-yl}-[1,3]dioxan-5-yl]-methylamine, cis- and trans-isomers, (Compound D);

2,2,2-trifluoro-N-[5-methyl-2-{5-(4-fluoro-phenyl)-4-pyridin-4-yl-1H-imidazol-2-yl}-[1,3]dioxan-5-yl]-acetamide, cis- and trans-isomers, (Compound E);

2,2,2-trifluoro-N-[5-methyl-2-{5-(4-fluoro-phenyl)-4-pyridin-4-yl-1H-imidazol-2-yl}-[1,3]dioxan-5-yl]-acetamide, cis-isomer, (Compound F);

2,2,2-trifluoro-N-[5-methyl-2-{5-(4-fluoro-phenyl)-4-pyridin-4-yl-1H-imidazol-2-yl}-[1,3]dioxan-5-yl]-acetamide, trans-isomer, (Compound G);

4-[2-(5-azidomethyl-5-methyl-[1,3]dioxan-2-yl)-5-(4-fluoro-phenyl)-1H-imidazol-4-yl]-pyridine, cis- and trans-isomers, (Compound H);

4-[2-(5-benzyl-[1,3]dioxan-2-yl)-5-(4-fluorophenyl)-1H-imidazol-4-yl]-pyridine, cis- adn trans-isomers, (Compound I);

2-[5-(4-fluoro-phenyl)-4-pyridin-4-yl-1H-imidazol-2-yl]-5-methyl-[1,3]dioxane-5-carboxylic acid methyl ester, cis- and trans-isomers, (Compound J);

4-[5-(4-fluoro-phenyl)-2-(1,8,10-trioxa-spiro[5.5]undec-9-yl)-1H-imidazol-4-yl]-pyridine, (Compound K);

4-[5-(4-fluoro-phenyl)-2-(1,7,9-trioxa-spiro[4.5]dec-8-yl)-1H-imidazol-4-yl]-pyridine, (Compound L);

4-[2-(5-methyl-[1,3]dioxan-2-yl)-5-(4-fluoro-phenyl)-3H-imidazol-4-yl]-pyridine, (Compound M);

4-[5-(4-fluoro-phenyl)-2-(5-methylene-[1,3]dioxan-2-yl)-3H-imidazol-4-yl]-pyridine, (Compound N);

4-[2-[1,3]dioxan-2-yl-5-(4-fluoro-phenyl)-3H-imidazol-4-yl]-pyridine, (Compound O);

4-[5-(4-fluoro-phenyl)-2-(4-methyl-[1,3]dioxan-2-yl)-3H-imidazol-4-yl]-pyridine, (R/S)(R/S) isomers, (Compound P);

4-[2-(4,6-dimethyl-[1,3]dioxan-2-yl)-5-(4-fluoro-phenyl)-3H-imidazol-4-yl]-pyridine, (R/S)(R/S)(R/S) isomers, (Compound Q);

4-[2-(5-benzyloxy-[1,3]dioxan-2-yl)-5-(4-fluoro-phenyl)-3H-imidazol-4-yl]-pyridine, cis- and trans-isomers, (Compound R);

4-[5-(4-fluoro-phenyl)-2-(5-phenyl-[1,3]dioxan-2-yl)-3H-imidazol-4-yl]-pyridine, (Compound S);

4-[5-(4-fluoro-phenyl)-2-(4-isopropyl-5,5-dimethyl-[1,3]dioxan-2-yl)-3H-imidazol-4-yl]-pyridine, (R/S)(R/S) isomers, (Compound T);

4-[2-(5,5-diethyl-[1,3]dioxan-2-yl)-5-(4-fluoro-phenyl)-3H-imidazol-4-yl]-pyridine, (Compound U);

4-[2-(2,4-dioxa-spiro[5.5]undec-8-en-3-yl)-5-(4-fluoro-phenyl)-3H-imidazol-4-yl]-pyridine, cis- and trans-isomers, (Compound V);

N-{2-[4-(4-fluoro-phenyl)-5-pyridin-4-yl-1H-imidazol-2-yl]-5-methyl-[1,3]dioxan-5-yl}-benxamide, cis- and trans-isomers, (Compound W);

1-(4-fluoro-phenyl)-3-{2-[4-(4-fluoro-phenyl)-5-pyridin-4-yl-1H-imidazol-2-yl]-5-methyl-[1,3]dioxan-5-yl}-thiourea, cis- and trans-isomers, (Compound X);

1-(2,6-dimethyl-phenyl)-3-{2-[4-(4-fluoro-phenyl)-5-pyridin-4-yl-1H-imidazol-2-yl]-5-methyl-[1,3]dioxan-5-yl}-thiourea, cis- and trans-isomers, (Compound Y);

4-[5-(4-fluoro-phenyl)-2-(5-methyl-5-pyrrol-1-yl-[1,3]dioxan-2-yl)-1H-imidazol-4-yl]-pyridine, cis- and trans-isomer, (Compound Z);

C-[5-methyl-2-{5-(4-fluoro-phenyl)-4-pyridin-4-yl-1H-imidazol-2-yl}-[1,3]dioxan-5-yl]-methylamine, trans-isomer, (Compound AA);

C-[5-methyl-2-{5-(4-fluoro-phenyl)-4-pyridin-4-yl-1H-imidazol-2-yl}-[1,3]dioxan-5-yl]-methylamine, cis-isomer, (Compound AB);

2,2,2-trifluoro-N-[5-methyl-2-{5-(4-fluoro-phenyl)-4-pyridin-4-yl-1H-imidazol-2-yl}-[1,3]dioxan-5-ylmethyl]-acetamide, trans-isomer, (Compound AC);

2,2,2-trifluoro-N-[5-methyl-2-{5-(4-fluoro-phenyl)-4-pyridin-4-yl-1H-imidazol-2-yl}-[1,3]dioxan-5-ylmethyl]-acetamide, cis-isomer, (Compound AD);

5-methyl-2-{5-(4-fluoro-phenyl)-4-pyridin-4-yl-1H-imidazol-2-yl}-[1,3]dioxan-5-ulamine, cis-isomer, (Compound AE);

5-methyl-2-{5-(4-fluoro-phenyl)-4-pyridin-4-yl-1H-imidazol-2-yl}-[1,3]dioxan-5-ylamine, trans-isomer, (Compound AF);

5-methyl-2-{5-(4-fluoro-phenyl)-4-pyridin-4-yl-1H-imidazol-2-yl}-[1,3]dioxan-5-ylamine, cis- and trans-isomers, (Compound AG);

2-[5-(4-fluoro-phenyl)-4-pyridin-4-yl-1H-imidazol-2-yl]-5-methyl-[1,3]dioxane-5-carboxylic acid, trans-isomer, (Compound AH);

2-[5-(4-fluoro-phenyl)-4-pyridin-4-yl-1H-imidazol-2-yl]-5-methyl-[1,3]dioxane-5-carboxylic acid, cis-isomer, (Compound AI);

2-[4-(4-fluoro-phenyl)-5-pyridin-4-yl-1H-imidazol-2-yl]-5-methyl-[1,3]dioxane-5-carboxylic acid benzylamide, cis-isomer, (Compound AJ);

2-[4-(4-fluoro-phenyl)-5-pyridin-4-yl-1H-imidazol-2-yl]-5-methyl-[1,3]dioxane-5-carboxylic acid benzylamide, trans-isomer, (Compound AK);

2-[4-(4-fluoro-phenyl)-5-pyridin-4-yl-1H-imidazol-2-yl]-5-methyl-[1,3]dioxane-5-carboxylic acid (2-hydroxy-ethyl)-amide, trans-isomer, (Compound AL);

2-[4-(4-fluoro-phenyl)-5-pyridin-4-yl-1H-imidazol-2-yl]-5-methyl-[1,3]dioxane-5-carboxylic acid (2-methoxy-ethyl)-amide, trans-isomer, (Compound AM);, 2-[4-(4-fluoro-phenyl)-5-pyridin-4-yl-1H-imidazol-2-yl]-5-methyl-[1,3]dioxane-5-carboxylic acid amide, trans-isomer, (Compound AN);

2-[4-(4-fluoro-phenyl)-5-pyridin-4-yl-1H-imidazol-2-yl]-5-methyl-[1,3]dioxane-5-carboxylic acid (pyridin-2-ylmethyl)-amide, trans-isomer, (Compound AO);

2-[4-(4-fluoro-phenyl)-5-pyridin-4-yl-1H-imidazol-2-yl]-5-methyl-[1,3]dioxane-5-carboxylic acid (pyridin-3-ylmethyl)-amide, trans-isomer, (Compound AP);

2-[4-(4-fluoro-phenyl)-5-pyridin-4-yl-1H-imidazol-2-yl]-5-methyl-[1,3]dioxane-5-carboxylic acid (pyridin-4-ylmethyl)-amide, trans-isomer, (Compound AQ);

{2-[4-(4-fluoro-phenyl)-5-pyridin-4-yl-1H-imidazol-2-yl]-5-methyl-[1,3]dioxan-5-yl}-(4-methyl-piperazin-1-yl)-methanone, trans-isomer, (Compound AR);

2-[4-(4-fluoro-phenyl)-5-pyridin-4-yl-1H-imidazol-2-yl]-5-methyl-[1,3]dioxane-5-carboxylic acid (3-dimethylamino-propyl)-amide, trans-isomer, (Compound AS);

2-[4-(4-fluoro-phenyl)-5-pyridin-4-yl-1H-imidazol-2-yl]-5-methyl-[1,3]dioxane-5-carboxylic acid [2-(1H-indol-3-yl)-ethyl]-amide, trans-isomer, (Compound AT);

2-[4-(4-fluoro-phenyl)-5-pyridin-4-yl-1H-imidazol-2-yl]-5-methyl-[1,3]dioxane-5-carboxylic acid (3-hydroxy-propyl)-amide, trans-isomer, (Compound AU);

2-[4-(4-fluoro-phenyl)-5-pyridin-4-yl-1H-imidazol-2-yl]-5-methyl-[1,3]dioxane-5-carboxylic acid (tetrahydro-furan-2-ylmethyl)-amide, trans-isomer, (Compound AV);

{2-[4-(4-fluoro-phenyl)-5-pyridin-4-yl-1H-imidazol-2-yl]-5-methyl-[1,3]dioxan-5-yl}-morpholin-4-yl-methanone, trans-isomer, (Compound AW);

{2-[4-(4-fluoro-phenyl)-5-pyridin-4-yl-1H-imidazol-2-yl]-5-methyl-[1,3]dioxan-5-yl}-pyrrolidin-1-yl-methanone, trans-isomer, (Compound AX);

2-[4-(4-fluoro-phenyl)-5-pyridin-4-yl-1H-imidazol-2-yl]-5-methyl-[1,3]dioxane-5-carboxylic acid butylamide, trans-isomer, (Compound AY);

2-[4-(4-fluoro-phenyl)-5-pyridin-4-yl-1H-imidazol-2-yl]-5-methyl-[1,3]dioxane-5-carboxylic acid dipropylamide, trans-isomer, (Compound AZ);

2-[4-(4-fluoro-phenyl)-5-pyridin-4-yl-1H-imidazol-2-yl]-5-methyl-[1,3]dioxane-5-carboxylic acid (3-methoxy-propyl)-amide, trans-isomer, (Compound BA);

2-[4-(4-fluoro-phenyl)-5-pyridin-4-yl-1H-imidazol-2-yl]-5-methyl-[1,3]dioxane-5-carboxylic acid phenethyl-amide, trans-isomer, (Compound BB);

2-[4-(4-fluoro-phenyl)-5-pyridin-4-yl-1H-imidazol-2-yl]-5-methyl-[1,3]dioxane-5-carboxylic acid (2-pyridin-2-yl-ethyl)-amide, trans-isomer, (Compound BC);

2-[4-(4-fluoro-phenyl)-5-pyridin-4-yl-1H-imidazol-2-yl]-5-methyl-[1,3]dioxane-5-carboxylic acid (furan-2-ylmethyl)-amide, trans-isomer, (Compound BD);

{2-[4-(4-fluoro-phenyl)-5-pyridin-4-yl-1H-imidazol-2-yl]-5-methyl-[1,3]dioxan-5-yl}-morpholin-4-yl-methanone, trans-isomer, (Compound BE);

2-[4-(4-fluoro-phenyl)-5-pyridin-4-yl-1H-imidazol-2-yl]-5-methyl-[1,3]dioxane-5-carboxylic acid dimethylamide, trans-isomer, (Compound BF);

2-[4-(4-fluoro-phenyl)-5-pyridin-4-yl-1H-imidazol-2-yl]-5-methyl-[1,3]dioxane-5-carboxylic acid propylamide, trans-isomer, (Compound BG);

2-[4-(4-fluoro-phenyl)-5-pyridin-4-yl-1H-imidazol-2-yl]-5-methyl-[1,3]dioxane-5-carboxylic acid cyclopropylamide, trans-isomer, (Compound BH);

2-[4-(4-fluoro-phenyl)-5-pyridin-4-yl-1H-imidazol-2-yl]-5-methyl-[1,3]dioxane-5-carboxylic acid cyclopentylamide, trans-isomer, Compound BI);

2-[4-(4-fluoro-phenyl)-5-pyridin-4-yl-1H-imidazol-2-yl]-5-methyl-[1,3]dioxane-5-carboxylic acid cyclohexylamide, trans-isomer, (Compound BJ);

2-[4-(4-fluoro-phenyl)-5-pyridin-4-yl-1H-imidazol-2-yl]-5-methyl-[1,3]dioxane-5-carboxylic acid (2-methoxy-ethyl)-amide, cis-isomer, (Compound BK);

2-[4-(4-fluoro-phenyl)-5-pyridin-4-yl-1H-imidazol-2-yl]-5-methyl-[1,3]dioxane-5-carboxylic acid (2-hydroxy-ethyl)-amide, cis-isomer, (Compound BL);

2-[4-(4-fluoro-phenyl)-5-pyridin-4-yl-1H-imidazol-2-yl]-5-methyl-[1,3]dioxane-5-carboxylic acid amide, cis-isomer, (Compound BM);

2-[4-(4-fluoro-phenyl)-5-pyridin-4-yl-1H-imidazol-2-yl]-5-methyl-[1,3]dioxane-5-carboxylic acid (pyridin-2-ylmethyl)-amide, cis-isomer, (Compound BN);

2-[4-(4-fluoro-phenyl)-5-pyridin-4-yl-1H-imidazol-2-yl]-5-methyl-[1,3]dioxane-5-carboxylic acid (pyridin-3-ylmethyl)-amide, cis-isomer, (Compound BO);

2-[4-(4-fluoro-phenyl)-5-pyridin-4-yl-1H-imidazol-2-yl]-5-methyl-[1,3]dioxane-5-carboxylic acid (pyridin-4-ylmethyl)-amide, cis-isomer, (Compound BP);

{2-[4-(4-fluoro-phenyl)-5-pyridin-4-yl-1H-imidazol-2-yl]-5-methyl-[1,3]dioxan-5-yl}-morpholin-4-yl-methanone, cis-isomer, (Compound BQ);

{2-[4-(4-fluoro-phenyl)-5-pyridin-4-yl-1H-imidazol-2-yl]-5-methyl-[1,3]dioxan-5-yl}-(4-methyl-piperazin-1-yl)-methanone, cis-isomer, (Compound BR);

2-[4-(4-fluoro-phenyl)-5-pyridin-4-yl-1H-imidazol-2-yl]-5-methyl-[1,3]dioxane-5-carboxylic acid (3-dimethylamino-propyl)-amide, cis-isomer, (Compound BS);

2-[4-(4-fluoro-phenyl)-5-pyridin-4-yl-1H-imidazol-2-yl]-5-methyl-[1,3]dioxane-5-carboxylic acid [2-(1H-indol-3-yl)-ethyl]-amide, cis-isomer, (Compound BT);

2-[4-(4-fluoro-phenyl)-5-pyridin-4-yl-1H-imidazol-2-yl]-5-methyl-[1,3]dioxane-5-carboxylic acid (3-hydroxy-propyl)-amide, cis-isomer, (Compound BU);

2-[4-(4-fluoro-phenyl)-5-pyridin-4-yl-1H-imidazol-2-yl]-5-methyl-[1,3]dioxane-5-carboxylic acid phenethyl-amide, cis-isomer, (Compound BV);

2-[4-(4-fluoro-phenyl)-5-pyridin-4-yl-1H-imidazol-2-yl]-5-methyl-[1,3]dioxane-5-carboxylic acid (3-methoxy-propyl)-amide, cis-isomer, (Compound BW);

2-[4-(4-fluoro-phenyl)-5-pyridin-4-yl-1H-imidazol-2-yl]-5-methyl-[1,3]dioxane-5-carboxylic acid (2-pyridin-2-yl-ethyl)-amide, cis-isomer, (Compound BX);

2-[4-(4-fluoro-phenyl)-5-pyridin-4-yl-1H-imidazol-2-yl]-5-methyl-[1,3]dioxane-5-carboxylic acid (furan-2-ylmethyl)-amide, cis-isomer, (Compound BY);

2-[4-(4-fluoro-phenyl)-5-pyridin-4-yl-1H-imidazol-2-yl]-5-methyl-[1,3]dioxane-5-carboxylic acid (tetrahydro-furan-2-ylmethyl)-amide, cis-isomer, (Compound BZ);

{2-[4-(4-fluoro-phenyl)-5-pyridin-4-yl-1H-imidazol-2-yl]-5-methyl-[1,3]dioxan-5-yl}-pyrrolidin-1-yl-methanone, cis-isomer, (Compound CA);

{2-[4-(4-fluoro-phenyl)-5-pyridin-4-yl-1H-imidazol-2-yl]-5-methyl-[1,3]dioxan-5-yl}-piperidin-1-yl-methanone, cis-isomer, (Compound CB);

2-[4-(4-fluoro-phenyl)-5-pyridin-4-yl-1H-imidazol-2-yl]-5-methyl-[1,3]dioxane-5-carboxylic acid propylamide, cis-isomer, (Compound CC);

2-[4-(4-fluoro-phenyl)-5-pyridin-4-yl-1H-imidazol-2-yl]-5-methyl-[1,3]dioxane-5-carboxylic acid butylamide, cis-isomer, (Compound CD);

2-[4-(4-fluoro-phenyl)-5-pyridin-4-yl-1H-imidazol-2-yl]-5-methyl-[1,3]dioxane-5-carboxylic acid cyclopropylamide, cis-isomer, (Compound CE);

2-[4-(4-fluoro-phenyl)-5-pyridin-4-yl-1H-imidazol-2-yl]-5-methyl-[1,3]dioxane-5-carboxylic acid cyclopentylamide, cis-isomer, (Compound CF);

2-[4-(4-fluoro-phenyl)-5-pyridin-4-yl-1H-imidazol-2-yl]-5-methyl-[1,3]dioxane-5-carboxylic acid cyclohexylamide, cis-isomer, (Compound CG);

2-[4-(4-fluoro-phenyl)-5-pyridin-4-yl-1H-imidazol-2-yl]-5-methyl-[1,3]dioxane-5-carboxylic acid methylamide, cis-isomer, (Compound CH);

2-[4-(4-fluoro-phenyl)-5-pyridin-4-yl-1H-imidazol-2-yl]-5-methyl-[1,3]dioxane-5-carboxylic acid (2-dimethylamino-ethyl)-amide, cis-isomer, (Compound CI);

2-[4-(4-fluoro-phenyl)-5-pyridin-4-yl-1H-imidazol-2-yl]-5-methyl-[1,3]dioxane-5-carboxylic acid dimethylamide, cis-isomer, (Compound CJ);

2-[4-(4-fluoro-phenyl)-5-pyridin-4-yl-1H-imidazol-2-yl]-5-methyl-[1,3]dioxane-5-carboxylic acid dipropylamide, cis-isomer, (Compound CK);

2-[4-(4-fluoro-phenyl)-5-pyridin-4-yl-1H-imidazol-2-yl]-5-methyl-[1,3]dioxane-5-carboxylic acid ethylamide, cis-isomer, (Compound CL);

2-[4-(4-fluoro-phenyl)-5-pyridin-4-yl-1H-imidazol-2-yl]-5-methyl-[1,3]dioxane-5-carboxylic acid methylamide, trans-isomer, (Compound CM);

2-[4-(4-fluoro-phenyl)-5-pyridin-4-yl-1H-imidazol-2-yl]-5-methyl-[1,3]dioxane-5-carboxylic acid dimethylamino-ethyl)-amide, trans-isomer, (Compound CN);

2-[4-(4-fluoro-phenyl)-5-pyridin-4-yl-1H-imidazol-2-yl]-5-methyl-[1,3]dioxane-5-carboxylic acid ethylamide, trans-isomer, (Compound CO);

1-{2-[4-(4-fluoro-phenyl)-5-pyridin-4-yl-1H-imidazol-2-yl]-5-methyl-[1,3]dioxan-5-yl}-3-phenyl-urea, cis-isomer, (Compound CP);

1-ethyl-3-{2-[4-(4-fluoro-phenyl)-5-pyridin-4-yl-1H-imidazol-2-yl]-5-methyl-[1,3]dioxan-5-yl}-urea, cis-isomer, (Compound CQ);

1-(3,5-dimethyl-isoxazol-4-yl)-3-{2-[4-(4-fluoro-phenyl)-5-pyridin-4-yl-1H-imidazol-2-yl]-5methyl-[1,3]dioxan-5-yl}-urea, cis-isomer, (Compound CR);

1-benzyl-3-{2-[4-(4-fluoro-phenyl)-5-pyridin-4-yl-1H-imidazol-2-yl]-5-methyl-[1,3]dioxan-5-yl}-urea, cis-isomer, (Compound CS);

1-{2-[4-(4-fluoro-phenyl)-5-pyridin-4-yl-1H-imidazol-2-yl]-5-methyl-[1,3]dioxan-5-yl}-3-(2-yl-ethyl)-urea, cis-isomer, (Compound CT);

1-(3-acetyl-phenyl)-3-{2-[4-(4-fluoro-phenyl)-5-pyridin-4-yl-1H-imidazol-2-yl]-5-methyl-[1,3]dioxan-5-yl}-urea, cis-isomer, (Compound CU);

1-{2-[4-(4-fluoro-phenyl)-5-pyridin-4-yl-1H-imidazol-2-yl]-5-methyl-[1,3]dioxan-5-yl}-3-phenyl-urea, trans-isomer, (Compound CV);

3-(3-{2-[4-(4-fluoro-phenyl)-5-pyridin-4-yl-1H-imidazol-2-yl]-5-methyl-[1,3]dioxan-5-yl}-ureido)-benzoic acid, trans-isomer, (Compound CW);

1-benzyl-3-{2-[4-(4-fluoro-phenyl)-5-pyridin-4-yl-1H-imidazol-2-yl]-5-methyl-[1,3]dioxan-5-yl}-urea, trans-isomer, (Compound CX);

1-ethyl-3-{2-[4-(4-fluoro-phenyl)-5-pyridin-4-yl-1H-imidazol-2-yl]-5-methyl-[1,3]dioxan-5-yl}-urea, trans-isomer, (Compound CY);

1-{2-[4-(4-fluoro-phenyl)-5-pyridin-4-yl-1H-imidazol-2-yl]-5-methyl-[1,3]dioxan-5-yl}-3-(2-thiophen-2-yl-ethyl)-urea, trans-isomer, (Compound CZ);

1-benzyl-3-{2-[4-(4-fluoro-phenyl)-5-pyridin-4-yl-1H-imidazol-2-yl]-5-methyl-[1,3]dioxan-5-ylmethyl}-urea, cis-isomer, (Compound DA);

1-ethyl-3-{2-[4-(4-fluoro-phenyl)-5-pyridin-4-yl-1H-imidazol-2-yl]-5-methyl-[1,3]dioxan-5-ylmethyl}-urea, cis-isomer, (Compound DB);

1-{2-[4-(4-fluoro-phenyl)-5-pyridin-4-yl-1H-imidazol-2-yl]-5-methyl-[1,3]dioxan-5-ylmethyl}-3-phenyl-urea, cis-isomer, (Compound DC);

1-{2-[4-(4-fluoro-phenyl)-5-pyridin-4-yl-1H-imidazol-2-yl]-5-methyl-[1,3]dioxan-5-ylmethyl}-3-phenyl-urea, trans-isomer, (Compound DD);

1-benzyl-3-{2-[4-(4-fluoro-phenyl)-5-pyridin-4-yl-1H-imidazol-2-yl]-5-methyl-[1,3]dioxan-5-ylmethyl}-urea, trans-isomer, (Compound DE);

1-ethyl-3-{2-[4-(4-fluoro-phenyl)-5-pyridin-4-yl-1H-imidazol-2-yl]-5-methyl-[1,3]dioxan-5-ylmethyl}-urea, trans-isomer, (Compound DF);

1-{2-[4-(4-fluoro-phenyl)-5-pyridin-4-yl-1H-imidazol-2-yl]-5-methyl-[1,3]dioxan-5-yl}-3-(2-morpholin-4-yl-ethyl)-thiourea, cis-isomer, (Compound DG);

1-{2-[4-(4-fluoro-phenyl)-5-pyridin-4-yl-1H-imidazol-2-yl]-5-methyl-[1,3]dioxan-5-yl}-3-furan-3-ylmethyl-thiourea, cis-isomer, (Compound DH);

1-{2-[4-(4-fluoro-phenyl)-5-pyridin-4-yl-1H-imidazol-2-yl]-5-methyl-[1,3]dioxan-5-yl}-3-pyridin-3-yl-thiourea, cis-isomer, (Compound DI);

1-benzo[1,3]dioxol-5-yl-3-{2-[4-(4-fluoro-phenyl)-5-pyridin-4-yl-1H-imidazol-2-yl]-5-methyl-[1,3]dioxan-5-yl}-thiourea, cis-isomer, (Compound DJ);

1-benzo[1,3]dioxol-5-ylmethyl-3-{2-[4-(4-fluoro-phenyl)-5-pyridin-4-yl-1H-imidazol-2-yl]-5-methyl-[1,3]dioxan-5-yl}-thiourea, cis-isomer, (Compound DK);

1-{2-[4-(4-fluoro-phenyl)-5-pyridin-4-yl-1H-imidazol-2-yl]-5-methyl-[1,3]dioxan-5-ylmethyl}-3-pyridin-3-yl-thiourea, trans-isomer, (Compound DL);

1-{2-[4-(4-fluoro-phenyl)-5-pyridin-4-yl-1H-imidazol-2-yl]-5-methyl-[1,3]dioxan-5-ylmethyl}-3-(2-morpholin-4-yl-ethyl)-thiourea, trans-isomer, (Compound DM);

1-{2-[4-(4-fluoro-phenyl)-5-pyridin-4-yl-1H-imidazol-2-yl]-5-methyl-[1,3]dioxan-5-ylmethyl}-3-furan-2-ylmethyl-thiourea, trans-isomer, (Compound DN);

1-benzo[1,3]dioxol-5-ylmethyl-3-{2-[4-(4-fluoro-phenyl)-5-pyridin-4-yl-1H-imidazol-2-yl]-5-methyl-[1,3]dioxan-5-ylmethyl}-thiourea, trans-isomer, (Compound DO);

1-benzo[1,3]dioxol-5-yl-3-{2-[4-(4-fluoro-phenyl)-5-pyridin-4-yl-1H-imidazol-2-yl]-5-methyl-[1,3]dioxan-5-ylmethyl}-thiourea, cis-isomer, (Compound DP);

1-{2-[4-(4-fluoro-phenyl)-5-pyridin-4-yl-1H-imidazol-2-yl]-5-methyl-[1,3]dioxan-5-ylmethyl}-3-furan-2-ylmethyl-thiourea, cis-isomer, (Compound DQ);

3-(3-{2-[4-(4-fluoro-phenyl)-5-pyridin-4-yl-1H-imidazol-2-yl]-5-methyl-[1,3]dioxan-5-ylmethyl}-thioureido)-benzoic acid, cis-isomer, (Compound DR);

1-{2-[4-(4-fluoro-phenyl)-5-pyridin-4-yl-1H-imidazol-2-yl]-5-methyl-[1,3]dioxan-5-ylmethyl}-3-pyridin-3-yl-thiourea, cis-isomer, (Compound DS);

1-{2-[4-(4-fluoro-phenyl)-5-pyridin-4-yl-1H-imidazol-2-yl]-5-methyl-[1,3]dioxan-5-ylmethyl}-3-(2-morpholin-4-yl-ethyl)-thiourea, cis-isomer, (Compound DT);

1-benzo[1,3]dioxol-5-ylmethyl-3-{2-[4-(4-fluoro-phenyl)-5-pyridin-4-yl-1H-imidazol-2-yl]-5-methyl-[1,3]dioxan-5-ylmethyl}-thiourea, cis-isomer, (Compound DU);

N-{2-[4-(4-fluoro-phenyl)-5-pyridin-4-yl-1H-imidazol-2-yl]-5-methyl-[1,3]dioxan-5-yl}-acetamide, cis-isomer, (Compound DV);

N-{2-[4-(4-fluoro-phenyl)-5-pyridin-4-yl-1H-imidazol-2-yl]-5-methyl-[1,3]dioxan-5-yl}-2-phenyl-acetamide, cis-isomer, (Compound DW);

cyclohexanecarboxylic acid {2-[4-(4-fluoro-phenyl)-5-pyridin-4-yl-1H-imidazol-2-yl]-5-methyl-[1,3]dioxan-5-yl}-amide, cis-isomer, (Compound DX);

2-benzyloxy-N-{2-[4-(4-fluoro-phenyl)-5-pyridin-4-yl-1H-imidazol-2-yl]-5-methyl-[1,3]dioxan-5-yl}-acetamide, trans-isomer, (Compound DY);

2-benzyloxy-N-{2-[4-(4-fluoro-phenyl)-5-pyridin-4-yl-1H-imidazol-2-yl]-5-methyl-[1,3]dioxan-5-yl}-acetamide, cis-isomer, (Compound DZ);

N-{2-[4-(4-fluoro-phenyl)-5-pyridin-4-yl-1H-imidazol-2-yl]-5-methyl-[1,3]dioxan-5-yl}-acetamide, trans-isomer, (Compound EA);

N-{2-[4-(4-fluoro-phenyl)-5-pyridin-4-yl-1H-imidazol-2-yl]-5-methyl-[1,3]dioxan-5-yl}-2-phenyl-acetamide, trans-isomer, (Compound EB);

cyclohexanecarboxylic acid {2-[4-(4-fluoro-phenyl)-5-pyridin-4-yl-1H-imidazol-2-yl]-5-methyl-[1,3]dioxan-5-yl}-amide, trans-isomer, (Compound EC);

N-{2-[4-(4-fluoro-phenyl)-5-pyridin-4-yl-1H-imidazol-2-yl]-5-methyl-[1,3]dioxan-5-yl}-2-phenyl-acetamide, cis-isomer, (Compound ED);

2-benzyloxy-N-{2-[4-(4-fluoro-phenyl)-5-pyridin-4-yl-1H-imidazol-2-yl]-5-methyl-[1,3]dioxan-5-ylmethyl}-acetamide, cis-isomer, (Compound EE);

N-{2-[4-(4-fluoro-phenyl)-5-pyridin-4-yl-1H-imidazol-2-yl]-5-methyl-[1,3]dioxan-5-ylmethyl}-2-phenyl-acetamide, cis-isomer, (Compound EF);

N-{2-[4-(4-fluoro-phenyl)-5-pyridin-4-yl-1H-imidazol-2-yl]-5-methyl-[1,3]dioxan-5-ylmethyl}-acetamide, cis-isomer, (Compound EG);

N-{2-[4-(4-fluoro-phenyl)-5-pyridin-4-yl-1H-imidazol-2-yl]-5-methyl-[1,3]dioxan-5-ylmethyl}-2-phenyl-acetamide, cis-isomer, (Compound EH);

cyclohexanecarboxylic acid {2-[4-(4-fluoro-phenyl)-5-pyridin-4-yl-1H-imidazol-2-yl]-5-methyl-[1,3]dioxan-5-ylmethyl}-amide, cis-isomer, (Compound EI);

N-{2-[4-(4-fluoro-phenyl)-5-pyridin-4-yl-1H-imidazol-2-yl]-5-methyl-[1,3]dioxan-5-ylmethyl}-acetamide, trans-isomer, (Compound EJ);

N-{2-[4-(4-fluoro-phenyl)-5-pyridin-4-yl-1H-imidazol-2-yl]-5-methyl-[1,3]dioxan-5-ylmethyl}-2-phenyl-acetamide, trans-isomer, (Compound EK);

cyclohexanecarboxylic acid {2-[4-(4-fluoro-phenyl)-5-pyridin-4-yl-1H-imidazol-2-yl]-5-methyl-[1,3]dioxan-5-ylmethyl}-amide, trans-isomer, (Compound EL);

N-{2-[4-(4-fluoro-phenyl)-5-pyridin-4-yl-1H-imidazol-2-yl]-5-methyl-[1,3]dioxan-5-ylmethyl}-2-phenyl-acetamide, trans-isomer, (Compound EM);

4-{2-[5-(4-fluoro-phenyl)-4-pyridin-4-yl-1H-imidazol-2-yl]-5-methyl-[1,3]dioxan-5-ylcarbamoyl}-butyric acid, cis-isomer, (Compound EN);

4-({2-[5-(4-fluoro-phenyl)-4-pyridin-4-yl-1H-imidazol-2-yl]-5-methyl-[1,3]dioxan-5-ylmethyl}-carbamoyl)-butyric acid, cis-isomer, (Compound EO);

4-{2-[5-(4-fluoro-phenyl)-4-pyridin-4-yl-1H-imidazol-2-yl]-5-methyl-[1,3]dioxan-5-ylcarbamoyl}-propionic acid, cis-isomer, (Compound EP);

4-({2-[5-(4-fluoro-phenyl)-4-pyridin-4-yl-1H-imidazol-2-yl]-5-methyl-[1,3]dioxan-5-ylmethyl}-carbamoyl)-propionic acid, cis-isomer, (Compound EQ);

4-({2-[5-(4-fluoro-phenyl)-4-pyridin-4-yl-1H-imidazol-2-yl]-5-methyl-[1,3]dioxan-5-ylcarbamoyl}-carbamoyl)-propionic acid, trans-isomer, (Compound ER);

N-{2-[5-(4-fluoro-phenyl)-4-pyridin-4-yl-1H-imidazol-2-yl]-5-methyl-[1,3]dioxan-5-yl}-methanesulphonamide, cis-isomer, (Compound ES);

N-{2-[4-(4-fluoro-phenyl)-5-pyridin-4-yl-1H-imidazol-2-yl]-5-methyl-[1,3]dioxan-5-ylmethyl}-methanesulphonamide, cis-isomer, (Compound ET);

N-{2-[4-(4-fluoro-phenyl)-5-pyridin-4-yl-1H-imidazol-2-yl]-5-methyl-[1,3]dioxan-5-ylmethyl}-benzenesulphonamide, cis-isomer, (Compound EU);

N-{2-[4-(4-fluoro-phenyl)-5-pyridin-4-yl-1H-imidazol-2-yl]-5-methyl-[1,3]dioxan-5-ylmethyl}-C-phenyl-methanesulphonamide, cis-isomer, (Compound EV);

thiophene-2-sulphonic acid {2-[4-(4-fluoro-phenyl)-5-pyridin-4-yl-1H-imidazol-2-yl]-5-methyl-[1,3]dioxan-5-ylmethyl}-amide, cis-isomer, (Compound EW);

3,5-dimethyl-isoxazole-4-sulphonic acid {2-[4-(4-fluoro-phenyl)-5-pyridin-4-yl-1H-imidazol-2-yl-]-5-methyl-[1,3]dioxan-5-ylmethyl}-amide, cis-isomer, (Compound EX);

N-{2-[4-(4-fluoro-phenyl)-5-pyridin-4-yl-1H-imidazol-2-yl]-5-methyl-[1,3]dioxan-5-ylmethyl}-methanesulphonamide, trans-isomer, (Compound EY);

N-{2-[4-(4-fluoro-phenyl)-5-pyridin-4-yl-1H-imidazol-2-yl]-5-methyl-[1,3]dioxan-5-ylmethyl}-benzenesulphonamide, trans-isomer, (Compound EZ);

thiophene-2-sulphonic acid {2-[4-(4-fluoro-phenyl)-5-pyridin-4-yl-1H-imidazol-2-yl]-5-methyl-[1,3]dioxan-5-ylmethyl}-amide, trans-isomer, (Compound FA);

3,5-dimethyl-isoxazole-4-sulphonic acid {2-[4-(4-fluoro-phenyl)-5-pyridin-4-yl-1H-imidazol-2-yl]-5-methyl-[1,3]dioxan-5-ylmethyl}-amide, trans-isomer, (Compound FB);

3-amino-N-{2-[4-(4-fluoro-phenyl)-5-pyridin-4-yl-1H-imidazol-2-yl]-5-methyl-[1,3]dioxan-5-yl}-propionamide, trans-isomer, (Compound FC);

3-amino-N-{2-[4-(4-fluoro-phenyl)-5-pyridin-4-yl-1H-imidazol-2-yl]-5-methyl-[1,3]dioxan-5-yl}-propionamide, cis-isomer, (Compound FD);

4-amino-N-{2-[4-(4-fluoro-phenyl)-5-pyridin-4-yl-1H-imidazol-2-yl]-5-methyl-[1,3]dioxan-5-yl}-butyramide, trans-isomer, (Compound FE);

4-amino-N-{2-[4-(4-fluoro-phenyl)-5-pyridin-4-yl-1H-imidazol-2-yl]-5-methyl-[1,3]dioxan-5-yl}-butyramide, cis-isomer, (Compound FF);

2-amino-N-{2-[4-(4-fluoro-phenyl)-5-pyridin-4-yl-1H-imidazol-2-yl]-5-methyl-[1,3]dioxan-5-yl}-acetamide, trans-isomer, (Compound FG);

2-amino-N-{2-[4-(4-fluoro-phenyl)-5-pyridin-4-yl-1H-imidazol-2-yl]-5-methyl-[1,3]dioxan-5-yl}-acetamide, cis-isomer, (Compound FH);

(3-{2-[4-(4-fluoro-phenyl)-5-pyridin-4-yl-1H-imidazol-2-yl]-5-methyl-[1,3]dioxan-5-ylcarbamoyl}-ethyl-carbamic acid benzyl ester, trans-isomer, (Compound FI);

(3-{2-[4-(4-fluoro-phenyl)-5-pyridin-4-yl-1H-imidazol-2-yl]-5-methyl-[1,3]dioxan-5-ylcarbamoyl}-ethyl-carbamic acid benzyl ester, cis-isomer, (Compound FJ);

(3-{2-[4-(4-fluoro-phenyl)-5-pyridin-4-yl-1H-imidazol-2-yl]-5-methyl-[1,3]dioxan-5-ylcarbamoyl}-propyl-carbamic acid benzyl ester, trans-isomer, (Compound FK);

(3-{2-[4-(4-fluoro-phenyl)-5-pyridin-4-yl-1H-imidazol-2-yl]-5-methyl-[1,3]dioxan-5-ylcarbamoyl}-propyl-carbamic acid benzyl ester, cis-isomer, (Compound FL);

(3-{2-[4-(4-fluoro-phenyl)-5-pyridin-4-yl-1H-imidazol-2-yl]-5-methyl-[1,3]dioxan-5-ylcarbamoyl}-propyl-carbamic acid benzyl ester, trans-isomer, (Compound FM);

(3-{2-[4-(4-fluoro-phenyl)-5-pyridin-4-yl-1H-imidazol-2-yl]-5-methyl-[1,3]dioxan-5-ylcarbamoyl}-methyl-carbamic acid benzyl ester, cis-isomer, (Compound FN);

4-dimethylamino-N-{2-[4-(4-fluoro-phenyl)-5-pyridin-4-yl-1H-imidazol-2-yl]-5-methyl-[1,3]dioxan-5-yl}-butyramide, cis- and trans-isomers, (Compound FO);

N-{2-[4-(4-fluoro-phenyl)-5-pyridin-4-yl-1H-imidazol-2-yl]-5-methyl-[1,3]dioxan-5-yl}-benzamide, trans-isomer, (Compound FR);

{2-[4-(4-fluoro-phenyl)-5-pyridin-4-yl-1H-imidazol-2-yl]-5-methyl-[1,3]dioxan-5-yl}-(4-hydroxy-piperdin-1-yl)-methanone, trans isomer, (Compound FS);

(1,4-dioxa-8-aza-spiro[4.5]dec-8-yl)-{2-[4-(4-fluoro-phenyl)-5-pyridin-4-yl-1H-imidazol-2-yl]-5-methyl-[1,3]dioxan-5-yl}-methanone, trans isomer, (Compound FT);

1-{2-[4-(4-fluoro-phenyl)-5-pyridin-4-yl-1H-imidazol-2-yl]-5-methyl-[1,3]dioxan-5-carbamoyl}-piperidine-4-carboxylic acid ethyl ester, trans isomer, (Compound FU);

1-{2-[4-(4-fluoro-phenyl)-5-pyridin-4-yl-1H-imidazol-2-yl]-5-methyl-[1,3]dioxan-5-carbamoyl}-piperidine-4-carboxylic acid, trans isomer, (Compound FV);

{2-[4-(4-fluoro-phenyl)-5-pyridin-4-yl-1H-imidazol-2-yl]-5-methyl-[1,3]dioxan-5-carbamoyl}-thiomorpholin-4-yl-methanone, trans isomer, (Compound FW);

(1,1-dioxothiomorpholin-4-yl)-{2-[4-(4-fluoro-phenyl)-5-pyridin-4-yl-1H-imidazol-2-yl]-5-methyl-[1,3]dioxan-5-yl}-methanone, trans isomer, (Compound FX);

{2-[4-(4-fluoro-phenyl)-5-pyridin-4-yl-1H-imidazol-2-yl]-5-methyl-[1,3]dioxan-5-carbamoyl}-(3-hydroxymethyl-piperidin-1-yl)-methanone, trans isomer, (Compound FY);

{2-[4-(4-fluoro-phenyl)-5-pyridin-4-yl-1H-imidazol-2-yl]-5-methyl-[1,3]dioxan-5-yl}-(3-hydroxy-piperidin-1-yl)-methanone, trans isomer, (Compound FZ);

(2,6-dimethyl-morpholin-4-yl)-{2-[4-(4-fluoro-phenyl)-5-pyridin-4-yl-1H-imidazol-2-yl]-5-methyl-[1,3]dioxan-5-yl}-methanone, trans isomer, (Compound GA);

{2-[4-(4-fluoro-phenyl)-5-pyridin-4-yl-1H-imidazol-2-yl]-5-methyl-[1,3]dioxan-5-yl}--(3-hydroxy-pyrrolidin-1-yl)-methanone, trans isomer, (Compound GB);

{2-[4-(4-fluoro-phenyl)-5-pyridin-4-yl-1H-imidazol-2-yl]-5-methyl-[1,3]dioxan-5-yl}-(4-methoxy-piperidin-1-yl)-methanone, trans isomer, (Compound GC);

{2-[4-(4-fluoro-phenyl)-5-pyridin-4-yl-1H-imidazol-2-yl]-5-methyl-[1,3]dioxan-5-yl}-[4-(2-hydroxy-ethyl)-piperidin-1-yl]-methanone, trans isomer, (Compound GD);

{5-Amino-2-[4-(4-fluoro-phenyl)-5-pyridin-4-yl-1H-imidazol-2-yl]-[1,3]dioxan-5-yl}-methanol, cis isomer, (Compound LE);

{5-Amino-2-[4-(4-fluoro-phenyl)-5-pyridin-4-yl-1H-imidazol-2-yl]-[1,3]dioxan-5-yl}-methanol, trans isomer, (Compound LF);

{2-[4-(4-Fluoro-phenyl)-5-pyridin-4-yl-1H-imidazol-2-yl]-5-nitro-[1,3]dioxan-5-yl}-methanol, cis isomer, (Compound LG);

{2-[4-(4-Fluoro-phenyl)-5-pyridin-4-yl-1H-imidazol-2-yl]-5-nitro-[1,3]dioxan-5-yl}-methanol, trans isomer, (Compound LH);

C-{2-[4-(4-fluoro-phenyl)-5-pyridin-4-yl-1H-imidazol-2-yl]-5,5-dimethyl-[1,3]dioxan-5-yl}-methylamine (Compound LI);

4-[2-(5,5-dimethyl-4-nitromethyl-[1,3]dioxan-2-yl)-5-(4-fluoro-phenyl)-3H-imidazol-4-yl]-pyridine (Compound LJ);

and the corresponding N-oxides, and their prodrugs; and pharmaceutically acceptable salts and solvates (e.g. hydrates) of such compounds and their N-oxides and prodrugs.

A further particular group of compounds of the invention are those selected from the following:

{2-[5-(2-cyclopropylamino-pyrimidin-4-yl)-4-(4-fluoro-phenyl)-1H-imidazol-2-yl]-5-methyl-[1,3]dioxan-5-yl}-morpholin-4-yl-methanone, trans isomer, (Compound GE);

2-[5-(2-Amino-pyrimidin-4-yl)-4-(4-fluoro-phenyl)-1H-imidazol-2-yl]-5-methyl-[1,3]dioxan-5-yl}-morpholin-4-yl-methanone, trans isomer, (Compound GI);

{(2-[5-(2-Dimethylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GJ);

(2-{4-(4-Fluoro-phenyl)-5-[2-(3-hydroxy-propylamino)-pyrimidin-4-yl]-1H-imidazol-2-yl}-5methyl-[1,3]dioxan-5-yl)-morpholin-4-yl-methanone, trans-isomer, (Compound GK);

(2-{4-(4-Fluoro-phenyl)-5-[2-(2-methoxy-ethylamino)-pyrimidin-4-yl]-1H-imidazol-2-yl }-5-methyl-[1,3]dioxan-5-yl)-morpholin-4-yl-methanone, trans-isomer, (Compound GL);

{2-[4-(4-Fluoro-phenyl)-5-(2-methylamino-pyrimidin-4-yl)-1H-imidazol-2-yl]-5-methyl-[1,3]dioxan-5-yl}-morpholin-4-yl-methanone, trans-isomer, (Compound GM);

(2-{4-(4-Fluoro-phenyl)-5-[2-(1-ethoxycarbonylpiperidin-4-ylamino)-pyrimidin-4-yl]-1H-imidazol-2-yl}-5-methyl-[1,3]dioxan-5-yl)-morpholin-4-yl-methanone, trans-isomer, (Compound GN);

{2-[5-(2-Cyclohexylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GO);

(2-{4-(4-Fluoro-phenyl)-5-[2-(2-hydroxy-ethylamino)-pyrimidin-4-yl]-1H-imidazol-2-yl}-5-methyl-[1,3]dioxan-5-yl)-morpholin-4-yl-methanone, trans-isomer, (Compound GP);

{2-[5-[2-(2-Amino-ethylamino)-pyrimidin-4-yl]-4-(4-fluoro-phenyl)-1H-imidazol-2-yl]5-methyl-[1,3]dioxan-5-yl}-morpholin-4-yl-methanone, trans-isomer, (Compound GQ);

[2-(4-(4-Fluoro-phenyl)-5-{2-[3-(5H-imidazol-1-yl)-propylamino]-pyrimidin-4-yl}-1H-imidaxol-2-yl)-5-methyl-[1,3]dioxan-5-yl]-morpholin-4-yl-methanone, trans-isomer, (Compound GR);

(2-{4-(4-Fluoro-phenyl)-5-[2-(3-morpholin-4-yl-propylamino)-pyrimidin-4-yl]-1H-imidazol-2-yl}-5-methyl-[1,3]dioxan-5-yl)-morpholin-4-yl-methanone, trans-isomer, (Compound GS);

2-[5-(2-Benzylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GT);

(2-{4-(4-Fluoro-phenyl)-5-[2-(1-phenyl-ethylamino)-pyrimidin-4-yl]-1H-imidazol-2-yl}-5methyl-[1,3]dioxan-5-yl)-morpholin-4-yl-methanone, R isomer, trans-isomer, (Compound GU);

(2-{4-(4-Fluoro-phenyl)-5-[2-(1-phenyl-ethylam ino)-pyrimidin-4-yl]-1H-imidazol-2-yl}-5-methyl-[1,3]dioxan-5-yl)-morpholin-4-yl-methanone, S isomer, trans-isomer, (Compound GV);

{2-[4-(4-Fluoro-phenyl)-5-(2-phenylamino-pyrimidin-4-yl)-1H-imidazol-2-yl]-5-methyl-[1,3]dioxan-5-yl}-morpholin-4-yl-methanone, trans-isomer, (Compound GW);

{2-[4-(4-Fluoro-phenyl)-5-(2-piperidin-1-yl-pyrimidin-4-yl)-1H-imidazol-2-yl]-5-methyl-[1,3]dioxan-5-yl}-morpholin-4-yl-methanone, trans-isomer, (Compound GX);

[2-(4-(4-Fluoro-phenyl)-5-{2-[(pyridin-4-ylmethyl)-amino]-pyrimidin-4-yl}-1H-imidazol-2-yl)-5-methyl-[1,3]dioxan-5-yl]-morpholin-4-yl-methanone, trans-isomer, (Compound GY);

[2-(4-(4-Fluoro-phenyl)-5-{2-[(pyridin-2-ylmethyl)-amino]-pyrimidin-4-yl}-1H-imidazol-2-yl)-5-methyl-[1,3]dioxan-5-yl]-morpholin-4-yl-methanone, trans-isomer, (Compound GZ);

[2-(4-(4-Fluoro-phenyl)-5-{2-[(pyridin-3-ylmethyl)-amino]-pyrimidin-4-yl}-1H-imidazol-2-yl)-5-methyl-[1,3]dioxan-5-yl]-morpholin-4-yl-methanone, trans-isomer, (Compound HA);

[2-(4-(4-Fluoro-phenyl)-5-{2-[(furan-2-ylmethyl)-amino]-pyrimidin-4-yl}-1H-imidazol-2-yl-)5-methyl-[1,3]dioxan-5-yl]-morpholin-4-yl-methanone, trans-isomer, (Compound HB);

[2-(4-(4-Fluoro-phenyl)-5-{2-[(thiophen-2-ylmethyl)-amino]-pyrimidin-4-yl}-1H-imidazol-2-yl)-5-methyl-[1,3]dioxan-5-yl]-morpholin-4-yl-methanone, trans-isomer, (Compound HC);

[2-(4-(4-Fluoro-phenyl)-5-{2-[(tetrahydro-furan-2-ylmethyl)-amino]-pyrimidin-4-yl}-1H-imidazol-2-yl)-5-methyl-[1,3]dioxan-5-yl]-morpholin-4-yl-methanone, trans-isomer, (Compound HD);

(2-{4-(4-Fluoro-phenyl)-5-[2-(4-methyl-piperazin-1-yl)-pyrimidin-4-yl]-1H-imidazol-2-yl}-5-methyl-[1,3]

dioxan-5-yl)-morpholin-4-yl-methanone, trans-isomer, (Compound HE);

{2-[4-(4-Fluoro-phenyl)-5-(2-morpholin-4-yl-pyrimidin-4-yl)-1H-imidazol-2-yl]-5-methyl-[1,3]dioxan-5-yl}-morpholin-4-yl-methanone, trans-isomer, (Compound HF);

(2-{4-(4-Fluoro-phenyl)-5-[2-(3-methoxy-propylamino)-pyrimidin-4-yl]-1H-imidazol-2-yl}-5-methyl-[1,3]dioxan-5-yl)-morpholin-4-yl-methanone, trans-isomer, (Compound FG);

{2-[5-[2-(3-Dimethylamino-propylamino)-pyrimidin-4-yl]-4-(4-fluoro-phenyl)-1H-imidazol-2-yl]-5-methyl-[[1,3]dioxan-5-yl}-morpholin-4-yl-methanone, trans-isomer, (Compound HH);

{2-[5-[2-(2-Dimethylamino-ethylamino)-pyrimidin-4-yl]-4-(4-fluoro-phenyl)-1H-imidazol-2-yl]-5-methyl-[[1,3]dioxan-5-yl}-morpholin-4-yl-methanone, trans-isomer, (Compound HI);

(4-{5-(4-Fluoro-phenyl)-2-[5-methyl-5-(morpholine-4-carbonyl)-[1,3]dioxan-2-yl]-3H-imidazol-4-yl}-pyrimidin-2-ylamino)-acetic acid, trans-isomer, (Compound HJ);

3-(4-{5-(4-Fluoro-phenyl)-2-[5-methyl-5-(morpholine-4-carbonyl)-[1,3]dioxan-2-yl]-3H-imidazol-4-yl}-pyrimidin-2-ylamino)-propionic acid, trans-isomer, (Compound HK);

4-[2-(5,5-dimethyl-[1,3]dioxan-2-yl)-5-(4-fluoro-phenyl)-3H-imidazol-4-yl]-pyrimidin-2-ylamine, (Compound HL);

{4-[2-(5,5-dimethyl-[1,3]dioxan-2-yl)-5-(4-fluoro-phenyl)-3H-imidazol-4-yl]-pyrimidin-2-yl}-methyl-amine, (Compound HM);

{4-[2-(5,5-dimethyl-[1,3]dioxan-2-yl)-5-(4-fluoro-phenyl)-3H-imidazol-4-yl]-pyrimidin-2-yl}-dimethyl-amine, (Compound HN);

cyclopropyl-{4-[2-(5,5-dimethyl-[1,3]dioxan-2-yl)-5-(4-fluoro-phenyl)-3H-imidazol-4-yl]-pyrimidin-2-yl}-amine, (Compound HO);

cyclohexyl-{4-[2-(5,5-dimethyl-[1,3]dioxan-2-yl)-5-(4-fluoro-phenyl)-3H-imidazol-4-yl]-pyrimidin-2-yl}-amine, (Compound HQ);

2-{4-[2-(5,5-dimethyl-[1,3]dioxan-2-yl)-5-(4-fluoro-phenyl)-3H-imidazol-4-yl]-pyrimidin-2-ylamino}-ethanol, (Compound HR);

N1-{4-[2-(5,5-dimethyl-[1,3]dioxan-2-yl)-5-(4-fluoro-phenyl)-3H-imidazol-4-yl]-pyrimidin-2-yl}-ethane-1,2-diamine, (Compound HS);

{4-[2-(5,5-dimethyl-[1,3]dioxan-2-yl)-5-(4-fluoro-phenyl)-3H-imidazol-4-yl]-pyrimidin-2-yl}-3(5H-imidazol-1-yl)-propyl]-amine, (Compound HT);

{4-[2-(5,5-dimethyl-[1,3]dioxan-2-yl)-5-(4-fluoro-phenyl)-3H-imidazol-4-yl]-pyrimidin-2-yl}-(3-morpholin-4-yl-propyl)-amine, (Compound HU);

3-{4-[2-(5,5-dimethyl-[1,3]dioxan-2-yl)-5-(4-fluoro-phenyl)-3H-imidazol-4-yl]-pyrimidin-2-ylamino}-propan-1-ol, (Compound HV);

benzyl-{4-[2-(5,5-dimethyl-[1,3]dioxan-2-yl)-5-(4-fluoro-phenyl)-3H-imidazol-4-yl]-pyrimidin-2-yl}-amine, (Compound HW);

{4-[2-(5,5-dimethyl-[1,3]dioxan-2-yl)-5-(4-fluoro-phenyl)-3H-imidazol-4-yl]-pyrimidin-2-yl}-(1-phenyl-ethyl)-amine, R-isomer, (Compound HX);

{4-[2-(5,5dimethyl-[1,3]dioxan-2-yl)-5-(4-fluoro-phenyl)-3H-imidazol-4-yl]-pyrimidin-2-yl}-(1-phenyl-ethyl)-amine, S-isomer, (Compound HY);

{4-[2-(5,5-dimethyl-[1,3]dioxan-2-yl)-5-(4-fluoro-phenyl)-3H-imidazol-4-yl]-pyrimidin-2-yl}-(1-phenyl-amine, (Compound HZ);

4-[2-(5,5-dimethyl-[1,3]dioxan-2-yl)-5-(4-fluoro-phenyl)-3H-imidazol-4-yl]-piperidin-1-yl-pyrimidine, (Compound IA);

{4-[2-(5,5-dimethyl-[1,3]dioxan-2-yl)-5-(4-fluoro-phenyl)-3H-imidazol-4-yl]-pyrimidin-2-yl}-pyridin-4-ylmethyl-amine, (Compound IB);

{4-[2-(5,5-dimethyl-[1,3]dioxan-2-yl)-5-(4-fluoro-phenyl)-3H-imidazol-4-yl]-pyrimidin-2-yl}-pyridin-2-ylmethyl-amine, (Compound IC);

{4-[2-(5,5-dimethyl-[1,3]dioxan-2-yl)-5-(4-fluoro-phenyl)-3H-imidazol-4-yl]-pyrimidin-2-yl}-pyridin-3-ylmethyl-amine, (Compound ID);

{4-[2-(5,5-dimethyl-[1,3]dioxan-2-yl)-5-(4-fluoro-phenyl)-3H-imidazol-4-yl]-pyrimidin-2-yl}-(furan-2-ylmethyl)-amine, (Compound IE);

{4-[2-(5,5-dimethyl-[1,3]dioxan-2-yl)-5-(4-fluoro-phenyl)-3H-imidazol-4-yl]-pyrimidin-2-yl}-(thiophen-2-ylmethyl)-amine, (Compound IF);

{4-[2-(5,5-dimethyl-[1,3]dioxan-2-yl)-5-(4-fluoro-phenyl)-3H-imidazol-4-yl]-pyrimidin-2-yl}-(tetrahydro-furan-2-ylmethyl)-amine, (Compound IG);

4-[2-(5,5-dimethyl-[1,3]dioxan-2-yl)-5-(4-fluoro-phenyl)-3H-imidazol-4-yl]-2-(4-methyl-piperazin-1-yl)-pyrimidine, (Compound IH);

4-{4-[2-(5,5-dimethyl-[1,3]dioxan-2-yl)-5-(4-fluoro-phenyl)-3H-imidazol-4-yl]-pyrimidin-2-yl}-morpholine, (Compound IJ);

{4-[2-(5,5-dimethyl-[1,3]dioxan-2-yl)-5-(4-fluoro-phenyl)-3H-imidazol-4-yl]-pyrimidin-2-yl}-(3-methoxy-propyl)-amine, (Compound IK);

{4-[2-(5,5-dimethyl-[1,3]dioxan-2-yl)-5-(4-fluoro-phenyl)-3H-imidazol-4-yl]-pyrimidin-2-yl}-(2-methoxy-ethyl)-amine, (Compound IL);

N-{4-[2-(5,5-dimethyl-[1,3]dioxan-2-yl)-5-(4-fluoro-phenyl)-3H-imidazol-4-yl]-pyrimidin-2-yl}-N',N'-dimethyl-propane-1,3-diamine, (Compound IM);

N-{4-[2-(5,5-dimethyl-[1,3]dioxan-2-yl)-5-(4-fluoro-phenyl)-3H-imidazol-4-yl]-pyrimidin-2-yl}-N',N'-dimethyl-ethane-1,2-diamine, (Compound IN);

{2-[5-(2-amino-pyrimidin-4-yl)-4-(4-fluoro-phenyl)-1H-imidazol-2-yl]-5-methyl-[1,3]dioxan-5-yl}-methanol, trans-isomer, (Compound IO)

{2-[4-(4-Fluoro-phenyl)-5-(2-methoxy-pyrimidin-4-yl)-1H-imidazol-2-yl]-5-methyl-[1,3]dioxan-5-yl}-morpholin-4-yl-methanone, trans-isomer, (Compound IP);

{2-[5-(2-Benzyloxy-pyrimidin-4-yl)-4-(4-fluoro-phenyl)-1H-imidazol-2-yl]-5-methyl-1,3]dioxan-5-yl}-morpholin-4-yl-methanone, trans-isomer, (Compound IQ);

{2-[4-(4-Fluoro-phenyl)-5-(2-phenoxy-pyrimidin-4-yl)-1H-imidazol-2-yl]-5-methyl-[1,3]dioxan-5-yl}-morpholin-4-yl-methanone, trans-isomer, (Compound IR);

(2-{4-(4-Fluoro-phenyl)-5-[2-(2-methoxy-ethoxy)-pyrimidin-4-yl]-1H-imidazol-2-yl}-5-methyl-[1,3]dioxan-5-yl)-morpholin-4-yl-methanone, trans-isomer, (Compound IS);

{2-[5-[2-(2-Dimethylamino-ethoxy)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound IT);

{2-[5-(2-Cyclohexyloxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound IU);

{2-[5-(2-Isopropoxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound IW);

4-[2-(5,5-dimethyl-[1,3]dioxan-2-yl)-5-(4-fluoro-phenyl)-3H-imidazol-4-yl]-2-methoxy-pyrimidine, (Compound IY);
2-benzyloxy-4-[2-(5,5-dimethyl-[1,3]dioxan-2-yl)-5-(4-fluoro-phenyl)-3H-imidazol-4-yl]-pyrimidine, (Compound IZ);
4-[2-(5,5-dimethyl-[1,3]dioxan-2-yl)-5-(4-fluoro-phenyl)-3H-imidazol-4-yl]-2-phenoxy-pyrimidine, (Compound JA);
4-[2-(5,5-dimethyl-[1,3]dioxan-2-yl)-5-(4-fluoro-phenyl)-3H-imidazol-4-yl]-2-(2-methoxy-ethoxy)-pyrimidine, (Compound JB);
(2-{4-[2-(5,5-dimethyl-[1,3]dioxan-2-yl)-5-(4-fluoro-phenyl)-3H-imidazol-4-yl]-pyrimidin-2-yloxy}-ethyl)-dimethyl-amine, (Compound JC);
2-cyclohexyloxy-4-[2-(5,5-dimethyl-[1,3]dioxan-2-yl)-5-(4-fluoro-phenyl)-3H-imidazol-4-yl]-pyrimidine, (Compound JD);
2-isopropoxy-4-[2-(5,5-dimethyl-[1,3]dioxan-2-yl)-5-(4-fluoro-phenyl)-3H-imidazol-4-yl]-pyrimidine, (Compound JE);
4-[2-(5-amino-5-methyl-[1,3]dioxan-2-yl)-5-(4-fluoro-phenyl)-3H-imidazol-4-yl]-pyrimidine-2-ylamine, cis-isomer, (Compound JF);
{4-[2-(5-amino-5-methyl-[1,3]dioxan-2-yl)-5-(4-fluoro-phenyl)-3H-imidazol-4-yl]-pyrimidine-2-yl}-methyl-amine, cis-isomer, (Compound JG);
{4-[2-(5-amino-5-methyl-[1,3]dioxan-2-yl)-5-(4-fluoro-phenyl)-3H-imidazol-4-yl]-pyrimidine-2-yl}-dimethyl-amine, cis-isomer, (Compound JH);
{4-[2-(5-amino-5-methyl-[1,3]dioxan-2-yl)-5-(4-fluoro-phenyl)-3H-imidazol-4-yl]-pyrimidine-2-yl}-cyclopropyl-amine, cis-isomer, (Compound JI);
{4-[2-(5-amino-5-methyl-[1,3]dioxan-2-yl)-5-(4-fluoro-phenyl)-3H-imidazol-4-yl]-pyrimidine-2-yl}-piperidin-4-yl-amine, cis-isomer, (Compound JJ);
{4-[2-(5-amino-5-methyl-[1,3]dioxan-2-yl)-5-(4-fluoro-phenyl)-3H-imidazol-4-yl]-pyrimidine-2-yl}-cyclohexyl-amine, cis-isomer, (Compound JK);
2-{4-[2-(5-amino-5-methyl-[1,3]dioxan-2-yl)-5-(4-fluoro-phenyl)-3H-imidazol-4-yl]-pyrimidine-2-ylamino}-ethanol, cis-isomer, (Compound JL);
N1-{4-[2-(5-amino-5-methyl-[1,3]dioxan-2-yl)-5-(4-fluoro-phenyl)-3H-imidazol-4-yl]-pyrimidine-2-yl}-ethane-1,2-diamine, cis-isomer, (Compound JM);
{4-[2-(5-amino-5-methyl-[1,3]dioxan-2-yl)-5-(4-fluoro-phenyl)-3H-imidazol-4-yl]-pyrimidine-2-yl}-[3-(5H-imidazol-1-yl)-propyl]-amine, cis-isomer, (Compound JN);
{4-[2-(5-amino-5-methyl-[1,3]dioxan-2-yl)-5-(4-fluoro-phenyl)-3H-imidazol-4-yl]-pyrimidine-2-yl}-(3-morpholin-4-yl-propyl)-amine, cis-isomer, (Compound JO);
3-{4-[2-(5-amino-5-methyl-[1,3]dioxan-2-yl)-5-(4-fluoro-phenyl)-3H-imidazol-4-yl]-pyrimidine-2-ylamino}-propan-1-ol, cis-isomer, (Compound JP);
{4-[2-(5-amino-5-methyl-[1,3]dioxan-2-yl)-5-(4-fluoro-phenyl)-3H-imidazol-4-yl]-pyrimidine-2-yl}-benzyl-amine, cis-isomer, (Compound JQ);
{4-[2-(5-amino-5-methyl-[1,3]dioxan-2-yl)-5-(4-fluoro-phenyl)-3H-imidazol-4-yl]-pyrimidine-2-yl}-(1-phenyl-ethyl)-amine, R isomer, cis-isomer, (Compound JR);
{4-[2-(5-amino-5-methyl-[1,3]dioxan-2-yl)-5-(4-fluoro-phenyl)-3H-imidazol-4-yl]-pyrimidine-2-yl}-(1-phenyl-ethyl)-amine, S isomer, cis-isomer, (Compound JS);
{4-[2-(5-amino-5-methyl-[1,3]dioxan-2-yl)-5-(4-fluoro-phenyl)-3H-imidazol-4-yl]-pyrimidine-2-yl}-phenyl-amine, cis-isomer, (Compound JT);
2-[4-(4-fluoro-phenyl)-5-(2-piperidin-1-yl-pyrimidin-4-yl)-1H-imidazol-2-yl]-5-methyl-[1,3]dioxan-5-ylamine, cis-isomer, (Compound JU);
{4-[2-(5-amino-5-methyl-[1,3]dioxan-2-yl)-5-(4-fluoro-phenyl)-3H-imidazol-4-yl]-pyrimidine-2-yl}-pyridin-4-ylmethyl-amine, cis-isomer, (Compound JV);
{4-[2-(5-amino-5-methyl-[1,3]dioxan-2-yl)-5-(4-fluoro-phenyl)-3H-imidazol-4-yl]-pyrimidine-2-yl}-pyridin-2-ylmethyl-amine, cis-isomer, (Compound JW);
{4-[2-(5-amino-5-methyl-[1,3]dioxan-2-yl)-5-(4-fluoro-phenyl)-3H-imidazol-4-yl]-pyrimidine-2-yl}-pyridin-3-ylmethyl-amine, cis-isomer, (Compound JX);
{4-[2-(5-amino-5-methyl-[1,3]dioxan-2-yl)-5-(4-fluoro-phenyl)-3H-imidazol-4-yl]-pyrimidine-2-yl}-(furan-2-ylmethyl)-amine, cis-isomer, (Compound JY);
{4-[2-(5-amino-5-methyl-[1,3]dioxan-2-yl)-5-(4-fluoro-phenyl)-3H-imidazol-4-yl]-pyrimidine-2-yl}-(thiophen-2-ylmethyl)-amine, cis-isomer, (Compound JZ);
{4-[2-(5-amino-5-methyl-[1,3]dioxan-2-yl)-5-(4-fluoro-phenyl)-3H-imidazol-4-yl]-pyrimidine-2-yl}-(tetrahydro-furan-2-ylmethyl)-amine, cis-isomer, (Compound KA);
2-{4-(4-fluoro-phenyl)-5-[2-(4-methyl-piperazin-1-yl)-pyrimidin-4-yl]-1H-imidazol-2-yl}-5-methyl-[1,3]dioxan-5-ylamine, cis-isomer, (Compound KB);
2-[4-(4-fluoro-phenyl)-5-(2-morpholin-4-yl-pyrimidin-4-yl)-1H-imidazol-2-yl]-5-methyl-[1,3]dioxan-5-ylamine, cis-isomer, (Compound KC);
{4-[2-(5-amino-5-methyl-[1,3]dioxan-2-yl)-5-(4-fluoro-phenyl)-3H-imidazol-4-yl]-pyrimidine-2-yl}-(3-methoxy-propyl)-amine, cis-isomer, (Compound KD);
{4-[2-(5-amino-5-methyl-[1,3]dioxan-2-yl)-5-(4-fluoro-phenyl)-3H-imidazol-4-yl]-pyrimidine-2-yl}-(2-methoxy-ethyl)-amine, cis-isomer, (Compound KE);
N-{4-[2-(5-amino-5-methyl-[1,3]dioxan-2-yl)-5-(4-fluoro-phenyl)-3H-imidazol-4-yl]-pyrimidine-2-yl}-N',N'-dimethyl-propane-1,3-diamine, cis-isomer, (Compound KF);
N-{4-[2-(5-amino-5-methyl-[1,3]dioxan-2-yl)-5-(4-fluoro-phenyl)-3H-imidazol-4-yl]-pyrimidine-2-yl}-N',N'-dimethyl-ethane-1,2-diamine, cis-isomer, (Compound KG);
{2-[4-(4-fluoro-phenyl)-5-(2-methylsulphonylpyrimidin-4-yl)-1H-imidazol-2-yl]-5-methyl-[1,3]dioxan-5-yl}-morpholin-4-yl-methanone, trans isomer, (Compound KH);
2-[4-(4-fluoro-phenyl)-5-(2-methylsulphonylpyrimidin-4-yl)-1H-imidazol-2-yl]-5,5-dimethyl-[1,3]dioxan (Compound KI);
{2-[4-(4-fluoro-phenyl)-5-(2-methylsulphonyl-pyrimidin-4-yl)-1H-imidazol-2-yl]-5-methyl-[1,3]dioxan-5-yl}-methanol, trans-isomer (Compound KJ);
{2-[4-(4-fluoro-phenyl)-5-(2-methylsulphonylpyrimidin-4-yl)-1H-imidazol-2-yl]-5-methyl-[1,3]dioxan-5-yl}-methanol, cis-isomer (Compound KK);
2-[4-(4-fluoro-phenyl)-5-(2-methylsulphonylpyrimidin-4-yl)-1H-imidazol-2-yl]-5-methylene-[1,3]dioxane (Compound KL).
4-[2-[1,3]dioxan-2-yl-5-(4-fluoro-phenyl)-3H-imidazol-4-yl]-2-methylsulphonyl-pyrimidine (Compound KM);
{2-[4-(4-fluoro-phenyl)-5-(2-methylsulphonylpyrimidin-4-yl)-1H-imidazol-2-yl]-[1,3]dioxan-5-yl}-methanol, trans-isomer (Compound KN);
{2-[4-(4-fluoro-phenyl)-5-(2-methylsulphonyl-pyrimidin-4-yl)-1H-imidazol-2-yl]-[1,3]dioxan-5-yl}-methanol, cis-isomer (Compound KO);
2,2,2-trifluoro-N-[2-{4-(4-fluoro-phenyl)-5-(2-methanesulphonylpyrimidin-4-yl)-1H-imidazol-2-yl}-5- methyl-[1,3]dioxan-5-yl]acetamide, cis-isomer (Compound KP);
{2-[4-(4-fluoro-phenyl)-5-(2-methylsulphanylpyrimidin-4-yl)-1H-imidazol-2-yl]-5-methyl-[1,3]dioxan-5-yl}-morpholin-4-yl-methanone, trans isomer, (Compound KQ);
2-[4-(4-fluoro-phenyl)-5-(2-methylsulphanylpyrimidin-4-yl)-1H-imidazol-2-yl]-5,5-dimethyl-[1,3]dioxane (Compound KR);
2,2,2-trifluoro-N-[2-{4-(4-fluoro-phenyl)-5-(2-methylsulphanyl-pyrimidin-4-yl)-1H-imidazol-2-yl}-5-methyl-[1,3]dioxan-5-yl]acetamide, cis-isomer, (Compound KS);
{2-[4-(4-fluoro-phenyl)-5-(2-methylsulfanyl-pyrimidin-4-yl)-1H-imidazol-2-yl]-5-methyl-[1,3]dioxan-5-yl}-methanol, cis isomer (Compound KT);
{2-[4-(4-fluoro-phenyl)-5-(2-methylsulfanyl-pyrimidin-4-yl)-1H-imidazol-2-yl]-5-methyl-[1,3]dioxan-5-yl}-methanol, trans isomer (Compound KU);
4-[5-(4-fluoro-phenyl)-2-(5-methylene-[1,3]dioxan-2-yl)-3H-imidazol-4-yl]-2-methylsulfanyl-pyrimidine (Compound KV);
4-[2-[1,3]dioxan-2-yl-5-(4-fluoro-phenyl)-3H-imidazol-4-yl]-2-methylsulphanyl-pyrimidine (Compound KW);
{2-[4-(4-fluoro-phenyl)-5-(2-methylsulphanyl-pyrimidin-4-yl)-1H-imidazol-2-yl]-[1,3]dioxan-5-yl}-methanol, trans-isomer (Compound KX);
{2-[4-(4-fluoro-phenyl)-5-(2-methylsulphanyl-pyrimidin-4-yl)-1H-imidazol-2-yl]-[1,3]dioxan-5-yl}-methanol, cis-isomer (Compound KY);
C-{2-[4-(4-fluoro-phenyl)-5-(2-methylsulfanyl-pyrimidin-4-yl)-1H-imidazol-2-yl]-5-methyl-[1,3]dioxan-5-yl}-methylamine, cis isomer (Compound KZ);
2-[4-(4-fluoro-phenyl)-5-(2-methylsulfanyl-pyrimidin-4-yl)-1H-imidazol-2-yl]-5-methyl-[1,3]dioxan-5-carboxylic acid amide, cis isomer Compound LA);
2-[4-(4-fluoro-phenyl)-5-(2-methylsulfanyl-pyrimidin-4-yl)-1H-imidazol-2-yl]-5-methyl-[1,3]dioxan-5-carboxylic acid, cis isomer (Compound LB);
2-[4-(4-fluorophenyl)-5-(2-methylsulphanylpyrimidin-4-yl)-1H-imidazol-2-yl]-5-methyl-[1,3]dioxan-5-carboxylic acid methyl ester, trans isomer, (Compound LC);
2-[4-(4-fluorophenyl)-5-(2-methylsulphanylpyrimidin-4-yl)-1H-imidazol-2-yl]-5-methyl-[1,3]dioxan-5-carboxylic acid methyl ester, cis isomer, (Compound LD);
2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, cis isomer, (Compound LK);
2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, trans isomer, (Compound LL);
2-[4-(4-fluorophenyl)-5-(2-methylsulphonylpyrimidin-4-yl)-1H-imidazol-2-yl]-5-methyl-[1,3]dioxan-5-carboxylic acid methyl ester, trans isomer, (Compound LM);
2-[4-(4-fluorophenyl)-5-(2-methylenesulphonylpyrimidin-4-yl)-1H-imidazol-2-yl]-5-methyl-[1,3]dioxan-5-carboxylic acid methyl ester, cis isomer (Compound LN);

and the corresponding N-oxides, and their prodrugs; and pharmaceutically acceptable salts and solvates (e.g. hydrates) of such compounds and their N-oxides and prodrugs.

Preferred compounds of the invention include:

{2-[5-(4-fluoro-phenyl)-4-pyridin-4-yl-1H-imidazol-2-yl]-5-methyl-[1,3]dioxan-5-yl}-methanol, cis-isomer, (Compound A);
C-[5-methyl-2-{5-(4-fluoro-phenyl)-4-pyridin-4-yl-1H-imidazol-2-yl}-[1,3]dioxan-5-yl]-methylamine, cis- and trans-isomers, (Compound D);
4-[5-(4-fluoro-phenyl)-2-(4-isopropyl-5,5-dimethyl-[1,3]dioxan-2-yl)-3H-imidazol-4-yl]-pyridine, (R/S)(R/S) isomers, (Compound T);
C-[5-methyl-2-(5-phenyl-4-pyridin-4-yl-1H-imidazol-2-yl)-[1,3]dioxan-5-yl]-methylamine, trans-isomer, (Compound AA);
C-[5-methyl-2-(5-phenyl-4-pyridin-4-yl-1H-imidazol-2-yl)-[1,3]dioxan-5-yl]-methylamine, cis-isomer, (Compound AB);
5-methyl-2-{5-(4-fluoro-phenyl)-4-pyridin-4-yl-1H-imidazol-2-yl}-[1,3]dioxan-5-ylamine, cis-isomer, (Compound AE);
5-methyl-2-{5-(4-fluoro-phenyl)-4-pyridin-4-yl-1H-imidazol-2-yl}-[1,3]dioxan-5-ylamine, trans-isomer, (Compound AF);
5-methyl-2-{5-(4-fluoro-phenyl)-4-pyridin-4-yl-1H-imidazol-2-yl}-[1,3]dioxan-5-ylamine, cis- and trans-isomers, (Compound AG);
2-[4-(4-fluoro-phenyl)-5-pyridin-4-yl-1H-imidazol-2-yl]-5-methyl-[1,3]dioxane-5-carboxylic acid amide, trans-isomer, (Compound AN);
{2-[4-(4-fluoro-phenyl)-5-pyridin-4-yl-1H-imidazol-2-yl]-5-methyl-[1,3]dioxan-5-yl}-morpholin-4-yl-methanone, trans-isomer, (Compound AW);
2-[4-(4-fluoro-phenyl)-5-pyridin-4-yl-1H-imidazol-2-yl]-5-methyl-[1,3]dioxane-5-carboxylic acid amide, cis-isomer, (Compound BM);
amino-N-{2-[4-(4-fluoro-phenyl)-5-pyridin-4-yl-1H-imidazol-2-yl]-5-methyl-[1,3]dioxan-5-yl}-acetamide, trans-isomer, (Compound FC);
amino-N-{2-[4-(4-fluoro-phenyl)-5-pyridin-4-yl-1H-imidazol-2-yl]-5-methyl-[1,3]dioxan-5-yl}-acetamide, cis-isomer, (Compound FD);
N-{2-[4-(4-fluoro-phenyl)-5-pyridin-4-yl-1H-imidazol-2-yl]-5-methyl-[1,3]dioxan-5-yl}-benzamide, trans-isomer, (Compound FR);

and the corresponding N-oxides, and their prodrugs; and pharmaceutically acceptable salts and solvates (e.g. hydrates) of such compounds and their N-oxides and prodrugs.

Further preferred compounds of the invention include:

{2-[5-(2-cyclopropylamino-pyrimidin-4-yl)-4-(4-fluoro-phenyl)-1H-imidazol-2-yl]-5-methyl-[1,3]dioxan-5-yl}-morpholin-4-yl-methanone, trans isomer, (Compound GE);
(2-{4-(4-fluoro-phenyl)-5-[2-(2-methoxy-ethylamino)-pyrimidin-4-yl]-1H-imidazol-2-yl}-5-methyl-[1,3]dioxan-5-yl)-morpholin-4-yl-methanone, trans isomer, (Compound GI);
2-{4-(4-fluoro-phenyl)-5-[2-(1-ethoxycarbonylpiperidin-4-ylamino)-pyrimidin-4-yl]-1H-imidazol-2-yl}-5-methyl-[1,3]dioxan-5-yl)-morpholin-4-yl-methanone, trans isomer, (Compound GK);
{2-[5-(2-cyclohexylamino-pyrimidin-4-yl)-4-(4-fluoro-phenyl)-1H-imidazol-2-yl]-5-methyl-[1,3]dioxan-5-yl}-morpholin-4-yl-methanone, trans isomer, (Compound GL);

and the corresponding N-oxides, and their prodrugs; and pharmaceutically acceptable salts and solvates (e.g. hydrates) of such compounds and their N-oxides and prodrugs.

A particularly preferred compound of the invention is {2-[4-(4-fluoro-phenyl)-5-pyridin-4-yl-1H-imidazol-2-yl]-5-methyl-[1,3]dioxan-5-yl}-morpholin-4-yl-methanone, trans-isomer, (Compound AW); and the corresponding N-oxide, and its prodrugs; and pharmaceutically acceptable salts and solvates (e.g. hydrates) of this compound and its N-oxide and prodrugs, especially its methane sulphonic acid salt as depicted by Compound FP.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention are inhibitors of the generation of tumour necrosis factor (TNF), especially TNF-alpha, according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of TNF, especially of TNF-alpha. For example, compounds of the present invention are useful in the treatment of joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, chronic pulmonary inflammatory diseases including asthma and adult respiratory distress syndrome, silicosis, pulmonary sarcoidosis, bone resorption diseases, osteoporosis, restenosis, heart failure and myocardial ischaemic syndromes, cardiac and renal reperfusion injury, thrombosis, glomerulamephritis, graft vs. host reaction, allograft rejection and leprosy. Furthermore, the compounds are useful in the treatment of infections such as viral infections, for example HIV, cytomegalovirus (CMV), influenza, adenovirus and the Herpes group of viruses, parasitic infections, for example malaria such as cerebral malaria, and yeast and fungal infections, for example fungal meningitis; fever and myalgias due to infection; AIDS; AIDS related complex (ARC); cachexia secondary to infection or malignancy; cachexia secondary to acquired immune deficiency syndrome (AIDS) or to. cancer; keloid and scar tissue formation; pyresis; diabetes; inflammatory bowel diseases such as Crohn's disease and ulcerative colitis; eczema; contact dermititis; psoriasis; sunburn and conjunctivitis.

Compounds of the invention are also useful in the treatment of diseases of, or injury to, the brain in which overproduction of TNF-alpha has been implicated, such as multiple sclerosis, Alzheimers disease, trauma, stroke and other ischaemic conditions.

Compounds of the invention may also be useful in inhibiting diseases associated with over-production of other pro-inflammatory cytokines, IL-1, IL-6 and IL-8.

A special embodiment of the therapeutic methods of the present invention is the treating of asthma.

Another special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of TNF, especially TNF-alpha, for example conditions as hereinbefore described, which comprises the administration to the patient of an effective amount of compound of the invention or a composition containing a compound of the invention. "Effective amount" is meant to describe an amount of compound of the present invention effective in inhibiting TNF and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended.in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature.

Compounds of the invention may be prepared by methods similar to those described in EP424195 and EP506437.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of this invention may be represented by the formula (Ic):

(Ic)

wherein $R^4$, $R^5$, $R^6$ and m are as hereinbefore defined and $T^1$ represents a group of the formula:

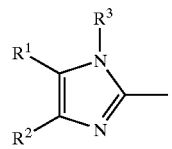

wherein $R^1$, $R^2$ and $R^3$ are as hereinbefore defined.

In a process (A), compounds of formula (I), wherein $R^1$, $R^2$, $R^4$, $R^5$, $R^6$ and m are as hereinbefore defined and $R^3$ is hydrogen, may be prepared by reaction of compounds of formula (II):

(II)

wherein $R^1$ and $R^2$ are as hereinbefore defined, $R^{19}$ is hydrogen or a suitable protecting group, such as 2-trimethylsilanyl-ethoxymethyl, which is subsequently removed under the acidic reaction conditions and $R^{20}$ is —CHO or —CH(OMe)$_2$, with compounds of formula (III):

(III)

wherein $R^4$, $R^5$, $R^6$ and m are as hereinbefore defined. The reaction may conveniently be carried out in the presence of an acid catalyst, such as pyridinium 4-toluene sulphonate or 4-toluene sulphonic acid, in an inert solvent, such as toluene, at reflux temperature, with azeotropic removal of the water formed in the reaction.

Compounds of formula (I), wherein $R^1$, $R^2$, $R^4$, $R^5$, $R^6$ and m are as hereinbefore defined and $R^3$ represents a group —$L^1$—$R^7$ (where $L^1$ and $R^7$ are as hereinbefore defined) or —$L^2$—$R^8$ (where $L^2$ is as hereinbefore defined and $R^8$ is aryl, cycloalkenyl, cycloalkyl, heteroaryl, heterocycloalkyl) may be similarly prepared by reaction of compounds of formula (II), wherein $R^1$, $R^2$ are as hereinbefore defined, $R^{19}$ represents a group —$L^1$—$R^7$ (where $L^1$ and $R^7$ are as hereinbefore defined) or —$L^2$—$R^8$ (where $L^2$ is as hereinbefore defined and $R^8$ is aryl, cycloalkenyl, cycloalkyl, heteroaryl, heterocycloalkyl) and $R^{20}$ is —CHO or —CH(OMe)$_2$, with compounds of formula (III) wherein $R^4$, $R^5$, $R^6$ and m are as hereinbefore defined.

In a process B, compounds of formula (I), wherein $R^2$, $R^3$, $R^4$, $R^5$, $R^6$ and m are as hereinbefore defined, and $R^1$ represents a group (IV):

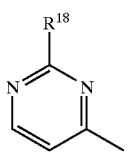
(IV)

wherein $R^{18}$ is $Y^4Y^5N-$ (in which $Y^4$ and $Y^5$ are as hereinbefore defined), may be prepared by:

(i) treating Merrifield resin (chloromethylpolystyrene resin) with potassium thioacetate in an inert solvent, such as dimethylformamide, at a temperature at about room temperature, to give Resin A;

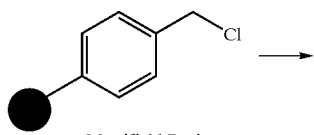
Merrifield Resin

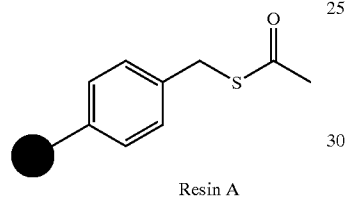
Resin A (ii) reaction of Resin A with lithium borohydride in an inert solvent, such as tetrahydrofuran, and at a temperature at about room temperature, to give Resin B;

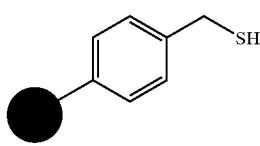
Resin B (iii) reaction of Resin B with an alkali metal hydride, such as sodium hydride, in an inert solvent, such as dimethylformamide, at a temperature at about room temperature, followed by treatment with compounds of formula (V);

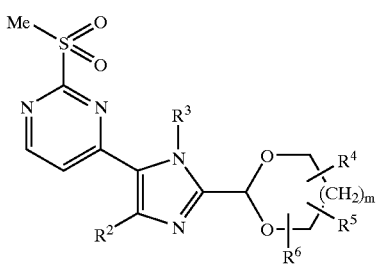
(V)

wherein $R^2$, $R^3$, $R^4$, $R^5$, $R^6$ and m are as hereinbefore defined, at a temperature from about room temperature to about 80° C., to give Resin C;

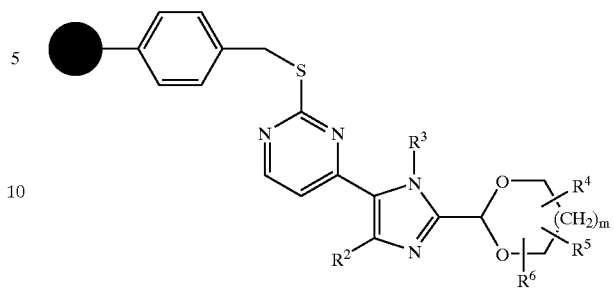
Resin C in which $R^2$, $R^3$, $R^4$, $R^5$, $R^6$ and m are as hereinbefore defined; followed by appropriate functional group interconversions, for example those described hereinafter.

(iv) reaction of Resin C, in which $R^2$, $R^3$, $R^4$, $R^5$, $R^6$ and m are as hereinbefore defined, with m-chloroperoxybenzoic acid, in an inert solvent or preferably in a mixture of inert solvents, such as a mixture of dichloromethane and methanol, to give resin D, in which $R^2$, $R^3$, $R^4$, $R^5$, $R^6$ and m are as hereinbefore defined;

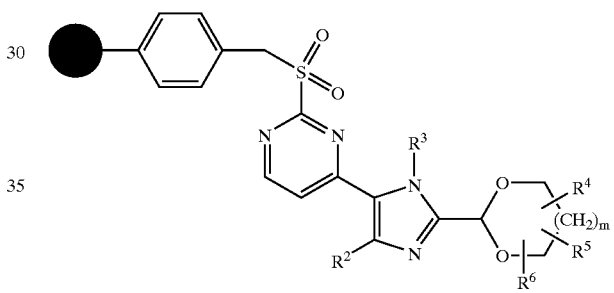
Resin D (v) reaction of Resin D, wherein $R^2$, $R^3$, $R^4$, $R^5$, $R^6$ and m are as hereinbefore defined, with amines of formula $HNY^4Y^5$, wherein $Y^4$ and $Y^5$ are as hereinbefore defined, in an inert solvent, such as dimethoxyethane, and at a temperature at about 70° C.

Compounds of formula (I), wherein $R^2$, $R^3$, $R^4$, $R^5$, $R^6$ and m are as hereinbefore defined and $R^1$ represents a group (IV), wherein $R^{18}$ is a $-OR^{17}$ or $-SR^{17}$ group (in which $R^{17}$ is as hereinbefore defined), may be prepared by reaction of Resin D, wherein $R^2$, $R^3$, $R^4$, $R^5$, $R^6$ and m are as hereinbefore defined, with compounds of formula $R^{17}OH$ or $R^{17}SH$ (in which $R^{17}$ is as hereinbefore defined), in the presence of an alkali metal hydride, such as sodium hydride, in an inert solvent, such as dimethylformamide, and at a temperature from about room temperature to about 80° C.

According to a further feature of the present invention, compounds of the invention may be prepared by interconversion of other compounds of the invention.

For example compounds of formula (I), wherein $R^1$, $R^2$, $R^4$, $R^5$, $R^6$ and m are as hereinbefore defined and $R^3$ is a group $-L^1-R^7$ (in which $L^1$ represents a straight- or branched-chain alkylene linkage containing from 1 to about 6 carbon atoms and $R^7$ is as hereinbefore defined), may be prepared by alkylation of compounds of formula (I) wherein $R^1$, $R^2$, $R^4$, $R^5$, $R^6$ and m are as hereinbefore defined and $R^3$ is hydrogen, with an alkyl halide of formula (IV):

$$X^1-L^1-R^7 \quad \text{(IV)}$$

wherein $L^1$ and $R^7$ are as hereinbefore defined immediately above and $X^1$ is a halogen atom, preferably a bromine atom. The alkylation may for example be carried out in the presence of a base, such as an alkali metal hydride, e.g. sodium hydride, in dimethylformamide, or dimethyl sulphoxide, at a temperature from about 0° C. to about 100° C.

As another example of the interconversion process, compounds of formula (I), wherein $R^1$, $R^2$, $R^4$, $R^5$, $R^6$ and m are as hereinbefore defined and $R^3$ is a group —$L^2$—$R^8$ (in which $L^2$ represents a straight- or branched-carbon chain comprising from 2 to about 6 carbon atoms and contains a double or triple carbon-carbon bond, and $R^8$ is aryl, cycloalkenyl, cycloalkyl, heteroaryl, heterocycloalkyl), may be similarly prepared by alkylation of compounds of formula (I), wherein $R^1$, $R^2$, $R^4$, $R^5$, $R^6$ and m are as hereinbefore defined and $R^3$ is hydrogen, with compounds of formula (V):

$X^1$—$L^2$—$R^8$ (V)

wherein $L^2$ and $R^8$ are as hereinbefore defined immediately above and $X^1$ is a halogen atom, preferably a bromine atom.

As another example of the interconversion process, compounds of formula (Ic), wherein $T^1$, $R^5$, $R^6$ and m are as hereinbefore defined and $R^4$ contains a —$NH_2$ group, may be prepared by reaction of compounds of formula (Ic) wherein $T^1$, $R^5$, $R^6$ and m are as hereinbefore defined, and $R^4$ contains a —NHC(=O)CF$_3$ group, with a base such as potassium or ammonium carbonate in methanol, or a mixture of methanol and water, at a temperature at about reflux temperature.

As another example of the interconversion process, compounds of formula (Ic), wherein $T^1$, $R^5$, $R^6$ and m are as hereinbefore defined and $R^4$ contains a —N($R^{10}$)—C(=O)—$R^{15}$ or —N($R^{10}$)—C(=O)—$L^4$—$R^{16}$ group (in which $R^{10}$, $R^{15}$, $R^{16}$ and $L^4$ are as hereinbefore defined), may be prepared by reaction of compounds of formula (Ic) wherein $T^1$, $R^5$, $R^6$ and m are as hereinbefore defined, and $R^4$ contains a —NHR$^{10}$ group (in which $R^{10}$ is as hereinbefore defined), with the appropriately substituted acid chloride Cl—C(=O)—$R^{15}$ or Cl—C(=O)—$L^4$—$R^{16}$ (in which $R^{15}$, $R^{16}$ and $L^4$ are as hereinbefore defined) in the presence of triethylamine in an inert solvent such as tetrahydrofuran and at a temperature at about room temperature.

As another example of the interconversion process, compounds of formula (Ic), wherein $T^1$, $R^5$, $R^6$ and m are as hereinbefore defined, and $R^4$ contains a —NH—C(=O)—$R^{15}$ or —NH—C(=O)—$L^4$—$R^{16}$ group (in which $R^{15}$, $R^{16}$ and $L^4$ are as hereinbefore defined), may be prepared by reaction of compounds of formula (Ic), wherein $T^1$, $R^5$, $R^6$ and m are as hereinbefore defined, and $R^4$ contains a —$NH_2$ group, with the appropriately substituted acid HO—C(=O)—$R^{15}$ or HO—C(=O)—$L^4$—$R^{16}$ (in which $R^{15}$, $R^{16}$ and $L^4$ are as hereinbefore defined) respectively, in the presence of O-(7-azabenzotriazol-1-yl)-1,1,3,3-tetramethyluronium hexafluorophosphate and diisopropylethylamine in dimethylformamide, at room temperature. Other standard peptide coupling procedures may be employed for the reaction, such as treatment with a carbodiimide, for example dicyclohexylcarbodiimide, in the presence of triethylamine, or treatment with 1-hydroxybenzotriazole and a carbodiimide, such as 1-(3-dimethylaminopropyl)-3-ethylcarbodiimide, in an inert solvent such as dimethylformamide and at a temperature at about room temperature.

As another example of the interconversion process, compounds of formula (Ic), wherein $T^1$, $R^5$, $R^6$ and m are as hereinbefore defined and $R^4$ contains a —NH—C(=O)—$R^{15}$ or a —NH—C(=O)—$L^4$—$R^{16}$ group (in which $R^{15}$, $R^{16}$ and $L^4$ are as hereinbefore defined), may be prepared by reaction of compounds of formula (Ic), wherein $T^1$, $R^5$, $R^6$ and m are as hereinbefore defined and $R^4$contains a —$NH_2$ group, with the appropriately substituted acid anhydride $R^{15}$—C(=O)—O—C(=O)—$R^{15}$ or $R^{16}$—$L^4$—C(=O)—O—C(=O)—$L^4$—$R^{16}$ (in which $R^{15}$, $R^{16}$ and $L^4$ are as hereinbefore defined) in the presence of triethylamine or pyridine, in an inert solvent, such as tetrahydrofuran, and at a temperature at about room temperature As another example of the interconversion process, compounds of formula (Ic), wherein $T^1$, $R^5$, $R^6$ and m are as hereinbefore defined and $R^4$ contains a —NH—C(=O)—NH—$R^{15}$ or —NH—C(=O)—NH—$L^4$—$R^{16}$ group (in which $R^{15}$, $R^{16}$ and $L^4$ are as hereinbefore defined), may be prepared by reaction of compounds of formula (Ic) wherein $T^1$, $R^5$, $R^6$ and m are as hereinbefore defined and $R^4$ contains a —$NH_2$ group, with the appropriately substituted isocyanate O=C=N—$R^{15}$ or O=C=N—$L^4$—$R^{16}$ (in which $R^{15}$, $R^{16}$ and $L^4$ are as hereinbefore defined), in an inert solvent, such as tetrahydrofuran, and at a temperature at about room temperature.

As another example of the interconversion process, compounds of formula (Ic) wherein $T^1$, $R^5$, $R^6$ and m are as hereinbefore defined, and $R^4$ contains a —NH—(C=S)—NH—$R^{15}$ or —NH—(C=S)—NH—$L^4$—$R^{16}$ group (in which $R^{15}$, $R^{16}$ and $L^4$ are as hereinbefore defined), may prepared by reaction of compounds of formula (Ic) wherein $T^1$, $R^5$, $R^6$ and m are as hereinbefore defined, and $R^4$contains a —$NH_2$ group, with the appropriately substituted isothiocyanate S=C=N—$R^{15}$ or S=C=N—$L^4$—$R^{16}$ (in which $R^{15}$, $R^{16}$ and $L^4$ are as hereinbefore defined), in an inert solvent, such as tetrahydrofuran, and at a temperature at about reflux temperature.

As another example of the interconversion process, compounds of formula (Ic), wherein $T^1$, $R^5$, $R^6$ and m re as hereinbefore defined and $R^4$ contains a —$CO_2H$ group, may be prepared by hydrolysis of corresponding compounds of formula (Ic), wherein $T^1$, $R^5$, $R^6$ and m are as hereinbefore defined and $R^4$ contains a —$CO_2R^{21}$ group (in which $R^{21}$ is as hereinbefore defined). The hydrolysis may conveniently be carried out by alkaline hydrolysis using a base, such as an alkali metal hydroxide or carbonate, in the presence of an aqueous/organic solvent mixture, using organic solvents such as dioxan, tetrahydrofuran or methanol, at a temperature from about ambient to about reflux. The hydrolysis may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example of the interconversion process, compounds of formula (Ic), wherein $T^1$, $R^5$, $R^6$ and m are as hereinbefore defined and $R^4$ contains a —C(=O)—NY$^4$Y$^5$ group (in which $Y^4$ and $Y^5$ are as hereinbefore defined), may be prepared by reaction of compounds of formula (Ic), wherein $T^1$, $R^5$, $R^6$ and m are as hereinbefore defined and $R^4$ contains a —$CO_2H$ group, with an appropriately substituted amine of formula HNY$^4$Y$^5$ (in which $Y^4$ and $Y^5$ are as hereinbefore defined). The coupling reaction may conveniently be carried out in the presence of 1-hydroxybenzotriazole and a carbodiimide such as 1-(3-dimethylaminopropyl)-3-ethylcarbodiimide in an inert solvent such as dimethylformamide and at a temperature at about room temperature. Alternatively the reaction may be carried out by initial conversion of the acid of formula (Ic), wherein $R^4$ contains a —$CO_2H$ group, to the corresponding acid chloride (for example by reaction with thionyl chloride or oxalyl chloride at room temperature) followed by treatment with an appropriately substituted amine of formula $HNY^4Y^5$.

As another example of the interconversion process, compounds of formula (I) containing sulphoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (Ic), wherein $T^1$, $R^5$, $R^6$ and m are as hereinbefore defined and $R^4$ contains a —$N(R^{10})$—$SO_2$—$R^{15}$ or —$N(R^{10})$—$SO_2$—$L^4$—$R^{16}$ group (in which $R^{10}$, $R^{15}$, $R^{16}$ and $L^4$ are as hereinbefore defined), may be prepared from the corresponding compounds of of formula (Ic) wherein $T^1$, $R^5$, $R^6$ and m are as hereinbefore defined and $R^4$ contains a —$NH_2$ group by treatment with the appropriately substituted acid chloride Cl—$SO_2$—$R^{15}$ or Cl—$SO_2$—$L^4$—$R^{16}$ (in which $R^{15}$, $R^{16}$ and $L^4$ are as hereinbefore defined), in the presence of a suitable base, such as triethylamine, in an inert solvent, such as tetrahydrofuran, and at a temperature at about room temperature.

As another example of the interconversion process, compounds of formula (I) containing sulphone linkages may be prepared by the oxidation of corresponding compounds containing —S— or sulphoxide linkages. For example, compounds of formula (Ib) where $R^{18}$ is —$SO_2Me$ may conveniently be prepared by means of reaction of compounds of formula (Ib) where $R^{18}$ is —SMe with a peroxyacid, e.g. 3-chloroperbenzoic acid, preferably in an inert solvent, such as dichloromethane, at a temperature from about 0° C. to about room temperature.

As another example of the interconversion process, compounds of formula (Ib), wherein $R^4$ and $R^5$ are as hereinbefore defined and $R^{18}$ is a —$NY^4Y^5$ group (in which $Y^4$ is hydrogen and $Y^5$ is as hereinbefore defined), may be prepared by reaction of compounds of formula (Ib), where $R^{18}$ is a —$SO_2Me$ group, with an appropriately substituted amine of formula $Y^5NH_2$ (in which $Y^5$ is as hereinbefore defined). The reaction may conveniently be carried out in an inert solvent such as dimethylformamide at a temperature up to about 100° C. When $Y^5$ is hydrogen the reaction may be conveniently carried out in a sealed vessel. When $Y^5$ is aryl, for example phenyl, the reaction may be conveniently carried out with the lithio-anion of the amine.

As another example of the interconversion process, compounds of formula (Ib), wherein $R^4$ and $R^5$ are as hereinbefore defined and $R^{18}$ is a —$OR^{17}$ group (in which $R^{17}$ is as hereinbefore defined), may be prepared by reaction of compounds of formula (Ib), where $R^{18}$ is a —$SO_2Me$ group, with an appropriately substituted alcohol of formula $R^{17}OH$ (in which $R^{17}$ is as hereinbefore defined). The reaction may conveniently be carried out in the presence of an alkali metal hydride, such as sodium hydride, in a mixture of inert solvents, for example tetrahydrofuran and dimethylformamide, and at a temperature at about room temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates. Additionally, in situations where tautomers of the compounds of formula (I) are possible, the present invention is intended to include all tautomeric forms of the compounds.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or an aqueous alcohol solution or other suitable solvents containing the appropriate acid and isolating the salt by evaporating the solution, or by reacting the free base and acid in an organic solvent, such as tetrahydrofuran, in which case the salt separates directly or can be obtained by concentration of the solution.

Compounds of this invention can be regenerated from their acid addition salts by the application or adaptation of known methods. For example, parent compounds of the invention can be regenerated from their acid addition salts by treatment with an alkali, e.g. aqueous sodium bicarbonate solution or aqueous ammonia solution.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from water.

The starting materials and intermediates may be prepared by the application or adaptation of known methods, for example methods as described in the Reference Examples or their obvious chemical equivalents.

Intermediates of formula (II), wherein $R^1$ and $R^2$ are as hereinbefore defined, $R^{19}$ is a 2-trimethylsilanyl-ethoxymethyl group and $R^{20}$ is —$CH(OMe)_2$, may be prepared by reaction of compounds of formula (II), wherein $R^1$ and $R^2$ are as hereinbefore defined, $R^{19}$ is a 2-trimethylsilanyl-ethoxymethyl group and $R^{20}$ is —CHO, with trimethylorthoformate in the presence of an acid catalyst, such as 4-toluene sulphonic acid, in methanol at reflux temperature.

Intermediates of formula (II), wherein $R^1$ and $R^2$ are as hereinbefore defined, $R^{19}$ is a 2-trimethylsilanyl-ethoxymethyl group and $R^{20}$ is —CHO, may be prepared by reaction of compounds of formula (1):

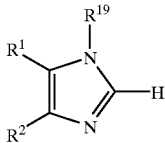

(1)

wherein $R^1$ and $R^2$ are as hereinbefore defined, $R^{19}$ is a 2-trimethylsilanyl-ethoxymethyl group, with an alkyllithium, such as butyllithium or lithium diisopropylamide, in an inert solvent, such as tetrahydrofuran, at a temperature at about −78° C., followed by reaction with N-formylmorpholine.

Intermediates of formula (II), wherein $R^1$ and $R^2$ are as hereinbefore defined, $R^{19}$ is hydrogen and $R^{20}$ is —CH(OMe)$_2$, may be prepared by reaction of compounds of formula (2):

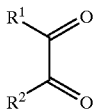

(2)

wherein $R^1$ and $R^2$ are as hereinbefore defined, with glyoxal 1,1-dimethylacetal and ammonium acetate. The reaction may conveniently be carried out in a mixture of inert solvents, such as tert-butylmethyl ether and methanol, and at a temperature at about room temperature.

Intermediates of formula (II), wherein $R^1$, $R^2$ are as hereinbefore defined, $R^{19}$ represents a —L$^1$—R$^7$ or —L$^2$—R$^8$ group (in which $R^7$, $L^1$ and $L^2$ is as hereinbefore defined and $R^8$ is aryl, cycloalkenyl, cycloalkyl, heteroaryl, heterocycloalkyl) and $R^{20}$ is —CHO, may be similarly prepared by reaction of compounds of formula (1), wherein $R^1$, $R^2$ and $R^{19}$ are as defined immediately above, with butyl lithium followed by reaction with N-formylmorpholine.

Intermediate 1,3-propanediols of formula (III), wherein $R^4$ is an azidomethyl group, $R^5$ is a methyl group, $R^6$ is hydrogen and m is 1, and where both $R^4$ and $R^5$ are attached in the 2-position, may be prepared by reaction of 5-azidomethyl-2,5-dimethyl-1,3-dioxane (prepared according to the procedure in J.Org.Chem., 1992, 57, page 6080) with a mineral acid, for example hydrochloric acid, in an aqueous organic solvent mixture such as tetrahydrofuran and water, at reflux temperature.

Intermediate 1,3-propanediols of formula (III), wherein $R^4$ is an —NHC(=O)CF$_3$ group, $R^5$ is a methyl group, $R^6$ is hydrogen and m is 1, and where both $R^4$ and $R^5$ are attached in the 2-position, may be prepared by reaction of 2-amino-2-methyl-1,3-propanediol with trifluoroacetic acid in the presence of a base, such as potassium carbonate, in an inert solvent, such as dimethylformamide, and at a temperature at about room temperature.

Intermediate 1,3-propanediols of formula (III), wherein $R^4$ is a —C(=O)—NY$^4$Y$^5$ group (in which Y$^4$ and Y$^5$ are as hereinbefore defined), $R^5$ is a methyl group, $R^6$ is hydrogen and m is 1, and where both $R^4$ and $R^5$ are attached in the 2-position, may be prepared by reaction of 2-carboxy-2-methyl-1,3-propanediol with an amine of formula HNY$^4$Y$^5$, wherein Y$^4$ and Y$^5$ are as hereinbefore defined.

The coupling may conveniently be carried out with a carbodiimide, such as dicyclohexylcarbodiimide, in the presence of 1-hydroxybenzotriazole and disisopropylethylamine, in an inert solvent, such as acetonitrile, and at a temperature from room temperature to about 55° C. Other standard peptide coupling procedures may be employed for the reaction, such as those described hereinbefore.

Resins of formula Resin C in which $R^3$, $R^5$, $R^6$ and m are as hereinbefore defined, and $R^4$ contains a —C(=O)—NY$^4$Y$^5$ group may be prepared from the corresponding Resin C, in which $R^3$, $R^5$, $R^6$ and m are as hereinbefore defined and $R^4$ contains a —C(=O)—OR$^{21}$ group (in which $R^{21}$ is alkyl, aryl or arylalkyl), by: (i) treatment with an alkali metal hydroxide, such as sodium hydroxide, in a mixture of water and a water miscible inert organic solvent, such as tetrahydrofuran,and at a temperature from about room temperature to about 70° C.; (ii) treatment of the resulting resin in which $R^4$ contains a —C(=O)—OH group with oxalyl chloride solution in an inert solvent, such as dichloromethane, at a temperature at about room temperature; (iii) treatment of the resulting resin in which $R^4$ contains a —C(=O)—Cl group with an amine of formula HNY$^4$Y$^5$ in an inert solvent, such as dichloromethane, at a temperature at about room temperature.

Resins of formula Resin C in which $R^3$, $R^5$, $R^6$ and m are as hereinbefore defined, and $R^4$ contains a —N(R$^{10}$)—C(=O)—R$^{15}$ or —N(R$^{10}$)—C(=O)—L$^4$—R$^{16}$ group (in which $R^{10}$, $R^{15}$, $R^{16}$ and $L^4$ are as hereinbefore defined), may be prepared from the corresponding Resin C, in which $R^3$, $R^5$, $R^6$ and m are as hereinbefore defined and $R^4$ contains a —NH$_2$ group by treatment with the appropriately substituted acid chloride Cl—C(=O)—R$^{15}$ or Cl—C(=O)—L$^4$—R$^{16}$ (in which $R^{15}$, $R^{16}$ and $L^4$ are as hereinbefore defined), in the presence of triethylamine, in an inert solvent, such as tetrahydrofuran, and at a temperature at about room temperature.

Resins of formula Resin C in which $R^3$, $R^5$, $R^6$ and m are as hereinbefore defined, and $R^4$ contains a —N(R$^{10}$)—SO$_2$—R$^{15}$ or —N(R$^{10}$)—SO$_2$—L$^4$—R$^{16}$ group (in which $R^{10}$, $R^{15}$, $R^{16}$ and $L^4$ are as hereinbefore defined), may be prepared from the corresponding Resin C, in which $R^3$, $R^5$, $R^6$ and m are as hereinbefore defined and $R^4$ contains a —NH$_2$ group by treatment with the appropriately substituted acid chloride Cl—SO$_2$—R$^{15}$ or Cl—SO$_2$—L$^4$—R$^{16}$ (in which $R^{15}$, $R^{16}$ and $L^4$ are as hereinbefore defined), in the presence of triethylamine, in an inert solvent, such as tetrahydrofuran, and at a temperature at about room temperature.

Compounds of formula (1), wherein $R^1$ and $R^2$ are as hereinbefore defined, $R^{19}$ is a 2-trimethylsilanyl-ethoxymethyl group, may be prepared by reaction of compounds of formula (1), wherein $R^1$ and $R^2$ are as hereinbefore defined, $R^{19}$ is a hydrogen atom, with 2-(trimethylsilyl)ethoxymethyl chloride in the presence of sodium hydride, in an inert solvent such as dimethylformamide, and at a temperature at about room temperature.

Compounds of formula (1) wherein $R^1$ and $R^2$ are as hereinbefore defined, $R^{19}$ represents a group —L$^1$—R$^7$ (where $L^1$ and $R^7$ are as hereinbefore defined) or —L$^2$—R$^8$ (where $L^2$ is as hereinbefore defined and $R^8$ is aryl, cycloalkenyl, cycloalkyl, heteroaryl, heterocycloalkyl) may be similarly prepared by reaction of compounds of formula (1), wherein $R^1$ and $R^2$ are as hereinbefore defined, $R^{19}$ is a hydrogen atom, with an alkyl halide of formula (V) or (VI) respectively, in the presence of sodium hydride.

Compounds of formula (1), wherein $R^1$ and $R^2$ are as hereinbefore defined, $R^{19}$ is a hydrogen atom, may be prepared by the application or adaptation of known literature methods, for example Boehm et. al., J.Med.Chem., 1996, 39, page 3829.

Intermediates of formulae (II), (III), (IV), Resin C and Resin D are novel compounds and, as such, they and their processes described herein for their preparation constitute further features of the present invention.

The present invention is further Exemplified but not limited by the following illustrative Examples and Reference Examples.

EXAMPLE 1
Compounds A, B and C

A solution of 4-[5(4)-(4-fluoro-phenyl)-2-formyl-1-[(2-(trimethylsilyl)ethoxy)methyl]-1H-imidazol-4(5)-yl]-pyridine (1.1 g, Reference Example 1), 1,1,1-tris (hydroxymethyl)-ethane (1.66 g) and pyridinium-4-toluenesulphonate (0.13 g) in dry toluene (20 ml) was gently refluxed for 20 hours with azeotropic removal of water. After cooling to room temperature the reaction mixture was treated with ethyl acetate (100 ml), then washed three times with water (20 ml), then dried over magnesium sulphate and then evaporated. The residual oil was subjected to flash chromatography, on silica, eluting with a mixture of dichloromethane and methanol (24:1, v/v) to give {2-[5-(4-fluoro-phenyl)-4-pyridin-4-yl-1H-imidazol-2-yl]-5-methyl-[1,3]dioxan-5-yl}-methanol, cis-isomer, (Compound A) as a white solid, m.p. 270–272° C. [Elemental analysis:- C,64.22; H,5.71;N,10.81; F,4.91%. Calculated for $C_{20}H_{20}FN_3O_3.H_2O$:-C,64.67; H,5.97; N,11.31; F,5.11%]; and {2-[5-(4-fluoro-phenyl)-4-pyridin-4-yl-1H-imidazol-2-yl]-5-methyl-[1,3]dioxan-5-yl}-methanol, trans-isomer, (Compound B) as a buff-coloured solid, m.p. 250–255° C. [Elemental analysis:- C,64.22; H,5.71; N,10.81; F,4.91 %. Calculated:- C,65.03; H,5.46; N,11.38; F,5.14%].

By proceeding in a similar manner but using 2,2-dimethyl-1,3-propanediol there was prepared 4-[2-(5,5-dimethyl-[1,3]dioxan-2-yl)-5-(4-fluoro-phenyl)-1H-imidazol-4-yl]-pyridine, (Compound C) as a cream solid, m.p. 248–249° C. (with decomposition). [Elemental analysis:- C,66.75; H,5.74; N,11.42%. Calculated for $C_{20}H_{20}FN_3O_2.0.5H_2O$:- C,66.28; H,5.84; N, 11.59%].

EXAMPLE 2
Compound D

A solution of 4-[2-(5-azidomethyl-5-methyl-[1,3]dioxan-2-yl)-5-(4-fluoro-phenyl)-1H-imidazol-4-yl]-pyridine, cis- and trans-isomers [1.56 g, Compound H] in methanol (100 ml) was treated with ammonium formate (1 g), then with 10% palladium on activated carbon (0.15 g). After stirring for 3.5 hours the reaction mixture was filtered through diatomaceous earth then evaporated. The residual orange solid was subjected to flash chromatography on silica eluting with a mixture of dichloromethane, pentane, methanol and concentrated ammonia (55:25:18:2 v/v/v/v) to give C-[5-methyl-2-{5-(4-fluoro-phenyl)-4-pyridin-4-yl-1H-imidazol-2-yl}-[1,3]dioxan-5-yl]-methylamine, cis- and trans-isomers, Compound D, (0.68 g) as a yellow solid.

EXAMPLE 3
Compounds E to Z

A stirred solution of 4-[2-dimethoxymethyl-5(4)-(4-fluoro-phenyl)-1H-imidazol-4(5)-yl]-pyridine (5.75 g, Reference Example 3), and 2-methyl-2-trifluoroacetamido-1,3-propanediol (7.38 g, Reference Example 4) and 4-toluenesulphonic acid (8.03 g) in dry tetrahydrofuran (200 ml) was heated at reflux for 6 hours. After cooling the mixture was stood at room temperature for 4 days then partitioned between ethyl acetate and saturated sodium bicarbonate solution. The organic phase was washed twice with water (100 ml), then with brine (100 ml), then dried over magnesium sulphate and then evaporated to give 2,2,2-trifluoro-N-[5-methyl-2-{5-(4-fluoro-phenyl)-4-pyridin-4-yl-1H-imidazol-2-yl}-[1,3]dioxan-5-yl]-acetamide, cis- and trans-isomers (Compound E). The residue was subjected to flash chromatography on silica eluting with a mixture of dichloromethane and methanol (95:5, v/v) to give: 2,2,2-trifluoro-N-[5-methyl-2-{5-(4-fluoro-phenyl)-4-pyridin-4-yl-1H-imidazol-2-yl}-[1,3]dioxan-5-yl]-acetamide, cis-isomer (Compound F); $MH^+$ 451; and 2,2,2-trifluoro-N-[5-methyl-2-{5-(4-fluoro-phenyl)-4-pyridin-4-yl-1H-imidazol-2yl}-[1,3]dioxan-5-yl]-acetamide, trans-isomer (Compound G). $MH^+$ 451.

By proceeding in a similar manner but using 2-azidomethyl-2-methyl-1,3-propanediol (Reference Example 5) there was prepared 4-[2-(5-azidomethyl-5-methyl-[1,3]dioxan-2-yl)-5-(4-fluoro-phenyl)-1H-imidazol-4-yl]-pyridine, cis- and trans-isomers (Compound H) as a white solid.

By proceeding in a similar manner but using 2-benzyl-1,3-propanediol and subjecting the crude product to preparative thick layer chromatography on silica eluting with a mixture of dichloromethane and methanol (9:1, v/v) there was prepared 4-[2-(5-benzyl-[1,3]dioxan-2-yl)-5-(4-fluoro-phenyl)-1H-imidazol-4-yl]-pyridine, cis- and trans-isomers (Compound I). $R_F$ 0.46 using a mixture of dichloromethane and methanol (9:1, v/v). $MH^+$ 416.

By proceeding in a similar manner but using methyl 2,2-bis(hydroxymethyl)propionate and subjecting the crude product to preparative thick layer chromatography on silica eluting with a mixture of dichloromethane and methanol (9:1, v/v) there was prepared 2-[5-(4-fluoro-phenyl)-4-pyridin-4-yl-1H-imidazol-2-yl]-5-methyl-[1,3]dioxane-5-carboxylic acid methyl ester, cis- and trans-isomers (Compound J). $R_F$ 0.71 using a mixture of dichloromethane and methanol (9:1, v/v). $MH^+$ 398.

By proceeding in a similar manner but using 2,2-bis(hydroxymethyl)-tetrahydropyran, carrying out the reaction in dimethylformamide at 50° C. and subjecting the crude product to preparative thick layer chromatography on silica eluting twice with a mixture of dichloromethane and methanol (19:1, v/v) there was prepared 4-[5-(4-fluoro-phenyl)-2-(1,8,10-trioxa-spiro[5.5]undec-9-yl)-1H-imidazol-4-yl]-pyridine, (Compound K), as a mixture of isomers. $R_F$ 0.45 and 0.48 using a mixture of dichloromethane and methanol (19:1, v/v) as eluent. $MH^+$ 396.

By proceeding in a similar manner but using 2,2-bis(hydroxymethyl)-tetrahydrofuran, carrying out the reaction in dimethylformamide at 50° C. and subjecting the crude product to preparative thick layer chromatography on silica eluting twice with a mixture of dichloromethane and methanol (19:1, v/v) there was prepared 4-[5-(4-fluoro-phenyl)-2-(1,7,9-trioxa-spiro[4.5]dec-8-yl)-1H-imidazol-4-yl]-pyridine, (Compound L), as a mixture of isomers. $R_F$ 0.39 and 0.45 using a mixture of dichloromethane and methanol (19:1, v/v)aseluent. $MH^+$ 382.

By proceeding in a similar manner but using the appropriately substituted 1,3-propanediols, carrying out the reaction in dichloromethane at room temperature over 3 days, and subjecting the crude product to preparative thick layer chromatography on silica, there were prepared the Compounds M to Z depicted in Table 1. For Compounds M to V and Compound Z the eluent used was a mixture of dichloromethane and methanol (9:1, v/v); for Compound W the eluent used was ethyl acetate then a mixture of dichloromethane and methanol (14:1, v/v); and for Compounds X and Y the eluent used was a mixture of dichloromethane and methanol (14:1, v/v).

TABLE 1

| STRUCTURE and Compound number | substituted 1,3-propanediol used in the reaction | $R_F$ | MOLECULAR FORMULA | MH+ (intensity) (MS-ESI) |
|---|---|---|---|---|
| Compound M | HO—/—OH (2-methyl-1,3-propanediol) | 0.41 | C19H18FN3O2 | 340 (100%) |
| Compound N | HO—/=/—OH (2-methylene-1,3-propanediol) | 0.40 | C19H16FN3O2 | 338 (100%) |
| Compound O | HO—CH2CH2CH2—OH (1,3-propanediol) | 0.37 | C18H16FN3O2 | 326 (100%) |
| Compound P | 1,3-butanediol | 0.40 | C19H18FN3O2 | 340 (100%) |
| Compound Q | 2,4-pentanediol | 0.44 | C20H20FN3O2 | 354 (50%) 169 (100%) |

TABLE 1-continued
| STRUCTURE and Compound number | substituted 1,3-propanediol used in the reaction | $R_F$ | MOLECULAR FORMULA | MH+ (intensity) (MS-ESI) |
|---|---|---|---|---|
| 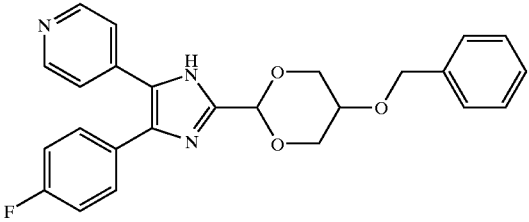<br>Compound R | 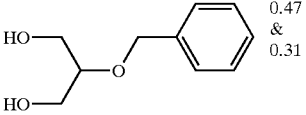 | 0.47 & 0.31 | C25H22FN3O3 | 432 (100%) |
| 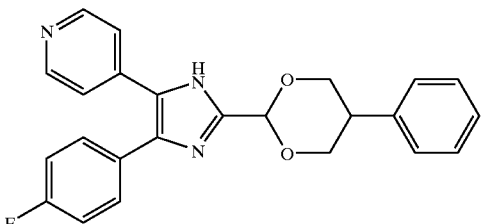<br>Compound S | 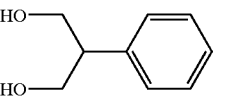 | 0.20 & 0.18 | C24H20FN3O2 | 402 (100%) |
| 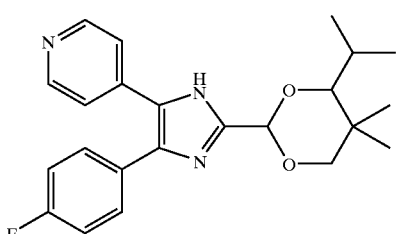<br>Compound T | 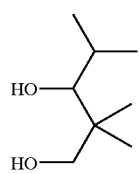 | 0.43 | C23H26FN3O2 | 396 (100%) |
| 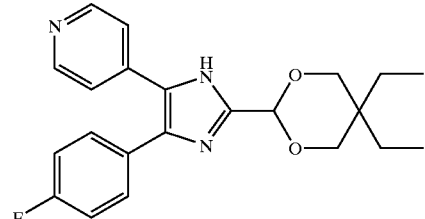<br>Compound U | 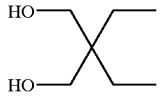 | 0.30 | C22H24FN3O2 | 382 (100%) |
| 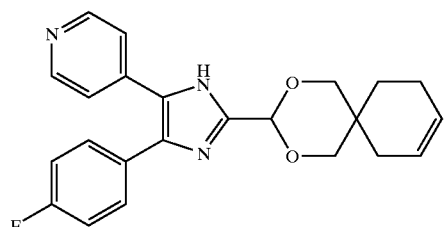<br>Compound V | 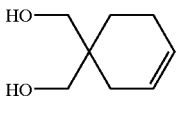 | 0.30 | C23H22FN3O2 | 392 (100%) |

TABLE 1-continued

| STRUCTURE and Compound number | substituted 1,3-propanediol used in the reaction | $R_F$ | MOLECULAR FORMULA | MH+ (intensity) (MS-ESI) |
|---|---|---|---|---|
| Compound W | | 0.14 | C26H23FN4O3 | 459 (100%) |
| Compound X | | 0.20 | C26H23F2N5O2S | 508 (100%) |
| Compound Y | | 0.25 & 0.18 | C28H28FN5O2S | 518 (100%) |
| Compound Z | | 0.31 | C23H21FN4O2 | 405 (100%) |

EXAMPLE 4

Compounds AA and AB

A solution of 2,2,2-trifluoro-N-[5-methyl-2-{5-(4-fluoro-phenyl)-4-pyridin-4-yl-1H-imidazol-2yl}-[1,3]dioxan-5-ylmethyl]-acetamide, trans-isomer [1.04 g, Compound AC] and potassium carbonate (1.55 g) in methanol (150 ml) was heated at reflux for 24 hours. After cooling to room temperature the mixture was partitioned between ethyl acetate and water. The aqueous layer was treated with sodium chloride then extracted three times with ethyl acetate (50 ml). The combined organic phases were evaporated. The residual oil was subjected to flash chromatography on silica eluting with a mixture of dichloromethane, pentane, methanol and concentrated ammonia (55:25:18:2, v/v/v/v) to give C-[5-methyl-2-(5-(4-fluoro-phenyl)-4-pyridin-4-yl-1H-imidazol-2-yl)-[1,3]dioxan-5-yl-methylamine, trans-isomer (0.51 g, Compound AA). MH+ 369.

By proceeding in a similar manner but using 2,2,2-trifluoro-N-[5-methyl-2-{5-(4-fluoro-phenyl)-4-pyridin-4-yl-1H-imidazol-2-yl}-[1,3]dioxan-5-ylmethyl]-acetamide, trans-isomer, [Compound AD] there was prepared C-[5-methyl-2-{5-(4-fluoro-phenyl)-4-pyridin-4-yl-1H-imidazol- 2-yl}-[1,3]dioxan-5-yl]-methylamine, cis-isomer (Compound AB). MH+ 369.

EXAMPLE 5
Compounds AC and AD

A suspension of C-[5-methyl-2-{5-(4-fluoro-phenyl)-4-pyridin-4-yl-1H-imidazol-2-yl}-[1,3]dioxan-5-yl]-methylamine (0.68 g, cis- and trans-isomers, Compound D) in dichloromethane (35 ml) was treated with triethylamine (0.72 ml) then with trifluoroacetic anhydride (0.72 ml). After stirring at room temperature for 4.5 hours the reaction mixture was partitioned between ethyl acetate and water. The organic phase was washed with water, then with brine, then dried over magnesium sulphate and then evaporated. The residue was subjected to flash chromatography on silica eluting with a mixture of ethyl acetate and methanol (9:1, v/v) to give 2,2,2-trifluoro-N-[5-methyl-2-{5-(4-fluoro-phenyl)-4-pyridin-4-yl-1H-imidazol-2-yl}-[1,3]dioxan-5-ylmethyl]-acetamide, cis- and trans-isomers. The mixture was subjected to preparative HPLC, using methanol and water 40/60 to 5/95 v/v over 20 minutes to give 2,2,2-trifluoro-N-[5-methyl-2-{5-(4-fluoro-phenyl)-4-pyridin-4-yl-1H-imidazol-2-yl}-[1,3]dioxan-5-ylmethyl]-acetamide, trans-isomer (0.75 g, Compound AC, $R_T$=11.99,) and 2,2,2-trifluoro-N-[5-methyl-2-{5-(4-fluoro-phenyl)-4-pyridin-4-yl-1H-imidazol-2-yl}-[1,3]dioxan-5-ylmethyl]-acetamide, cis-isomer -acetamide, cis-isomer (0.3 g, Compound AD, $R_T$=10.8).

EXAMPLE 6
Compounds AE, AF and AG

A stirred solution of 2,2,2-trifluoro-N-[5-methyl-2-{5-(4-fluoro-phenyl)-4-pyridin-4-yl-1H-imidazol-2-yl}-[1,3]dioxan-5-yl]-acetamide, cis-isomer (1.75 g, Compound F) and potassium carbonate (1.07 g) in a mixture of methanol (200 ml) and water (5 ml) was heated at reflux for 8 hours. After cooling to room temperature the mixture evaporated and then azeotroped with toluene. The residue was treated with silica and filtered through a pad of silica washing with a mixture of dichloromethane and methanol (4:1 ,v/v) to give 5-methyl-2-{5-(4-fluoro-phenyl)-4-pyridin-4-yl-1H-imidazol-2-yl}-[1,3]dioxan-5-ylamine, cis-isomer (1.3 g, Compound AE) as a yellow solid.

By proceeding in a similar manner but using Compound G there was prepared 5-methyl-2-{5-(4-fluoro-phenyl)-4-pyridin-4-yl-1H-imidazol-2-yl}-[1,3]dioxan-5-ylamine, trans-isomer (Compound AF).

By proceeding in a similar manner but using Compound E there was prepared 5-methyl-2-{5-(4-fluoro-phenyl)-4-pyridin-4-yl-1H-imidazol-2-yl}-[1,3]dioxan-5-ylamine, cis- and trans-isomers (Compound AG).

EXAMPLE 7
Compounds AH and AI

A solution of 2-[5-(4-fluoro-phenyl)-4-pyridin-4-yl-1H-imidazol-2-yl]-5-methyl-[1,3]dioxane-5-carboxylic acid methyl ester, cis- and trans-isomers (0.34 g, Compound J) in methanol (15 ml) was treated with aqueous sodium hydroxide solution (1.71 ml, 1N) then heated at reflux for 7 hours. After cooling to room temperature the reaction mixture was evaporated. The residual cream powder was dissolved in methanol (10 ml) and the solution acidified to pH 5–6 by addition of glacial acetic acid. The resulting white precipitate was filtered and washed with pentane to give 2-[5-(4-fluoro-phenyl)-4-pyridin-4-yl-1H-imidazol-2-yl]-5-methyl-[1,3]dioxane-5-carboxylic acid, trans-isomer (0.11 g, Compound AH). $R_F$ 0.15 ($CH_2Cl_2/CH_3OH$, 9:1 developed five times), MH+ 384. The filtrate plus washings were absorbed onto silica and subjected to flash chromatography on silica eluting with a mixture of dichloromethane and methanol (9:1, v/v) to give 2-[5-(4-fluoro-phenyl)-4-pyridin-4-yl-1H-imidazol-2-yl]-5-methyl-[1,3]dioxane-5-carboxylic acid, cis-isomer (0.14 g, Compound AI,) as a white solid. $R_F$ 0.25 ($CH_2Cl_2/CH_3OH$, 9:1, developed five times), MH+ 384.

EXAMPLE 8
Compounds AJ to CO and FS to GD

A solution of 2-[5-(4-fluoro-phenyl)-4-pyridin-4-yl-1H-imidazol-2-yl]-5-methyl-[1,3]dioxane-5-carboxylic acid, cis- or trans-isomer (1 equivalent, Compound AH or AI) an appropriately substituted amine of formula $HNY^4Y^5$ [1.1 equivalents, see table 2], 1-(3-dimethylamino-propyl)-3-ethylcarbodiimide [1.1 equivalents], 1-hydroxybenzotriazol hydrate [1.1 equivalents] and N,N-diisopropylethylamine [3 equivalents] in dry dimethylformamide was stirred at room temperature for 18 hours. The reaction mixture was evaporated and the residue was partitioned between ethyl acetate and water. The organic phase was washed with brine then evaporated to give Compounds AJ to GD and FS to GD depicted in Table 2 (Compound FV was obtained following alkaline hydrolysis of the intermediate ester). The $R_F$ values indicated were determined using a mixture of dichloromethane and methanol (9:1, v/v) as eluent [* in one case a mixture of ethyl acetate and methanol (9:1, v/v) was used].

TABLE 2

| STRUCTURE and Compound number | $HNY^4Y^5$ | $R_F$ | MOLECULAR FORMULA | MH+ (Intensity) |
|---|---|---|---|---|
| 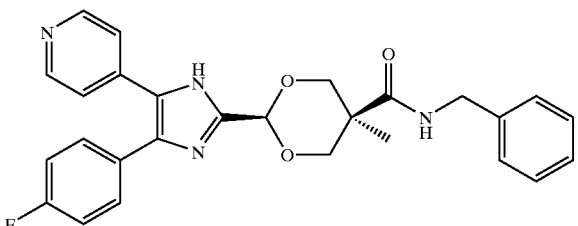 Compound AJ | 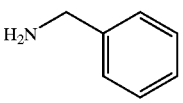 | 0.33 | C27H25FN4O3 | 473 (70%) 418 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 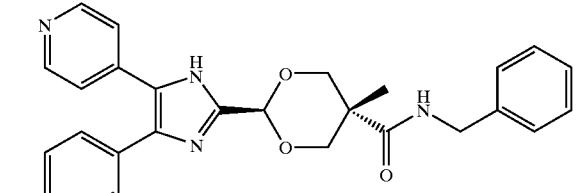 Compound AK | H₂N-CH₂-C₆H₅ | 0.35 | C27H25FN4O3 | 473 (20%) 418 (100%) |
| 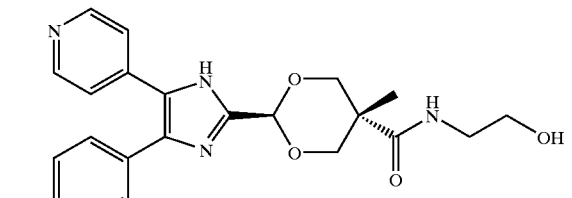 Compound AL | H₂N-CH₂CH₂-OH | 0.13 | C22H23FN4O4 | 427 (100%) |
| 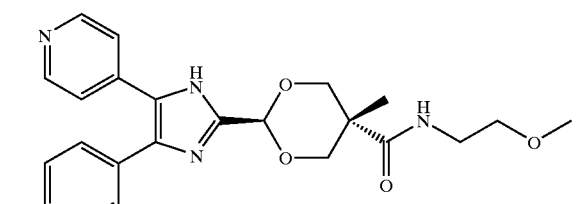 Compound AM | H₂N-CH₂CH₂-O-CH₃ | 0.28 | C23H25FN4O4 | 441 (20%) 384 (100%) |
| 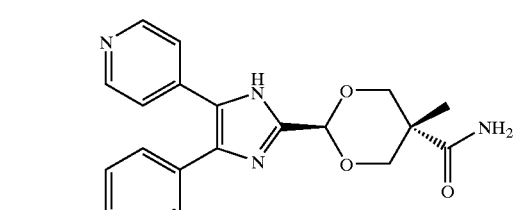 Compound AN | NH₃ | 0.14 | C20H19FN4O3 | 383 (100%) |
| 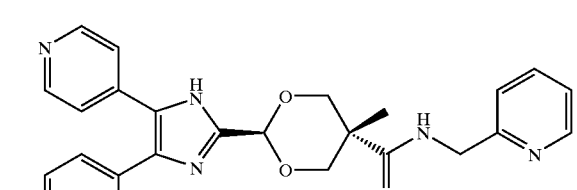 Compound AO | H₂N-CH₂-(2-pyridyl) | 0.29 | C26H24FN5O3 | 474 (100%) |

TABLE 2-continued

| STRUCTURE and Compound number | HNY⁴Y⁵ | $R_F$ | MOLECULAR FORMULA | MH⁺ (Intensity) |
|---|---|---|---|---|
| Compound AP | H₂N-CH₂-(3-pyridyl) | 0.18 | C26H24FN5O3 | 474 (100%) |
| Compound AQ | H₂N-CH₂-(4-pyridyl) | 0.16 | C26H24FN5O3 | 474 (100%) |
| Compound AR | HN(1-methylpiperazine) | 0.09 | C25H28FN5O3 | 466 (100%) |
| Compound AS | H₂N(CH₂)₃N(CH₃)₂ | 0.14 | C25H30FN5O3 | 468 (100%) |
| Compound AT | H₂N-CH₂CH₂-(indol-3-yl) | 0.25 | C30H28FN5O3 | 526 (100%) |

TABLE 2-continued
| STRUCTURE and Compound number | HNY⁴Y⁵ | R_F | MOLECULAR FORMULA | MH+ (Intensity) |
|---|---|---|---|---|
| 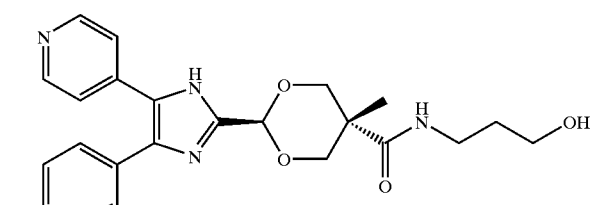 Compound AU | H2N~~~OH | 0.09 | C23H25FN4O4 | 441 (100%) |
| 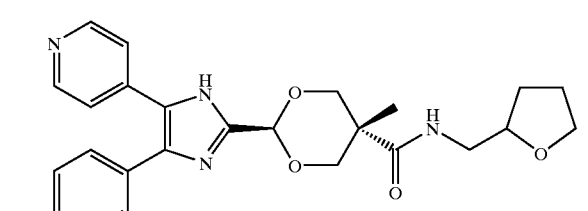 Compound AV | H2N-CH2-(tetrahydrofuran-2-yl) | 0.32 | C25H27FN4O4 | 467 (100%) |
| 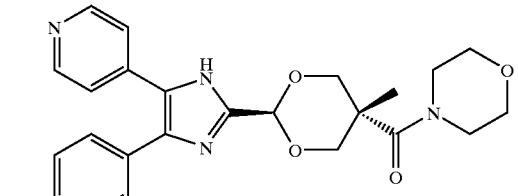 Compound AW | morpholine (HN-O) | 0.32 | C24H25FN4O4 | 453 (100%) |
| 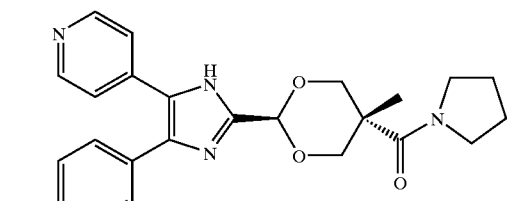 Compound AX | pyrrolidine (HN) | 0.39 | C24H25FN4O3 | 437 (50%) 384 (100%) |
| 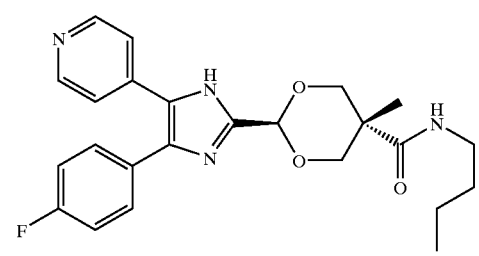 Compound AY | H2N-n-butyl | 0.33 | C24H27FN4O3 | 439 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 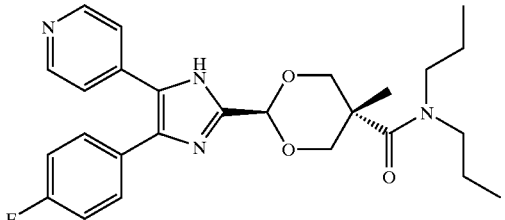 Compound AZ | 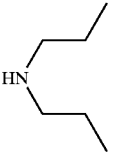 | 0.41 | C26H31FN4O3 | 467 (100%) |
| 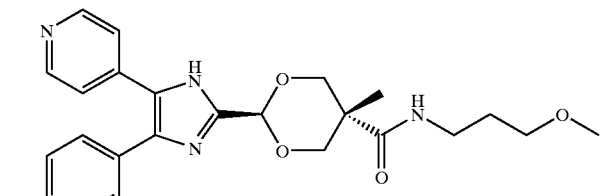 Compound BA | 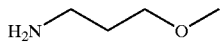 | 0.29 | C24H27FN4O4 | 455 (40%) 384 (100%) |
| 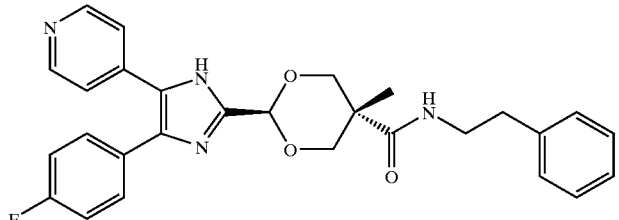 Compound BB | 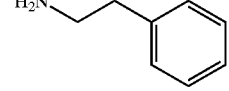 | 0.33 | C28H27FN4O3 | 487 (100%) |
| 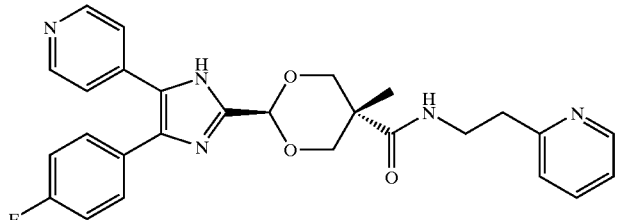 Compound BC | 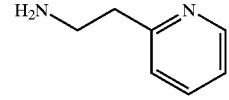 | 0.24 | C27H26FN5O3 | 488 (100%) |
| 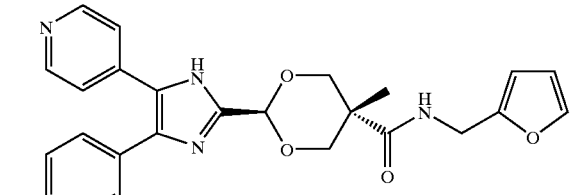 Compound BD | 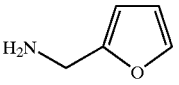 | 0.32 | C25H23FN4O4 | 463 (100%) |

TABLE 2-continued

| STRUCTURE and Compound number | HNY⁴Y⁵ | $R_F$ | MOLECULAR FORMULA | MH⁺ (Intensity) |
|---|---|---|---|---|
| Compound BE | piperidine | 0.36 | C25H27FN4O3 | 451 (30%) 384 (100%) |
| Compound BF | HN(CH₃)₂ (dimethylamine) | 0.28 | C22H23FN4O3 | 411 (11%) 384 (100%) |
| Compound BG | H₂N-propyl | 0.29 | C23H25FN4O3 | 425 (70%) 384 (100%) |
| Compound BH | H₂N-cyclopropyl | 0.22 | C23H23FN4O3 | 423 (25%) 384 (100%) |
| Compound BI | H₂N-cyclopentyl | 0.32 | C25H27FN4O3 | 451 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 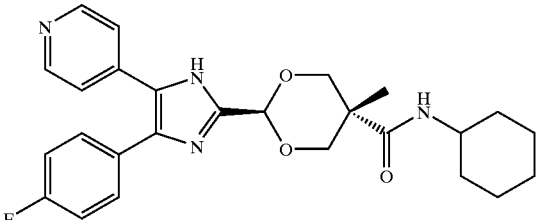 Compound BJ | 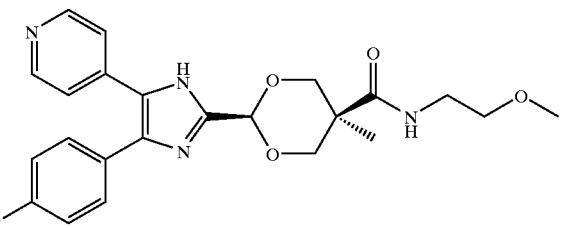 | 0.36 | C26H29FN4O3 | 465 (100%) |
| 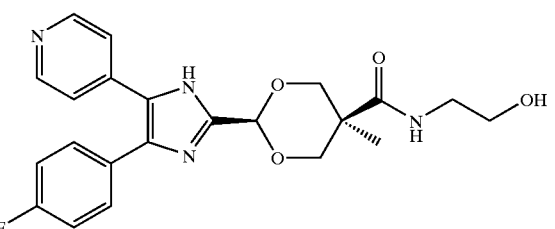 Compound BK | H₂N͡͡͡͡͡͡͡͡OCH₃ | 0.29 | C23H25FN4O4 | 441 (100%) |
| 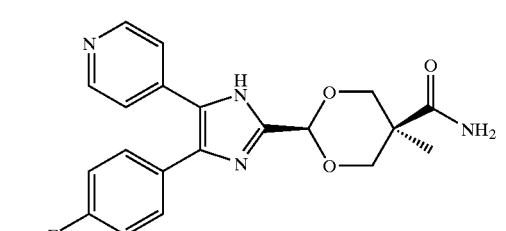 Compound BL | H₂N͡͡͡͡͡͡͡͡OH | 0.18 | C22H23FN4O4 | 427 (100%) |
| Compound BM | NH₃ | 0.16 | C20H19FN4O3 | 383 (100%) |
| 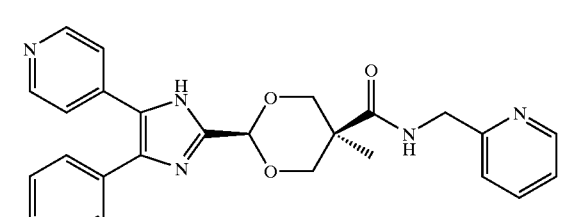 Compound BN | | 0.25 | C26H24FN5O3 | 474 (100%) |

TABLE 2-continued

| STRUCTURE and Compound number | HNY⁴Y⁵ | $R_F$ | MOLECULAR FORMULA | MH⁺ (Intensity) |
|---|---|---|---|---|
| Compound BO | H₂N-CH₂-(3-pyridyl) | 0.13 | C26H24FN5O3 | 474 (100%) |
| Compound BP | H₂N-CH₂-(4-pyridyl) | 0.10 | C26H24FN5O3 | 474 (100%) |
| Compound BQ | morpholine (HN-morpholine) | 0.36 | C24H25FN4O4 | 453 (100%) |
| Compound BR | N-methylpiperazine | 0.08 | C25H28FN5O3 | 466 (100%) |
| Compound BS | H₂N(CH₂)₃N(CH₃)₂ | 0.13 | C25H30FN5O3 | 468 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 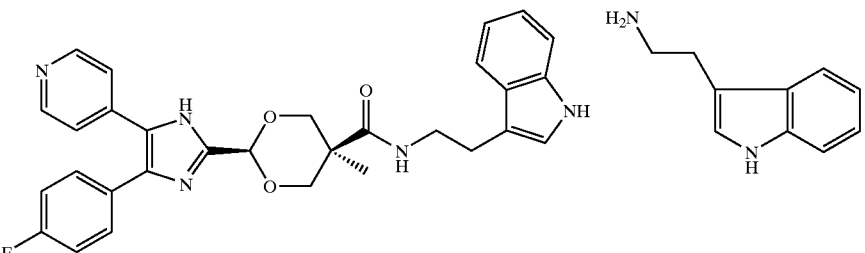 Compound BT | 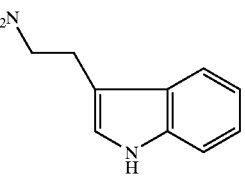 | 0.28 | C30H28FN5O3 | 526 (100%) |
| 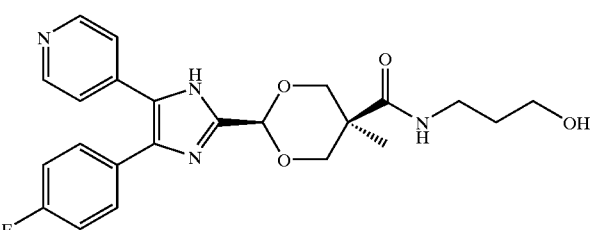 Compound BU | 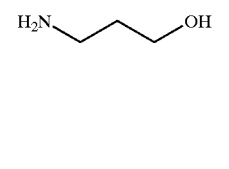 | 0.08 | C23H25FN4O4 | 441 (100%) |
| 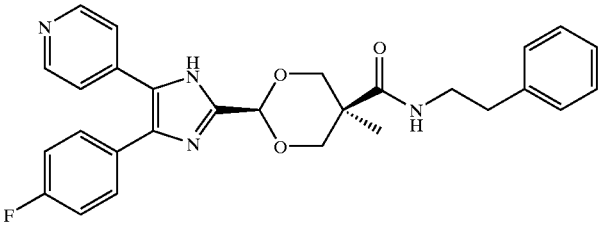 Compound BV | 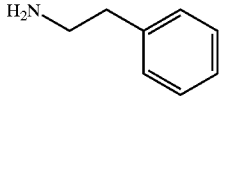 | 0.37 | C28H27FN4O3 | 487 (100%) |
| 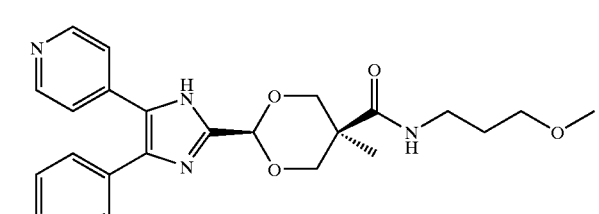 Compound BW | 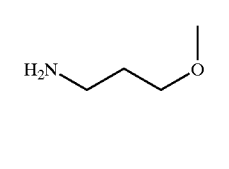 | 0.28 | C24H27FN4O4 | 455 (100%) |
| 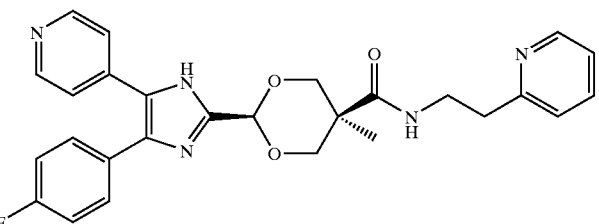 Compound BX | 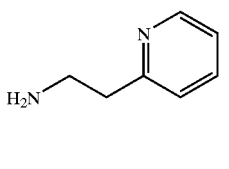 | 0.25 | C27H26FN5O3 | 488 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 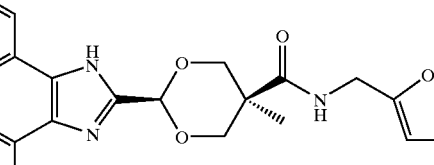 Compound BY | 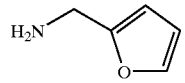 | 0.33 | C25H23FN4O4 | 463 (100%) |
| 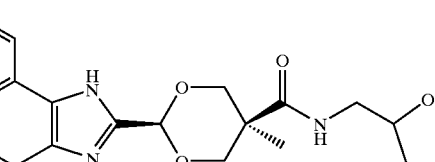 Compound BZ | 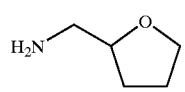 | 0.34 | C25H27FN4O4 | 467 (100%) |
| 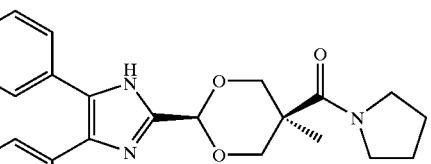 Compound CA | 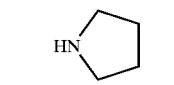 | 0.38 | C24H25FN4O3 | 437 (10%) 384 (100%) |
| 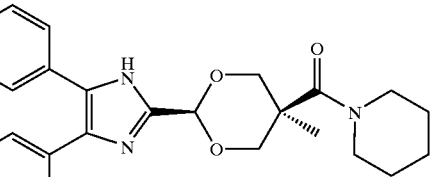 Compound CB |  | 0.40 | C25H27FN4O3 | 451 (60%) 384 (100%) |
| 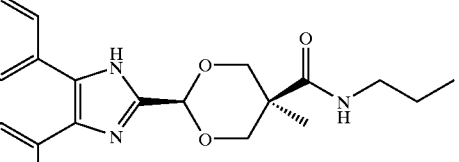 Compound CC | 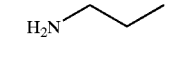 | 0.26 | C23H25FN4O3 | 425 (40%) 384 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 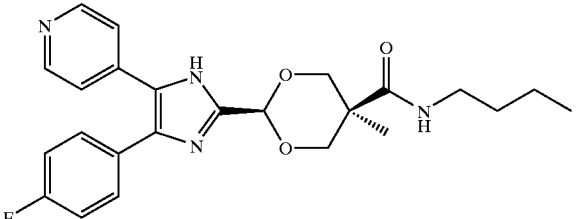 Compound CD |  H₂N-butyl | 0.31 | C24H27FN4O3 | 439 (100%) |
| 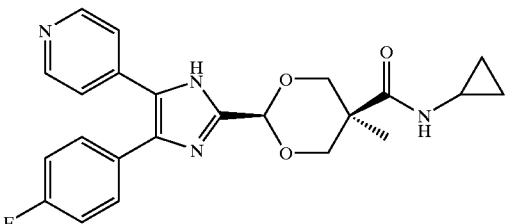 Compound CE | H₂N-cyclopropyl | 0.24 | C23H23FN4O3 | 423 (15%) 384 (100%) |
| 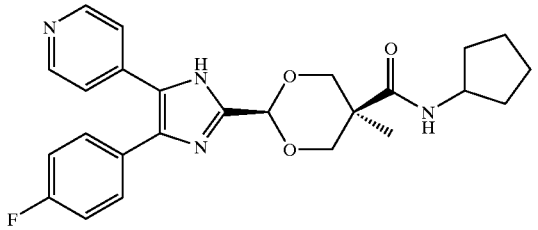 Compound CF | H₂N-cyclopentyl | 0.32 | C25H27FN4O3 | 451 (35%) 384 (100%) |
| 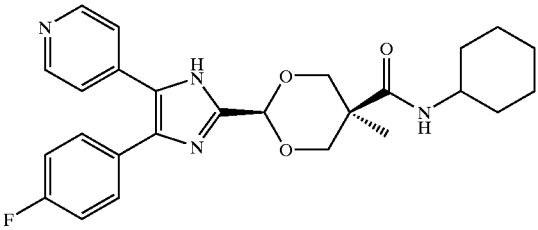 Compound CG | H₂N-cyclohexyl | 0.32 | C26H29FN4O3 | 465 (100%) |
| 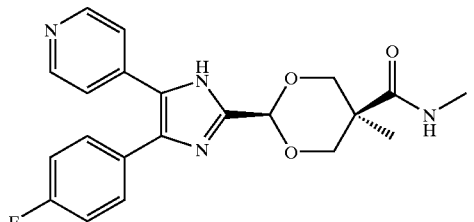 Compound CH | H₂N—CH₃·HCl | 0.22 | C21H21FN4O3 | 397 (50%) 384 (100%) |

TABLE 2-continued

| STRUCTURE and Compound number | HNY⁴Y⁵ | R_F | MOLECULAR FORMULA | MH⁺ (Intensity) |
|---|---|---|---|---|
| Compound CI | H₂N~~~N(CH₃)₂ (N,N-dimethylethylenediamine) | 0.11 | C24H28FN5O3 | 454 (100%) |
| Compound CJ | HN(CH₃)₂·HCl | 0.33 | C22H23FN4O3 | 411 (70%) 384 (100%) |
| Compound CK | HN(propyl)₂ | 0.40 | C26H31FN4O3 | 467 (100%) |
| Compound CL | H₂N-ethyl·HCl | 0.30 | C22H23FN4O3 | 411 (60%) 384 (100%) |
| Compound CM | H₂N—CH₃·HCl | 0.15 | C21H21FN4O3 | 397 (45%) 384 (100%) |

TABLE 2-continued

| STRUCTURE and Compound number | HNY⁴Y⁵ | R_F | MOLECULAR FORMULA | MH⁺ (Intensity) |
|---|---|---|---|---|
| Compound CN | H₂N−CH₂CH₂−N(CH₃)₂ | 0.07 | C24H28FN5O3 | 454 (40%) 418 (100%) |
| Compound CO | H₂N−Et · HCl | 0.23 | C22H23FN4O3 | 411 (34%) 384 (100%) |
| Compound FS | H−N(piperidine)−OH | 0.55 | C27H29FN4O5 | 467 (100%) |
| Compound FT | H−N(1,4-dioxa-8-azaspiro[4.5]decane) | 0.71 | C25H27FN4O4 | 509 (100%) |
| Compound FU | H−N(piperidine)−C(O)OEt | 0.73 | C28H31FN4O5 | 523 (100%) |

TABLE 2-continued
| STRUCTURE and Compound number | HNY⁴Y⁵ | $R_F$ | MOLECULAR FORMULA | MH⁺ (Intensity) |
|---|---|---|---|---|
| 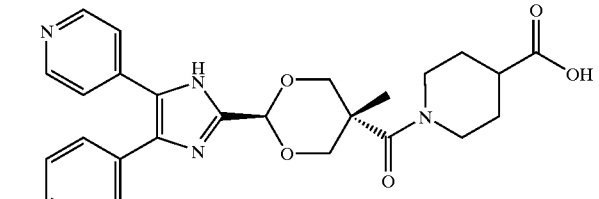 Compound FV | 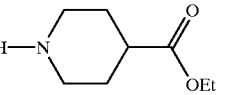 | 0.29 | C26H27FN4O5 | 495 (100%) |
| 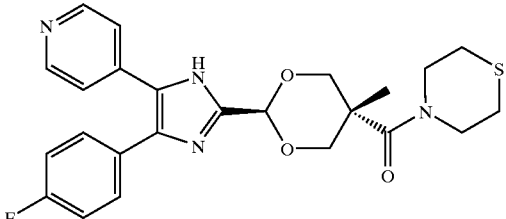 Compound FW | 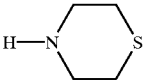 | 0.76 | C24H25FN4O3S | 469 (100%) |
| 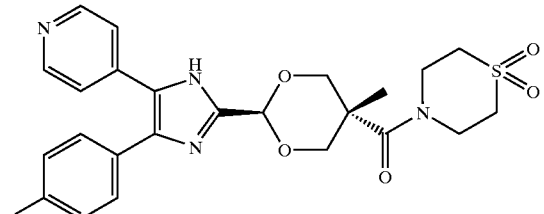 Compound FX | 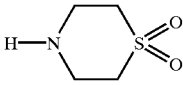 | 0.4 | C24H25FN4O5S | 501 (100%) |
| 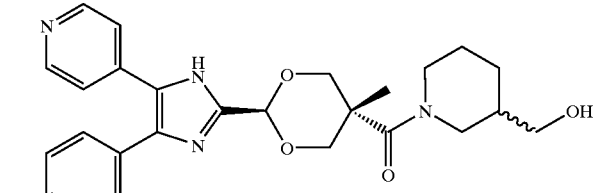 Compound FY |  | 0.62 | C26H29FN4O4 | 481 (100%) |
| 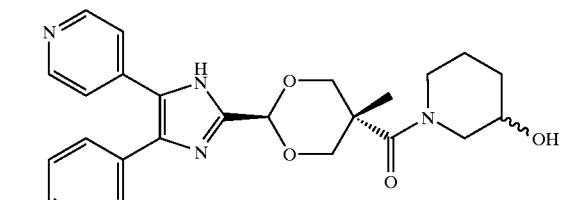 Compound FZ | 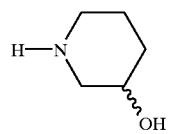 | 0.59 | C25H27FN4O4 | 467 (100%) |

TABLE 2-continued

| STRUCTURE and Compound number | HNY⁴Y⁵ | $R_F$ | MOLECULAR FORMULA | MH⁺ (Intensity) |
|---|---|---|---|---|
| Compound GA | (cis-2,6-dimethylmorpholine) | 0.71 | C26H29FN4O4 | 481 (100%) |
| Compound GB | (3-hydroxypyrrolidine) | 0.53 | C24H25FN4O4 | 453 (100%) |
| Compound GC | (4-methoxypiperidine) | 0.58* | C26H29FN4O4 | 481 (100%) |
| Compound GD | (4-(2-hydroxyethyl)piperidine) | 0.72 | C27H31FN4O4 | 495 (100%) |

EXAMPLE 9

Compounds CP to DF

A solution of 5-methyl-2-{5-(4-fluoro-phenyl)-4-pyridin-4-yl-1H-imidazol-2-yl}-[1,3]dioxan-5-ylamine, cis- or trans-isomer (1 equivalent, Compound AE or AF), and an appropriately substituted isocyanate of formula O=C=N—R¹⁵ or O=C=N—L⁴—R¹⁶ [1 equivalent, see Table 3] in dry tetrahydrofuran was stirred at room temperature for 30 minutes. The reaction mixture was evaporated in vacuo to give Compounds CP to CZ depicted in Table 3. The $R_F$ values indicated were determined using a mixture of dichloromethane and methanol (9:1 ,v/v) as eluent.

By proceeding in a similar manner but using Compound AA or Compound AB, there were prepared Compounds DA to DF depicted in Table 3. The $R_F$ values indicated were determined using a mixture of dichloromethane and methanol (9:1,v/v) as eluent.

TABLE 3
| STRUCTURE and Compound number | O=C=N—R15 or O=C=N—L4—R16 | R_F | MOLECULAR FORMULA | MH+ (Intensity) |
|---|---|---|---|---|
| 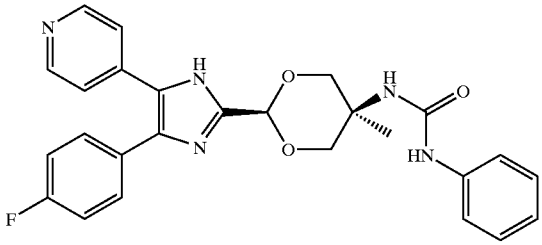 Compound CP | 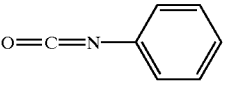 | 0.46 | C26H23FN5O3 | 474 (100%) |
| 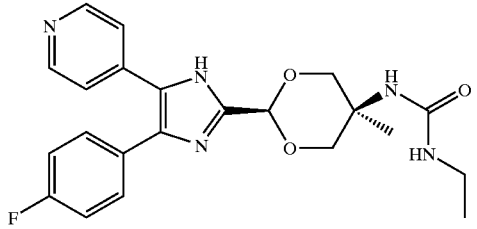 Compound CQ | O=C=N—CH2CH3 | 0.41 | C22H24FN5O3 | 426 (100%) |
| 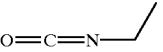 Compound CR | 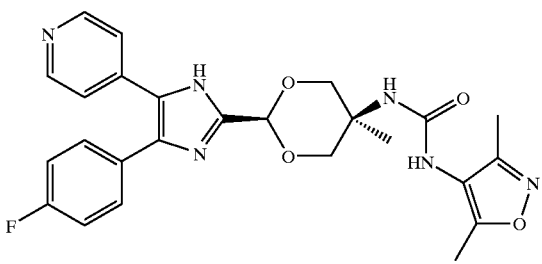 | 0.41 | C25H25FN6O4 | 493 (100%) |
| 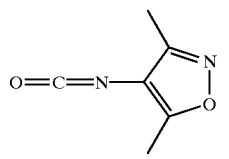 Compound CS | 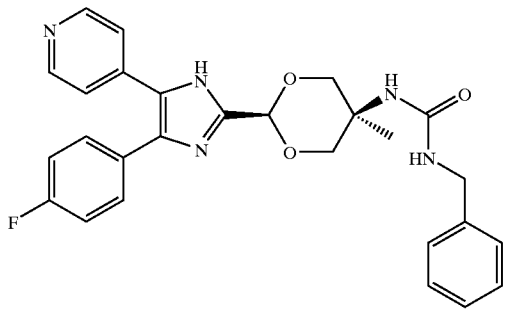 | 0.50 | C27H26FN5O3 | 488 (70%) 423 (100%) |
| 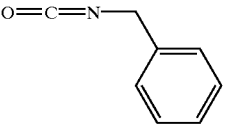 Compound CT | 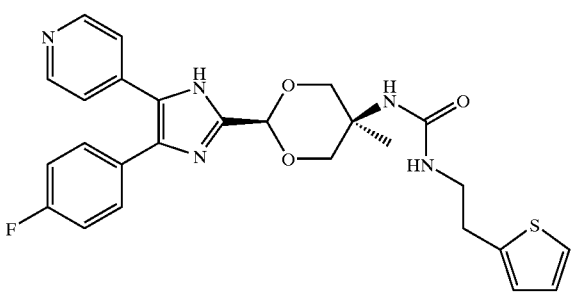 | 0.50 | C26H26FN5O3S | 508 (100%) |

TABLE 3-continued
| STRUCTURE and Compound number | O=C=N—R¹⁵ or O=C=N—L⁴—R¹⁶ | $R_F$ | MOLECULAR FORMULA | MH⁺ (Intensity) |
|---|---|---|---|---|
| 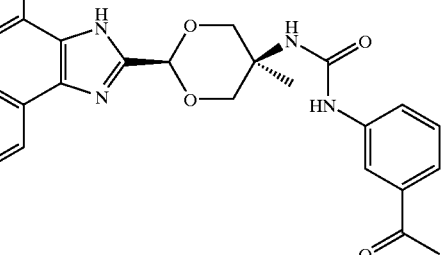 Compound CU | 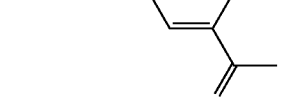 | 0.51 | C28H26FN5O4 | 516 (100%) |
| 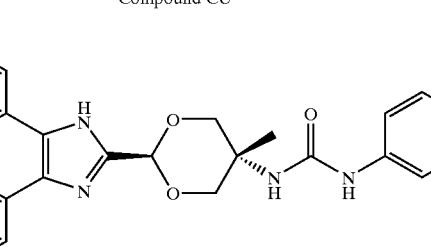 Compound CV | 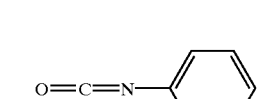 | 0.40 | C26H24FN5O3 | 474 (100%) |
| 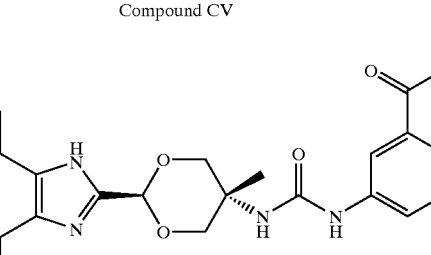 Compound CW | 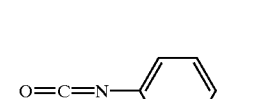 | 0.36 | C27H24FN5O5 | MH⁻ 516 (100%) |
| 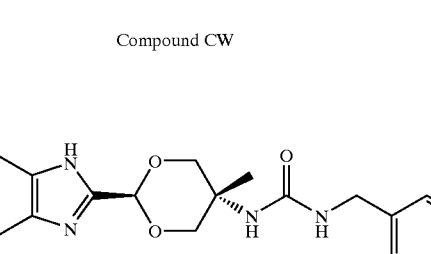 Compound CX |  | 0.39 | C27H26FN5O3 | 488 (100%) |
| 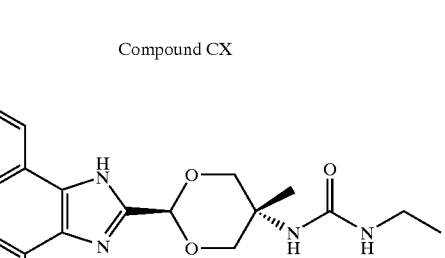 Compound CY |  | 0.24 | C22H24FN5O3 | 426 (100%) |

TABLE 3-continued
| STRUCTURE and Compound number | O=C=N—R¹⁵ or O=C=N—L⁴—R¹⁶ | $R_F$ | MOLECULAR FORMULA | MH⁺ (Intensity) |
|---|---|---|---|---|
| 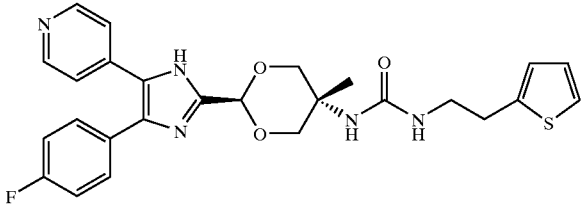 Compound CZ | 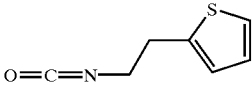 | 0.40 | C26H26FN5O3S | 508 (100%) |
| 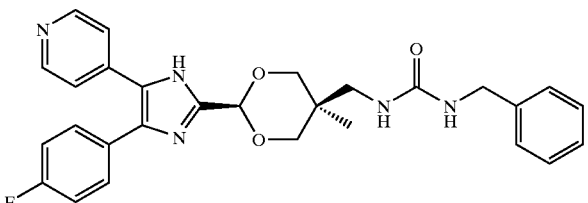 Compound DA | 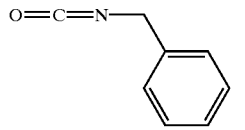 | 0.46 | C28H28FN5O3 | 502 (100%) |
| 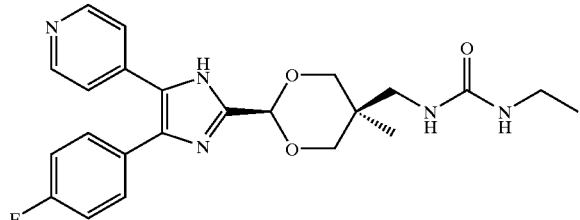 Compound DB | 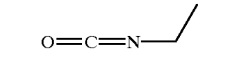 | 0.39 | C23H26FN5O3 | 440 (100%) |
| 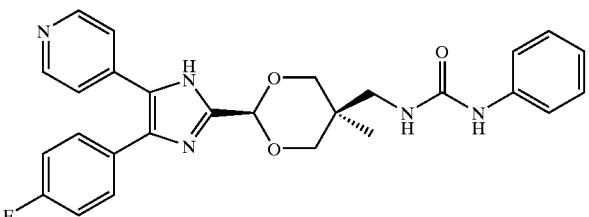 Compound DC | 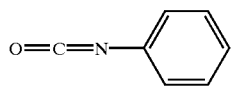 | 0.48 | C27H26FN5O3 | 489 (100%) |
| 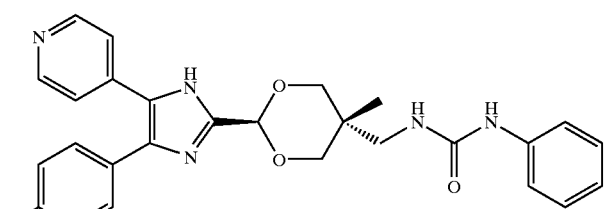 Compound DD | 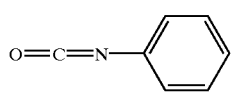 | 0.42 | C27H26FN5O3 | 488 (100%) |

TABLE 3-continued

| STRUCTURE and Compound number | O=C=N—R[15] or O=C=N—L[4]—R[16] | $R_F$ | MOLECULAR FORMULA | MH+ (Intensity) |
|---|---|---|---|---|
| 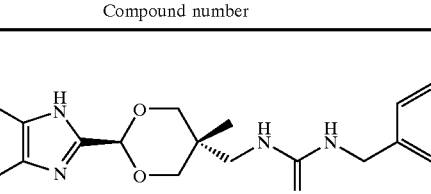 Compound DE |  | 0.40 | C28H28FN5O3 | 502 (100%) |
| 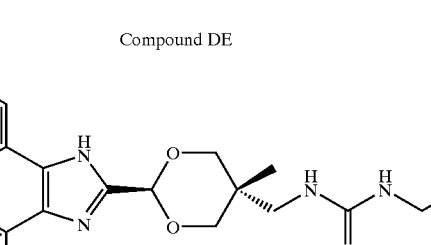 Compound DF |  | 0.23 | C23H26FN5O3 | 440 (100%) |

EXAMPLE 10

Compounds DG to DU

A solution of 5-methyl-2-{5-(4-fluoro-phenyl)-4-pyridin-4-yl-1H-imidazol-2-yl}-[1,3]dioxan-5-ylamine, cis- or trans-isomer (1 equivalent, Compound AE or AF), an appropriately substituted isothiocyanate of formula S=C=N—R[15] or S=C=N—L[4]—R[16] [1 equivalent, see Table 3] [1 equivalent] in dry tetrahydrofuran was heated to reflux for 18 hours. After cooling the reaction mixture was evaporated in vacuo and purified by preparative chromatography on silica gel, eluting with a mixture of dichloromethane and methanol (9:1 v/v) to give Compounds DG to DK depicted in Table 4. The $R_F$ values indicated were determined using a mixture of dichloromethane and methanol (9:1,v/v) as eluent.

By proceeding in a similar manner but using Compound AA or Compound AB, there were prepared Compounds DL to DU depicted in Table 4. The $R_F$ values indicated were determined using a mixture of dichloromethane and methanol (9:1,v/v) as eluent.

TABLE 4
| STRUCTURE and Compound number | S=C=N—R¹⁵ or S=C=N—L⁴—R¹⁶ | $R_F$ | MOLECULAR FORMULA | MH⁺ (Intensity) |
|---|---|---|---|---|
|  Compound DG | 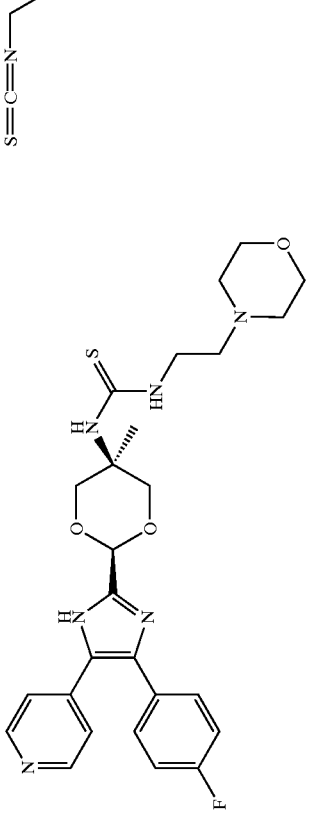 | 0.46 | C26H31FN6O3S | 527 (100%) |
| 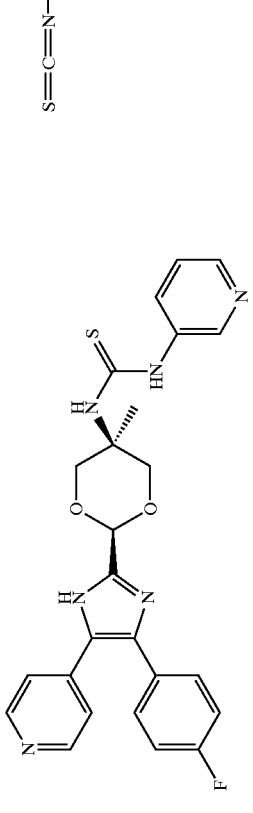 Compound DH |  | 0.46 | C25H24FN5O3S | 494 (100%) |
|  Compound DI | 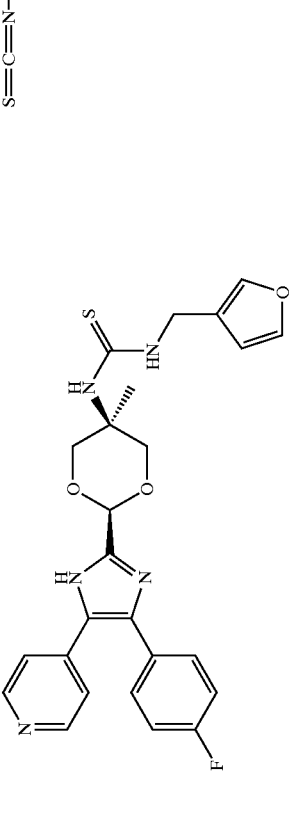 | 0.32 | C25H23FN6O2S | 491 (100%) |

TABLE 4-continued
| STRUCTURE and Compound number | S=C=N—R[15] or S=C=N—L[4]—R[16] | $R_F$ | MOLECULAR FORMULA | MH+ (Intensity) |
|---|---|---|---|---|
| Compound DJ | 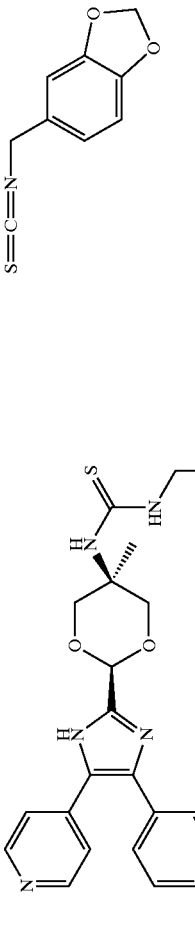 | 0.50 | C28H26FN5O4S | 548 (100%) |
| Compound DK |  | 0.24 | C27H24FN5O4S | 534 (100%) |
| Compound DL |  | 0.23 | C26H25FN6O2S | 505 (100%) |

TABLE 4-continued
| STRUCTURE and Compound number | S=C=N—R[15] or S=C=N—L[4]—R[16] | $R_F$ | MOLECULAR FORMULA | MH+ (Intensity) |
|---|---|---|---|---|
| 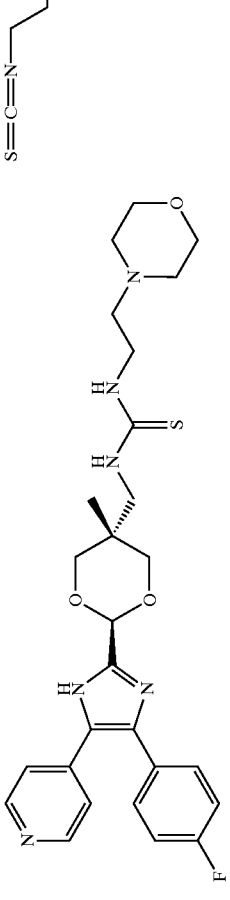 Compound DM | | 0.16 | C27H33FN6O3S | 541 (100%) |
| 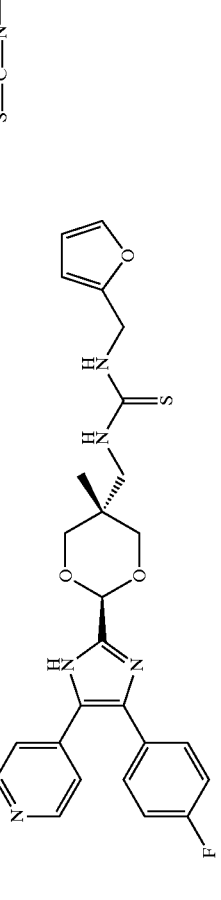 Compound DN | | 0.37 | C26H26FN5O3S | 508 (100%) |
| 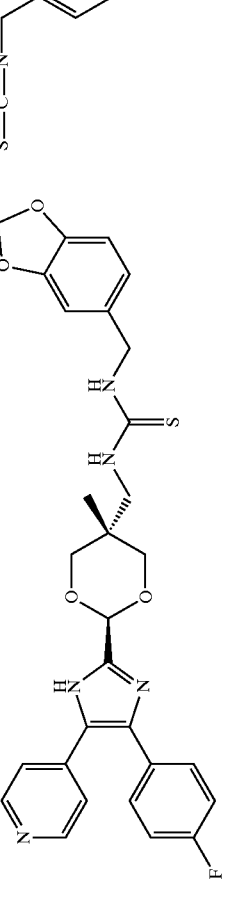 Compound DO | | 0.40 | C29H28FN5O4S | 562 (100%) |

TABLE 4-continued

| STRUCTURE and Compound number | S=C=N—R15 or S=C=N—L4—R16 | RF | MOLECULAR FORMULA | MH+ (Intensity) |
|---|---|---|---|---|
| Compound DP | benzo[1,3]dioxol-5-yl isothiocyanate | 0.48 | C29H28FN5O4S | 562 (100%) |
| Compound DQ | furan-2-ylmethyl isothiocyanate | 0.46 | C26H26FN5O3S | 508 (100%) |
| Compound DR | 4-isothiocyanato-benzoic acid | 0.13 | C28H26FN5O4S | 548 (100%) |

TABLE 4-continued

| STRUCTURE and Compound number | S=C=N—R$^{15}$ or S=C=N—L$^4$—R$^{16}$ | R$_F$ | MOLECULAR FORMULA | MH$^+$ (Intensity) |
|---|---|---|---|---|
| Compounds DS | 3-pyridyl isothiocyanate | 0.28 | C26H25FN6O2S | 505 (100%) |
| Compound DT | morpholinoethyl isothiocyanate | 0.35 | C27H33FN6O3S | 541 (100%) |
| Compound DU | benzo[1,3]dioxol-5-yl isothiocyanate | 0.50 | C28H26FN5O4S | 548 (100%) |

EXAMPLE 11

Compounds DV to EM

A stirred solution of 5-methyl-2-{5-(4-fluoro-phenyl)-4-pyridin-4-yl-1H-imidazol-2-yl}-1,3]dioxan-5-ylamine, cis- or trans-isomer (1 equivalent, Compound AE or AF) and triethylamine [1 equivalent] in dry tetrahydrofuran was treated with an appropriately substituted acid chloride of formula Cl—C(=O)—R$^{15}$ or Cl—C(=O)—L$^4$—R$^{16}$[1 equivalent, see Table 4]. After stirring at room temperature for 18 hours the reaction mixture was evaporated to give Compounds DV to ED depicted in Table 5. The R$_F$ values indicated were determined using a mixture of dichloromethane and methanol (9:1,v/v) as eluent.

By proceeding in a similar manner using Compound AA or AA, there were prepared Compounds EF to EM depicted in Table 4. The R$_F$ values indicated were determined using a mixture of dichloromethane and methanol (9:1,v/v) as eluent.

TABLE 5

| STRUCTURE and Compound number | Cl—C(=O)—R$^{15}$ or Cl—C(=O)—L$^4$—R$^{16}$ | R$_F$ |
|---|---|---|
| 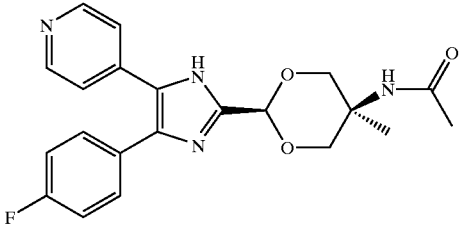 Compound DV |  | 0.41 |
| 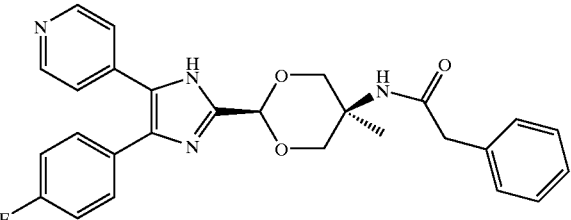 Compound DW | 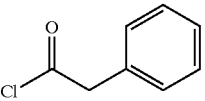 | 0.42 |
| 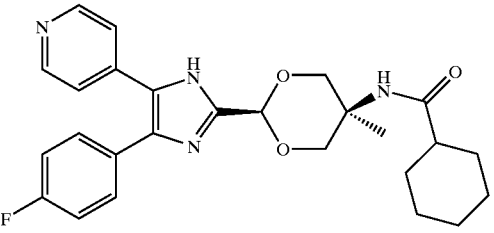 Compound DX | 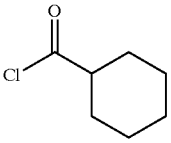 | 0.46 |
| 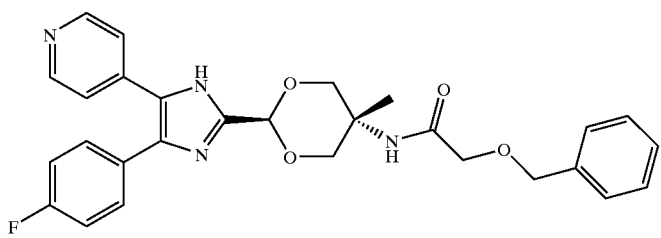 Compound DY | 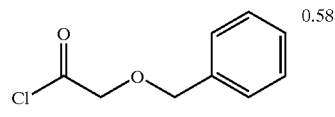 | 0.58 |

TABLE 5-continued
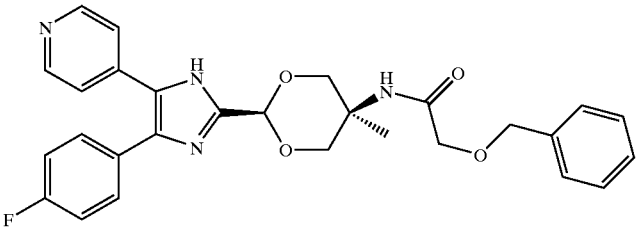
Compound DZ
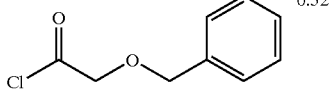
0.52
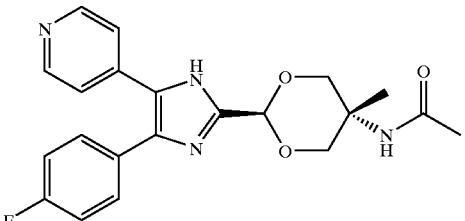
Compound EA
0.34
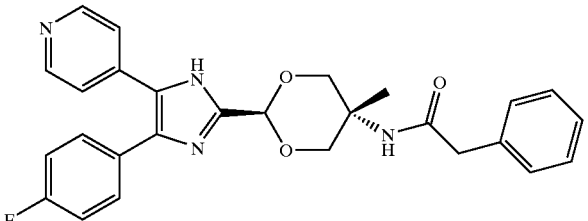
Compound EB
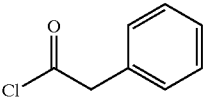
0.49
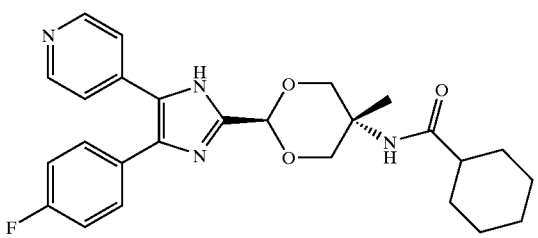
Compound EC
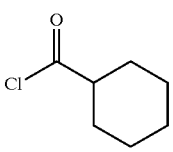
0.51
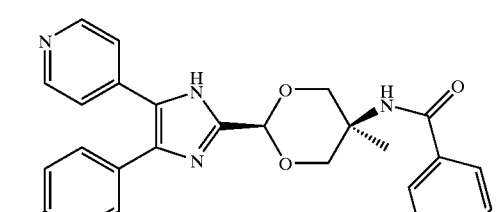
Compound ED
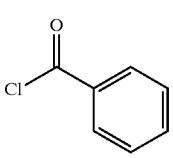
0.52

TABLE 5-continued
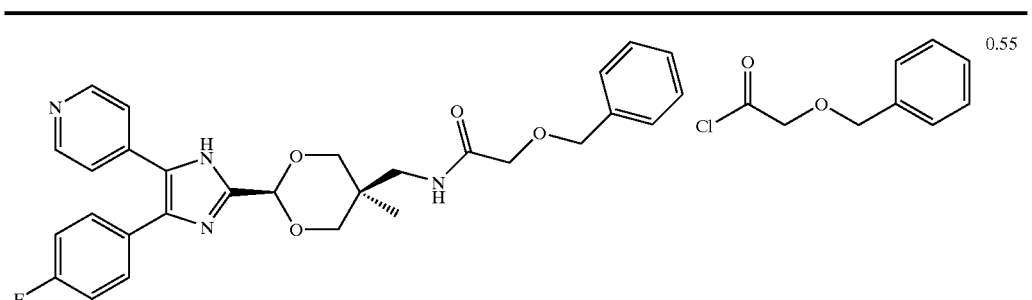
Compound EE    0.55
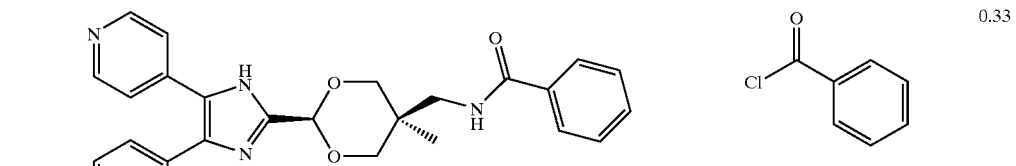
Compound EF    0.33
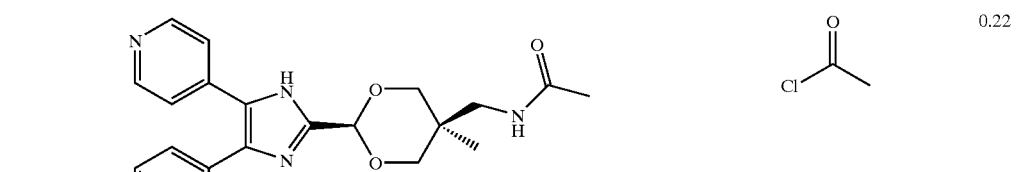
Compound EG    0.22
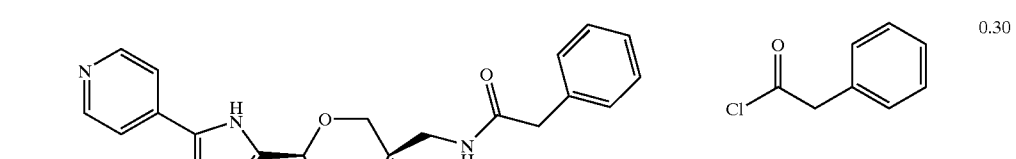
Compound EH    0.30
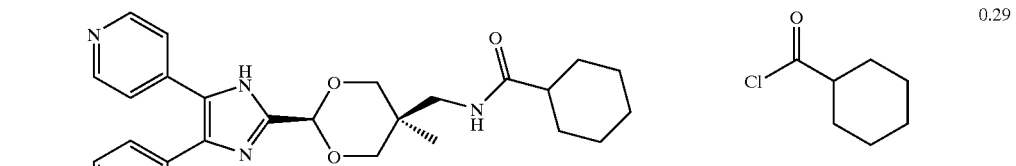
Compound EI    0.29

TABLE 5-continued
| STRUCTURE and Compound number | | |
|---|---|---|
| 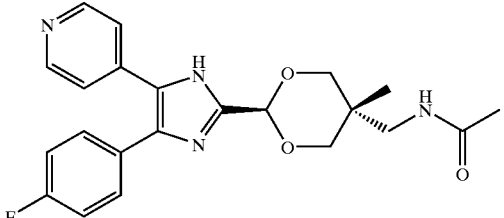<br>Compound EJ | 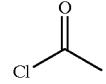 | 0.18 |
| 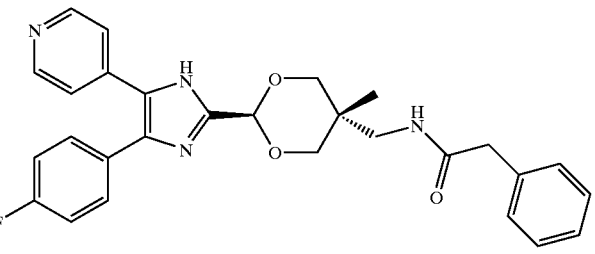<br>Compound EK | 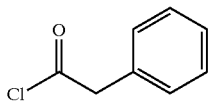 | 0.45 |
| 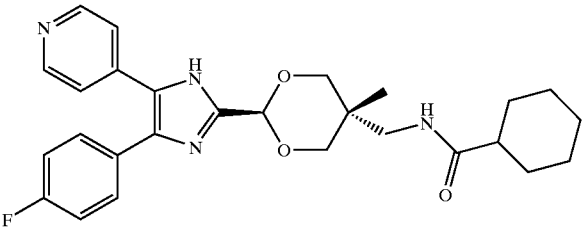<br>Compound EL | 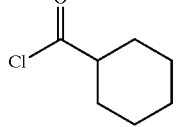 | 0.45 |
| 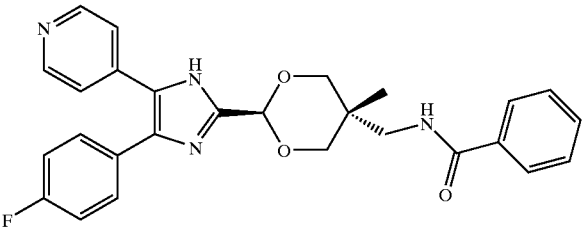<br>Compound EM | 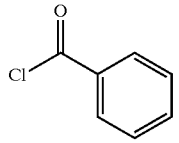 | 0.45 |
| STRUCTURE and Compound number | MOLECULAR FORMULA | MH+ (Intensity) |
|---|---|---|
| 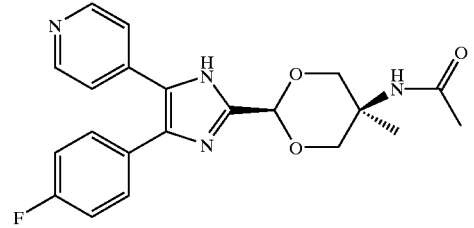<br>Compound DV | C21H21FN4O3 | 397 (100%) |

TABLE 5-continued
| | | |
|---|---|---|
| 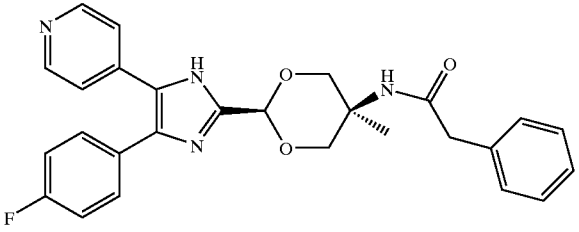       Compound DW | C27H25FN4O3 | 473 (100%) |
| 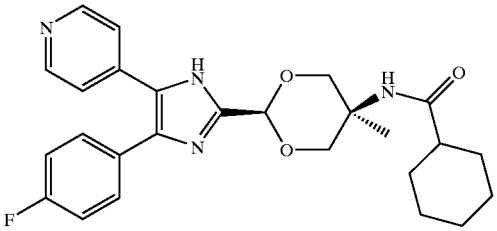       Compound DX | C26H29FN4O3 | 465 (100%) |
| 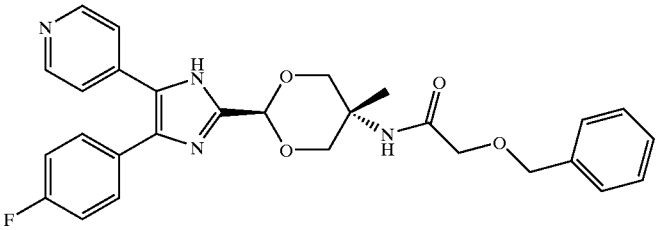       Compound DY | C28H27FN4O4 | MH−501 (100%) |
| 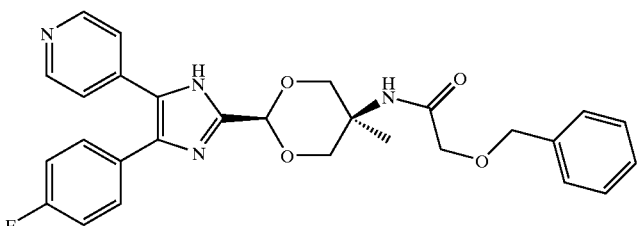       Compound DZ | C28H27FN4O4 | 503 (100%) |
| 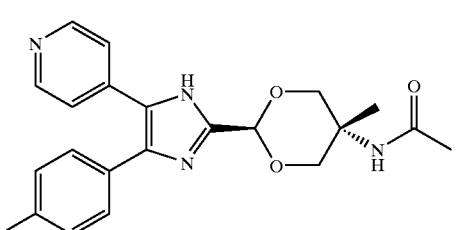       Compound EA | C21H21FN4O3 | 397 (100%) |
| 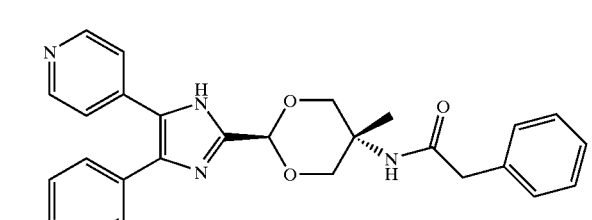       Compound EB | C27H25FN4O3 | 473 (100%) |

TABLE 5-continued
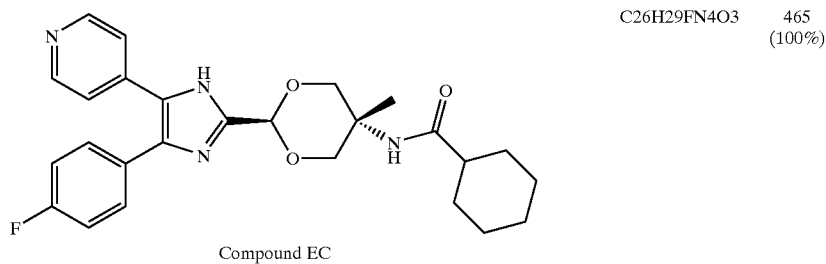
Compound EC
C26H29FN4O3  465 (100%)
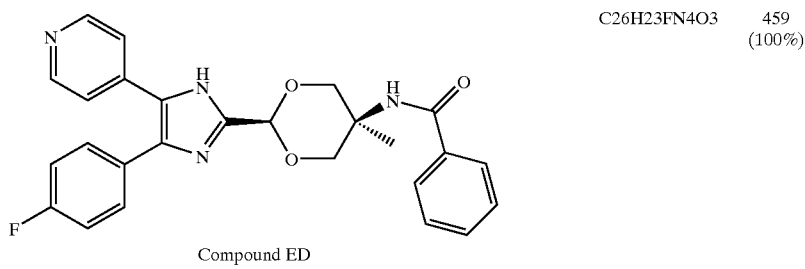
Compound ED
C26H23FN4O3  459 (100%)
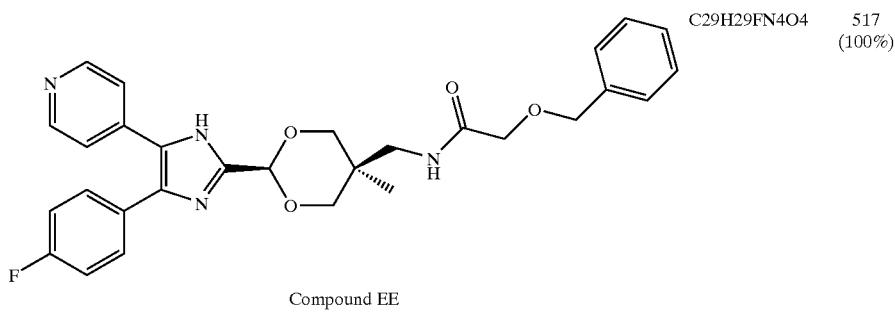
Compound EE
C29H29FN4O4  517 (100%)
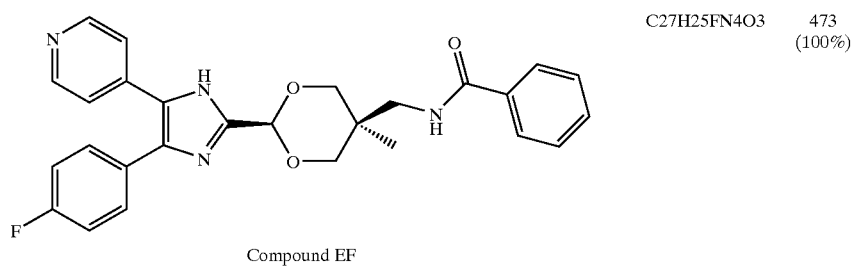
Compound EF
C27H25FN4O3  473 (100%)
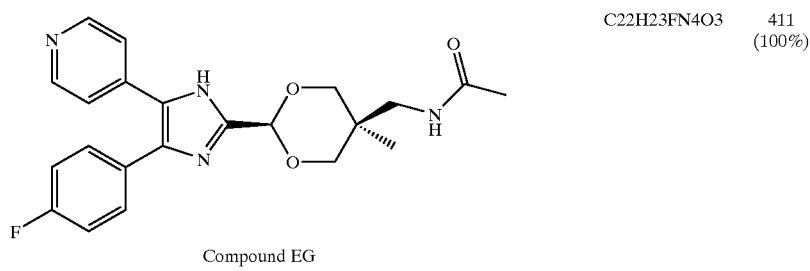
Compound EG
C22H23FN4O3  411 (100%)

TABLE 5-continued
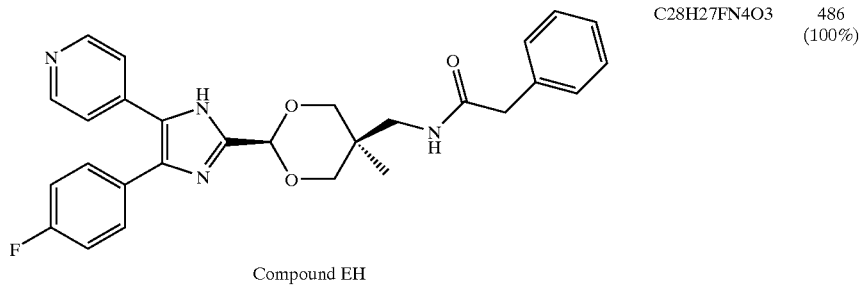
Compound EH
C28H27FN4O3   486
              (100%)
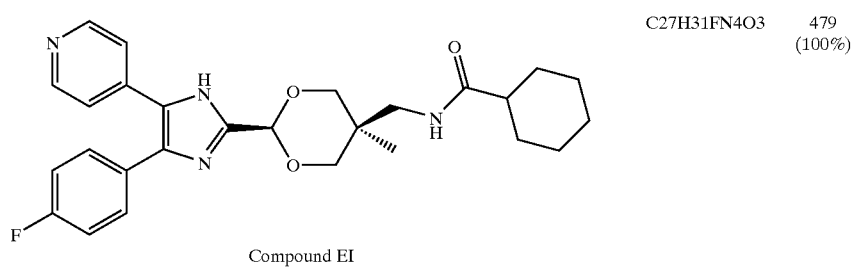
Compound EI
C27H31FN4O3   479
              (100%)
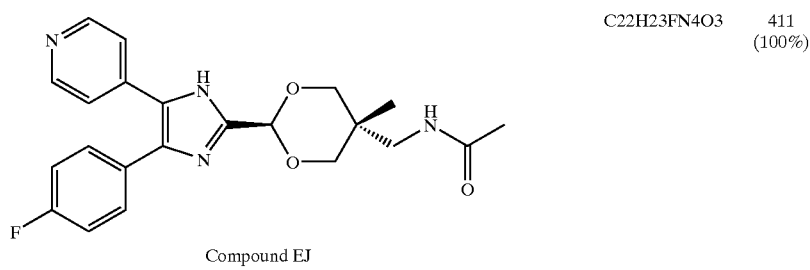
Compound EJ
C22H23FN4O3   411
              (100%)
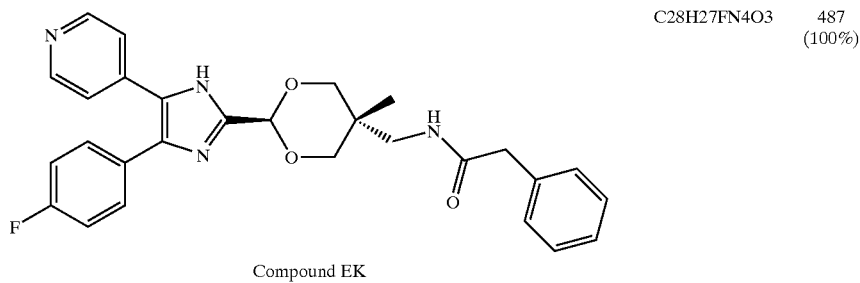
Compound EK
C28H27FN4O3   487
              (100%)
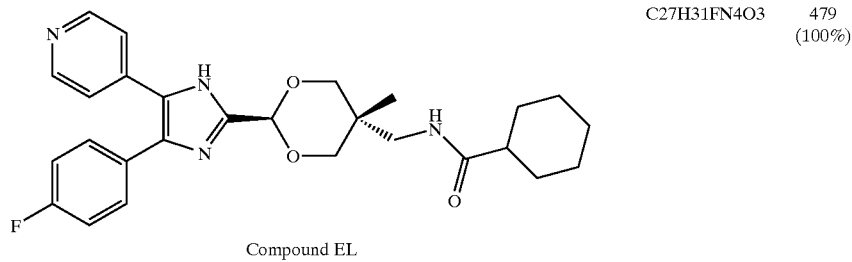
Compound EL
C27H31FN4O3   479
              (100%)

TABLE 5-continued

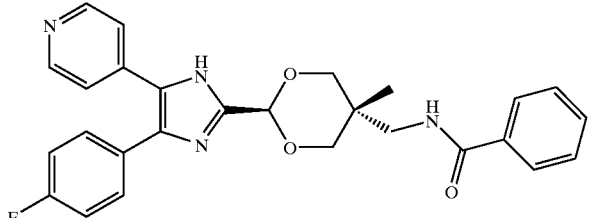

Compound EM

C27H25FN4O3  473 (100%)

EXAMPLE 12
Compounds EN to ER

A solution of 5-methyl-2-{5-(4-fluoro-phenyl)-4-pyridin-4-yl-1H-imidazol-2-yl}-[1,3]dioxan-5-ylamine, cis-isomer (1 equivalent, Compound AE), triethylamine (1.2 equivalents) and glutaric anhydride (1 equivalent) in dry tetrahydrofuran was heated to reflux for 8 hours. The reaction mixture was evaporated to give 4-{2-[5-(4-fluoro-phenyl)-4-pyridin-4-yl-1H-imidazol-2-yl]-5-methyl-[1,3]dioxan-5-ylcarbamoyl}-butyric acid, cis-isomer (Compound EN). MH$^+$ 469. R$_F$ 0.12 {determined using a mixture of dichloromethane and methanol (9:1,v/v) as eluent}.

By proceeding in a similar manner but using Compound AB and glutaric anhydride, there was prepared 4-({2-[5-(4-fluoro-phenyl)-4-pyridin-4-yl-1H-imidazol-2-yl]-5-methyl-[1,3]dioxan-5-ylmethyl}-carbamoyl)-butyric acid, cis-isomer (Compound EO). MH$^+$ 483. R$_F$ 0.10 {determined using a mixture of dichloromethane, pentane, methanol and ammonia (55:25:18:2,v/v) as eluent}.

By proceeding in a similar manner but using Compound AE and succinic anhydride there was prepared 4-{2-[5-(4-fluoro-phenyl)-4-pyridin-4-yl-1H-imidazol-2-yl]-[1,3]dioxan-5-ylcarbamoyl}-propionic acid, cis-isomer (Compound EP). MH$^+$ 455. R$_F$ 0.18 {determined using a mixture of dichloromethane and methanol (9:1,v/v) as eluent}.

By proceeding in a similar manner but using Compound AB and succinic anhydride there was prepared 4-({2-[5-(4-fluoro-phenyl)-4-pyridin-4-yl-1H-imidazol-2-yl]-5-methyl-[1,3]dioxan-5-ylmethyl}-carbamoyl)-propionic acid, cis-isomer (Compound EQ). MH$^+$ 469. R$_F$ 0.10 {determined using a mixture of dichloromethane, pentane, methanol and ammonia (55:25:18:2,v/v) as eluent}.

By proceeding in a similar manner but using Compound AA and succinic anhydride there was prepared 4-({2-[5-(4-fluoro-phenyl)-4-pyridin-4-yl-1H-imidazol-2-yl]-5-methyl-[1,3]dioxan-5-ylmethyl}-carbamoyl)-propionic acid, trans-isomer (Compound ER). MH$^+$ 469. R$_F$ 0.11 {determined using a mixture of dichloromethane, pentane, methanol and ammonia (55:25:18:2,v/v) as eluent}.

EXAMPLE 13
Compounds ES to FB

A solution of 5-methyl-2-{5-(4-fluoro-phenyl)-4-pyridin-4-yl-1H-imidazol-2-yl}-[1,3]dioxan-5-ylamine, cis-isomer [1 equivalent, Compound AE], and triethylamine [1 equivalent] in tetrahydrofuran was treated with methane sulphonyl chloride [1 equivalent]. After stirring at room temperature for 48 hours the reaction mixture was evaporated and the residue was subjected to preparative thick chromatography on silica, eluting with a mixture of dichloromethane and methanol (9:1, v/v), to give N-{2-[5-(4-fluoro-phenyl)-4-pyridin-4-yl-1H-imidazol-2-yl]-5-methyl-[1,3]dioxan-5-yl}-methanesulphonamide, cis-isomer (Compound ES). MH$^+$ 433. R$_F$ 0.42 {determined using a mixture of dichloromethane and methanol (9:1,v/v) as eluent}.

By proceeding in a similar manner but using Compound AA or Compound AB and an appropriately substituted sulphonyl chloride of formula Cl—SO$_2$—R$^{15}$ or Cl—SO$_2$—L$^4$—R$^{15}$ there was prepared Compounds ET to FB depicted in Table 6. The RF values indicated were determined using a mixture of dichloromethane and methanol (9:1,v/v) as eluent.

TABLE 6

| STRUCTURE and EXAMPLE NUMBER | Cl—SO$_2$—R$^{15}$ or Cl—SO$_2$—L$^4$—R$^{15}$ | R$_F$ | MOLECULAR FORMULA | MH$^+$ (Intensity) |
|---|---|---|---|---|
| 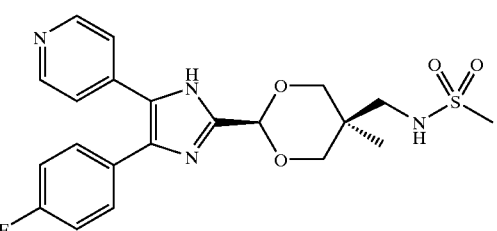 Compound ET | | 0.21 | C21H23FN4O4S | 447 (100%) |

TABLE 6-continued

| STRUCTURE and EXAMPLE NUMBER | Cl—SO$_2$—R$^{15}$ or Cl—SO$_2$—L$^4$—R$^{15}$ | R$_F$ | MOLECULAR FORMULA | MH$^+$ (Intensity) |
|---|---|---|---|---|
| Compound EU | benzenesulfonyl chloride | 0.28 | C26H25FN4OS | 509 (100%) |
| Compound EV | phenylmethanesulfonyl chloride | 0.29 | C27H27FN4O4S | 523 (100%) |
| Compound EW | thiophene-2-sulfonyl chloride | 0.30 | C24H23FN4O4S2 | 515 (100%) |
| Compound EX | 3,5-dimethylisoxazole-4-sulfonyl chloride | 0.30 | C25H26FN5O5S | 528 (100%) |
| Compound EY | methanesulfonyl chloride | 0.32 | C21H23FN4O4S | 447 (100%) |

TABLE 6-continued

| STRUCTURE and EXAMPLE NUMBER | Cl—SO₂—R¹⁵ or Cl—SO₂—L⁴—R¹⁵ | $R_F$ | MOLECULAR FORMULA | MH⁺ (Intensity) |
|---|---|---|---|---|
| 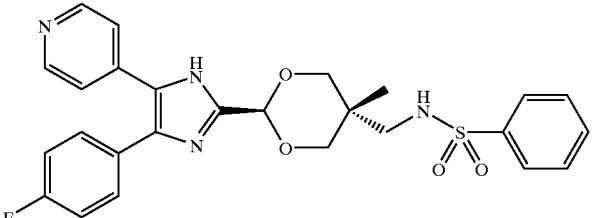 Compound EZ | | 0.53 | C26H25FN4O4S | 509 (100%) |
| 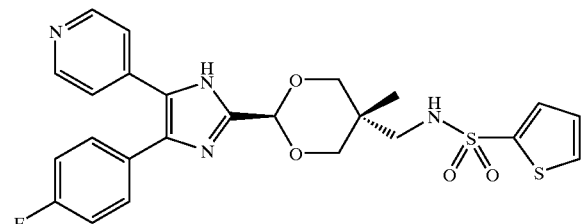 Compound FA | | 0.50 | C24H23FN4O4S2 | 515 (100%) |
| 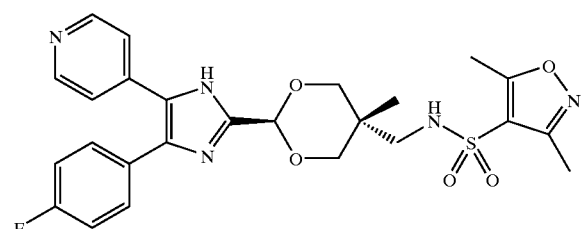 Compound FB | | 0.50 | C25H26FN5O5S | 528 (100%) |

EXAMPLE 14
Compounds FC to FJ

A solution of ({2-[5-(4-fluoro-phenyl)-4-pyridin-4-yl-1H-imidazol-2-yl]-5-methyl-[1,3]dioxon-5-ylcarbamoyl}-ethyl)-carbamic acid benzyl ester, trans-isomer (Compound FI) was treated with palladium, 5% activated on carbon and stirred at room temperature under a hydrogen atmosphere for 8 hours. The reaction mixture was filtered through a pad of diatomaceous earth and evaporated to dryness. The residue was subjected to preparative thick layer chromatography on silica, eluting with dichloromethane and methanol (7:3 v/v) to give 3-amino-N-{2-[4-(4-fluoro-phenyl)-5-pyridin-4-yl-1H-imidazol-2yl]-5-methyl-[1,3]dioxan-5-yl}-propionamide, trans-isomer (Compound FC). MH⁺ 426. $R_F$ 0.04 determined using a mixture of dichloromethane and methanol (7:3, v/v) as eluent.

By proceeding in a similar manner but using Compound FJ there was prepared 3-amino-N-{2-[4-(4-fluoro-phenyl)-5-pyridin-4-yl-1H-imidazol-2-yl]-5-methyl-[1,3]dioxan-5-yl}-propionamide, cis-isomer (Compound FD). MH⁺ 426. $R_F$ 0.04 determined using a mixture of dichloromethane and methanol (7:3, v/v) as eluent.

By proceeding in a similar manner but using Compound FK there was prepared 4-amino-N-{2-[4-(4-fluoro-phenyl)-5-pyridin-4-yl-1H-imidazol-2-yl]-5-methyl-[1,3]dioxan-5-yl}-butyramide, trans-isomer (Compound FE). MH⁺ 440. $R_F$ 0.03 determined using a mixture of dichloromethane and methanol (7:3, v/v) as eluent.

By proceeding in a similar manner but using Compound FL there was prepared 4-amino-N-{2-[4-(4-fluoro-phenyl)-5-pyridin-4-yl-1H-imidazol-2-yl]-5-methyl-[1,3]dioxan-5-yl}-butyramide, cis-isomer (Compound FF). MH⁺ 440. $R_F$ 0.03 determined using a mixture of dichloromethane and methanol (7:3, v/v) as eluent.

By proceeding in a similar manner but using Compound FM there was prepared 2-amino-N-{2-[4-(4-fluoro-phenyl)-5-pyridin-4-yl-1H-imidazol-2-yl]-5-methyl-[1,3]dioxan-5-yl}-acetamide, trans-isomer (Compound FG). MH⁺ 412. $R_F$ 0.01 determined using a mixture of dichloromethane and methanol (9:1, v/v) as eluent with two developments.

By proceeding in a similar manner but using Compound FN there was prepared 2-amino-N-{2-[4-(4-fluoro-phenyl)-5-pyridin-4-yl-1H-imidazol-2-yl]-5-methyl-[1,3]dioxan-5-yl}-acetamide, cis-isomer (Compound FH). MH⁺ 412. $R_F$ 0.03 determined using a mixture of dichloromethane and methanol (9:1, v/v) as eluent with two developments.

EXAMPLE 15
Compounds FI to FP

A solution of 5-methyl-2-{5-(4-fluoro-phenyl)-4-pyridin-4-yl-1H-imidazol-2-yl}-[1,3]dioxan-5-ylamine, cis- and trans-isomers [1 equivalent, Compound AG], N-benzyloxycarbonyl-β-alanine, [1 equivalent], 1-(3-dimethylaminopropyl)-3-ethylcarbodiimide hydrochloride [1.1 equivalents], N,N-diisopropylethylamine [3 equivalents] and 1-hydroxybenzotriazole hydrate [1.1 equivalents] in dry dimethylformamide was heated at 90° C.

for 2.5 hours. The reaction mixture was cooled to room temperature, then evaporated. The residue was partitioned between ethyl acetate (12 ml) and water (12 ml). The organic phase was separated and allowed to stand at room temperature. The solid which crystallised was filtered to give (3-{2-[4-(4-fluoro-phenyl)-5-pyridin-4-yl-1H-imidazol-2-yl]-5-methyl-[1,3]dioxan-5-ylcarbamoyl}-ethyl)-carbamic acid benzyl ester, trans-isomer (Compound FI). The filtrate was subjected to preparative chromatography on silica, eluting with a mixture of dichloromethane and pentane (9:1, v/v) to give (3-{2-[4-(4-fluoro-phenyl)-5-pyridin-4-yl-1H-imidazol-2-yl]-5-methyl-[1,3]dioxan-5-ylcarbamoyl}-ethyl)-carbamic acid benzyl ester, cis-isomer (Compound FJ).

By proceeding in a similar manner but using N-benzyloxycarbonyl-4-aminobutyric acid there was prepared (3-{2-[4-(4-fluoro-phenyl)-5-pyridin-4-yl-1H-imidazol-2-yl]-5-methyl-[1,3]dioxan-5-ylcarbamoyl}-propyl)-carbamic acid benzyl ester, trans-isomer, (Compound FK) and (3-{2-[4-(4-fluoro-phenyl)-5-pyridin-4-yl-1H-imidazol-2-yl]-5-methyl-[1,3]dioxan-5-ylcarbamoyl}-propyl)-carbamic acid benzyl ester, cis-isomer (Compound FL).

By proceeding in a similar manner but using N-benzyloxycarbonylglycine there was prepared (3-{2-[4-(4-fluoro-phenyl)-5-pyridin-4-yl-1H-imidazol-2-yl]-5-methyl-[1,3]dioxan-5-ylcarbamoyl}-methyl)-carbamic acid benzyl ester, trans-isomer (Compound FM) and (3-{2-[4-(4-fluoro-phenyl)-5-pyridin-4-yl-1H-imidazol-2-yl]-5-methyl-[1,3]dioxan-5-ylcarbamoyl}-methyl)-carbamic acid benzyl ester, cis-isomer (Compound FN).

By proceeding in a similar manner but using 3-dimethylamino-propionic acid there was prepared 4-dimethylamino-N-{2-[4-(4-fluoro-phenyl)-5-pyridin-4-yl-1H-imidazol-2-yl]-5-methyl-[1,3]dioxan-5-yl}-butyramide, cis- and trans-isomers Compound FO. MH$^+$ 468. $R_F$ 0.32 determined using a mixture of dichloromethane and methanol (7:3, v/v) as eluent.

EXAMPLE 16
Compound FP

A solution of {2-[4-(4-fluoro-phenyl)-5-pyridin-4-yl-1H-imidazol-2-yl]-5-methyl-[1,3]dioxan-5-yl}-morpholin-4-yl-methanone, trans-isomer (7.43 g, Compound AW) in hot tetrahydrofuran (500 ml) was treated with a solution of methane sulphonic acid (1.578 g) in tetrahydrofuran. After standing at room temperature for 18 hours the reaction mixture was filtered and the solid recrystallised from acetonitrile with hot filtration through celite to give {2-[4-(4-fluoro-phenyl)-5-pyridin-4-yl-1H-imidazol-2-yl]-5-methyl-[1,3]dioxan-5-yl}-morpholin-4-yl-methanone methane sulphonic acid salt, trans-isomer (6.00 g, Compound FP) as a pale yellow crystalline solid, m.p. 242–246° C. (with decomposition). [Elemental analysis:—C, 54.76; H,5.25; N,10.44; S, 5.89%. Calculated for $C_{24}H_{25}FN_4O_4 \cdot CH_3SO_3H$:—C, 54.73; H, 5.32; N, 10.21; S, 5.84%].

EXAMPLE 17
Compound FQ A solution of N-{2-[4-(4-fluoro-phenyl)-5-pyridin-4-yl-1H-imidazol-2-yl]-5-methyl-[1,3]dioxan-5-yl}-benzamide, trans-isomer (0.85 g, Compound FR) in tetrahydrofuran (100 ml) was treated with methane sulphonic acid (0.178 g). The reaction mixture was agitated for 5 minutes then evaporated to dryness and dried under high vacuum. The residual solid was recrystallised from ethyl acetate containing a minimum volume of acetonitrile to give N-{2-[4-(4-fluoro-phenyl)-5-pyridin-4-yl-1H-imidazol-2-yl]-5-methyl-(1,3)dioxan-5-yl}-benzamide, methane sulphonic acid salt, trans-isomer (1.20 g, Compound FQ) as a yellow crystalline solid, m.p. 165–169° C. [Elemental analysis:—C, 57.93; H,5.41; N,8.73%. Calculated for $C_{26}H_{23}FN_4O_3 \cdot CH_3SO_3H \cdot CH_3CO_2C_2H_5$:—C, 52.94; H, 5.123; N, 9.88%].

EXAMPLE 18
Compound FR

A stirred suspension of 5-methyl-2-{5-(4-fluoro-phenyl)-4-pyridin-4-yl-1H-imidazol-2-yl}-[1,3]dioxan-5-ylamine, trans isomer (1.76 g, Compound AF), benzoic acid (0.67 g) and diisopropylethylamine (1.39 ml) in dry dimethylformamide (50 ml) was treated with {O-(7-Azabenzotriazol-1-yl)-1,1,3,3-tetramethyluronium hexafluorophosphate} (1.88 g) under a nitrogen atmosphere. After stirring at room temperature for 2 hours the reaction mixture was evaporated to dryness. The residue was partitioned between ethyl acetate (70 ml) and saturated sodium bicarbonate (50 ml). The organic phase was washed twice with water (50 ml), then with brine (30 ml) and then evaporated. The residue was subjected to flash chromatography on silica eluting with ethyl acetate to give N-{2-[4-(4-fluoro-phenyl)-5-pyridin-4-yl-1H-imidazol-2-yl]-5-methyl-[1,3]dioxan-5-yl}-benzamide, trans-isomer (0.85 g, Compound FR) as a cream coloured solid, m.p. 235–236° C. $R_F$: 0.42 determined using a mixture of dichloromethane and methanol (9:1, v/v) as eluent. MH$^+$ 459.

EXAMPLE 19
Compound AW

Method A: 2-[5-(4-fluoro-phenyl)-4-pyridin-4-yl-1H-imidazol-2-yl]-5-methyl-[1,3]dioxane-5-carboxylic acid, trans-isomer (7.70 g, Compound AH) was added portionwise to stirred thionyl chloride. The reaction mixture was stirred at room temperature for 1.25 hours then evaporated. The residue was azeotroped with dry toluene to yield the crude acid chloride. This was treated with dry dichloromethane (150 ml) followed by morpholine (30 ml) under nitrogen. The mixture was stirred at room temperature for 2.5 hours then evaporated. The residue was partitioned between ethyl acetate (250 ml) and saturated sodium bicarbonate (200 ml). The insoluble product at the interface was filtered off and washed with methanol (10 ml), then with water (20 ml) and then with diethyl ether (20 ml) to give {2-[4-(4-fluoro-phenyl)-5-pyridin-4-yl-1H-imidazol-2-yl]-5-methyl-[1,3]dioxan-5-yl}-morpholin-4-yl-methanone, trans-isomer (7.63 g, Compound AW), m.p. 288–291° C. MH$^+$ 453.

Method B: 4-[2-(Dimethoxymethyl)-5-(4-fluorophenyl)-1H-4-imidazolyl]pyridine (62.7 g) and 3-hydroxy-2-(hydroxymethyl)-2-methyl-1-morpholino-1-propanone (44.8 g, Reference Example 6) were added to toluene (440 ml), under nitrogen. The mixture was stirred and heated to reflux under a Dean and Stark trap for 20 minutes. N,N-dimethylformamide (160 ml) and methanesulphonic acid (2 ml) were added and the mixture heated to a gentle reflux over 4 hours, removing a total of 150 ml distillate at a fairly uniform rate. The reaction mixture was then evaporated in vacuo to remove as much toluene as possible. The resulting suspension was treated with triethylamine (8 ml) and then water (600 ml) was added dropwise over 1 hour. The mixture was filtered to give a damp, crude solid mixture of cis- and trans-isomers after washing with water and allowing the cake to suck on the filter for 1 hour. This material was stirred in methanol (350 ml), then the mixture was heated to reflux for 15 minutes and then cooled to 5° C. The solid was filtered and then washed with methanol to give {2-[4-(4-fluoro-phenyl)-5-pyridin-4-yl-1H-imidazol-2-yl]-5-methyl-[1,3]dioxan-5-yl}-morpholin-4-yl-methanone, trans-isomer (46.4 g, Compound AW), m.p. 214° C. (with decomposition). $^1$H NMR ($\delta$, CDCl$_3$): 8.52 (d, 0.6H); 8.39 (d, 1.4H); 7.32–7.49 (m, 4H); 7.29 (t, 1.4H); 7.13 (t, 0.6H); 5.59 (s, 1H); 4.07 (s, 4H); 3.51 (bd, 8H); 1.56 (s, 3H).

EXAMPLE 20

Compound GE

A stirred suspension of {2-[4-(4-fluoro-phenyl)-5-pyridin-4-yl-1H-imidazol-2-yl]-5-methyl-[1,3]dioxan-5-yl}-morpholin-4-yl-methanone, trans-isomer (4.52 g, Compound AW) in a mixture of ethanol and methanol (45 ml, 95:5, v/v) was treated with aqueous hydrobromic acid (1.2 ml, 48%). The mixture was heated to reflux, then water (15 ml) was added and then the mixture was heated again to reflux. The solution formed was allowed to cool to room temperature then filtered. The solid was washed three times with a mixture of ethanol and methanol (10 ml, 95:5, v/v) to give {2-[4-(4-fluoro-phenyl)-5-pyridin-4-yl-1H-imidazol-2-yl]-5methyl-[1,3]dioxan-5-yl}-morpholin-4-yl-methanone monohydrobromide dihydrate, trans-isomer (4.5 g, Compound GE) as an off-white crystalline solid, m.p. 276–277° C. (with decomposition). $^1$H NMR (CD$_3$)$_2$SO: $\delta$1.53 (s, 3H), 3.49 (bd, 8H), 4.08 (s, 4H), 5.64 (s, 1H), 7.36 (t, 2H), 7.53–7.58 (m, 2H), 7.84 (d, 2H), 8.63 (d, 2H).

EXAMPLE 21

Compound GF

{2-[4-(4-Fluoro-phenyl)-5-pyridin-4-yl-1H-imidazol-2-yl]-5-methyl-[1,3]dioxan-5-yl}-morpholin-4-yl-methanone, trans-isomer (25.2 g, Compound AW), stirred in isopropanol (300 ml), was treated with concentrated hydrochloric acid (5 ml) and water (440 ml) and the mixture was heated to reflux for 15 minutes. The mixture was cooled to room temperature and then filtered. The solid was washed with isopropanol to give {2-[4-(4-fluoro-phenyl)-5-pyridin-4-yl-1H-imidazol-2-yl]-5-methyl-[1,3]dioxan-5-yl}-morpholin-4-yl-methanone monohydrochloride dihydrate, trans-isomer (22.5 g, Compound GF) as an off-white solid, m.p. 245–248° C. (with decomposition). $^1$H NMR (CD$_3$)$_2$SO: $\delta$1.58 (s, 3H), 3.55 (bd, 8H), 4.12 (s, 4H), 5.68 (s, 1H), 7.49 (t, 2H), 7.58–7.62 (m, 2H), 7.89 (d, 2H), 8.68 (d, 2H).

EXAMPLE 22

Compound GG

{2-[4-(4-Fluoro-phenyl)-5-pyridin-4-yl-1H-imidazol-2-yl]-5-methyl-[1,3]dioxan-5-yl}-morpholin-4-yl-methanone, trans-isomer (4.52 g, Compound AW), stirred in a mixture of ethanol and methanol (45 ml, 95:5, v/v), was treated with d-10-camphorsulphonic acid (2.55 g). The mixture was heated to reflux and the resulting solution allowed to cool to room-temperature. The resulting solid was collected by filtration and washed three times with a mixture of ethanol and methanol (10 ml, 95:5, v/v) to give {2-[4-(4-fluoro-phenyl)-5-pyridin-4-yl-1H-imidazol-2-yl]-5-methyl-[1,3]dioxan-5-yl}-morpholin-4-yl-methathanone d-10-camphorsulphonic acid salt, trans-isomer (6.0 g, Compound GG) as pale yellow crystals, m.p. 265–267° C. (with decomposition). $^1$H NMR (CD$_3$)$_2$SO: $\delta$0.74 (s, 3H), 1.05 (s, 3H), 1.33–1.43 (m, 2H), 1.58 (s, 3H), 1.80 (d, 1H), 1.81–1.89 (m, 1H), 1.94 (t, 1H), 2.24 (dt, 1H), 2.49 (d, 1H), 2.64–2.72 (m, 1H), 2.89 (d, 1H), 33.53 (d, 8H), 4.12 (s, 4H), 5.69 (s, 1H), 7.40 (t, 2H), 7.57–7.63 (m, 2H), 7.90 (d, 2H), 8.68 (d, 2H).

EXAMPLE 23

Compounds GH to HK (a) A solution of {2-[4-(4-fluoro-phenyl)-5-(2-methanesulphonylpyrimidin-4-yl)-1H-imidazol-2-yl]-5-methyl-[1,3]dioxan-5-yl}-morpholin-4-yl-methanone, trans isomer (1 equivalent, Compound KH) and cyclopropylamine (5 equivalents ) in dry dimethylformamide was heated at 100° C. for 16 hours. The solvent was evaporated and the residue subjected to high pressure liquid chromatography on a C18 Dynamax 60 Å column using gradient elution with a mixture of acetonitrile and water as the mobile phase (0–2 minutes 20% acetonitrile; 3–16 minutes ramp up to 80% acetonitrile; 17 minutes to end of run 80% acetonitrile) and UV detection at 238 nm to give {2-[5-(2-cyclopropylaminopyrimidin-4-yl)-4-(4-fluoro-phenyl)-1H-imidazol-2-yl]-5-methyl-[1,3]dioxan-5-yl}-morpholin-4-yl-methanone, trans isomer (Compound GH), HPLC retention time=8.0 minutes. MH$^+$ 509.

(b) By proceeding in a similar manner to Example 23(a), but replacing cyclopropylamine with an appropriately substituted amine of formula HNY$^4$Y$^5$ [5 equivalents, see Table 7], there were prepared Compounds GI to HK in Table 7. For Compound GI the reaction was carried out in the absence of dimethylformamide in a sealed vessel. For Compound GW the lithio-anion of the aniline (generated by reaction of aniline with butyl lithium in tetrahydrofuran according to standard reaction conditions) was used to replace the cyclopropylamine. Compounds GI to GL were obtained as solids on treating the crude reaction product with acetonitrile. The R$_T$ values indicated in Table 7 refer to high pressure liquid chromatography retention times determined on a C18 Dynamax 60 Å column using gradient elution with a mixture of acetonitrile and water as the mobile phase (0–12 minutes 5% acetonitrile ramp up to 80% acetonitrile; 12 minutes to end of run 80% acetonitrile). The R$_F$ values indicated in Table 7 were determined using a mixture of ethyl acetate and methanol (19:1, v/v) [the eluant for Compounds HJ and HK was a mixture of dichloromethane and methanol (9:1, v/v)].

TABLE 7

| STRUCTURE and Compound number | HNY⁴Y⁵ | $R_T$ | $R_F$ | MOLECULAR FORMULA | MH⁺ (Intensity) |
|---|---|---|---|---|---|
| Compound GI | NH₃ | | 9 | C23H25FN6O4 | 469 (100%) |
| Compound GJ | HN(CH₃)₂ | | 0.5 | C25H29FN6O4 | 497 (100%) |
| Compound GK | H₂N-CH₂CH₂CH₂-OH | | 0.07 | C26H31FN6O5 | 527 (100%) |
| Compound GL | H₂N-CH₂CH₂-O-CH₃ | | 0.19 | C26H31FN6O5 | 527 (100%) |

TABLE 7-continued
| STRUCTURE and Compound number | HNY⁴Y⁵ | $R_T$ | $R_F$ | MOLECULAR FORMULA | MH⁺ (Intensity) |
|---|---|---|---|---|---|
| 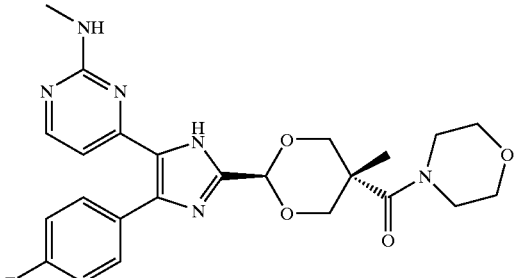  Compound GM | 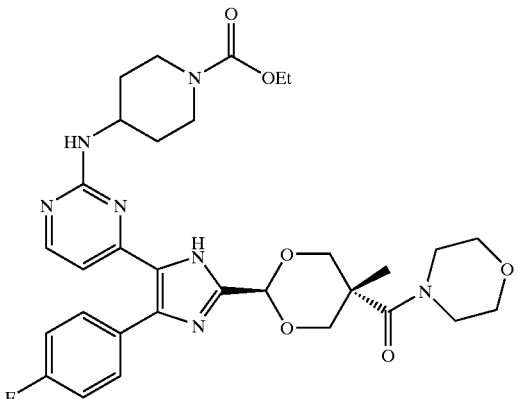 H₂N— | 9 | | C24H27FN6O4 | 483 (100%) |
| 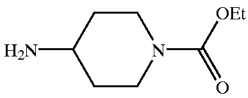  Compound GN | 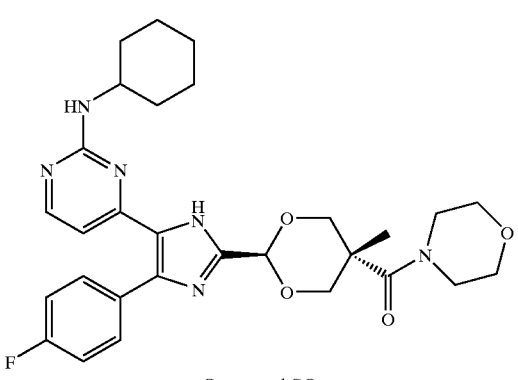 | 10 | | C31H38FN7O6 | 624 (100%) |
| 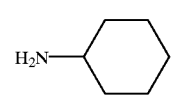  Compound GO | 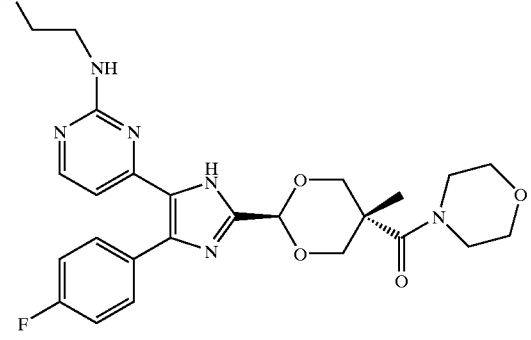 | 11 | | C29H35FN6O4 | 551 (100%) |
|   Compound GP | H₂N⏦OH | 8 | | C25H29FN6O5 | 513 (100%) |

TABLE 7-continued
| STRUCTURE and Compound number | HNY⁴Y⁵ | $R_T$ | $R_F$ | MOLECULAR FORMULA | MH⁺ (Intensity) |
|---|---|---|---|---|---|
| 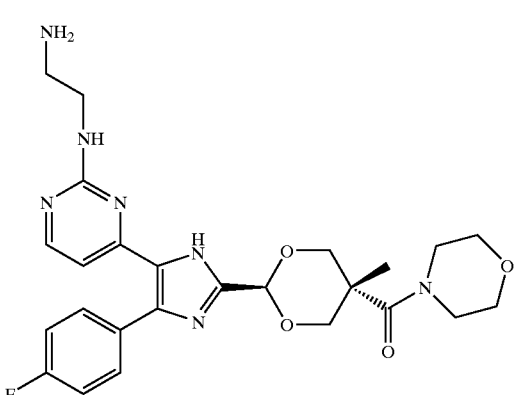<br>Compound GQ | 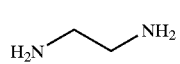 | 6 | | C25H30FN7O4 | 512 (100%) |
| 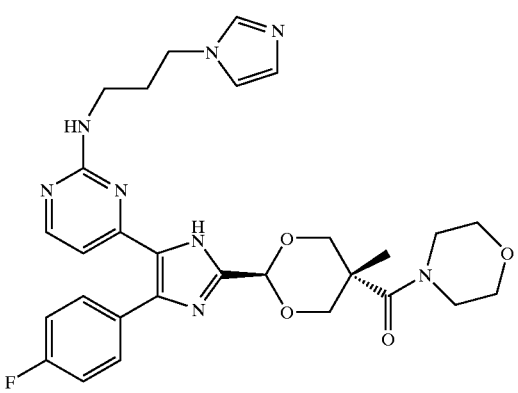<br>Compound GR | 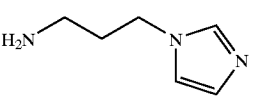 | 7 | | C29H33FN8O4 | 577 (100%) |
| 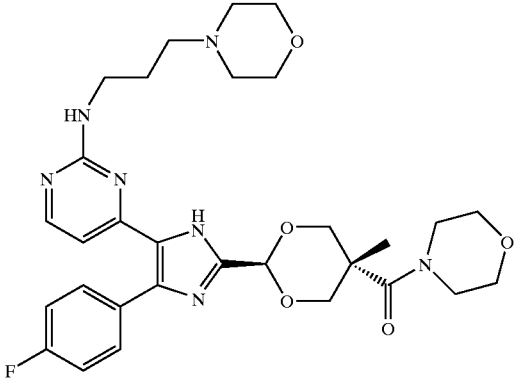<br>Compound GS | 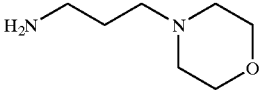 | 7 | | C30H38FN7O5 | 596 (100%) |

TABLE 7-continued
| STRUCTURE and Compound number | HNY⁴Y⁵ | $R_T$ | $R_F$ | MOLECULAR FORMULA | MH⁺ (Intensity) |
|---|---|---|---|---|---|
| 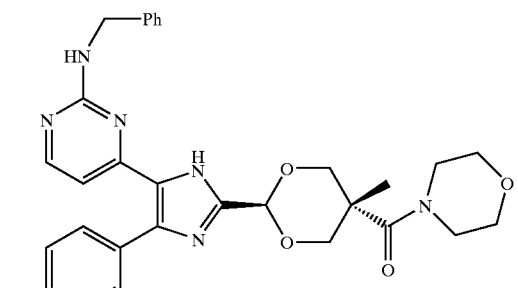 Compound GT | H₂N—CH₂—Ph | 11 | | C30H31FN6O4 | 559 (100%) |
| 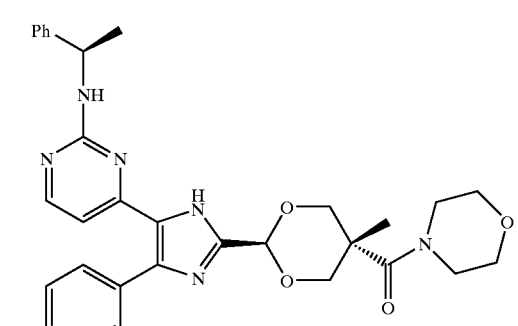 Compound GU | H₂N—CH(CH₃)Ph | 11 | | C31H33FN6O4 | 573 (100%) |
| 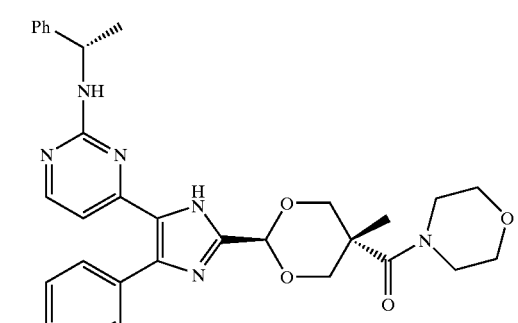 Compound GV | H₂N—CH(CH₃)Ph | 11 | | C31H33FN6O4 | 573 (100%) |
| 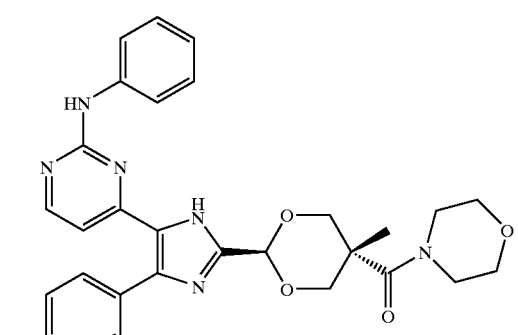 Compound GW | H₂N—Ph | 11.5 | | C29H29FN6O4 | 545 (100%) |

TABLE 7-continued
| STRUCTURE and Compound number | HNY⁴Y⁵ | R_T | R_F | MOLECULAR FORMULA | MH⁺ (Intensity) |
|---|---|---|---|---|---|
| 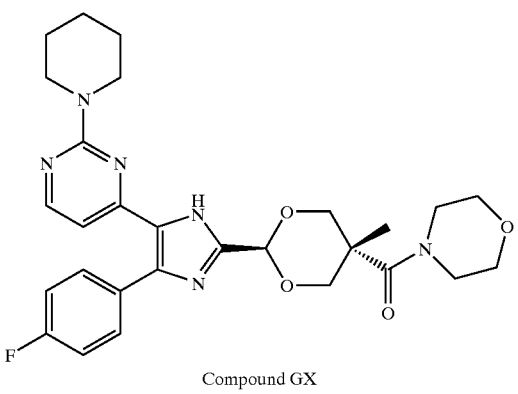 Compound GX | 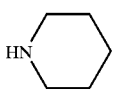 | 10 | | C28H33FN6O4 | 537 (100%) |
| 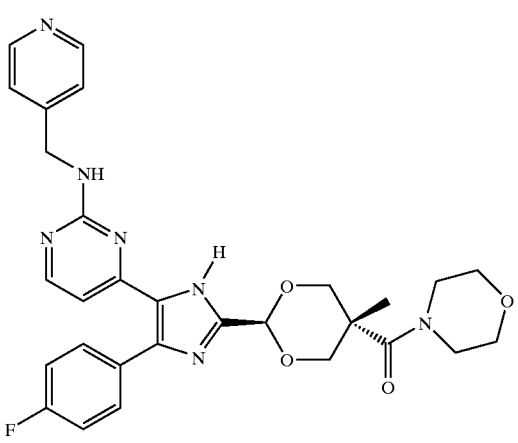 Compound GY | 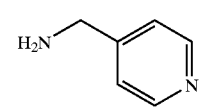 | 7 | | C29H30FN7O4 | 560 (100%) |
| 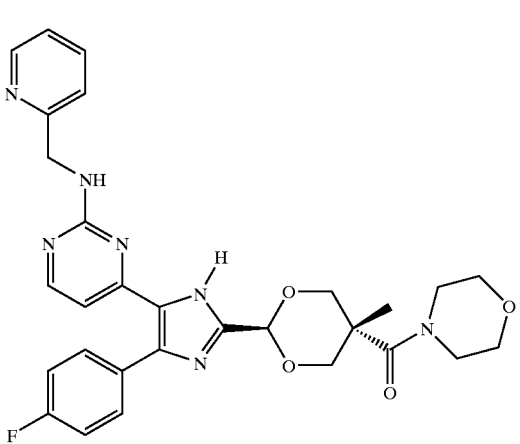 Compound GZ | 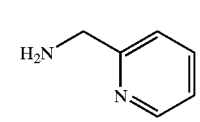 | 7 | | C29H30FN7O4 | 560 (100%) |

TABLE 7-continued
| STRUCTURE and Compound number | HNY⁴Y⁵ | R_T | R_F | MOLECULAR FORMULA | MH⁺ (Intensity) |
|---|---|---|---|---|---|
| 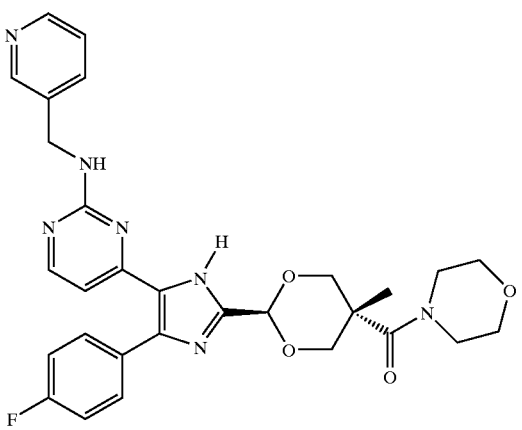<br>Compound HA | 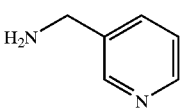 | 7 | | C29H30FN7O4 | 560 (100%) |
| 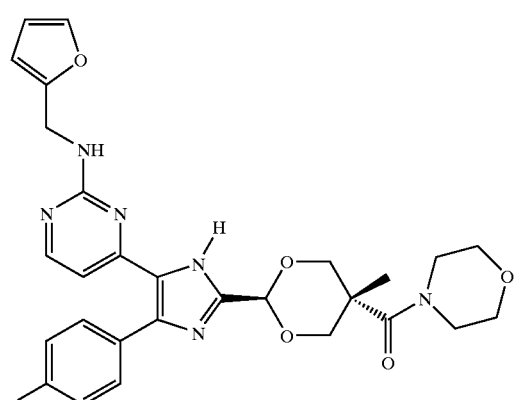<br>Compound HB | 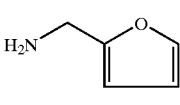 | 10.5 | | C28H29FN6O5 | 549 (100%) |
| 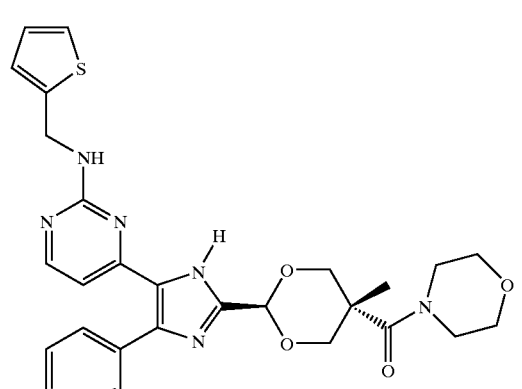<br>Compound HC | 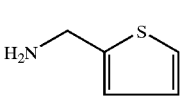 | 13 | | C28H29FN6O4S | 565 (100%) |

TABLE 7-continued
| STRUCTURE and Compound number | HNY⁴Y⁵ | R_T | R_F | MOLECULAR FORMULA | MH⁺ (Intensity) |
|---|---|---|---|---|---|
| 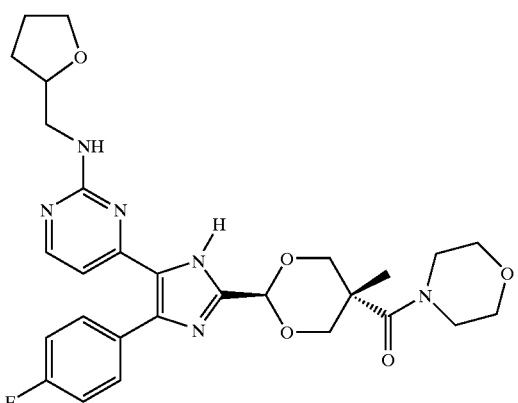 Compound HD | 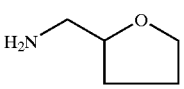 | 9 | | C28H33FN6O5 | 553 (100%) |
| 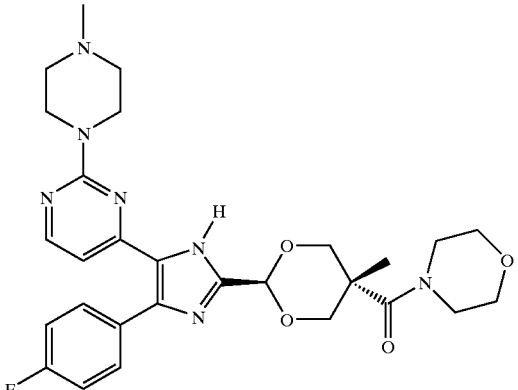 Compound HE | 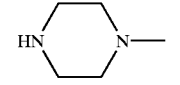 | 7 | | C28H34FN7O4 | 552 (100%) |
| 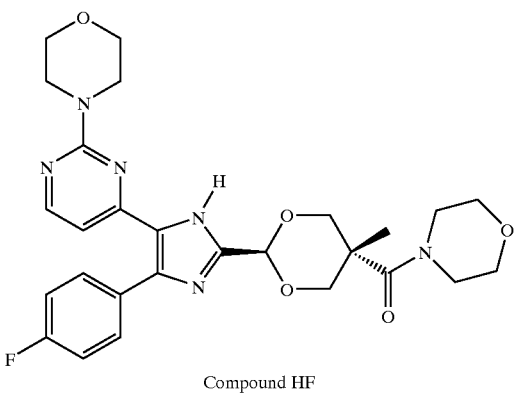 Compound HF |  | 9 | | C27H31FN6O5 | 539 (100%) |

TABLE 7-continued
| STRUCTURE and Compound number | HNY⁴Y⁵ | $R_T$ | $R_F$ | MOLECULAR FORMULA | MH⁺ (Intensity) |
|---|---|---|---|---|---|
| 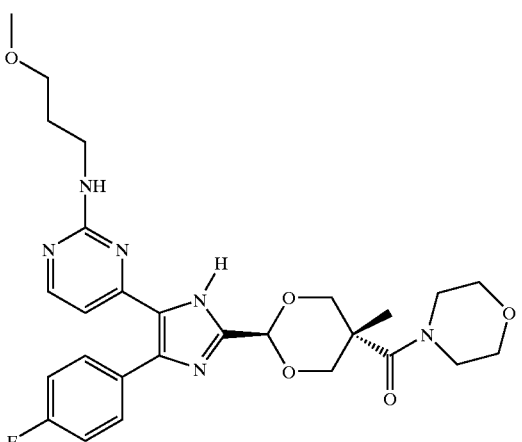  Compound HG | H₂N~~~O~ | 8 | | C27H33FN6O5 | 541 (100%) |
| 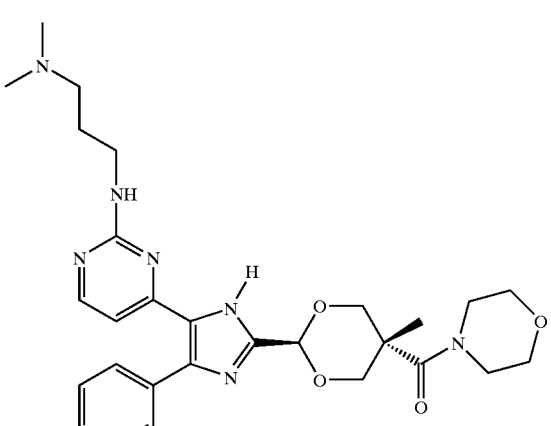  Compound HH | H₂N~~~N(CH₃)₂ | 7 | | C28H36FN7O4 | 554 (100%) |
| 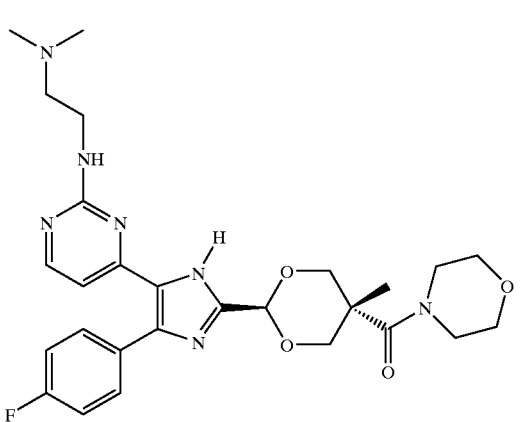  Compound HI | H₂N~~N(CH₃)₂ | 7 | | C27H34FN7O4 | 540 (100%) |

TABLE 7-continued

| STRUCTURE and Compound number | HNY⁴Y⁵ | $R_T$ | $R_F$ | MOLECULAR FORMULA | MH⁺ (Intensity) |
|---|---|---|---|---|---|
| 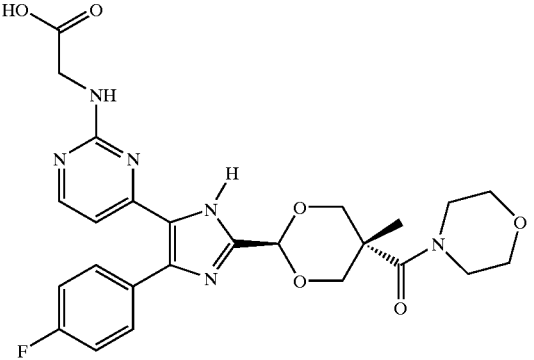<br>Compound HJ | 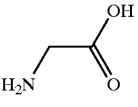 | | 0.22 | C25H27FN6O6 | 527 (100%) |
| 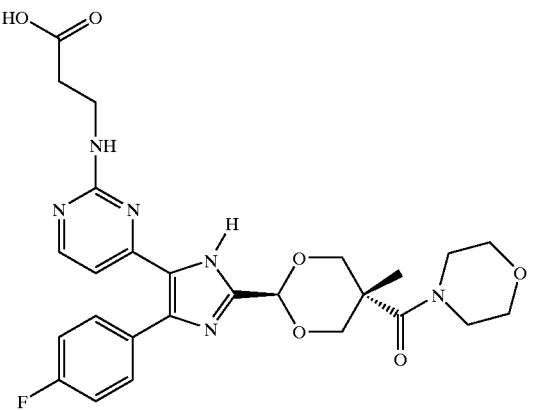<br>Compound HK | 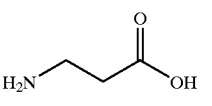 | | 0.24 | C26H29FN6O6 | 541 (100%) |

(c) By proceeding in the same manner to Example 23 (b) and using the appropriately substituted amine of formula HNY⁴Y⁵ there are prepared Compounds A1 to A16.

{2-[4-(4-fluoro-phenyl)-5-(2-isopropylamino-pyrimidin-4-yl)-1H-imidazol-2-yl]-5-methyl-[1,3]dioxan-5-yl}-morpholin-4-yl-methanone, trans-isomer, (Compound A1);

{2-[5-(2-allylamino-pyrimidin-4-yl)-4-(4-fluoro-phenyl)-1H-imidazol-2-yl]-5-methyl-[1,3]dioxan-5yl}-morpholin-4-yl-methanone, trans-isomer, trans-isomer, (Compound A2);

{2-[5-[2-(cyclopropylmethyl-amino)-pyrimidn-4yl]-4-(4fluoro-phenyl)-1H-imidazol-2-yl]-5-methyl-[1,3]dioxan-5-yl}-morpholin-4-yl-methanone, trans-isomer, (Compound A3);

(4-{5-(4-fluoro-phenyl)-2-[5-methyl-5-(morpholine-4-carbonyl)-[1,3]dioxan-2-yl]-3H-imidazol-4-yl}-pyrimidin-2-ylamino)-acetonitrile, trans-isomer, (Compound A4);

3-(4-{5-(4-fluoro-phenyl)-2-[5-methyl-5-(morpholine-4-carbonyl)-[1,3]dioxan-2-yl]-3H-imidazol-4-yl}-pyrimidin-2-ylamino)-propionitrile, trans-isomer, (Compound A5);

(2-{4-(4-fluoro-phenyl)-5-[2-(pyridin-3-ylamino)-pyrimidin-4-yl]-1H-imidazol-2-yl}-5-methyl-[1,3]dioxan-5-yl)-morpholin-4-yl-methanone, trans-isomer, (Compound A6);

(2-{4-(4-fluoro-phenyl)-5-[2-(pyridin-4-ylamino)-pyrimidin-4-yl]-1H-imidazol-2-yl}-5-methyl-[1,3]dioxan-5-yl)-morpholin-4-yl-methanone, trans-isomer, (Compound A7);

2-(4-{5-(4-fluoro-phenyl)-2-[5-methyl-5-(morpholine-4-carbonyl)-[1,3]dioxan-2yl]-3H-imidazol-4-yl}-pyrimidin-2-ylamino)-acetamide, trans-isomer, (Compound A8);

3-(4-{5-(4-fluoro-phenyl)-2-[5-methyl-5-(morpholine-4-carbonyl)-[1,3]dioxan-2yl]-3H-imidazol-4-yl}-pyrimidin-2-ylamino)-propionamide, trans-isomer, (Compound A9);

{2-[4-(4-fluoro-phenyl)-5-(2-propylamino-pyrimidin-4-yl)-1H-imidazol-2-yl]-5methyl-[1,3]dioxan-5-yl}-morpholin-4-yl-methanone, trans-isomer, (Compound A 10);

{2-[4-(4-fluoro-phenyl)-5-(2-pyrrolidin-1-yl-pyrimidin-4-yl)-1H-imidazol-2-yl]-5-methyl-[1,3]dioxan-5-yl}-morpholin-4-yl-methanone, trans-isomer, (Compound A11);

2-[5-(2-(4-fluorobenzyl)amino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A12);

2-[5-(2-(4-methoxybenzyl)amino-pyrimidin-4-yl)-4-(4-fluoro-phenyl)-1H-imidazol-2-yl]-5methyl-[1,3]dioxan-5-yl}-morpholin-4-yl-methanone, trans-isomer, (Compound A13);

{2-[4-(4-fluoro-phenyl)-5-(2-(4-fluorophenyl)amino-pyrimidin-4-yl)-1H-imidazol-2yl]-5-methyl-[1,3]dioxan-5-yl}-morpholin-4-yl-methanone, trans-isomer, (Compound A14);

{2-[4-(4-fluoro-phenyl)-5-(2-(3,4-difluorophenyl)amino-pyrimidin-4-yl)-1H-imidazol-2-yl]-5-methyl-[1,3]dioxan-5-yl}-morpholin-4-yl-methanone, trans-isomer, (Compound A15);

{2-[4-(4-fluoro-phenyl)-5-(2-(3-methoxyphenyl)amino-pyrimidin-4-yl)-1H-imidazol-2-yl]-5-methyl-[1,3]dioxan-5-yl}-morpholin-4-yl-methanone, trans-isomer, (Compound A16);

(d) By proceeding in a similar manner to Example 23 (b) but using 2-[4-(4-fluoro-phenyl)-5-(2-methylsulphonylpyrimidin-4-yl)-1H-imidazol-2-yl]-5,5-dimethyl-[1,3]dioxane (Compound KI) there were prepared Compounds HL to IN in Table 7a.

TABLE 7a

| STRUCTURE and COMPOUND NUMBER | HNY⁴Y⁵ | R_T | MOLECULAR FORMULA | MH⁺ (Intensity) |
|---|---|---|---|---|
| 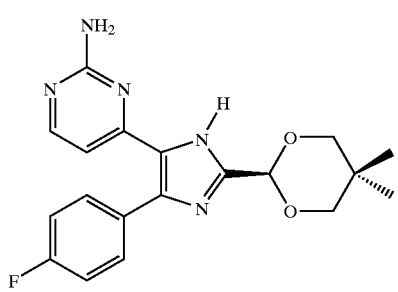 Compound HL | NH₃ | 10.31 | C19H20FN5O2 | 370 (100%) |
| 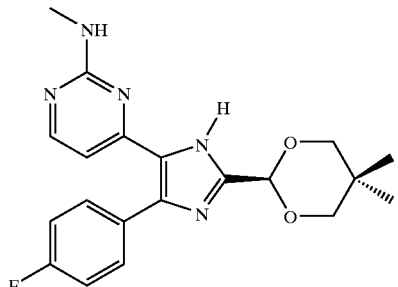 Compound HM | H₂N─ | 10.58 | C20H22FN5O2 | 384 (100%) |
| 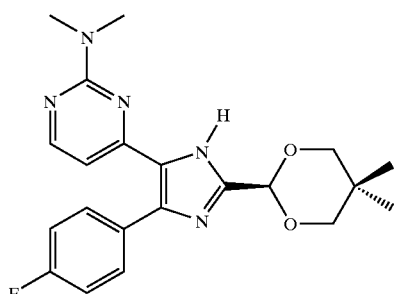 Compound HN | HN(─)(─) | 10.88 | C21H24FN5O2 | 398 (100%) |

TABLE 7a-continued
| STRUCTURE and COMPOUND NUMBER | HNY⁴Y⁵ | R_T | MOLECULAR FORMULA | MH⁺ (Intensity) |
|---|---|---|---|---|
| 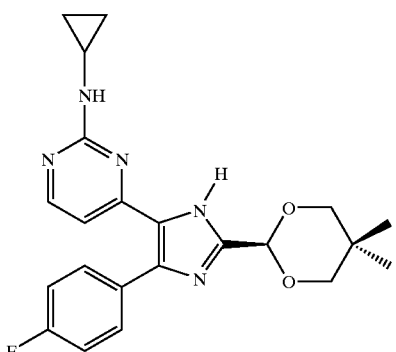 Compound HO | 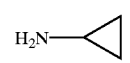 | 11.05 | C22H24FN5O2 | 410 (100%) |
| 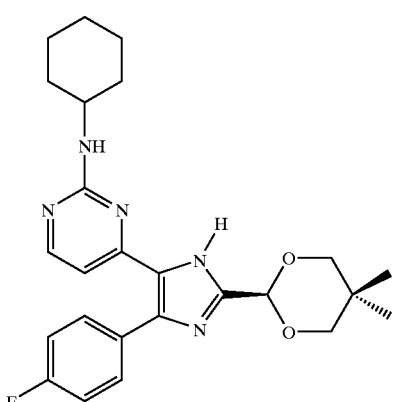 Compound HQ | 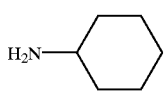 | 12.7 | C25H30FN5O2 | 452 (100%) |
| 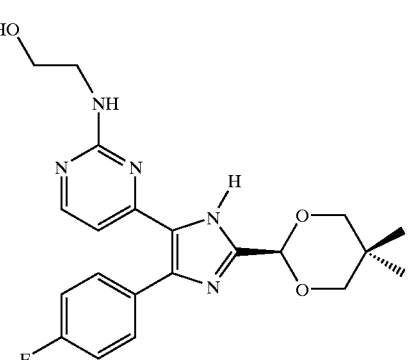 Compound HR | 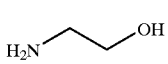 | 9.76 | C21H24FN5O3 | 414 (100%) |

TABLE 7a-continued
| STRUCTURE and COMPOUND NUMBER | HNY⁴Y⁵ | $R_T$ | MOLECULAR FORMULA | MH⁺ (Intensity) |
|---|---|---|---|---|
| 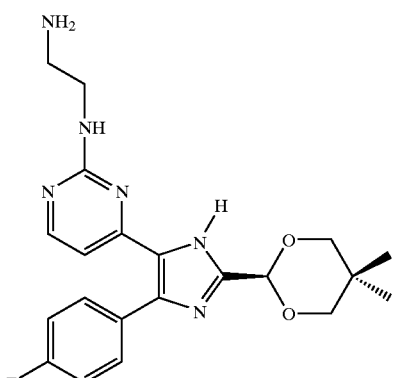 Compound HS | H₂N–CH₂CH₂–NH₂ | 8.85 | C21H25FN6O2 | 413 (100%) |
| 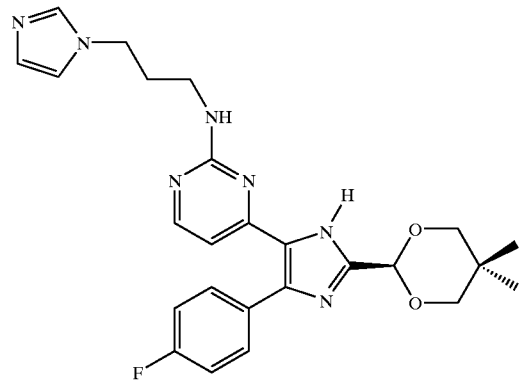 Compound HT | H₂N–(CH₂)₃–imidazole | 9.16 | C25H25FN7O2 | 478 (100%) |
| 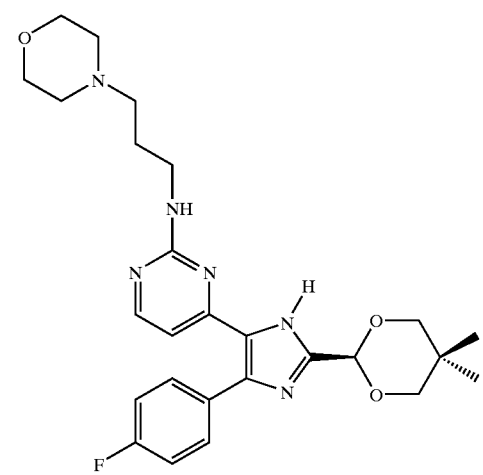 Compound HU | H₂N–(CH₂)₃–morpholine | 9.15 | C26H33FN6O3 | 497 (100%) |

TABLE 7a-continued
| STRUCTURE and COMPOUND NUMBER | HNY⁴Y⁵ | $R_T$ | MOLECULAR FORMULA | MH⁺ (Intensity) |
|---|---|---|---|---|
| 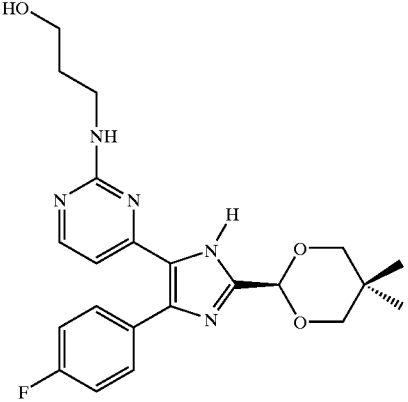 Compound HV | H₂N⌒⌒OH | 9.68 | C22H26FN5O2 | 428 (100%) |
| 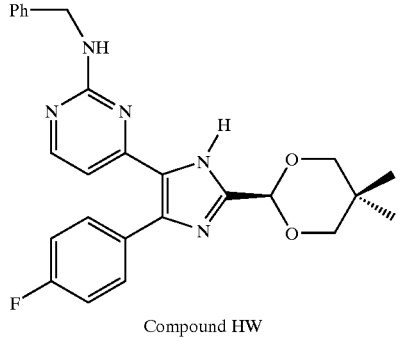 Compound HW | H₂N−Ph | 12.4 | C26H26FN5O2 | 446 (100%) |
| 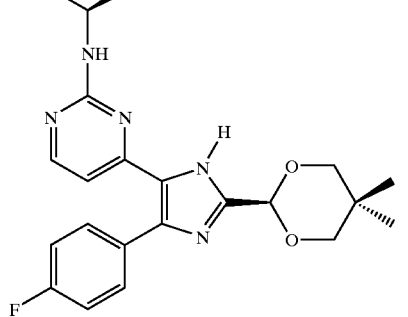 Compound HX | H₂N−CH(Ph)CH₃ | 13.01 | C27H28FN5O2 | 474 (100%) |
| 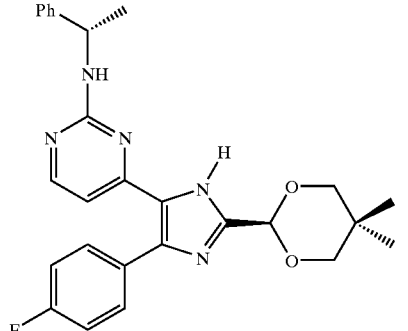 Compound HY | H₂N−CH(Ph)CH₃ | 13.01 | C27H28FN5O2 | 474 (100%) |

TABLE 7a-continued
| STRUCTURE and COMPOUND NUMBER | HNY⁴Y⁵ | R_T | MOLECULAR FORMULA | MH⁺ (Intensity) |
|---|---|---|---|---|
| 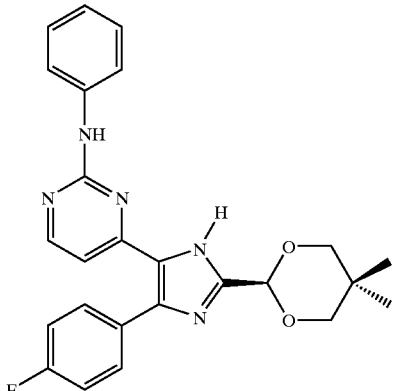 Compound HZ | 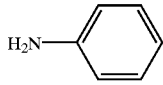 | 12.53 | C25H24FN5O2 | 446 (100%) |
| 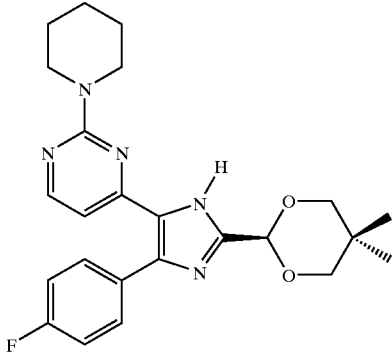 Compound IA | 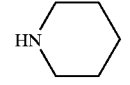 | 12.23 | C24H28FN5O2 | 438 (100%) |
| 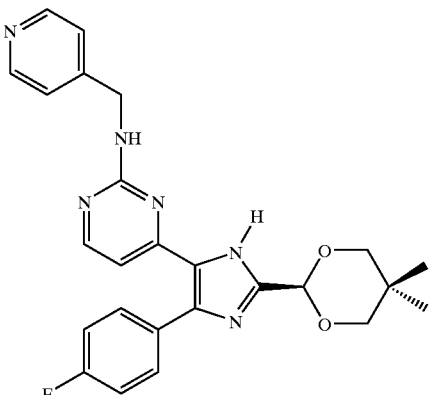 Compound IB | 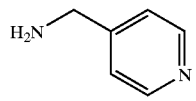 | 8.97 | C25H25FN6O2 | 461 (100%) |

TABLE 7a-continued
| STRUCTURE and COMPOUND NUMBER | HNY⁴Y⁵ | R_T | MOLECULAR FORMULA | MH⁺ (Intensity) |
|---|---|---|---|---|
| 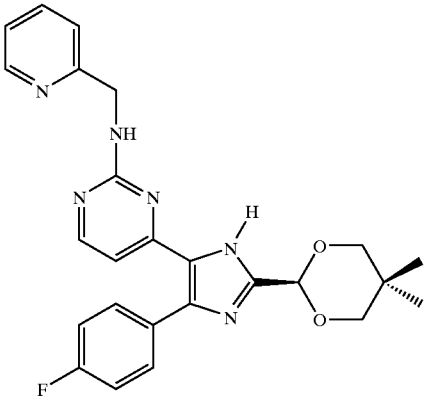<br>Compound IC | 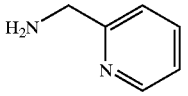 | 8.87 | C25H25FN6O2 | 461 (100%) |
| 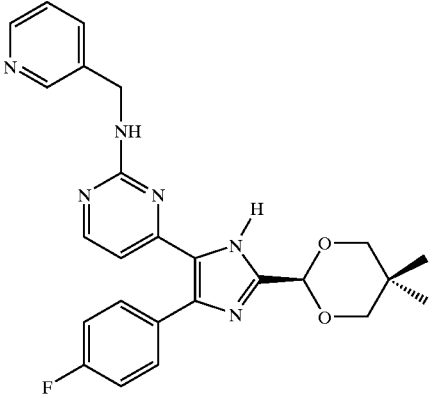<br>Compound ID | 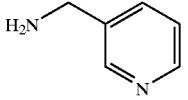 | 8.94 | C25H25FN6O2 | 461 (100%) |
| 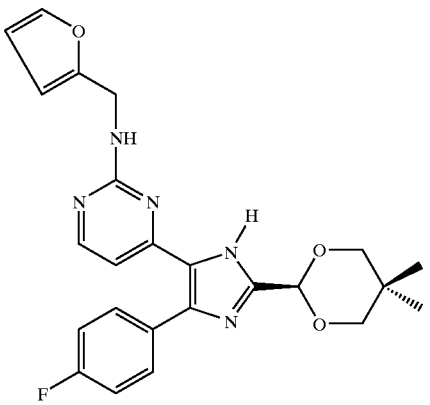<br>Compound IE | 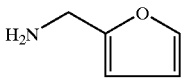 | 11.99 | C24H24FN5O3 | 450 (100%) |

TABLE 7a-continued
| STRUCTURE and COMPOUND NUMBER | HNY⁴Y⁵ | R_T | MOLECULAR FORMULA | MH⁺ (Intensity) |
|---|---|---|---|---|
| 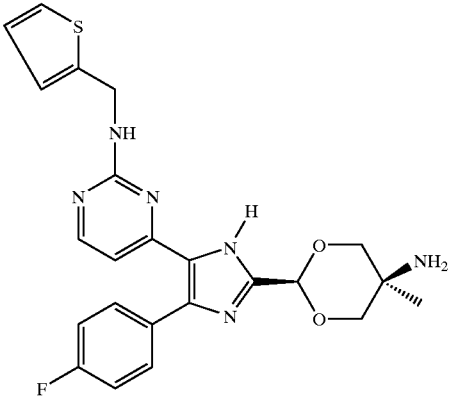 Compound IF | 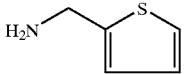 | 12.3 | C24H24FN5O2S | 466 (100%) |
| 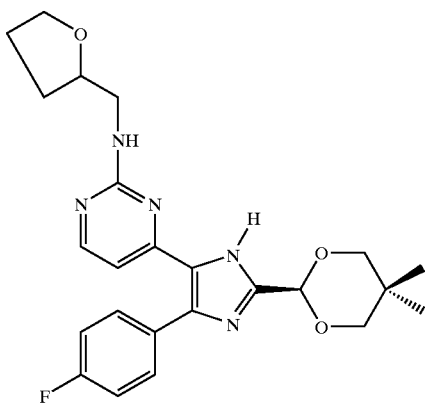 Compound IG | 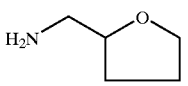 | 11.29 | C24H28FN5O3 | 454 (100%) |
| 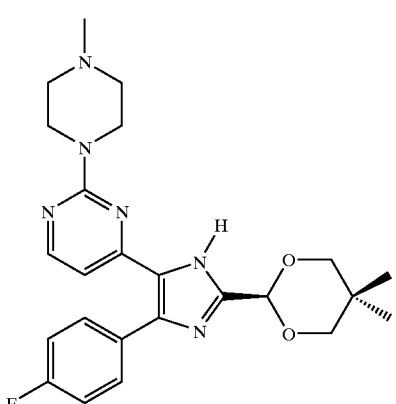 Compound IH | 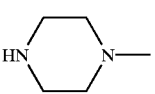 | 9.43 | C24H29FN6O2 | 453 (100%) |

TABLE 7a-continued
| STRUCTURE and COMPOUND NUMBER | HNY⁴Y⁵ | R_T | MOLECULAR FORMULA | MH⁺ (Intensity) |
|---|---|---|---|---|
| 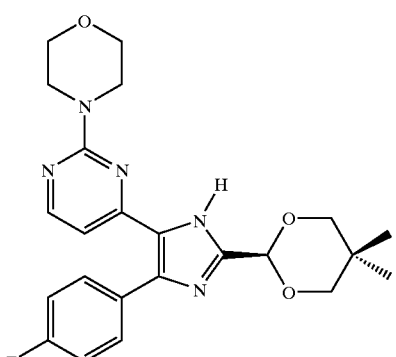 Compound IJ |  | 11.1 | C23H26FN5O3 | 440 (100%) |
| 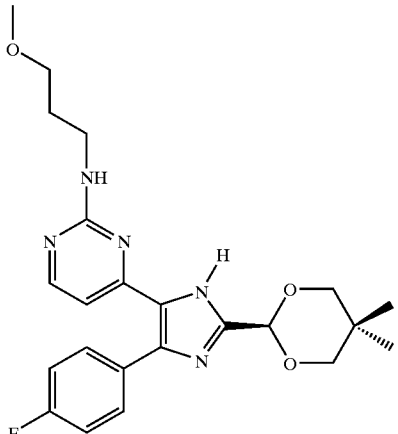 Compound IK | 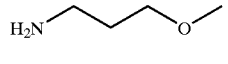 | 11.1 | C23H28FN5O3 | 442 (100%) |
| 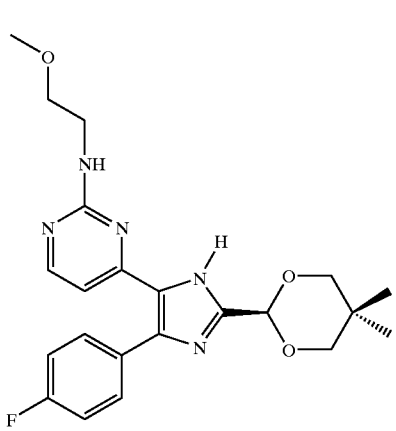 Compound IL | 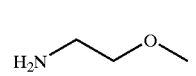 | 10.78 | C22H26FN5O3 | 428 (100%) |

TABLE 7a-continued

| STRUCTURE and COMPOUND NUMBER | HNY⁴Y⁵ | $R_T$ | MOLECULAR FORMULA | MH⁺ (Intensity) |
|---|---|---|---|---|
| 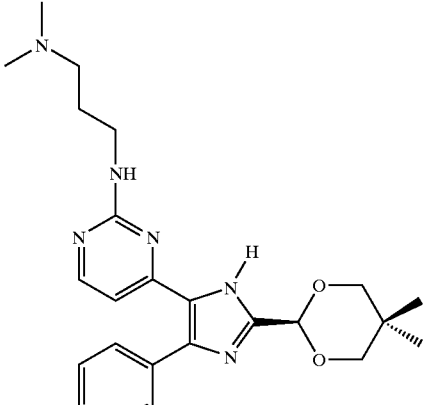<br>Compound IM | 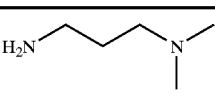 | 9.07 | C24H31FN6O2 | 455 (100%) |
| 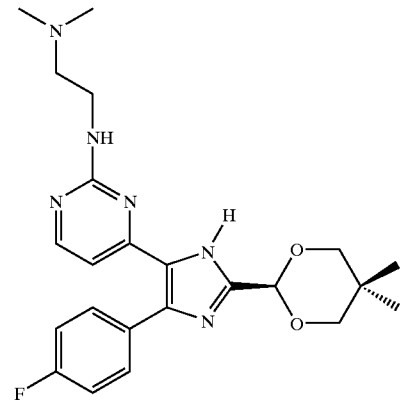<br>Compound IN | 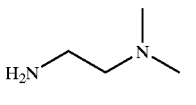 | 9.14 | C23H29FN6O2 | 441 (100%) |

(e) By proceeding in a similar manner to Example 23 (d) and using the appropriately substituted amine of formula HNY⁴Y⁵ there are prepared Compounds A17 to A35.

{4-[2-(5,5-dimethyl-[1,3]dioxan-2-yl)-5-(4-fluoro-phenyl)-3H-imidazol-4-yl]-pyrimidin-2-ylamino}-acetic acid, (Compound A17);

3-{4-[2-(5,5-dimethyl-[1,3]dioxan-2-yl)-5-(4-fluoro-phenyl)-3H-imidazol-4-yl]-pyrimidin-2-ylamino}-propionic acid, (Compound A18);

{4-[2-(5,5-dimethyl-[1,3]dioxan-2-yl)-5-(4-fluoro-phenyl)-3H-imidazol-4-yl]-pyrimidin-2-yl}-piperidin-4-yl-amine, (Compound A19);

{4-[2-(5,5-dimethyl-[1,3]dioxan-2-yl)-5-(4-fluoro-phenyl)-3H-imidazol-4-yl]-pyrimidin-2-yl}-isopropyl-amine, (Compound A20);

allyl-{4-[2-(5,5-dimethyl-[1,3]dioxan-2-y)-5-(4-fluoro-phenyl)-3H-imidazol-4-yl]-pyrimidin-2-yl}-amine, (Compound A21);

cyclopropylmethyl-{4-[2-(5,5-dimethyl-[1,3]dioxan-2-yl)-5-(4-fluoro-phenyl)-3H-imidazol-4-yl]-pyrimidin-2-yl}-amine, (Compound A22);

{4-[2-(5,5-dimethyl-[1,3]dioxan-2-yl)-5-(4-fluoro-phenyl)-3H-imidazol-4-yl]-pyrimidin-2-ylamino}-acetonitrile, (Compound A23);

3-{4-[2-(5,5-dimethyl-[1,3]dioxan-2-yl)-5-(4-fluoro-phenyl)-3H-imidazol-4yl]-pyrimidin-2-ylamino}-propionitrile, (Compound A24);

{4-[2-(5,5-dimethyl-[1,3]dioxan-2-yl)-5-(4-fluoro-phenyl)-3H-imidazol-4-yl]-pyrimidin-2-yl}-pyridin-3-yl-amine, (Compound A25);

{4-[2-(5,5-dimethyl-[1,3]dioxan-2-yl)-5-(4-fluoro-phenyl)-3H-imidazol-4-yl]-pyrimidin-2-yl}-pyridin-4-yl-amine, (Compound A26);

2-{4-[2-(5,5-dimethyl-[1,3]dioxan-2-yl)-5-(4-fluoro-phenyl)-3H-imidazol-4-yl]-pyrimidin-2-ylamino}-acetamide, (Compound A27);

3-{4-[2-(5,5-dimethyl-[1,3]dioxan-2-yl)-5-(4-fluoro-phenyl)-3H-imidazol-4-yl]-pyrimidin-2-ylamino}-propionamide, (Compound A28);

{4-[2-(5,5-dimethyl-[1,3]dioxan-2-yl)-5-(4-fluoro-phenyl)-3H-imidazol-4-yl]-pyrimidin-2-yl}-propyl-amine, (Compound A29);

4-[2-(5,5-dimethyl-[1,3]dioxan-2-yl)-5-(4-fluoro-phenyl)-3H-imidazol-4-yl]-2-pyrrolidin-1-yl-pyrimidime, (Compound A30);

4-fluorobenzyl-{4-[2-(5,5-dimethyl-[1,3]dioxan-2-yl)-5-(4-fluoro-phenyl)-3H-imidazol-4-yl]-pyrimidin-2-yl}-amine, (Compound A31);

4-methoxybenzyl-{4-[2-(5,5-dimethyl-[1,3]dioxan-2-yl)-5-(4-fluoro-phenyl)-3H-imidazol-4-yl]-pyrimidin-2-yl}-amine, (Compound A32);

{4-[2-(5,5-dimethyl-[1,3]dioxan-2-yl)-5-(4-fluoro-phenyl)-3H-imidazol-4-yl]-pyrimidin-2-yl}-4-fluorophenyl-amine, (Compound A33);

{4-[2-(5,5-dimethyl-[1,3]dioxan-2-yl)-5-(4-fluoro-phenyl)-3H-imidazol-4-yl]-pyrimidin-2-yl}-3,4-difluorophenyl-amine, (Compound A34);

{4-[2-(5,5-dimethyl-[1,3]dioxan-2-yl)-5-(4-fluoro-phenyl)-3H-imidazol-4-yl]-pyrimidin-2-yl}-3-methoxyphenyl-amine, (Compound A35);

(f) By proceeding in a similar manner to Example 23(a), but using {2-[4-(4-fluoro-phenyl)-5-(2-methylsulphonyl-pyrimidin-4-yl)-1H-imidazol-2-yl]-5-methyl-[1,3]dioxan-5-yl}-methanol, trans isomer, (Compound KJ) and replacing cyclopropylamine with liquid ammonia and carrying out the reaction under pressure for 2 days, there was prepared following preparative thin layer chromatography on silica gel [eluting with a mixture of dichloromethane, methanol and ammonia (90:10:2, v/v/v)] {2-[5-(2-amino-pyrimidin-4-yl)-4-(4-fluoro-phenyl)-1H-imidazol-2-yl]-5-methyl-[1,3]dioxan-5-yl)-methanol, trans-isomer (Compound IO) as a white solid. MH$^+$ 386. R$_F$: 0.41 (solvent as described immediately above).

(g) By proceeding in a similar manner to Example 23 (b) but using {2-[4-(4-fluoro-phenyl)-5-(2-methylsulphonyl-pyrimidin-4-yl)-1H-imidazol-2-yl]-5-methyl-[1,3]dioxan-5-yl}-methanol, trans isomer, (Compound KJ) there are prepared Compounds A36 to A79:

{2-[4-(4-fluoro-phenyl)-5-(2-methylamino-pyrimidin-4-yl)-1H-imidazol-2-yl]-5methyl-[1,3]dioxan-5-yl}-methanol, trans-isomer, (Compound A36);

{2-[5-(2-dimethylamino-pyrimidin-4-yl)-4-(4-fluoro-phenyl)-1H-imidazol-2-yl]-5-methyl-[1,3]dioxan-5-yl}-methanol, trans-isomer, (Compound A37);

{2-[5-(2-cyclopropylamino-pyrimidin-4-yl)-4-(4-fluoro-phenyl)-1H-imidazol-2-yl]-5-methyl-[1,3]dioxan-5-yl}-methanol, trans-isomer, (Compound A38);

(2-{4-(4-fluoro-phenyl)-5-[2-(piperidin-4-ylamino)-pyrimidin-4-yl]-1H-imidazol-2-yl}-5-methyl-[1,3]dioxan-5-yl)-methanol, trans-isomer, (Compound A39);

{2-[5-(2-cyclohexylamino-pyrimidin-4-yl)-4-(4-fluoro-phenyl)-1H-imidazol-2-yl]-5-methyl-[1,3]dioxan-5-yl}-methanol, trans-isomer, (Compound A40);

2-{4-[5-(4-fluoro-phenyl)-2-(5-hydroxymethyl-5-methyl-[1,3]dioxan-2-yl)-3H-imidazol-4-yl]-pyrimidin-2-ylamino}-ethanol, trans-isomer, (Compound A41);

{2-[5-[2-(2-amino-ethylamino)-pyrimidin-4-yl]-4-(4-fluoro-phenyl)-1H-imidazol-2-yl]-5-methyl-[1,3]dioxan-5-yl}-methanol, trans-isomer, (Compound A42);

[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-yl]-methanol, trans-isomer, (Compound A43);

(2-{4-(4-fluoro-phenyl)-5-[2-(3-morpholin-4-yl-propylamino)-pyrimidin-4-yl]-1H-imidazol-2-yl}-5-methyl-[1,3]dioxan-5-yl)-methanol, trans-isomer, (Compound A44);

3-{4-[5-(4-fluoro-phenyl)-2-(5-hydroxymethyl-5-methyl-[1,3]dioxan-2-yl)-3H-imidazol-4-yl]-pyrimidin-2-ylamino}-propan-1-ol, trans-isomer, (Compound A45);

{2-[5-(2-benzylamino-pyrimidin-4-yl)-4-(4-fluoro-phenyl)-1H-imidazol-2-yl]-5-methyl-[1,3]dioxan-5-yl}-methanol, trans-isomer, (Compound A46);

{2-[5-(2-(4-fluorobenzyl)amino-pyrimidin-4-yl)-4-(4-fluoro-phenyl)-1H-imidazol-2-yl]-5-methyl-[1,3]dioxan-5-yl}-methanol, trans-isomer, (Compound A47);

{2-[5-(2-(4-methoxybenzyl)amino-pyrimidin-4-yl)-4-(4-fluoro-phenyl)-1H-imidazol-2-yl]-5-methyl-[1,3]dioxan-5-yl}-methanol, trans-isomer, (Compound A48);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-methanol, R isomer, trans-isomer, (Compound A49);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-methanol, S isomer, trans-isomer, (Compound A50);

{2-[4-(4-fluoro-phenyl)-5-(2-phenylamino-pyrimidin-4-yl)-1H-imidazol-2-yl]-5-methyl-[1,3]dioxan-5-yl}-methanol, trans-isomer, (Compound A51);

{2-[4-(4-fluoro-phenyl)-5-(2-(4-fluorophenyl)amino-pyrimidin-4-yl)-1H-imidazol-2-yl]-5-methyl-[1,3]dioxan-5-yl}-methanol, trans-isomer, (Compound A52);

2-[4-(4-fluoro-phenyl)-5-(2-(3,4-difluorophenyl)amino-pyrimidin-4-yl)-1H-imidazol-2-yl]-5-methyl-[1,3]dioxan-5-yl}-methanol, trans-isomer, (Compound A53);

{2-[4-(4-fluoro-phenyl)-5-(2-(3-methoxyphenyl)amino-pyrinidin-4-yl)-1H-imidazol-2-yl]-5-methyl-[1,3]dioxan-5-yl}-methanol, trans-isomer, (Compound A54);

{2-[4-(4-fluoro-phenyl)-5-(2-piperidin-1-yl-pyrimidin-4-yl)-1H-imidazol-2-yl]-5-methyl-[1,3]dioxan-5-yl}-methanol, trans-isomer, (Compound A55);

[2-(4-(4-fluoro-phenyl)-5-{2-[(pyridin-4-ylmethyl)-amino]-pyrimidin-4-yl}-1H-imidazol-2-5-methyl-[1,3]dioxan-5-yl]-methanol, trans-isomer, (Compound A56);

[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-yl]-methanol, trans-isomer, (Compound A57);

[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-yl]-methanol, trans-isomer, (Compound A58);

[2-(4-(4-fluoro-phenyl)-5-{2-[(furan-2-ylmethyl)-amino]-pyrimidin-4-yl}-1H-imidazol-2-yl)-5-methyl-[1,3]dioxan-5-yl]-methanol, trans-isomer, (Compound A59);

[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-yl]-methanol, trans-isomer, (Compound A60);

[2-(4-(4-fluoro-phenyl)-5-{2-[(tetrahydro-furan-2-ylmethyl)-amino]-pyrimidin-4-yl}1H-imidazol-2-yl)-5-methyl-[1,3]dioxan-5-yl]-methanol, trans-isomer, (Compound A61);

(2-{4-(4-fluoro-phenyl)-5-[2-(4-methyl-piperazin-1-yl)-pyrimidin-4-yl]-1H-imidazol-2yl}-5-methyl-[1,3]dioxan-5-yl)-methanol, trans-isomer, (Compound A62);

{2-[4-(4-fluoro-phenyl)-5-(2-morpholin-4-yl-pyrimidin-4-yl)-1H-imidazol-2-yl]-5-methyl-[1,3]dioxan-5-yl}-methanol, trans-isomer, (Compound A63);

(2-{4-(4-fluoro-phenyl)-5-[2-(3-methoxy-propylamino)-pyrimidin-4-yl]-1H-imidazol-2-yl}-5-methyl-[1,3]dioxan-5-yl)-methanol, trans-isomer, (Compound A64);

(2-{4-(4-fluoro-phenyl)-5-[2-(2-methoxy-ethylamino)-pyrimidin-4-yl]-1H-imidazol-2-yl}-5-methyl-[1,3]dioxan-5-yl)-methanol, trans-isomer, (Compound A65);

{2-[5-[2-(3-dimethylamino-propylamino)-pyrimidin-4-yl]-4-(4-fluoro-phenyl)-1H-imidazol-2-yl]-5-methyl-[1,3]dioxan-5-yl}-methanol, trans-isomer, (Compound A66);

{2-[5-[2-(2-dimethylamino-ethylamino)-pyrimidin-4-yl]-4-(4-fluoro-phenyl)-1H-imidazol-2-yl]-5-methyl-[1,3]dioxan-5-yl}-methanol, trans-isomer, (Compound A67);

{4-[5-(4-fluoro-phenyl)-2-(5-hydroxymethyl-5-methyl-[1,3]dioxan-2-yl)-3H-imidazol-4-yl]-pyrimidin-2-ylamino}-acetic acid, trans-isomer, (Compound A68);

3-{4-[5-(4-fluoro-phenyl)-2-(5-hydroxymethyl-5-methyl-[1,3]dioxan-2-yl)-3H-imidazol-4-yl]-pyrimidin-2-ylamino}-propionic acid, trans-isomer, (Compound A69);

{2-[4-(4-fluoro-phenyl)-5-(2-isopropylamino-pyrimidin-4-yl)-1H-imidazol-2-yl]-5-methyl-[1,3]dioxan-5-yl}-methanol, trans-isomer, (Compound A70);

{2-[5-(2-allylamino-pyrimidin-4-yl)-4-(4-fluoro-phenyl)-1H-imidazol-2-yl]-5-methyl-[1,3]dioxan-5yl}-methanol, trans-isomer, (Compound A71);

{2-[5-[2-(cyclopropylmethyl-amino)-pyrimidin-4-yl]-4-(4-fluoro-phenyl)-1H-imidazol-2-yl]-5-methyl-[1,3]dioxan-5-yl}-methanol, trans-isomer, (Compound A72);

{4-[5-(4-fluoro-phenyl)-2-(5-hydroxymethyl-5-methyl-[1,3]dioxan-2-yl)-3H-imidazol-4-yl]-pyrimidin-2-ylamino}-acetonitrile, trans-isomer, (Compound A73);

3-{4-[5-(4-fluoro-phenyl)-2-(5-hydroxymethyl-5-methyl-[1,3]dioxan-2-yl)-3H-imidazol-4-yl]-pyrimidin-2-ylamino}-propionitrile, trans-isomer, (Compound A74);

(2-{4-(4-fluoro-phenyl)-5-[2-(pyridin-3-ylamino)-pyrimidin-4-yl]-1H-imidazol-2-yl}-5-methyl-[1,3]dioxan-5-yl)-methanol, trans-isomer, (Compound A75);

(2-{4-(4-fluoro-phenyl)-5-[2-(pyridin-4-ylamino)-pyrimidin-4-yl]-1H-imidazol-2-yl}-5-methyl-[1,3]dioxan-5-yl)-methanol, trans-isomer, (Compound A76);

2-{4-[5-(4-fluoro-phenyl)-2-(5-hydroxymethyl-5-methyl-[1,3]dioxan-2-yl)-3H-imidazol-4-yl]-pyrimdin-2-ylamino}-acetamide, trans-isomer, (Compound A77);

3-{4-[5-(4-fluoro-phenyl)-2-(5-hydroxymethyl-5-methyl-[1,3]dioxan-2-yl)-3H-imidazol-4-pyrimidin-2-ylamino}-propionamide, trans-isomer, (Compound A78);

{2-[4-(4-fluoro-phenyl)-5-(2-propylamino-pyrimidin-4-yl)-1H-imidazol-2-yl]-5-methyl-[1,3]dioxan=5-yl}-methanol, trans-isomer, (Compound A79);

(h) By proceeding in a similar manner to Example 23 (g) but using {2-[4-(4-fluoro-phenyl)-5-(2-methylsulphonyl-pyrimidin-4-yl)-1H-imidazol-2-yl]-5-methyl-[1,3]dioxan-5-yl}-methanol, cis-isomer, (Compound KK) there are prepared the corresponding cis-isomers of Compounds A36 to A79.

(i) By proceeding in a similar manner to Example 23 (b) but using 2-[4-(4-fluoro-phenyl)-5-(2-methylsulphonylpyrimidin-4-yl)-1H-imidazol-2-yl]-5-methylene-[1,3]dioxane (Compound KL) there are prepared compounds A80 to A125:

4-[5-(4-fluoro-phenyl)-2-(5-methylene-[1,3]dioxan-2-yl)-3H-imidazol-4-yl]-pyrimidin-2-ylamine, (Compound A80);

{4-[5-(4-fluoro-phenyl)-2-(5-methylene-[1,3]dioxan-2-yl)-3H-imidazol-4-yl]-pyrimidin-2-yl}-methyl-amine, (Compound A81);

{4-[5-(4-fluoro-phenyl)-2-(5-methylene-[1,3]dioxan-2-yl)-3H-imidazol-4-yl]-pyrimidin-2-2-yl}-dimethyl-amine, (Compound A82);

cyclopropyl-{4-[5-(4-fluoro-phenyl)-2-(5-methylene-[1,3]dioxan-2-yl)-3H-imidazol-4-]-pyrimidin-2-yl}-amine, (Compound A83);

{4-[5-(4-fluoro-phenyl)-2-(5-methylene-[1,3]dioxan-2-yl)-3H-imidazol-4-yl]-pyrimidin-2-yl}-piperdin-4-yl-amine, (Compound A84);

cyclohexyl-{4-[5-(4-fluoro-phenyl)-2-(5-methylene-[1,3]dioxan-2-yl)-3H-imidazol-4-yl]-pyrimidin-2-yl}-amine, (Compound A85);

2-{4-[5-(4-fluoro-phenyl)-2-(5-methylene-[1,3]dioxan-2-yl)-3H-imidazol-4-yl]-pyrimidin-2-ylamino}-ethanol, (Compound A86);

N1-{4-[5-(4-fluoro-phenyl)-2-(5-methylene-[1,3]dioxan-2-yl)-3H-imidazol-4-yl]-pyrimidin-2-yl}-ethane-1,2-diamine, (Compound A87);

{4-[5-(4-fluoro-phenyl)-2-(5-methylene-[1,3]dioxan-2-yl)-3H-imidazol-4-yl]-pyrimidin-2-yl}-[3-(5H-imidazol-1-yl)-propyl]-amine, (Compound A88);

{4-[5-(4-fluoro-phenyl)-2-(5-methylene-[1,3]dioxan-2-yl)-3H-imidazol-4-yl]-pyrimidin-2-yl}-(3-morpholin-4-yl-propyl)-amine, (Compound A89);

3-{4-[5-(4-fluoro-phenyl)-2-(5-methylene-[1,3]dioxan-2-yl)-3H-imidazol-4-yl]-pyrimidin-2-ylamino}-propan-1-ol, (Compound A90);

benzyl-{4-[5-(4-fluoro-phenyl)-2-(5-methylene-[1,3]dioxan-2-yl)-3H-imidazol-4-yl]-pyrimidin-2-yl}-amine, (Compound A91);

4-fluorobenzyl-{4-[5-(4-fluoro-phenyl)-2-(5-methylene-[1,3]dioxan-2-yl)-3H-imidazol-4-yl]-pyrimidin-2-yl}-amine, (Compound A92);

4-methoxybenzyl-{4-[5-(4-fluoro-phenyl)-2-(5-methylene-[1,3]dioxan-2-yl)-3H-imidazol-4-yl]-pyrimidin-2-yl}-amine, (Compound A93);

{4-[5-(4-fluoro-phenyl)-2-(5-methylene-[1,3]dioxan-2-yl)-3H-imidazol-4-yl]-pyrimidin-2-yl}-(1-phenyl-ethyl)-amine, R isomer, (Compound A94);

{4-[5-(4-fluoro-phenyl)-2-(5-methylene-[1,3]dioxan-2-yl)-3H-imidazol-4-yl]-pyrimidin-2-yl}-(1-phenyl-ethyl)-amine, S isomer, (Compound A95);

{4-[5-(4-fluoro-phenyl)-2-(5-methylene-[1,3]dioxan-2-yl)-3H-imidazol-4-yl]-pyrimidin-2-yl}-phenyl-ethyl-amine, (Compound A96);

{4-[5-(4-fluoro-phenyl)-2-(5-methylene-[1,3]dioxan-2-yl)-3H-imidazol-4-yl]-pyrimidin-2-yl}-4-fluorophenyl-amine, (Compound A97);

{4-[5-(4-fluoro-phenyl)-2-(5-methylene-[1,3]dioxan-2-yl)-3H-imidazol-4-yl]-pyrimidin-2-yl}-3,4-difluorophenyl-amine, (Compound A98);

{4-[5-(4-fluoro-phenyl)-2-(5-methylene-[1,3]dioxan-2-yl)-3H-imidazol-4-yl]-pyrimidin-2-yl}-3-methoxyphenyl-amine, (Compound A99);

4-[5-(4-fluoro-phenyl)-2-(5-methylene-[1,3]dioxan-2-yl)-3H-imidazol-4yl]-2-piperidin-1-pyrimidine, (Compound A100);

{4-[5-(4-fluoro-phenyl)-2-(5-methylene-[1,3]dioxan-2-yl)-3H-imidazol-4-yl]-pyrimidin-2-yl}-pyridin-4-ylmethyl-amine, (Compound A101);

{4-[5-(4-fluoro-phenyl)-2-(5-methylene-[1,3]dioxan-2-yl)-3H-imidazol-4-yl]-pyrimidin-2-yl}-pyridin-3-ylmethyl-amine, (Compound A102);

{4-[5-(4-fluoro-phenyl)-2-(5-methylene-[1,3]dioxan-2-yl)-3H-imidazol-4-yl]-pyrimidin-2-yl}-pyridin-2-ylmethyl-amine, (Compound A103);

{4-[5-(4-fluoro-phenyl)-2-(5-methylene-[1,3]dioxan-2-yl)-3H-imidazol-4-yl]-pyrimidin-2-yl}-(furan-2-ylmethyl)-amine, (Compound A104);

{4-[5-(4-fluoro-phenyl)-2-(5-methylene-[1,3]dioxan-2-yl)-3H-imidazol-4-yl]-pyrimidin-2-yl}-(thiophen-2-ylmethyl)-amine, (Compound A105);

{4-[5-(4-fluoro-phenyl)-2-(5-methylene-[1,3]dioxan-2-yl)-3H-imidazol-4-yl]-pyrimidin-2-yl}-(tetrahydro-furan-2-ylmethyl)-amine, (Compound A106);

4-[5-(4-fluoro-phenyl)-2-(5-methylene-[1,3]dioxan-2-yl)-3H-imidazol-4-yl]-2-(4-methyl-piperazin-1-yl)-pyrimidine, (Compound A107);

4-{4-[5-(4-fluoro-phenyl)-2-(5-methylene-[1,3]dioxan-2-yl)-3H-imidazol-4-yl]-pyrimidin-2yl}-morpholine, (Compound A108);

{4-[5-(4-fluoro-phenyl)-2-(5-methylene-[1,3]dioxan-2-yl)-3H-imidazol-4-yl]-pyrimidin-2yl}-(3-methoxy-propyl)-amine, (Compound A109);

{4-[5-(4-fluoro-phenyl)-2-(5-methylene-[1,3]dioxan-2-yl)-3H-imidazol-4-yl]-pyrimidin-2yl}-(2-methoxy-ethyl)-amine, (Compound A110);

N-{4-[5-(4-fluoro-phenyl)-2-(5-methylene-[1,3]dioxan-2-yl)-3H-imidazol-4-yl]-pyrimidin-2yl}-N',N'-dimethyl-propane-1,3-diamine, (Compound A111);

N-{4-[5-(4-fluoro-phenyl)-2-(5-methylene-[1,3]dioxan-2-yl)-3H-imidazol-4-yl]-pyrimidin-2yl}-N',N'-dimethyl-ethane-1,2-diamine, (Compound A112);

{4-[5-(4-fluoro-phenyl)-2-(5-methylene-[1,3]dioxan-2-yl)-3H-imidazol-4yl]-pyrimidin-2-ylamino}-acetic acid, (Compound A113);

3-{4-[5-(4-fluoro-phenyl)-2-(5-methylene-[1,3]dioxan-2-yl)-3H-imidazol-4-yl]-pyrimidin-2-ylamino}-propionic acid, (Compound A114);

{4-[5-(4-fluoro-phenyl)-2-(5-methylene-[1,3]dioxan-2-yl)-3H-imidazol-4-yl]-pyrimidin-2-yl}-isoprop1-amine, (Compound A115);

allyl-{4-[5-(4-fluoro-phenyl)-2-(5-methylene-[1,3]dioxan-2-yl)-3H-imidazol-4-yl]-pyrimidin-2-yl}-amine, (Compound A116);

cyclopropylmethyl-{4-[5-(4-fluoro-phenyl)-2-(5-methylene-[1,3]dioxan-2-yl)-3H-imidazol-4-yl]-pyrimidin-2-yl}-amine, (Compound A117);

{4-[5-(4-fluoro-phenyl)-2-(5-methylene-[1,3]dioxan-2-yl)-3H-imidazol-4-yl]-pyrimidin-2-ylamino}-acetonitrile, (Compound A118);

3-{4-[5-(4-fluoro-phenyl)-2-(5-methylene-[1,3]dioxan-2-yl)-3H-imidazol-4-yl]-pyrimidin-2-ylamino}-propionitrile, (Compound A119);

{4-[5-(4-fluoro-phenyl)-2-(5-methylene-[1,3]dioxan-2-yl)-3H-imidazol-4-yl]-pyrimidin-2-yl}-pyridin-3-yl-amine, (Compound A120);

{4-[5-(4-fluoro-phenyl)-2-(5-methylene-[1,3]dioxan-2-yl)-3H-imidazol-4-yl]-pyrimidin-2-yl}-pyridin-4-yl-amine, (Compound A121);

2-{4-[5-(4-fluoro-phenyl)-2-(5-methylene-[1,3]dioxan-2-yl)-3H-imidazol-4-yl]-pyrimidin-2-ylamino}-acetamide, (Compound A122);

3-{4-[5-(4-fluoro-phenyl)-2-(5-methylene-[1,3]dioxan-2-yl)-3H-imidazol-4-yl]-pyrimidin-2-ylamino}-propionamide, (Compound A123);

{4-[5-(4-fluoro-phenyl)-2-(5-methylene-[1,3]dioxan-2-yl)-3H-imidazol-4-yl]-pyrimidin-2-yl}-propyl-amine, (Compound A124);

4-[5-(4-fluoro-phenyl)-2-(5-methylene-[1,3]dioxan-2-yl)-3H-imidazol-4-yl]-2-pyrimidin-1-yl-pyrimidine, (Compound A125);

(j) By proceeding in a similar manner to Example 23(b) but using 4-[2-[1,3]dioxan-2-yl-5-(4-fluoro-phenyl)-3H-imidazol-4-yl]-2-methylsulphonyl-pyrimidine (Compound KM) there are prepared Compounds A126 to A170:

4-[2-[1,3]dioxan-2-yl-5-(4-fluoro-phenyl)-3H-imidazol-4-yl]-pyrimidin-2-ylamine, (Compound A126);

{4-[2-[1,3]dioxan-2-yl-5-(4-fluoro-phenyl)-3H-imidazol-4-yl]-pyrimidin-2-yl}-methyl-amine, (Compound A127);

{4-[2-[1,3]dioxan-2-yl-5-(4-fluoro-phenyl)-3H-imidazol-4-yl]-pyrimidin-2-yl}-dimethyl-amine, (Compound A128);

cyclopropyl-{4-[2-[1,3]dioxan-2-yl-5-(4-fluoro-phenyl)-3H-imidazol-4-yl]-pyrimidin-2-yl}-amine, (Compound A129);

{4-[2-[1,3]dioxan-2-yl-5-(4-fluoro-phenyl)-3H-imidazol-4-yl]-pyrimidin-2-yl}-piperidin-4-yl-amine, (Compound A130);

cyclohexyl-{4-[2-[1,3]dioxan-2-yl-5-(4-fluoro-phenyl)-3H-imidazol-4-yl]-pyrimidin-2-yl}-amine, (Compound A131);

2-{4-[2-[1,3]dioxan-2-yl-5-(4-fluoro-phenyl)-3H-imidazol-4-yl]-pyrimidin-2-ylamino}-ethanol, (Compound A132);

N1-{4-[2-[1,3]dioxan-2-yl-5-(4-fluoro-phenyl)-3H-imidazol-4-yl]-pyrimidin-2-yl}-ethane-1,2-diamine, (Compound A133);

{4-[2-[1,3]dioxan-2-yl-5-(4-fluoro-phenyl)-3H-imidazol-4-yl]-pyrimidin-2-yl}-[3-(5H-imidazol-1-yl)-propyl]-amine, (Compound A134);

{4-[2-[1,3]dioxan-2-yl-5-(4-fluoro-phenyl)-3H-imidazol-4-yl]-pyrimidin-2-yl}-(3-morpholin-4-yl-propyl)-amine, (Compound A135);

3-{4-[2-[1,3]dioxan-2-yl-5-(4-fluoro-phenyl)-3H-imidazol-4-yl]-pyrimidin-2-ylamino}-propan-1-ol, (Compound A136);

benzyl-{4-[2-[1,3]dioxan-2-yl-5-(4-fluoro-phenyl)-3H-imidazol-4-yl]-pyrimidin-2-yl}-amine, (Compound A137);

4-fluorobenzyl-{4-[2-[1,3]dioxan-2-yl-5-(4-fluoro-phenyl)-3H-imidazol-4-yl]-pyrimidin-2-yl}-amine, (Compound A138);

4-methoxybenzyl-{4-[2-[1,3]dioxan-2-yl-5-(4-fluoro-phenyl)-3H-imidazol-4-yl]-pyrimidin-2-yl}-amine, (Compound A139);

{4-[2-[1,3]dioxan-2-yl-5-(4-fluoro-phenyl)-3H-imidazol-4-yl]-pyrimidin-2-yl}-(1-phenyl-ethyl)-amine, R isomer, (Compound A140);

{4-[2-[1,3]dioxan-2-yl-5-(4-fluoro-phenyl)-3H-imidazol-4-yl]-pyrimidin-2-yl}-(1-phenyl-ethyl)-amine, S isomer, (Compound A141);

{4-[2-[1,3]dioxan-2-yl-5-(4-fluoro-phenyl)-3H-imidazol-4-yl]-pyrimidin-2-yl}-phenyl-amine, (Compound A142);

{4-[2-[1,3]dioxan-2-yl-5-(4-fluoro-phenyl)-3H-imidazol-4-yl]-pyrimidin-2-yl}-(4-fluorophenyl)-amine, (Compound A143);

{4-[2-[1,3]dioxan-2-yl-5-(4-fluoro-phenyl)-3H-imidazol-4-yl]-pyrimidin-2-yl}-(3,4-difluorophenyl)-amine, (Compound A144);

{4-[2-[1,3]dioxan-2-yl-5-(4-fluoro-phenyl)-3H-imidazol-4-yl]-pyrimidin-2-yl}-(4-methoxyphenyl)-amine, (Compound A145);

4-[2-[1,3]dioxan-2-yl-5-(4-fluoro-phenyl)-3H-imidazol-4-yl]-2-piperidin-1-yl-pyrimidine, (Compound A146);

{4-[2-[1,3]dioxan-2-yl-5-(4-fluoro-phenyl)-3H-imidazol-4-yl]-pyrimidin-2-yl}-pyridin-4-ylmethyl-amine, (Compound A147);

{4-[2-[1,3]dioxan-2-yl-5-(4-fluoro-phenyl)-3H-imidazol-4-yl]-pyrimidin-2-yl}-pyridin-3-ylmethyl-amine, (Compound A148);

{4-[2-[1,3]dioxan-2-yl-5-(4-fluoro-phenyl)-3H-imidazol-4-yl]-pyrimidin-2-yl}-pyridin-2-ylmethyl-amine, (Compound A149);

{4-[2-[1,3]dioxan-2-yl-5-(4-fluoro-phenyl)-3H-imidazol-4-yl]-pyrimidin-2-yl}-(furan-2-ylmethyl)-amine, {4-[2-[1,3]dioxan-2-yl-5-(4-fluoro-phenyl)-3H-imidazol-4-yl]-pyrimidin-2-yl}-(thiophen-2-ylmethyl)-amine, (Compound A150);

{4-[2-[1,3]dioxan-2-yl-5-(4-fluoro-phenyl)-3H-imidazol-4-yl]-pyrimidin-2-yl}-(tetrahydro-furan -2-ylmethyl-amine, (Compound A151);

4-[2-[1,3]dioxan-2-yl-5-(4-fluoro-phenyl)-3H-imidazol-4-yl]-2-(4-methyl-piperazin-1-yl)-pyrimidine, (Compound A152);

4-{4-[2-[1,3]dioxan-2-yl-5-(4-fluoro-phenyl)-3H-imidazol-4-yl]-pyrimidin-2yl}morpholine, (Compound A153);

{4-[2-[1,3]dioxan-2-yl-5-(4-fluoro-phenyl)-3H-imidazol-4-yl]-pyrimidin-2-yl}-(3-methoxy-propyl)-amine, (Compound A154);

{4-[2-[1,3]dioxan-2-yl-5-(4-fluoro-phenyl)-3H-imidazol-4-yl]-pyrimidin-2-yl}-(2-methoxy-ethyl)-amine, (Compound A155);

N-{4-[2-[1,3]dioxan-2-yl-5-(4-fluoro-phenyl)-3H-imidazol-4-yl]-pyrimidin-2-yl}-N',N'-dimethyl-propane-1,3-diamine, (Compound A156);

N-{4-[2-[1,3]dioxan-2-yl-5-(4-fluoro-phenyl)-3H-imidazol-4-yl]-pyrimidin-2-yl}-N',N'-dimethyl-ethane-1,2-diamine, (Compound A157);

{4-[2-[1,3]dioxan-2-yl-5-(4-fluoro-phenyl)-3H-imidazol-4-yl]-pyrimidin-2-ylamino}-acetic acid, (Compound A158);

3-{4-[2-[1,3]dioxan-2-yl-5-(4-fluoro-phenyl)-3H-imidazol-4-yl]-pyrimidin-2-ylamino}-propionic acid, (Compound A159);

{4-[2-[1,3]dioxan-2-yl-5-(4-fluoro-phenyl)-3H-imidazol-4-yl]-pyrimidin-2-yl}-isopropyl-amine, (Compound A160);

allyl-{4-[2-[1,3]dioxan-2-yl-5-(4-fluoro-phenyl)-3H-imidazol-4-yl]-pyrimidin-2-yl}-amine, (Compound A161);

cyclopropylmethyl-{4-[2-[1,3]dioxan-2-yl-5-(4-fluoro-phenyl)-3H-imidazol-4-yl]-pyrimidin-2-yl}amine, (Compound A162);

{4-[2-[1,3]dioxan-2-yl-5-(4-fluoro-phenyl)-3H-imidazol-4-yl]-pyrimidin-2-ylamino}-acetonitrile, (Compound A163);

3-{4-[2-[1,3]dioxan-2-yl-5-(4-fluoro-phenyl)-3H-imidazol-4-yl]-pyrimidin-2-ylamino}-propionitrile, (Compound A164);

{4-(2-[1,3]dioxan-2-yl-5-(4-fluoro-phenyl)-3H-imidazol-4-yl]-pyrimidin-2yl}-pyridin-3-yl-amine, (Compound A165);

{4-[2-[1,3]dioxan-2-yl-5-(4-fluoro-phenyl)-3H-imidazol-4-yl]-pyrimidin-2yl}-pyridin-4-yl-amine, (Compound A166);

2-{4-[2-[1,3]dioxan-2-yl-5-(4-fluoro-phenyl)-3H-imidazol-4-yl]-pyrimidin-2-ylamino}-acetamide, (Compound A167);

3-{4-[2-[1,3]dioxan-2-yl-5-(4-fluoro-phenyl)-3H-imidazol-4-yl]-pyrimidin-2-ylamino}-propionamide, (Compound A168);

{4-[2-[1,3]dioxan-2-yl-5-(4-fluoro-phenyl)-3H-imidazol-4-yl]-pyrimidin-2-yl}-propyl-amine, (Compound A169);

4-[2-[1,3]dioxan-2-yl-5-(4-fluoro-phenyl)-3H-imidazol-4-yl]-2-pyrrolidin-1-yl-pyrimidine, (Compound A170);

(k) By proceeding in a similar manner to Example 23 (b) but using {2-[4-(4-fluoro-phenyl)-5-(2-methylsulphonyl-pyrimidin-4-yl)-1H-imidazol-2-yl]-[1,3]dioxan-5-yl}-methanol, trans-isomer, (Compound KN) there are prepared Compounds A171 to A215:

{2-[5-(2-amino-pyrimidin-4-yl)-4-(4-fluoro-phenyl)-1H-imidazol-2-yl]-[1,3]dioxan-5-yl}-methanol, trans-isomer, (Compound A171);

{2-[4-(4-fluoro-phenyl)-5-(2-methylamino-pyrimidin-4-yl)-1H-imidazol-2-yl]-[1,3]dioxan-5-yl}-methanol, trans-isomer, (Compound A172);

{2-[5-(2-dimethylamino-pyrimidin-4-yl)-4-(4-fluoro-phenyl)-1H-imidazol-2-yl]-[1,3]dioxan-5-yl}-methanol, trans-isomer, (Compound A173);

{2-[5-(2-cyclopropylamino-pyrimidin-4-yl)-4-(4-fluoro-phenyl)-1H-imidazol-2-yl]-[1,3]dioxan-5-yl}-methanol, trans-isomer, (Compound A174);

(2-{4-(4-fluoro-phenyl)-5-[2-(piperidin-4-ylamino)-pyrimidin-4-yl]-1H-imidazol-2-yl}-[1,3]dioxan-5-yl)-methanol, trans-isomer, (Compound A175);

{2-[5-(2-cyclohexylamino-pyrimidin-4-yl)-4-(4-fluoro-phenyl)-1H-imidazol-2-yl]-[1,3]dioxan-5-yl}-methanol, trans-isomer, (Compound A176);

2-{4-[5-(4-fluoro-phenyl)-2-(5-hydroxymethyl-[1,3]dioxan-2-yl)-3H-imidazol-4-yl]-pyrimidin-2-ylamino}-ethanol, trans-isomer, (Compound A177);

{2-[5-[2-(2-amino-ethylamino)-pyrimidin-4-yl]-4-(4-fluoro-phenyl)-1H-imidazol-2-yl]-[1,3]dioxan-5-yl}-methanol, trans-isomer, (Compound A178);

[2-(4-(4-fluoro-phenyl)-5-{2-[3-(5H-imidazol-1-yl)-propylamino]-pyrimidin-4-yl}-1H-imidazol-2-yl)-[1,3]dioxan-5-yl]-methanol, trans-isomer, (Compound A179);

(2-{4-(4-fluoro-phenyl)-5-[2-(3-morpholin-4-yl-propylamino)-pyrimidin-4-yl]-1H-imidazol-2-yl}-[1,3]dioxan-5-yl)-methanol, trans-isomer, (Compound A180);

3-{4-[5-(4-fluoro-phenyl)-2-(5-hydroxymethyl-[1,3]dioxan-2-yl)-3H-imidazol-4-yl]-pyrimidin-2-ylamino}-propan-1-ol, trans-isomer, (Compound A181);

{2-[5-(2-benzylamino-pyrimidin-4-yl)-4-(4-fluoro-phenyl)-1H-imidazol-2-yl]-[1,3]dioxan-5-yl}-methanol, trans-isomer, (Compound A182);

{2-[5-(2-(4-fluorobenzyl)amino-pyrimidin-4-yl)-4-(4-fluoro-phenyl)-1H-imidazol-2-yl]-[1,3]dioxan-5-yl}-methanol, trans-isomer, (Compound A183);

{2-[5-(2-(4-methoxybenzyl)amino-pyrimidin-4-yl)-4-(4-fluoro-phenyl)-1H-imidazol-2-yl]-[1,3]dioxan-5-yl}-methanol, trans-isomer, (Compound A184);

(2-{4-(4-fluoro-phenyl)-5-[2-(1-phenyl-ethylamino)-pyrimidin-4-yl]-1H-imidazol-2-yl}-[1,3]dioxan-5-yl)-methanol, R isomer, trans-isomer, (Compound A185);

(2-{4-(4-fluoro-phenyl)-5-[2-(1-phenyl-ethylamino)-pyrimidin-4-yl]-1H-imidazol-2-yl}-[1,3]dioxan-5-yl)-methanol, S isomer, trans-isomer, (Compound A186);

{2-[4-(4-fluoro-phenyl)-5-(2-phenylamino-pyrimidin-4-yl)-1H-imidazol-2-yl]-[1,3]dioxan-5-yl}-methanol, trans-isomer, (Compound A187);

{2-[4-(4-fluoro-phenyl)-5-(2-(4-fluorophenyl)amino-pyrimidin-4-yl)-1H-imidazol-2-yl]-[1,3]dioxan-5-yl}-methanol, trans-isomer, (Compound A188);

{2-[4-(4-fluoro-phenyl)-5-(2-(3,4-difluorophenyl)amino-pyrimidin-4-yl)-1H-imidazol-2-yl]-[1,3]dioxan-5-yl}-methanol, trans-isomer, (Compound A189);

{2-[4-(4-fluoro-phenyl)-5-(2-(4-methoxyphenyl)amino-pyrimidin-4-yl)-1H-imidazol-2-yl]-[1,3]dioxan-5-yl}-methanol, trans-isomer, (Compound A190);

{2-[4-(4-fluoro-phenyl)-5-(2-piperidin-1-yl-pyrimidin-4-yl)-1H-imidazol-2-yl]-[1,3]dioxan-5-yl}-methanol, trans-isomer, (Compound A191);

[2-(4-(4-fluoro-phenyl)-5-{2-[(pyridin-4-ylmethyl)-amino]-pyrimidin-4-yl}-1H-imidazol-2-yl)-[1,3]dioxan-5-yl]-methanol, trans-isomer, (Compound A192);

[2-(4-(4-fluoro-phenyl)-5-{2-[(pyridin-3-ylmethyl)-amino]-pyrimidin-4-yl}-1H-imidazol-2-yl)-[1,3]dioxan-5-yl]-methanol, trans-isomer, (Compound A193);

[2-(4-(4-fluoro-phenyl)-5-{2-[(pyridin-2-ylmethyl)-amino]-pyrimidin-4-yl}-1H-imidazol-2-yl)-[1,3]dioxan-5-yl]-methanol, trans-isomer, (Compound A194);

[2-(4-(4-fluoro-phenyl)-5-{2-[(furan-2-ylmethyl)-amino]-pyrimidin-4-yl}-1H-imidazol-2-yl)-[1,3]dioxan-5-yl]-methanol, trans-isomer, (Compound A195);

[2-(4-(4-fluoro-phenyl)-5-{2-[(thiophen-2-ylmethyl)-amino]-pyrimidin-4-yl}-1H-imidazol-2-yl)-[1,3]dioxan-5-yl]-methanol, trans-isomer, (Compound A196);

[2-(4-(4-fluoro-phenyl)-5-{2-[(tetrahydro-furan-2-ylmethyl)-amino]-pyrimidin-4-yl}-1H-imidazol-2-yl)-[1,3]dioxan-5-yl]-methanol, trans-isomer, (Compound A197);

(2-{4-(4-fluoro-phenyl)-5-[2-(4-methyl-piperazin-1-yl)-pyrimidin-4-yl]-1H-imidazol-2-yl}-[1,3]dioxan-5-yl)-methanol, trans-isomer, (Compound A198);

{2-[4-(4-fluoro-phenyl)-5-(2-morpholin-4-yl-pyrimidin-4-yl)-1H-imidazol-2-yl]-[1,3]dioxan-5-yl}-methanol, trans-isomer, (Compound A199);

(2-{4-(4-fluoro-phenyl)-5-[2-(3-methoxy-propylamino)-pyrimidin-4-yl]-1H-imidazol-2-yl}-[1,3]dioxan-5-yl)-methanol, trans-isomer, (Compound A200);

(2-{4-(4-fluoro-phenyl)-5-[2-(2-methoxy-ethylamino)-pyrimidin-4-yl]-1H-imidazol-2-yl}-[1,3]dioxan-5-yl)-methanol, trans-isomer, (Compound A201);

{2-[5-[2-(3-dimethylamino-propylamino)-pyrimidin-4-yl]-4-(4-fluoro-phenyl)-1H-imidazol-2-yl]-[1,3]dioxan-5-yl}-methanol, trans-isomer, (Compound A202);

{2-[5-[2-(2-dimethylamino-ethylamino)-pyrimidin-4-yl]-4-(4-fluoro-phenyl)-1H-imidazol-2yl]-[1,3]dioxan-5-yl}-methanol, trans-isomer, (Compound A203);

{4-[5-(4-fluoro-phenyl)-2-(5-hydroxymethyl-[1,3]dioxan-2-yl)-3H-imidazol-4-yl]-pyrimidin-2-ylamino}-acetic acid, trans-isomer, (Compound A204);

3-{4-[5-(4-fluoro-phenyl)-2-(5-hydroxymethyl-[1,3]dioxan-2-yl)-3H-imidazol-4-yl]-pyrimidin-2-ylamino}-propionic acid, trans-isomer, (Compound A205);

{2-[4-(4-fluoro-phenyl)-5-(2-isopropylamino-pyrimidin-4-yl)-1H-imidazol-2-yl]-[1,3]dioxan-5-yl}-methanol, trans-isomer, (Compound A206);

{2-[5-(2-allylamino-pyrimidin-4-yl)-4-(4-fluoro-phenyl)-1H-imidazol-2-yl]-[1,3]dioxan-5-yl}-methanol, trans-isomer, (Compound A207);

{2-[5-[2-(isopropylmethyl-amino)-pyrimidin-4-yl]-4-(4-fluoro-phenyl)-1H-imidazol-2-yl]-[1,3]dioxan-5-yl}-methanol, trans-isomer, (Compound A208);

{4-[5-(4-fluoro-phenyl)-2-(5-hydroxymethyl-[1,3]dioxan-2-yl)-3H-imidazol-4-yl]-pyrimidin-2-ylamino}-acetonitrile, trans-isomer, (Compound A209);

3-{4-[5-(4-fluoro-phenyl)-2-(5-hydroxymethyl-[1,3]dioxan-2-yl)-3H-imidazol-4yl]-pyrimidin-2-ylamino}-propionitrile, trans-isomer, (Compound A210);

(2-{4-(4-fluoro-phenyl)-5-[2-(pyridin-3-ylamino)-pyrimidin-4-yl]-1H-imidazol-2-yl)}-[1,3]dioxan-5-yl)-methanol, trans-isomer, (Compound A211);

(2-{4-(4-fluoro-phenyl)-5-[2-(pyridin-4-ylamino)-pyrimidin-4-yl]-1H-imidazol-2-yl}-[1,3]dioxan-5-yl)-methanol, trans-isomer, (Compound A212);

2-{4-[5-(4-fluoro-phenyl)-2-(5-hydroxymethyl-[1,3]dioxan-2-yl)-3H-imidazol-4-yl]-pyrimidin-2-ylamino}-acetamide, trans-isomer, (Compound A213);

3-{4-[5-(4-fluoro-phenyl)-2-(5-hydroxymethyl-[1,3]dioxan-2-yl)-3H-imidazol-4-yl]-pyrimidin-2-ylamino}-propionamide, trans-isomer, (Compound A214);

{2-[4-(4-fluoro-phenyl)-5-(2-propylamino-pyrimidin-4-yl)-1H-imidazol-2-yl]-[1,3]dioxan-5-yl}-methanol, trans-isomer, (Compound A215);

(l) By proceeding in a similar manner to Example 23(k) but using {2-[4-(4-fluoro-phenyl)-5-(2-methylsulphonyl-pyrimidin-4-yl)-1H-imidazol-2-yl]-[1,3]dioxan-5-yl}-methanol, cis-isomer, (Compound KO) there are prepared the corresponding cis-isomers of Compounds A1171 to A215.

EXAMPLE 24

Compounds IP to IW (a) A stirred solution of {2-[4-(4-fluoro-phenyl)-5-(2-methanesulphonylpyrimidin-4-yl)-1H-imidazol-2-yl]-5-methyl-[1,3]dioxan-5-yl}-morpholin-4-yl-methanone, trans isomer, (1 equivalent, Compound KB) and an appropriately substituted alcohol or phenol [5 equivalents, see table 8] in dry dimethylformamide, at room temperature, was treated with sodium hydride [6 equivalents]. After stirring for 16 hours the reaction mixture was evaporated and the residue partitioned between water and ethyl acetate. The organic phase was evaporated to give Compounds IP to IW depicted in Table 8. The $R_F$ values indicated in Table 8 were determined using a mixture of ethyl acetate and methanol (9:1, v/v) as eluant [the eluant for Compound IT was a mixture of ethyl acetate and methanol (1:1, v/v)].

TABLE 8

| STRUCTURE and Compound number | $R^{17}OH$ | $R_F$ | MOLECULAR FORMULA | MH+ (Intensity) |
|---|---|---|---|---|
| 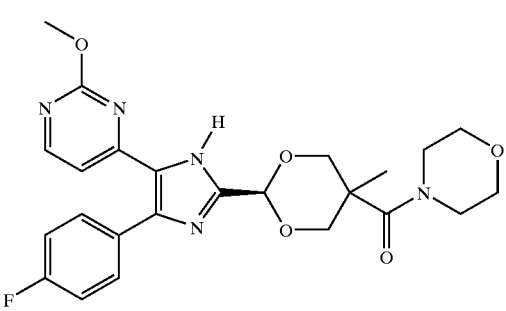 Compound IP |  | 0.37 | C24H26FN5O5 | 484 (100%) |

TABLE 8-continued
| STRUCTURE and Compound number | R¹⁷OH | $R_F$ | MOLECULAR FORMULA | MH⁺ (Intensity) |
|---|---|---|---|---|
| 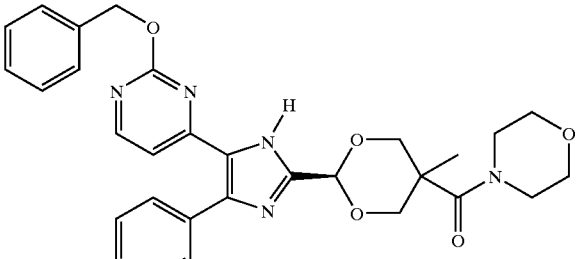 Compound IQ | 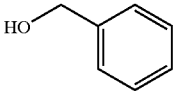 | 0.45 | C30H30FN5O5 | 560 (100%) |
| 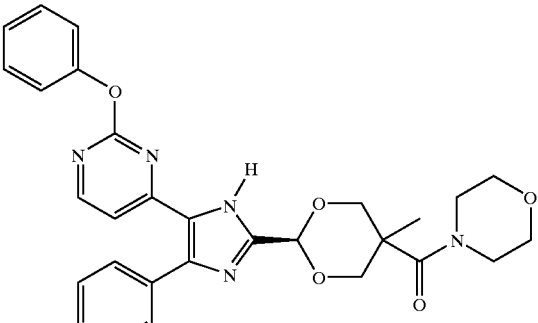 Compound IR | 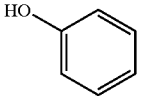 | 0.41 | C29H28FN5O5 | 546 (100%) |
| 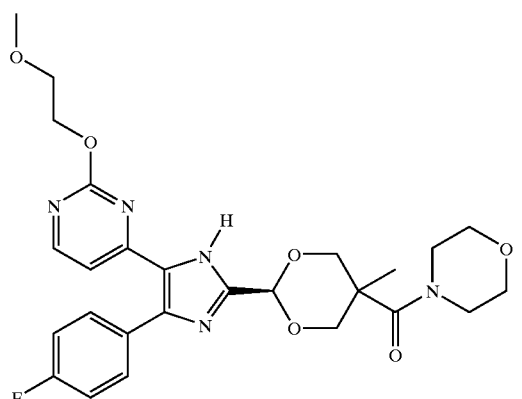 Compound IS | 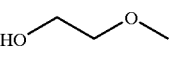 | 0.28 | C26H30FN5O6 | 528 (100%) |

TABLE 8-continued

| STRUCTURE and Compound number | R¹⁷OH | $R_F$ | MOLECULAR FORMULA | MH⁺ (Intensity) |
|---|---|---|---|---|
| 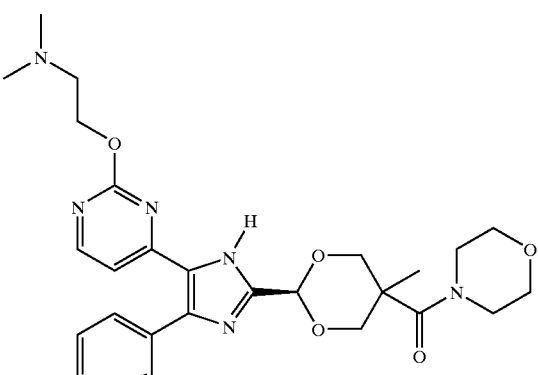<br>Compound IT | 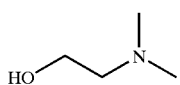 | 0.19 | C27H33FN6O5 | 541 (100%) |
| 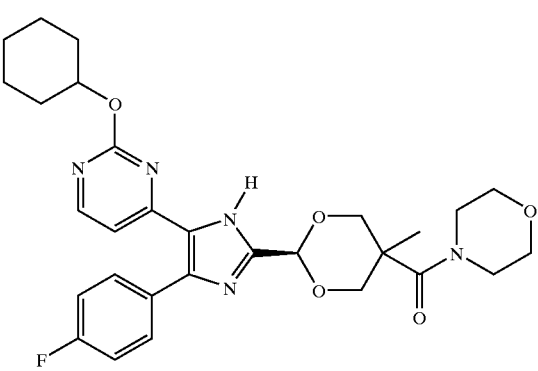<br>Compound IU | 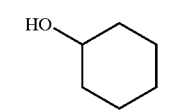 | 0.43 | C29H34FN5O5 | 552 (100%) |
| 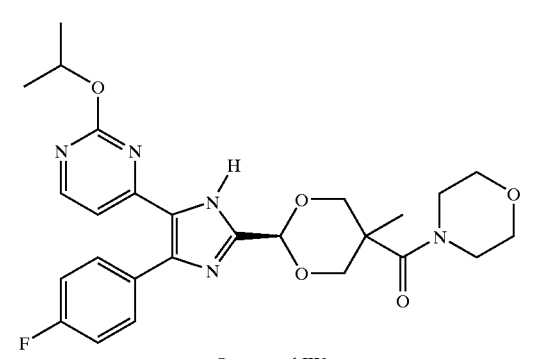<br>Compound IW | 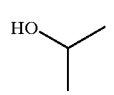 | 0.43 | C26H30FN5O5 | 512 (100%) |

(b) By proceeding in the same manner to Example 24(a) there are prepared Compounds A216 to A219.

{2-[4-(4-fluoro-phenyl)-5-(2-hydroxypyrimidin-4-yl)-1H-imidazol-2-yl]-5-methyl-[1,3]dioxan-5-yl}-morpholin-4-yl-methanone, trans-isomer, (Compound A216);

{2-[4-(4-fluoro-phenyl)-5-(2-propoxy-pyrimidin-4-yl)-1H-imidazol-2-yl]-5-methyl-[1,3]dioxan-5-yl}-morpholin-4-yl-methanone, trans-isomer, (Compound A217);

(2-{4-(4-fluoro-phenyl)-5-[2-(2-hydroxy-ethoxy)-pyrimidin-4-yl]-1H-imidazol-2-yl}-5-methyl-[1,3]dioxan-5-yl)-morpholin-4-yl-methanone, trans-isomer, (Compound A218);

(2-{4-(4-fluoro-phenyl)-5-[2-(3-hydroxy-propoxy)-pyrimidin-4-yl]-1H-imidazol-2-yl}-5-methyl-[1,3]dioxan-5-yl)-morpholin-4-yl-methanone, trans-isomer, (Compound A219);

(c) By proceeding in a similar manner to Example 24(a) but using 2-[4-(4-fluoro-phenyl)-5-(2-methylsulphonylpyrimidin-4-yl)-1H-imidazol-2-yl]-5,5-dimethyl-[1,3]dioxane (Compound KI) there were prepared Compounds IY to JE in Table 8a.

TABLE 8a
| Structure | Reagent | RT | Formula | MW |
|---|---|---|---|---|
| 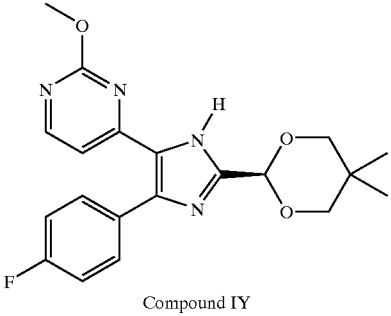<br>Compound IY |  | 11.44 | C20H21FN4O3 | 386 (100%) |
| 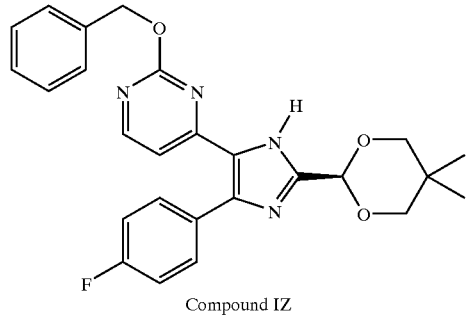<br>Compound IZ | 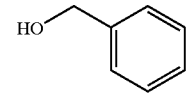 | 13.40 | C26H25FN4O3 | 461 (100%) |
| 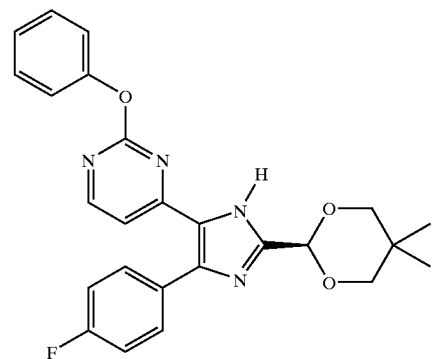<br>Compound JA | 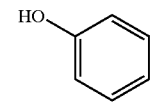 | 13.15 | C25H23FN4O3 | 447 (100%) |
| 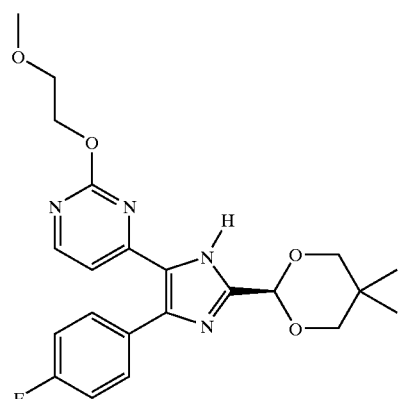 | 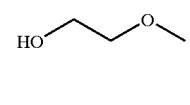 | 11.08 | C22H25FN4O4 | 429 (100%) |

TABLE 8a-continued

| Structure | Reagent | RT | Formula | MW |
|---|---|---|---|---|
| Compound JC | HO-CH2CH2-N(CH3)2 | 9.60 | C23H28FN5O3 | 442 (100%) |
| Compound JD | HO-cyclohexyl | 13.52 | C25H29FN4O3 | 453 (100%) |
| Compound JE | HO-iPr | 12.14 | C22H25FN4O3 | 413 (100%) |

(d) By proceeding in the same manner to Example 24(c) there are prepared Compounds A220 to A222.

4-[2-(5,5-dimethyl-[1,3]dioxan-2-yl)-5-(4-fluoro-phenyl)-3H-imidazol-4-yl]-2-propoxy-pyrimidine, (Compound A220);

2-{4-[2-(5,5-dimethyl-[1,3]dioxan-2-yl)-5-(4-fluoro-phenyl)-3H-imidazol-4-yl]-pyrimidin-2-yloxy}-ethanol, (Compound A221);

3-{4-[2-(5,5-dimethyl-[1,3]dioxan-2-yl)-5-(4-fluoro-phenyl)-3H-imidazol-4-yl]-pyrimidin-2-yloxy}-propan-1-ol, (Compound A222);

(e) By proceeding in a similar manner to Example 24(a) but using {2-[5-(2-methanesulphonyl-pyrimidin-4-yl)-4-(4-fluoro-phenyl)-1H-imidazol-2-yl]-5-methyl-[1,3]dioxan-5-yl}-methanol, trans-isomer, (Compound KJ) there are prepared Compounds A223 to A232:

{2-[4-(4-fluoro-phenyl)-5-(2-methoxy-pyrimidin-4-yl)-1H-imidazol-2-yl]-5-methyl-[1,3]dioxan-5-yl}-methanol, trans-isomers, trans-isomer, (Compound A223);

{2-[5-(2-benzyloxy-pyrimidin-4-yl)-4-(4-fluoro-phenyl)-1H-imidazol-2-yl]-5-methyl-[1,3]dioxan-5-yl}-methanol, trans-isomer, (Compound A224);

{2-[4-(4-fluoro-phenyl)-5-(2-phenoxy-pyrimidin-4-yl)-1H-imidazol-2-yl]-5-methyl-[1,3]dioxan-5-yl}-methanol, trans-isomer, (Compound A225);

(2-{4-(4-fluoro-phenyl)-5-[2-(2-methoxy-ethoxy)-pyrimidin-4-yl]-1H-imidazol-2-yl}-methyl-[1,3]dioxan-5-yl)-methanol, trans-isomer, (Compound A226);

{2-[5-[2-(2-dimethylamino-ethoxy)-pyrimidin-4-yl]-4-(4-fluoro-phenyl)-1H-imidazol-2-yl]-5-methyl-[1,3]dioxan-5-yl}-methanol, trans-isomer, (Compound A227);

{2-[5-(2-cyclohexyloxy-pyrimidin-4-yl)-4-(4-fluoro-phenyl)-1H-imidazol-2-yl]-5-methyl-[1,3]dioxan-5-yl}-methanol, trans-isomer, (Compound A228);

{2-[5-(2-isopropoxy-pyrimidin-4-yl)-4-(4-fluoro-phenyl)-1H-imidazol-2-yl]-5-methyl-[1,3]dioxan-5-yl}-methanol, trans-isomer, (Compound A229);

{2-[4-(4-fluoro-phenyl)-5-(2-propoxy-pyrimidin-4-yl)-1H-imidazol-2-yl]-5-methyl-[1,3]dioxan-5-yl}-methanol, trans-isomer, (Compound A230);

2-{4-[5-(4-fluoro-phenyl)-2-(5-hydroxymethyl-5-methyl-[1,3]dioxan-2-yl)-3H-imidazol-4yl]-pyrimidin-2-yloxy}-ethanol, trans-isomer, (Compound A231);

3-{4-[5-(4-fluoro-phenyl)-2-(5-hydroxymethyl-5-methyl-[1,3]dioxan-2-yl)-3H-imidazol-4yl]-pyrimidin-2-yloxy}-propan-1-ol., trans-isomer, (Compound A232);

(f) By proceeding in a similar manner to Example 24(e) but using {2-[5-(2-methanesulphonyl-pyrimidin-4-yl)-4-(4-fluoro-phenyl)-1H-imidazol-2-yl]-5-methyl-[1,3]dioxan-5-yl}-methanol, cis-isomer, (Compound KK) there are prepared the corresponding cis-isomers of Compounds A223 to A232.

(g) By proceeding in a similar manner to Example 24(a) but using {2-[4-(4-fluoro-phenyl)-5-(2-methylsulphonyl-pyrimidin-4-yl)-1H-imidazol-2-yl]-[1,3]dioxan-5-yl}-methanol, trans-isomer, (Compound KN) there are prepared Compounds A233 to A242:

{2-[4-(4-fluoro-phenyl)-5-(2-methoxy-pyrimidin-4-yl)-1H-imidazol-2-yl]-[1,3]dioxan-5-yl}-methanol, trans-isomer, (Compound A233);

{2-[5-(2-benzyloxy-pyrimidin-4-yl)-4-(4-fluoro-phenyl)-1H-imidazol-2-yl]-[1,3]dioxan-5-yl}-methanol, trans-isomer, (Compound A234);

{2-[4-(4-fluoro-phenyl)-5-(2-phenoxy-pyrimidin-4-yl)-1H-imidazol-2-yl]-[1,3]dioxan-5-yl}-methanol, trans-isomer, (Compound A235);

(2-{4-(4-fluoro-phenyl)-5-[2-(2-methoxy-ethoxy)-pyrimidin-4-yl]-1H-imidazol-2-yl}-[1,3]dioxan-5-yl)-methanol, trans-isomer, (Compound A236);

{2-[5-[2-(2-dimethylamino-ethoxy)-pyrimidin-4-yl]-4-(4-fluoro-phenyl)-1H-imidazol-2-yl]-[1,3]dioxan-5-yl}-methanol, trans-isomer, (Compound A237);

{2-[5-(2-cyclohexyloxy-pyrimidin-4-yl)-4-(4-fluoro-phenyl)-1H-imidazol-2-yl]-[1,3]dioxan-5-yl}-methanol, trans-isomer, (Compound A238);

{2-[5-(2-isopropoxy-pyrimidin-4-yl)-4-(4-fluoro-phenyl)-1H-imidazol-2-yl]-[1,3]dioxan-5-yl}-methanol, trans-isomer, (Compound A239);

{2-[4-(4-fluoro-phenyl)-5-(2-propoxy-pyrimidin-4-yl)-1H-imidazol-2-yl]-[1,3]dioxan-5-yl}-methanol, trans-isomer, (Compound A240);

2-{4-[5-(4-fluoro-phenyl)-2-(5-hydroxymethyl-[1,3]dioxan-2-yl)-3H-imidazol-4yl]-pyrimidin-2-yloxy}-ethanol, trans-isomer, (Compound A241);

3-{4-[5-(4-fluoro-phenyl)-2-(5-hydroxymethyl-[1,3]dioxan-2-yl)-3H-imidazol-4yl]-pyrimidin-2-yloxy}-propan-1-ol, trans-isomer, (Compound A242);

(h) By proceeding in a similar manner to Example 24(g) but using {2-[4-(4-fluoro-phenyl)-5-(2-methylsulphonyl-pyrimidin-4-yl)-1H-imidazol-2-yl]-[1,3]dioxan-5-yl}-methanol, cis-isomer, (Compound KO) there are prepared the corresponding cis-isomers of Compounds A233 to A242.

(i) By proceeding in a similar manner to Example 24(a) but using 4-[5-(4-fluoro-phenyl)-2-(5-methylene-[1,3]dioxan-2-yl)-3H-imidazol-4-yl]-2-methylsulphonyl-pyrimidine (Compound KL) there are prepared Compounds A243 to A252:

4-[5-(4-fluoro-phenyl)-2-(5-methylene-[1,3]dioxan-2-yl)-3H-imidazol-4-yl]-2-methoxy-pyrimidine, (Compound A243);

2-benzyloxy-4-[5-(4-fluoro-phenyl)-2-(5-methylene-[1,3]dioxan-2-yl)-3H-imidazol-4-yl]-pyrimidine, (Compound A244);

4-[5-(4-fluoro-phenyl)-2-(5-methylene-[1,3]dioxan-2-yl)-3H-imidazol-4-yl]-2-phenoxy-pyrimidine, (Compound A245);

4-[5-(4-fluoro-phenyl)-2-(5-methylene-[1,3]dioxan-2-yl)-3H-imidazol-4-yl]-2-(2-methoxy-ethoxy)-pyrimidine, (Compound A246);

(2-{4-[5-(4-fluoro-phenyl)-2-(5-methylene-[1,3]dioxan-2-yl)-3H-imidazol-4-yl]-pyrimidin-2-yloxy}-ethyl)-dimethyl-amine, (Compound A247);

2-cyclohexyloxy-4-[5-(4-fluoro-phenyl)-2-(5-methylene-[1,3]dioxan-2-yl)-3H-imidazol4-yl]-pyrimidin, (Compound A248);

2-cyclopropoxy-4-[5-(4-fluoro-phenyl)-2-(5-methylene-[1,3]dioxan-2-yl)-3H-imidazol-4-yl]-pyrimidin, (Compound A249);

4-[5-(4-fluoro-phenyl)-2-(5-methylene-[1,3]dioxan-2-yl)-3H-imidazol-4-yl]-2-propoxy-pyrimidine, (Compound A250);

2-{4-[5-(4-fluoro-phenyl)-2-(5-methylene-[1,3]dioxan-2-yl)-3H-imidazol-4-yl]-pyrimidin-2-yloxy}-ethanol, (Compound A251);

3-{4-[5-(4-fluoro-phenyl)-2-(5-methylene-[1,3]dioxan-2-yl)-3H-imidazol-4-yl]-pyrimidin-2-yloxy}-propan-1-ol, (Compound A252);

(j) By proceeding in a similar manner to Example 24(a) but using 4-[2-[1,3]dioxan-2-yl-5-(4-fluoro-phenyl)-3H-imidazol-4-yl]-2-methylsulphonyl-pyrimidine (Compound KM) there are prepared Compounds A253 to A262:

4-[2-[1,3]dioxan-2-yl-5-(4-fluoro-phenyl)-3H-imidazol-4-yl]-2-methoxy-pyrimidine, (Compound A253);

2-benzyloxy-4-[2-[1,3]dioxan-2-yl-5-(4-fluoro-phenyl)-3H-imidazol-4-yl]-pyrimidine, (Compound A254);

4-[2-[1,3]dioxan-2-yl-5-(4-fluoro-phenyl)-3H-imidazol-4-yl]-2-phenoxy-pyrimidine, (Compound A255);

4-[2-[1,3]dioxan-2-yl-5-(4-fluoro-phenyl)-3H-imidazol-4-yl]-2-(2-methoxy-ethoxy)-pyrimidine, (Compound A256);

(2-{4-[2-[1,3]dioxan-2-yl-5-(4-fluoro-phenyl)-3H-imidazol-4-yl]-pyrimidin-2-yloxy}-ethyl)-dimethyl-amine, (Compound A257);

2-cyclohexyloxy-4-[2-[1,3]dioxan-2-yl-5-(4-fluoro-phenyl)-3H-imidazol-4-yl]-pyrimidine, (Compound A258);

2-isopropyloxy-4-[2-[1,3]dioxan-2-yl-5-(4-fluoro-phenyl)-3H-imidazol-4-yl]-pyrimidine, (Compound A259);

4-[2-[1,3]dioxan-2-yl-5-(4-fluoro-phenyl)-3H-imidazol-4-yl]-2-propoxy-pyrimidine, (Compound A260);

2-{4-[2-[1,3]dioxan-2-yl-5-(4-fluoro-phenyl)-3H-imidazol-4-yl]-pyrimidin-2-yloxy}-ethanol, (Compound A261);

3-{4-[2-[1,3]dioxan-2-yl-5-(4-fluoro-phenyl)-3H-imidazol-4-yl]-pyrimidin-2-yloxy}-propan-1-ol, (Compound A262);

EXAMPLE 25

Compounds JF to KG (a) A solution of 2,2,2-trifluoro-N-[2-{4-(4-fluorophenyl)-5-(2-methanesulphonylpyrimidin-4-yl)-1H-imidazol-2-yl}-5-methyl-[1,3]dioxan-5-yl]acetamide, cis-isomer, (1 equivalent, Compound KP) and an appropriately substituted amine of formula $HNY^4Y^5$ [5 equivalents, see Table 9] in dry dimethylformamide was heated at 100° C. for 8 hours (or in the case of JF reacted without a solvent in a pressure vessel). The reaction mixture was then treated with aqueous potassium carbonate solution (2 equivalents) and then heated at 100° C. for 24 hours. The mixture was partitioned between water and dichloromethane. The organic phase was separated, evaporated and the residue subjected to high pressure liquid chromatography, on a C18 Dynamax 60 Å column using gradient elution with a mixture of acetonitrile and water as the mobile phase (0–3 minutes 20% acetonitrile; 2–15 minutes ramp up to 80% acetonitrile; 16 minutes to end of run 80% acetonitrile) and UV detection at 254 nm, to give Compounds JF to KG depicted in Table 9. The $R_T$ values indicated in Table 9 refer to the high pressure liquid chromatography retention times determined as described above.

TABLE 9

| STRUCTURE and EXAMPLE NUMBER | $HNY^4Y^5$ | $R_T$ (minutes) | MOLECULAR FORMULA | $MH^+$ (Intensity) |
|---|---|---|---|---|
| 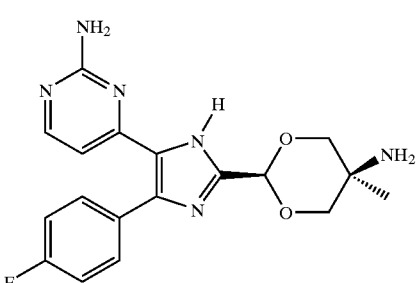<br>Compound JF | $NH_3$ | 11.41 | C18H19FN6O2 | 371 (100%) |
| 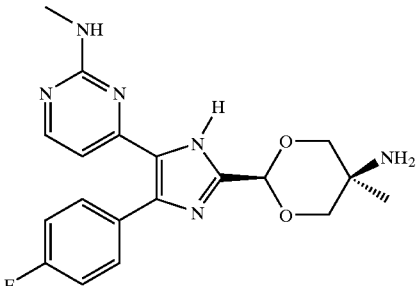<br>Compound JG |  | 11.65 | C19H21FN6O2 | 385 (100%) |
| 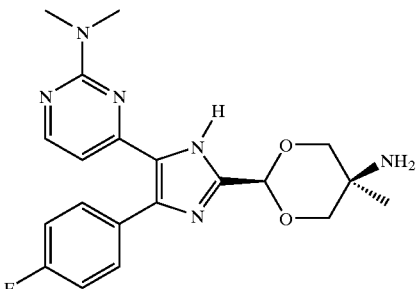<br>Compound JH |  | 11.85 | C20H23FN6O2 | 399 (100%) |

TABLE 9-continued
| STRUCTURE and EXAMPLE NUMBER | HNY⁴Y⁵ | R$_T$ (minutes) | MOLECULAR FORMULA | MH⁺ (Intensity) |
|---|---|---|---|---|
| 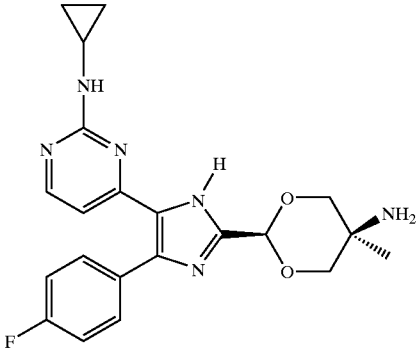<br>Compound JI | 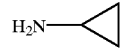 | 12.10 | C21H23FN6O2 | 411 (100%) |
| 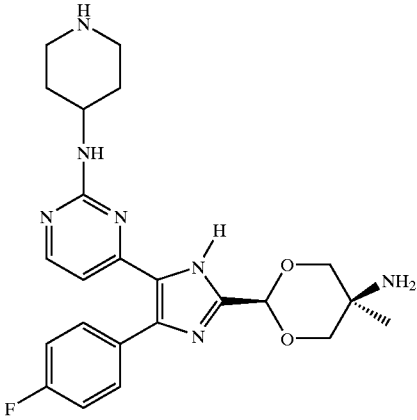<br>Compound JJ | 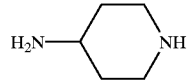 | 2.70 | C23H28FN7O2 | 454 (100%) |
| 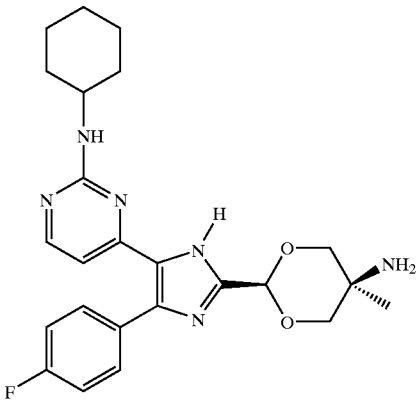<br>Compound JK | 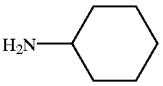 | 10.91 | C24H29FN6O2 | 453 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 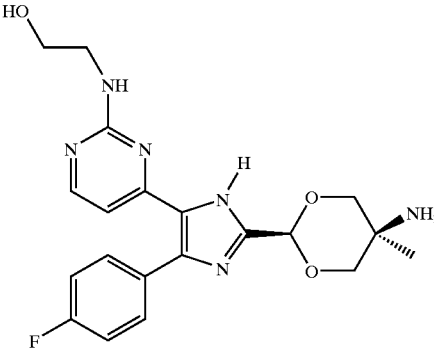 Compound JL | 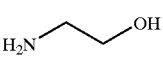 | 10.30 | C20H23FN6O3 | 415 (100%) |
| 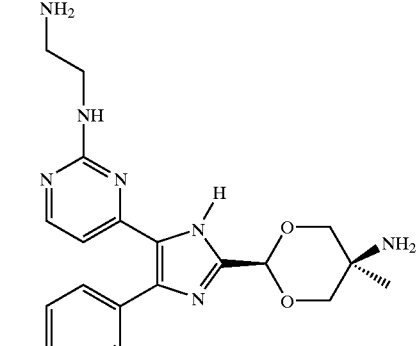 Compound JM | 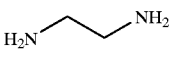 | 1.96 | C20H24FN7O2 | 414 (100%) |
| 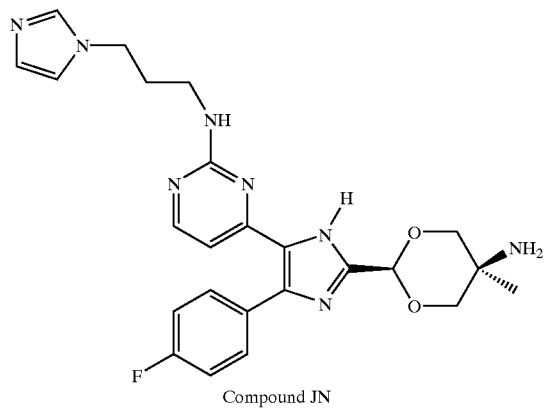 Compound JN | 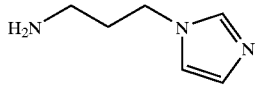 | 1.98 | C24H27FN8O2 | 479 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 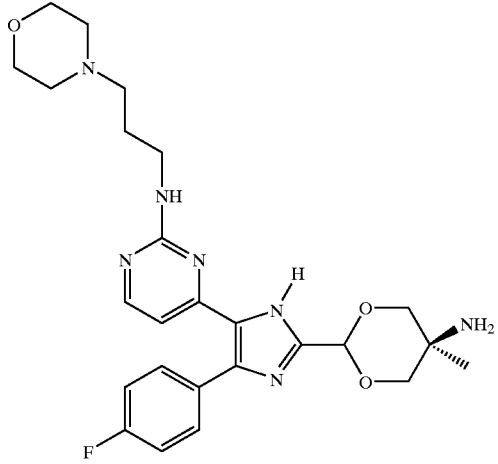<br>Compound JO | 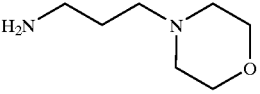 | 2.02 | C25H32FN7O3 | 498 (100%) |
| 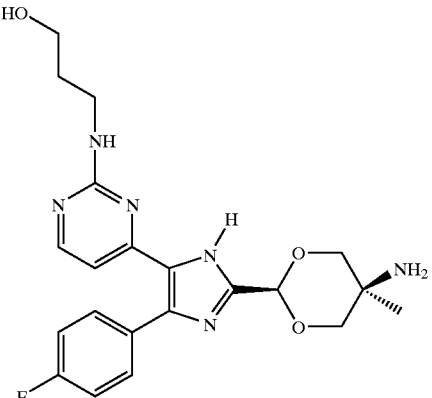<br>Compound JP | 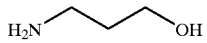 | 10.40 | C21H25FN6O2 | 413 (100%) |
| 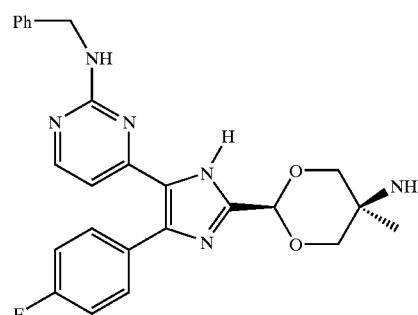<br>Compound JQ | 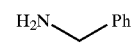 | 10.18 | C25H25FN6O2 | 461 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 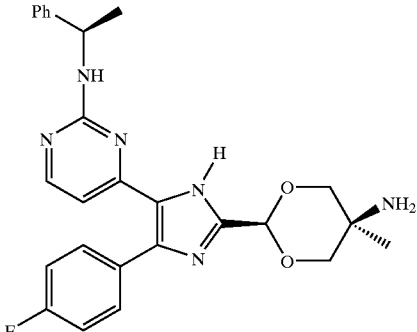<br>Compound JR | 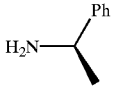 | 10.91 | C26H27FN6O2 | 475 (100%) |
| 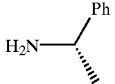<br>Compound JS | 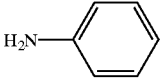 | 10.91 | C26H27FN6O2 | 475 (100%) |
| Compound JT | | 11.01 | C24H23FN6O2 | 447 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 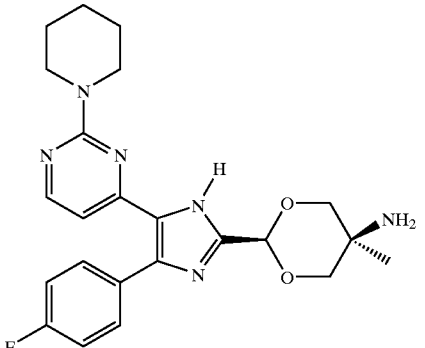<br>Compound JU |  | 13.15 | C23H27FN6O2 | 439 (100%) |
| 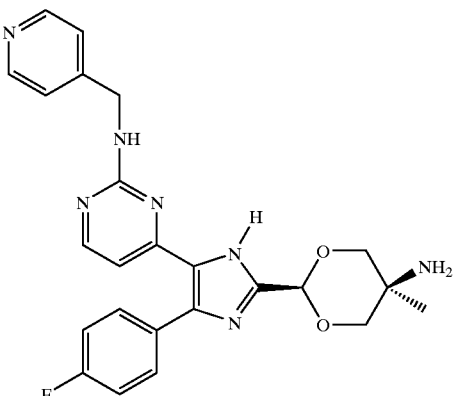<br>Compound JV | 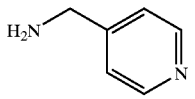 | 3.95 | C24H24FN7O2 | 462 (100%) |
| 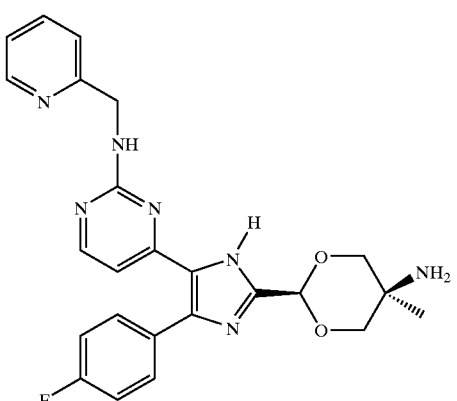<br>Compound JW | 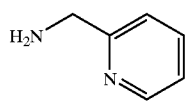 | 2.14 | C24H24FN7O2 | 462 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 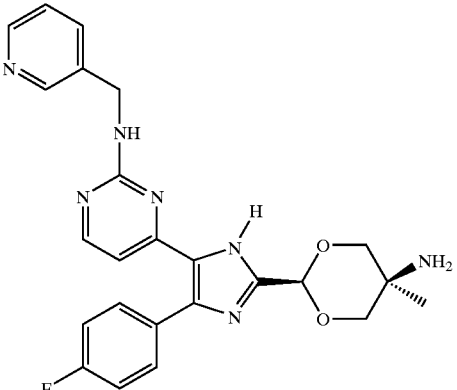 Compound JX | 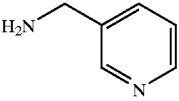 | 1.96 | C24H24FN7O2 | 462 (100%) |
| 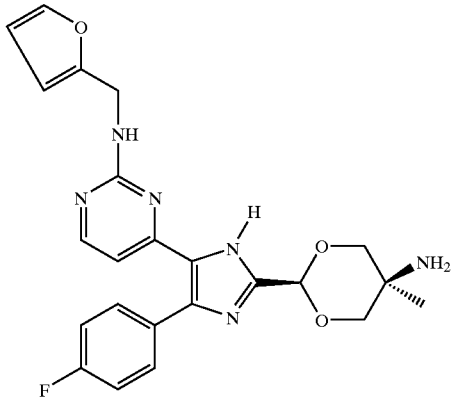 Compound JY | 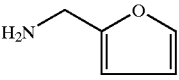 | 11.93 | C23H23FN6O3 | 451 (100%) |
| 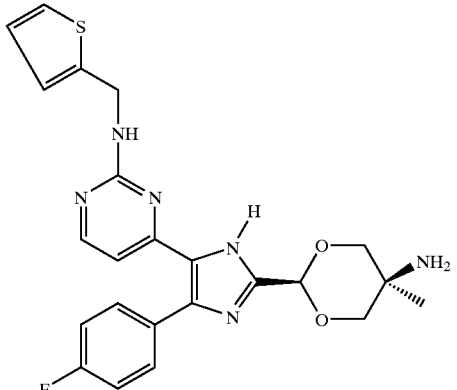 Compound JZ | 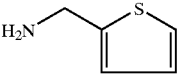 | 12.10 | C23H23FN6O2S | 467 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 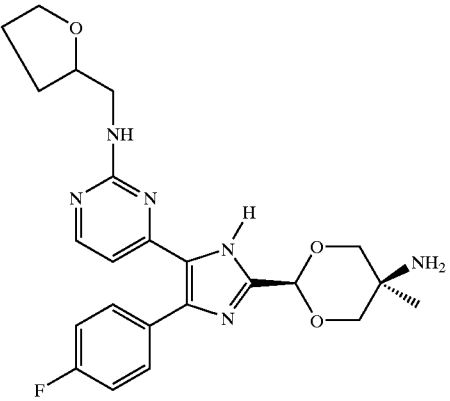 Compound KA | 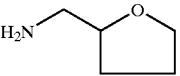 | 12.44 | C23H27FN6O3 | 455 (100%) |
| 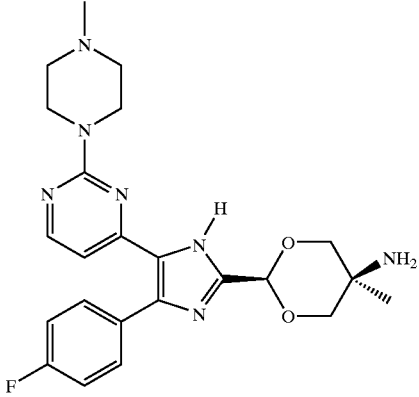 Compound KB | 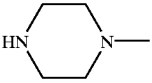 | 2.10 | C23H28FN7O2 | 454 (100%) |
| 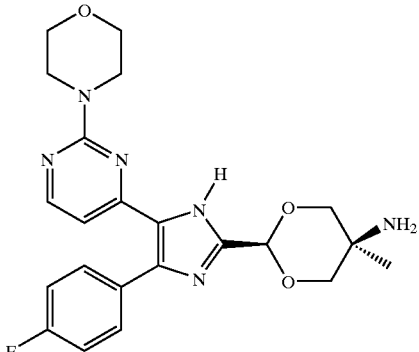 Compound KC | 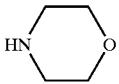 | 12.20 | C22H25FN6O3 | 441 (100%) |

TABLE 9-continued
| STRUCTURE and EXAMPLE NUMBER | HNY⁴Y⁵ | R_T (minutes) | MOLECULAR FORMULA | MH⁺ (Intensity) |
|---|---|---|---|---|
| 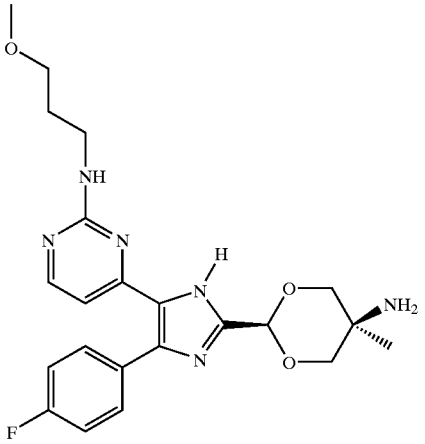 Compound KD | H₂N~~~O~ | 11.10 | C22H27FN6O3 | 443 (100%) |
| 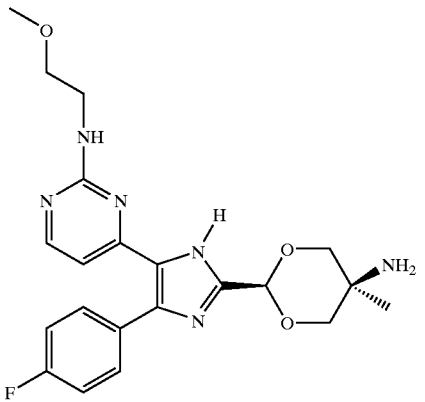 Compound KE | H₂N~~O~ | 11.86 | C21H25FN6O3 | 429 (100%) |
| 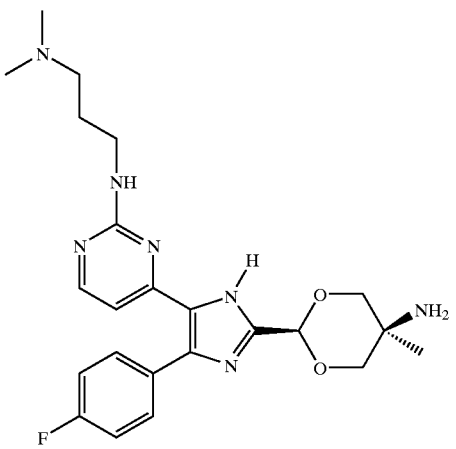 Compound KF | H₂N~~~N(CH₃)₂ | 2.02 | C23H30FN7O2 | 456 (100%) |

TABLE 9-continued

| STRUCTURE and EXAMPLE NUMBER | HNY⁴Y⁵ | $R_T$ (minutes) | MOLECULAR FORMULA | MH⁺ (Intensity) |
|---|---|---|---|---|
| 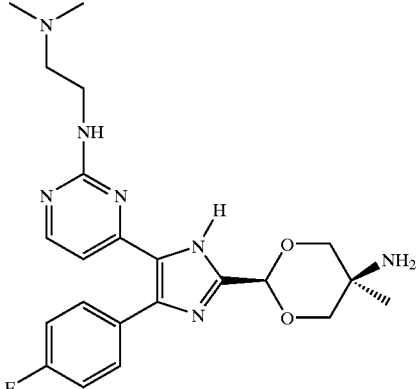<br>Compound KG | 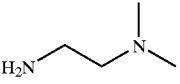 | 2.04 | C22H28FN7O2 | 442 (100%) |

(b) By proceeding in the same manner Example 25(a) there are prepared Compounds A263 to A280.

{4-[2-(5-amino-5-methyl-[1,3]dioxan-2-yl)-5-(4-fluoro-phenyl)-3H-imidazol-4-yl]-pyrimidin-2-ylamino}-acetic acid, cis-isomer, (Compound A263);

3-{4-[2-(5-amino-5-methyl-[1,3]dioxan-2-yl)-5-(4-fluoro-phenyl)-3H-imidazol-4-yl]-pyrimidin-2-ylamino}-propionic acid, cis-isomer, (Compound A264);

{4-[2-(5-amino-5-methyl-[1,3]dioxan-2-yl)-5-(4-fluoro-phenyl)-3H-imidazol-4-yl]-pyrimidin-2-yl}-isopropyl-amine, cis-isomer, (Compound A265);

allyl-{4-[2-(5-amino-5-methyl-[1,3]dioxan-2-yl)-5-(4-fluoro-phenyl)-3H-imidazol-4-yl]-pyrimidin-2-yl}-amine, cis-isomer, (Compound A266);

{4-[2-(5-amino-5-methyl-[1,3]dioxan-2-yl)-5-(4-fluoro-phenyl)-3H-imidazol-4-yl]-pyrimidin-2-yl}-cyclopropylmethyl-aminer, cis-isomer (Compound A267);

{4-[2-(5-amino-5-methyl-[1,3]dioxan-2-yl)-5-(4-fluoro-phenyl)-3H-imidazol-4-yl]-pyrimidin-2-ylamino}-acetonitrile, cis-isomer, (Compound A268);

3-{4-[2-(5-amino-5-methyl-[1,3]dioxan-2-yl)-5-(4-fluoro-phenyl)-3H-imidazol-4-yl]-pyrimidin-2-ylamino}-propionitrile, cis-isomer, (Compound A269);

{4-[2-(5-amino-5-methyl-[1,3]dioxan-2-yl)-5-(4-fluoro-phenyl)-3H-imidazol-4-yl]-pyrimidin-2-yl}-pyridin-3-yl-amine, cis-isomer, (Compound A270);

{4-[2-(5-amino-5-methyl-[1,3]dioxan-2-yl)-5-(4-fluoro-phenyl)-3H-imidazol-4-yl]-pyrimidin-2-yl}-pyridin-4-yl-amine, cis-isomer, (Compound A271);

2-{4-[2-(5-amino-5-methyl-[1,3]dioxan-2-yl)-5-(4-fluoro-phenyl)-3H-imidazol-4-yl]-pyrimidin-2-ylamino}-acetamide, cis-isomer, (Compound A272);

3-{4-[2-(5-amino-5-methyl-[1,3]dioxan-2-yl)-5-(4-fluoro-phenyl)-3H-imidazol-4-yl]-pyrimidin-2-ylamino}-propionamide, cis-isomer, (Compound A273);

{4-[2-(5-amino-5-methyl-[1,3]dioxan-2-yl)-5-(4-fluoro-phenyl)-3H-imidazol-4-yl]-pyrimidin-2-yl}-propyl-amine, cis-isomer, (Compound A274);

2-[4-(4-fluoro-phenyl)-5-(2-pyrrolidin-1-yl-pyrimidin-4-yl)-1H-imidazol-2-yl]-5-methyl-[1,3]dioxan-5-ylamine, cis-isomer, (Compound A275);

{4-[2-(5-amino-5-methyl-[1,3]dioxan-2-yl)-5-(4-fluoro-phenyl)-3H-imidazol-4-yl]-pyrimidin-2-yl}-(4-fluorobenzyl)-amine, cis-isomer, (Compound A276);

{4-[2-(5-amino-5-methyl-[1,3]dioxan-2-yl)-5-(4-fluoro-phenyl)-3H-imidazol-4-yl]-pyrimidin-2-yl}-(4-methoxybenzyl)-amine, cis-isomer, (Compound A277);

{4-[2-(5-amino-5-methyl-[1,3]dioxan-2-yl)-5-(4-fluoro-phenyl)-3H-imidazol-4-yl]-pyrimidin-2-yl}-(4-fluorophenyl)-amine, cis-isomer, (Compound A278);

{4-[2-(5-amino-5-methyl-[1,3]dioxan-2-yl)-5-(4-fluoro-phenyl)-3H-imidazol-4-yl]-pyrimidin-2-yl}-(3,4-difluorophenyl)-amine, cis-isomer, (Compound A279);

{4-[2-(5-amino-5-methyl-[1,3]dioxan-2-yl)-5-(4-fluoro-phenyl)-3H-imidazol-4-yl]-pyrimidin-2-yl}-(4-methoxyphenyl)-amine, cis-isomer, (Compound A280);

(c) By proceeding in a similar manner to Example 25(a) but replacing the amine with a single equivalent of the sodium salt of an appropriately substituted alcohol or phenol there are prepared Compounds A281 to A290.

2-[4-(4-fluoro-phenyl)-5-(2-methoxy-pyrimidin-4-yl)-1H-imidazol-2-yl]-5-methyl-[1,3]dioxan-5-ylamine, cis-isomer, (Compound A281);

2-[5-(2-benzyloxy-pyrimidin-4-yl)-4-(4-fluoro-phenyl)-1H-imidazol-2-yl]-5-methyl-[1,3]dioxan-5-ylamine, cis-isomer, (Compound A282);

2-[4-(4-fluoro-phenyl)-5-(2-phenoxy-pyrimidin-4-yl)-1H-imidazol-2-yl]-5-methyl-[1,3]dioxan-5-ylamine, cis-isomer, (Compound A283);

2-{4-(4-fluoro-phenyl)-5-[2-(2-methoxy-ethoxy)-pyrimidin-4-yl]-1H-imidazol-2-yl}-5-methyl-[1,3]dioxan-5-ylamine, cis-isomer, (Compound A284);

2-[5-[2-(2-dimethylamino-ethoxy)-pyrimidin-4-yl]-4-(4-fluoro-phenyl)-1H-imidazol-2-yl]-5-methyl-[1,3]dioxan-5-ylamine, cis-isomer, (Compound A285);

2-[5-(2-cyclohexyloxy-pyrimidin-4-yl)-4-(4-fluoro-phenyl)-1H-imidazol-2-yl]-5-methyl-[1,3]dioxan-5-ylamine, cis-isomer, (Compound A286);

2-[5-(2-Isolopropoxy-pyrimidin-4-yl)-4-(4-fluoro-phenyl)-1H-imidazol-2-yl]-5-methyl-[1,3]dioxan-5-ylamine, cis-isomer, (Compound A287);

2-[4-(4-fluoro-phenyl)-5-(2-propoxy-pyrimidin-4-yl)-1H-imidazol-2-yl]-5-methyl-[1,3]dioxan-5-ylamine, cis-isomer, (Compound A288);

2-{4-[2-(5-amino-5-methyl-[1,3]dioxan-2-yl)-5-(4-fluoro-phenyl)-3H-imidazol-4-yl]-pyrimidin-2-yloxy}-ethanol, cis-isomer, (Compound A289);

3-{4-[2-(5-amino-5-methyl-[1,3]dioxan-2-yl)-5-(4-fluoro-phenyl)-3H-imidazol-4-yl]-pyrimidin-2-yloxy}-propan-1-ol, cis-isomer, (Compound A290);

(d) By proceeding in a similar manner to Example 25(a) but using 2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, trans isomer (Compound LL) there are prepared Compounds A291 to A337.

4-[2-(5-aminomethyl-5-methyl-[1,3]dioxan-2-yl)-5-(4-fluoro-phenyl)-3H-imidazol-4-yl]-pyrimidin-2-ylamine, trans-isomer, (Compound A291);

{4-[2-(5-aminomethyl-5-methyl-[1,3]dioxan-2-yl)-5-(4-fluoro-phenyl)-3H-imidazol-4-yl]-pyrimidin-2-yl}-methyl-amine, trans-isomer, (Compound A292);

{4-[2-(5-aminomethyl-5-methyl-[1,3]dioxan-2-yl)-5-(4-fluoro-phenyl)-3H-imidazol-4-yl]-pyrimidin-2-yl}-dimethyl-amine, trans-isomer, (Compound A293);

{4-[2-(5-aminomethyl-5-methyl-[1,3]dioxan-2-yl)-5-(4-fluoro-phenyl)-3H-imidazol-4-yl]-pyrimidin-2-yl}-cyclopropyl-amine, trans-isomer, (Compound A294);

{4-[2-(5-aminomethyl-5-methyl-[1,3]dioxan-2-yl)-5-(4-fluoro-phenyl)-3H-imidazol-4-yl]pyrimidin-2-yl}-piperidin-4-yl-amine, trans-isomer, (Compound A295);

{4-[2-(5-aminomethyl-5-methyl-[1,3]dioxan-2-yl)-5-(4-fluoro-phenyl)-3H-imidazol-4-yl]-pyrimidin-2-yl}-cyclohexyl-amine, trans-isomer, (Compound A296);

2-{4-[2-(5-aminomethyl-5-methyl-[1,3]dioxan-2-yl)-5-(4-fluoro-phenyl)-3H-imidazol-4-yl]-pyrimidin-2-ylamino}-ethanol, trans-isomer, (Compound A297);

N1-{4-[2-(5-aminomethyl-5-methyl-[1,3]dioxan-2-yl)-5-(4-fluoro-phenyl)-3H-imidazol-4-yl]-pyrimidin-2-yl}-ethane-1,2-diamine, trans-isomer, (Compound A298);

{4-[2-(5-aminomethyl-5-methyl-[1,3]dioxan-2-yl)-5-(4-fluoro-phenyl)-3H-imidazol-4-yl ]-pyrimidin-2-yl}-[3-(5H-imidazol-1-yl)-propyl]-amine, trans-isomer, (Compound A299);

{4-[2-(5-aminomethyl-5-methyl-[1,3]dioxan-2-yl)-5-(4-fluoro-phenyl)-3H-imidazol-4-yl]-pyrimidin-2-yl}-(3-morpholin-4-yl-propyl)-amine, trans-isomer, (Compound A300);

3-{4-[2-(5-aminomethyl-5-methyl-[1,3]dioxan-2-yl)-5-(4-fluoro-phenyl)-3H-imidazol-4-yl]-pyrimidin-2-ylamino}-propan-1-ol, trans-isomer, (Compound A301);

{4-[2-(5-aminomethyl-5-methyl-[1,3]dioxan-2-yl)-5-(4-fluoro-phenyl)-3H-imidazol-4-yl]-pyrimidin-2-yl}-benzyl-amine, trans-isomer, (Compound A302);

{4-[2-(5-aminomethyl-5-methyl-[1,3]dioxan-2-yl)-5-(4-fluoro-phenyl)-3H-imidazol-4-yl]-pyrimidin-2-yl}-(4-fluorobenzyl)-amine, trans-isomer, (Compound A303);

{4-[2-(5-aminomethyl-5-methyl-[1,3]dioxan-2-yl)-5-(4-fluoro-phenyl)-3H-imidazol-4-yl]-pyrimidin-2-yl}-(4-methoxybenzyl)-amine, trans-isomer, (Compound A304);

{4-[2-(5-aminomethyl-5-methyl-[1,3]dioxan-2-y)-5-(4-fluoro-phenyl)-3H-imidiazol-4-yl]-pyrimidin-2-yl}(1-phenyl-ethyl)-amine, R isomer, trans-isomer, (Compound A305);

{4-[2-(5-aminomethyl-5-methyl-[1,3]dioxan-2-yl)-5-(4-fluoro-phenyl)-3H-imidazol-4-yl]-pyrimidin-2-yl}-(1-phenyl-ethyl)-amine, S isomer, trans-isomer, (Compound A306);

{4-[2-(5-aminomethyl-5-methyl-[1,3]dioxan-2-yl)-5-(4-fluoro-phenyl)-3H-imidazol-4-yl]-pyrimidin-2-yl}-phenyl-amine, trans-isomer, (Compound A307);

{4-[2-(5-aminomethyl-5-methyl-[1,3]dioxan-2-yl)-5-(4-fluoro-phenyl)-3H-imidazol-4-yl]-pyrimidin-2-yl}-(4-fluorophenyl)-amine, trans-isomer, (Compound A308);

{4-[2-(5-aminomethyl-5-methyl-[1,3]dioxan-2-yl)-5-(4-fluoro-phenyl)-3H-imidazol-4-yl]-pyrimidin-2-yl}-(3,4-difluorophenyl)-amine, trans-isomer, (Compound A309);

{4-[2-(5-aminomethyl-5-methyl-[1 ,3]dioxan-2-yl)-5-(4-fluoro-phenyl)-3H-imidazol-4-yl]-pyrimidin-2-yl}-(3-methoxyphenyl)-amine, trans-isomer, (Compound A3 10);

C-{2-[4-(4-fluoro-phenyl)-5-(2-piperidin-1-yl-pyrimidin-4-yl)-1H-imidazol-2-yl]-5-methyl-[1,3]dioxan5-yl}-methylamine, trans-isomer, (Compound A311);

{4-[2-(5-aminomethyl-5-methyl-[1,3]dioxan-2-yl)-5-(4-fluoro-phenyl)-3H-imidazol-4-yl]-pyrimidin-2-yl}-pyridin-4-ylmethyl-amine, trans-isomer, (Compound A312);

{4-[2-(5-aminomethyl-5-methyl-[1,3]dioxan-2-yl)-5-(4-fluoro-phenyl)-3H-imidazol-4-yl]-pyrimidin-2-yl}-pyridin-3-ylmethyl-amine, trans-isomer, (Compound A313);

{4-[2-(5-aminomethyl-5-methyl-[1,3]dioxan-2-yl)-5-(4-fluoro-phenyl)-3H-imidazol-4-yl]-pyrimidin-2-yl}-pyridin-2-ylmethyl-amine, trans-isomer, (Compound A314);

{4-[2-(5-aminomethyl-5-methyl-[1,3]dioxan-2-yl)-5-(4-fluoro-phenyl)-3H-imidazol-4-yl]-pyrimidin-2-yl}-(furan-2-ylmethyl)-amine, trans-isomer, (Compound A315);

{4-[2-(5-aminomethyl-5-methyl-[1,3]dioxan-2-yl)-5-(4-fluoro-phenyl)-3H-imidazol-4-yl]-pyrimidin-2-yl}-(thiophen-2-ylmethyl)-amine, trans-isomer, (Compound A316);

{4-[2-(5-aminomethyl-5-methyl-[1,3]dioxan-2-yl)-5-(4-fluoro-phenyl)-3H-imidazol-4-yl]-pyrimidin-2-yl}-(tetrahydro-furan-2-ylmethyl)-amine, trans-isomer, (Compound A317);

C-(2-{4-(4-fluoro-phenyl)-5-[2-(4-methyl-piperazin-1-yl)-pyrimidin-4-yl]-1H-imidazol-2-yl}-5-methyl-[1,3]dioxan-5-yl)-methylamine, trans-isomer, (Compound A318);

C-{2-[4-(4-fluoro-phenyl)-5-(2-morpholin-4-yl-pyrimidin-4-yl)-1H-imidazol-2-yl]-5-methyl-[1,3]dioxan-5-yl}-methylamine, trans-isomer, (Compound A319);

{4-[2-(5-aminomethyl-5-methyl-[1,3]dioxan-2-yl)-5-(4-fluoro-phenyl)-3H-imidazol-4-yl]-pyrimidin-2-yl}-(3-methoxy-propyl)-amine, trans-isomer, (Compound A320);

{4-[2-(5-aminomethyl-5-methyl-[1,3]dioxan-2-yl)-5-(4-fluoro-phenyl)-3H-imidazol-4-yl]-pyrimidin-2-yl}-(2-methoxy-ethyl)-amine, trans-isomer, (Compound A321);

N-{4-[2-(5-aminomethyl-5-methyl-[1,3]dioxan-2-yl)-5-(4-fluoro-phenyl)-3H-imidazol-4-yl]-pyrimidin-2-yl}-N',N'-dimethyl-propane-1,3-diamine, trans-isomer, (Compound A322);

N-{4-[2-(5-aminomethyl-5-methyl-[1,3]dioxan-2-yl)-5-(4-fluoro-phenyl)-3H-imidazol-4-yl]-pyrimidin-2-yl}-N',N'-dimethyl-ethane-1,2-diamine, trans-isomer, (Compound A323);

{4-[2-(5-aminomethyl-5-methyl-[1,3]dioxan-2-yl)-5-(4-fluoro-phenyl)-3H-imidazol-4-yl]-pyrimidin-2-ylamino}-acetic acid, trans-isomer, (Compound A324);

3-{4-[2-(5-aminomethyl-5-methyl-[1,3]dioxan-2-yl)-5-(4-fluoro-phenyl)-3H-imidazol-4-yl]-pyrimidin-2-ylamino}-propionic acid, trans-isomer, (Compound A325);

C-{2-[4-(4-fluoro-phenyl)-5-(2-methylsulfanyl-pyrimidin-4-yl)-1H-imidazol-2-yl]-5-methyl-[1,3]dioxan-5-yl}-methylamine, trans-isomer, (Compound A326);

{4-[2-(5-aminomethyl-5-methyl-[1,3]dioxan-2-yl)-5-(4-fluoro-phenyl)-3H-imidazol-4-yl]-pyrimidin-2-yl}-isopropyl-amine, trans-isomer, (Compound A327);

allyl-{4-[2-(5-aminomethyl-5-methyl-[1,3]dioxan-2-yl)-5-(4-fluoro-phenyl)-3H-imidazol-4-yl]-pyrimidin-2-yl}-amine, trans-isomer, (Compound A328);

{4-[2-(5-aminomethyl-5-methyl-[1,3]dioxan-2-yl)-5-(4-fluoro-phenyl)-3H-imidazol-4-yl]-pyrimidin-2-yl}-cyclopropylmethyl-amine, trans-isomer, (Compound A329);

{4-[2-(5-aminomethyl-5-methyl-[1,3]dioxan-2-yl)-5-(4-fluoro-phenyl)-3H-imidazol-4-yl]-pyrimidin-2-ylamino}-acetonitrile, trans-isomer, (Compound A330);

3-{4-[2-(5-aminomethyl-5-methyl-[1,3]dioxan-2-yl)-5-(4-fluoro-phenyl)-3H-imidazol-4-yl]-pyrimidin-2-ylamino}-propionitrile, trans-isomer, (Compound A331);

{4-[2-(5-aminomethyl-5-methyl-[1,3]dioxan-2-yl)-5-(4-fluoro-phenyl)-3H-imidazol-4-yl]-pyrimidin-2-yl}-pyridin-3-yl-amine, trans-isomer, (Compound A332);

{4-[2-(5-aminomethyl-5-methyl-[1,3]dioxan-2-yl)-5-(4-fluoro-phenyl)-3H-imidazol-4-yl]-pyrimidin-2-yl}-pyridin-4-yl-amine, trans-isomer, (Compound A333);

2-{4-[2-(5-aminomethyl-5-methyl-[1,3]dioxan-2-yl)-5-(4-fluoro-phenyl)-3H-imidazol-4-yl]-pyrimidin-2-ylamino}-acetamide, trans-isomer, (Compound A334);

3-{4-[2-(5-aminomethyl-5-methyl-[1,3]dioxan-2-yl)-5-(4-fluoro-phenyl)-3H-imidazol-4-yl]-pyrimidin-2-ylamino}-propionamide, trans-isomer, (Compound A335);

{4-[2-(5-aminomethyl-5-methyl-[1,3]dioxan-2-yl)-5-(4-fluoro-phenyl)-3H-imidazol-4-yl]-pyrimidin-2-yl}-propyl-amine, trans-isomer, (Compound A336);

C-{2-[4-(4-fluoro-phenyl)-5-(2-pyrrolidin-1-yl-pyrimidin-4-yl)-1H-imidazol-2-yl]-5-methyl-[1,3]dioxan-5-yl}-methylamine, trans-isomer, (Compound A337);

(e) By proceeding in a similar manner to Example 25(d) but using 2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, cis isomer (Compound LK) there are prepared the corresponding cis isomers of Compounds A291 to A337.

(f) By proceeding in a similar manner to Example 25(e) but using 2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, trans isomer (Compound LL) there are prepared Compounds A338 to A347.

C-{2-[4-(4-fluoro-phenyl)-5-(2-methoxy-pyrimidin-4-yl)-1H-imidazol-2-yl]-5-methyl-[1,3]dioxan-5-yl}-methylamine, trans-isomer, (Compound A338);

C-{2-[5-(2-benzyloxy-pyrimidin-4-yl)-4-(4-fluoro-phenyl)-1H-imidazol-2-yl]-5-methyl-[1,3]dioxan-5-yl}-methylamine, trans-isomer, (Compound A339);

C-{2-[4-(4-fluoro-phenyl)-5-(2-phenoxy-pyrimidin-4-yl)-1H-imidazol-2-yl]-5-methyl-[1,3]dioxan-5-yl}-methylamine, trans-isomer, (Compound A340);

C-(2-{4-(4-fluoro-phenyl)-5-[2-(2-methoxy-ethoxy)-pyrimidin-4-yl]-1H-imidazol-2-yl}-5-methyl-[1,3]dioxan-5-yl)-methylamine, trans-isomer, (Compound A341);

(2-{4-[2-(5-aminomethyl-5-methyl-[1,3]dioxan-2-yl)-5-(4-fluoro-phenyl)-3H-imidazol-4-yl]-pyrimidin-2-yloxy}-ethyl)-dimethyl-amine, trans-isomer, (Compound A342);

C-{2-[5-(2-cyclohexyloxy-pyrimidin-4-yl)-4-(4-fluoro-phenyl)-1H-imidazol-2-yl]-5-methyl-[1,3]dioxan-5-yl}-methylamine, trans-isomer, (Compound A343);

C-{2-[5-(2-isopropoxy-pyrimidin-4-yl)-4-(4-fluoro-phenyl)-1H-imidazol-2-yl]-5-methyl-[1,3]dioxan-5-yl}-methylamine, trans-isomer, (Compound A344);

C-{2-[4-(4-fluoro-phenyl)-5-(2-propoxy-pyrimidin-4-yl)-1H-imidazol-2-yl]-5-methyl-[1,3]dioxan-5-yl}-methylamine, trans-isomer, (Compound A345);

2-{4-[2-(5-aminomethyl-5-methyl-[1,3]dioxan-2-yl)-5-(4-fluoro-phenyl)-3H-imidazol-4-yl]-pyrimidin-2-yloxy}-ethanol, trans-isomer, (Compound A346);

3-{4-[2-(5-aminomethyl-5-methyl-[1,3]dioxan-2-yl)-5-(4-fluoro-phenyl)-3H-imidazol-4-yl]-pyrimidin-2-yloxy}-propan-1-ol, trans-isomer, (Compound A347);

(g) By proceeding in a similar manner to Example 25(f) but using 2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, cis isomer, (Compound LK) there are prepared the corresponding cis isomers of Compounds A338 to A347.

EXAMPLE 26

Compounds A348 to A575

(a)
(i) Treatment of C-{2-[4-(4-fluoro-phenyl)-5-(2-methylsulphanyl-pyrimidin-4-yl)-1H-imidazol-2-yl]-5-methyl-[1,3]dioxan-5-yl}-methylamine, cis-isomer (Compound KZ) with either acetyl chloride, benzoyl chloride, phenylacetyl chloride according to method described in Example 11 or methanesulphonyl chloride according to method described in Example 13;

(ii) Treatment of compounds obtained from (i) with m-chloroperbenzoic acid according to method described for Example 27;

(iii) Treatment of compounds from (ii) with amines of formula HNY$^4$Y$^5$ or sodium salts of appropriately substituted alcohols or phenols according to methods described in Example 23 or Example 24; gives compounds A348 to A575:

N-{2-[5-(2-amino-pyrimidin-4-yl)-4-(4-fluoro-phenyl)-1H-imidazol-2-yl]-5-methyl-[1,3]dioxan-5-ylmethyl}-acetamide, cis-isomer, (Compound A348);

N-{2-[4-(4-fluoro-phenyl)-5-(2-methylamino-pyrimidin-4-yl)-1H-imidazol-2-yl]-5-methyl-[1,3]dioxan-5-ylmethyl}-acetamide, cis-isomer, (Compound A349);

N-{2-[5-(2-dimethylamino-pyrimidin-4-yl)-4-(4-fluoro-phenyl)-1H-imidazol-2-yl]-5-methyl-[1,3]dioxan-5-ylmethyl}-acetamide, cis-isomer, (Compound A350);

N-{2-[5-(2-cyclopropylamino-pyrimidin-4-yl)-4-(4-fluoro-phenyl)-1H-imidazol-2-yl]-5-methyl-[1,3]dioxan-5-ylmethyl}-acetamide, cis-isomer, (Compound A351);

N-(2-{4-(4-fluoro-phenyl)-5-[2-(piperidin-4-ylamino)-pyrimidin-4-yl]-1H-imidazol-2-yl}-5-methyl-[1,3]dioxan-5-ylmethyl)-acetamide, cis-isomer, (Compound A352);

N-{2-[5-(2-cyclohexylamino-pyrimidin-4-yl)-4-(4-fluoro-phenyl)-1H-imidazol-2-yl]-5-methyl-[1,3]dioxan-5-ylmethyl}-acetamide, cis-isomer, (Compound A353);

N-(2-{4-(4-fluoro-phenyl)-5-[2-(2-hydroxy-ethylamino)-pyrimidin-4-yl]-1H-imidazol-2-yl}-5-methyl-[1,3]dioxan-5-ylmethyl)-acetamide, cis-isomer, (Compound A354);

N-{2-[5-[2-(2-amino-ethylamino)-pyrimidin-4-yl]-4-(4-fluoro-phenyl)-1H-imidazol-2-yl]-5-methyl-[1,3]dioxan-5-ylmethyl}-acetamide, cis-isomer, (Compound A355);

N-[2-(4-(4-fluoro-phenyl)-5-{2-[3-(5H-imidazol-1-yl)-propylamino]-pyrimidin-4-yl}-1H-imidazol-2-yl)-5- methyl-[1,3]dioxan-5-ylmethyl]-acetamide, cis-isomer, (Compound A356);

N-(2-{4-(4-fluoro-phenyl)-5-[2-(3-morpholin-4-yl-propylamino)-pyrimidin-4-yl]-1H-imidazol-2-yl}-5-methyl-[1,3]dioxan-5-ylmethyl)-acetamide, cis-isomer, (Compound A357);

N-(2-{4-(4-fluoro-phenyl)-5-[2-(3-hydroxy-propylamino)-pyrimidin-4-yl]-1H-imidazol-2-yl}-5-methyl-[1,3]dioxan-5-ylmethyl)-acetamide, cis-isomer, (Compound A358);

N-{2-[5-(2-benzylamino-pyrimidin-4-yl)-4-(4-fluoro-phenyl)-1H-imidazol-2-yl]-5-methyl-[1,3]dioxan-5-ylmethyl}-acetamide, cis-isomer, (Compound A359);

N-{2-[5-(2-(4-fluorobenzyl)amino-pyrimidin-4-yl)-4-(4-fluoro-phenyl)-1H-imidazol-2-yl]-5-methyl-[1,3]dioxan-5-ylmethyl}-acetamide, cis-isomer, (Compound A360);

N-{2-[5-(2-(4-methoxybenzyl)amino-pyrimidin-4-yl)-4-(4-fluoro-phenyl)-1H-imidazol-2-yl]-5-methyl-[1,3]dioxan-5-ylmethyl}-acetamide, cis-isomer, (Compound A361);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-acetamide, R isomer, cis-isomer, (Compound A362);

N-(2-{4-(4-fluoro-phenyl)-5-[2-(1-phenyl-ethylamino)-pyrimidin-4-yl]-1H-imidazol-2-yl -}-5-methyl-[1,3]dioxan-5-ylmethyl)-acetamide, S isomer, cis-isomer, (Compound A363);

N-{2-[4-(4-fluoro-phenyl)-5-(2-phenylamino-pyrimidin-4-yl)-1H-imidazol-2-yl]-5-methyl-[1,3]dioxan-5-ylmethyl}-acetamide, cis-isomer, (Compound A364);

N-{2-[4-(4-fluoro-phenyl)-5-(2-(4-fluorophenyl)amino-pyrimidin-4-yl)-1H-imidazol-2-yl]-5-methyl-[1,3]dioxan-5-ylmethyl}-acetamide, cis-isomer, (Compound A365);

N-{2-[4-(4-fluoro-phenyl)-5-(2-(3,4-difluorophenyl)amino-pyrimidin-4-yl)-1H-imidazol-2-yl]-5-methyl-[1,3]dioxan-5-ylmethyl}-acetamide, cis-isomer, (Compound A366);

N-{2-[4-(4-fluoro-phenyl)-5-(2-(3-methoxyphenyl)amino-pyrimidin-4-yl)-1H-imidazol-2-yl]-5-methyl-[1,3]dioxan-5-ylmethyl}-acetamide, cis-isomer, (Compound A367);

N-{2-[4-(4-fluoro-phenyl)-5-(2-piperidin-1-yl-pyrimidin-4-yl)-1H-imidazol-2-yl]-5-methyl-[1,3]dioxan-5-ylmethyl}-acetamide, cis-isomer, (Compound A368);

N-[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-ylmethyl]-acetamide, cis-isomer, (Compound A369);

N-[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-ylmethyl]-acetamide, cis-isomer, (Compound A370);

N-[2-(4-(4-fluoro-phenyl )-5-{2-[(pyridin-2-ylmethyl)-amino]-pyrimidin-4-yl}-1H-imidazol-2-yl)-5-methyl-[1,3]dioxan-5-ylmethyl]-acetamide, cis-isomer, (Compound A371);

N-[2-(4-(4-fluoro-phenyl)-5-{2-[(furan-2-ylmethyl)-amino]-pyrimidin-4-yl}-1H-imidazol-2-yl)-5-methyl-[1,3]dioxan-5-ylmethyl]-acetamide, cis-isomer, (Compound A372);

N-[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-ylmethyl]-acetamide, cis-isomer, (Compound A373);

N-[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-ylmethyl]-acetamide, cis-isomer, (Compound A374);

N-(2-{4-(4-fluoro-phenyl)-5-[2-(4-methyl-piperazin-1-yl)-pyrimidin-4-yl]-1H-imidazol-2-yl}-5-methyl-[1,3]dioxan-5-ylmethyl)-acetamide, cis-isomer, (Compound A375);

N-{2-[4-(4-fluoro-phenyl)-5-(2-morpholin-4-yl-pyrimidin-4-yl)-1H-imidazol-2-yl]-5-methyl-[1,3]dioxan-5-ylmethyl}-acetamide, cis-isomer, (Compound A376);

N-(2-{4-(4-fluoro-phenyl)-5-[2-(3-methoxy-propylamino)-pyrimidin-4-yl]-1H-imidazol-2-yl}-5-methyl-[1,3]dioxan-5-ylmethyl)-acetamide, cis-isomer, (Compound A377);

N-(2-{4-(4-fluoro-phenyl)-5-[2-(2-methoxy-ethylamino)-pyrimidin-4-yl]-1H-imidazol-2-yl}-5-methyl-[1,3]dioxan-5-ylmethyl)-acetamide, cis-isomer, (Compound A378);

N-{2-[5-[2-(3-dimethylamino-propylamino)-pyrimidin-4-yl]-4-(4-fluoro-phenyl)-1H-imidazol-2-yl]-5-methyl-[1,3]dioxan-5-ylmethyl}-acetamide, cis-isomer, (Compound A379);

N-{2-[5-[2-(2-dimethylamino-ethylamino)-pyrimidin-4-yl]-4-(4-fluoro-phenyl)-1H-imidazol-2-yl]-5-methyl-[1,3]dioxan-5-ylmethyl}-acetamide, cis-isomer, (Compound A380);

{4-[2-[5-(acetylamino-methyl)-5-methyl-[1,3]dioxan-2-yl]-5-(4-fluoro-phenyl)-3H-imidazol-4-yl]-pyrimidin-2-ylamino}-acetic acid, cis-isomer, (Compound A381);

3-{4-[2-[5-(acetylamino-methyl)-5-methyl-[1,3]dioxan-2-yl]-5-(4-fluoro-phenyl)-3H-imidazol-4-yl]-pyrimidin-2-ylamino}-propionic acid, cis-isomer, (Compound A382);

N-{2-[4-(4-fluoro-phenyl)-5-(2-methylsulfanyl-pyrimidin-4-yl)-1H-imidazol-2-yl]-5-methyl-[1,3]dioxan-5-ylmethyl}-acetamide, cis-isomer, (Compound A383);

N-{2-[4-(4-fluoro-phenyl)-5-(2-methoxy-pyrimidin-4-yl)-1H-imidazol-2-yl]-5-methyl-[1,3]dioxan-5-ylmethyl}-acetamide, cis-isomer, (Compound A384);

N-{2-[5-(2-benzyloxy-pyrimidin-4-yl)-4-(4-fluoro-phenyl)-1H-imidazol-2-yl]-5-methyl-[1,3]dioxan-5-ylmethyl}-acetamide, cis-isomer, (Compound A385);

N-{2-[4-(4-fluoro-phenyl)-5-(2-phenoxy-pyrimidin-4-yl)-1H-imidazol-2-yl]-5-methyl-[1,3]dioxan-5-ylmethyl}-acetamide, cis-isomer, (Compound A386);

N-(2-{4-(4-fluoro-phenyl)-5-[2-(2-methoxy-ethoxy)-pyrimidin-4-yl]-1H-imidazol-2-yl}-5-methyl-[1,3]dioxan-5-ylmethyl)-acetamide, cis-isomer, (Compound A387);

N-{2-[5-[2-(2-dimethylamino-ethoxy)-pyrimidin-4-yl]-4-(4-fluoro-phenyl)-1H-imidazol-2-yl]-5-methyl-[1,3]dioxan-5-ylmethyl}-acetamide, cis-isomer, (Compound A388);

N-{2-[5-(2-cyclohexyloxy-pyrimidin-4-yl)-4-(4-fluoro-phenyl)-1H-imidazol-2-yl]-5-methyl-[1,3]dioxan-5-ylmethyl}-acetamide, cis-isomer, (Compound A389);

N-{2-[5-(2-Isopropoxy-pyrimidin-4-yl)-4-(4-fluoro-phenyl)-1H-imidazol-2-yl]-5-methyl-[1,3]dioxan-5-ylmethyl}-acetamide, cis-isomer, (Compound A390);

N-{2-[4-(4-fluoro-phenyl)-5-(2-isopropylamino-pyrimidin-4-yl)-1H-imidazol-2-yl]-5-methyl-[1,3]dioxan-5-ylmethyl}-acetamide, cis-isomer, (Compound A391);

N-{2-[5-(2-allylamino-pyrimidin-4-yl)-4-(4-fluoro-phenyl)-1H-imidazol-2-yl]-5-methyl-[1,3]dioxan-5-ylmethyl}-acetamide, cis-isomer, (Compound A392);

N-{2-[5-[2-(cyclopropylmethyl-amino)-pyrimidin-4-yl]-4-(4-fluoro-phenyl)-1H-imidazol-2-yl]-5-methyl-[1,3]dioxan-5-ylmethyl}-acetamide, cis-isomer, (Compound A393);

N-{2-[5-[2-(cyanomethyl-amino)-pyrimidin-4-yl]-4-(4-fluoro-phenyl)-1H-imidazol-2-yl]-5-methyl-[1,3]dioxan-5-ylmethyl}-acetamide, cis-isomer, (Compound A394);

N-{2-[5-[2-(2-cyano-ethylamino)-pyrimidin-4-yl]-4-(4-fluoro-phenyl)-1H-imidazol-2-yl]-5-methyl-[1,3]dioxan-5-ylmethyl}-acetamide, cis-isomer, (Compound A395);

N-(2-{4-(4-fluoro-phenyl)-5-[2-(pyridin-3-ylamino)-pyrimidin-4-yl]-1H-imidazol-2-yl}-5-methyl-[1,3]dioxan-5-ylmethyl)-acetamide, cis-isomer, (Compound A396);

N-(2-{4-(4-fluoro-phenyl)-5-[2-(pyridin-4-ylamino)-pyrimidin-4-yl]-1H-imidazol-2-yl}-5-methyl-[1,3]dioxan-5-ylmethyl)-acetamide, cis-isomer, (Compound A397);

2-{4-[2-[5-(acetylamino-methyl)-5-methyl-[1,3]dioxan-2-yl]-5-(4-fluoro-pheny)-3H-imidazol-4-yl]-pyrimidin-2-ylamino}-acetamide, cis-isomer, (Compound A398);

3-{4-[2-[5-(acetylamino-methyl)-5-methyl-[1,3]dioxan-2-yl]-5-(4-fluoro-phenyl)-3-imidazol-4-yl]-pyrimidin-2-ylamino}-propionamide, cis-isomer, (Compound A399);

N-{2-[4-(4-fluoro-phenyl)-5-(2-propoxy-pyrimidin-4-yl)-1H-imidazol-2-yl]-5-methyl-[1,3]dioxan-5-ylmethyl}-acetamide, cis-isomer, (Compound A400);

N-(2-{4-(4-fluoro-phenyl)-5-[2-(2-hydroxy-ethoxy)-pyrimidin-4-yl]-1H-imidazol-2-yl}-5-methyl-[1,3]dioxan-5-ylmethyl)-acetamide, cis-isomer, (Compound A401);

N-(2-{4-(4-fluoro-phenyl)-5-[2-(3-hydroxy-propoxy)-pyrimidin-4-yl]-1H-imidazol-2-yl}-5-methyl-[1,3]dioxan-5-ylmethyl)-acetamide, cis-isomer, (Compound A402);

N-{2-[4-(4-fluoro-phenyl)-5-(2-propylamino-pyrimidin-4-yl)-1H-imidazol-2-yl]-5-methyl-[1,3]dioxan-5-ylmethyl}-acetamide, cis-isomer, (Compound A403);

N-{2-[4-(4-fluoro-phenyl)-5-(2-pyrrolidin-1-yl-pyrimidin-4-yl)-1H-imidazol-2-yl]-5-methyl-[1,3]dioxan-5-ylmethyl}-acetamide, cis-isomer, (Compound A404);

N-{2-[5-(2-amino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A405);

N-{2-[4-(4-fluoro-phenyl)-5-(2-methylamino-pyrimidin-4-yl)-1H-imidazol-2-yl]-5-methyl-[1,3]dioxan-5-ylmethyl}-methanesulfonamide, cis-isomer, (Compound A406);

N-{2-[5-(2-dimethylamino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A407);

N-{2-[5-(2-cyclopropylamino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A408);

N-(2-{4-(4-fluoro-phenyl)-5-[2-(piperidin-4-ylamino)-pyrimidin-4-yl]-1H-imidazol-2-yl}-methyl-[1,3]dioxan-5-ylmethyl)-methanesulfonamide, cis-isomer, (Compound A409);

N-{2-[5-(2-cyclohexylamino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A410);

N-(2-{4-(4-fluoro-phenyl)-5-[2-(2-hydroxy-ethylamino)-pyrimidin-4-yl]-1H-imidazol-2-yl}-methyl-[1,3]dioxan-5-ylmethyl)-methanesulfonamide, cis-isomer, (Compound A411);

N-{2-[5-[2-(2-amino-ethylamino)-pyrimidin-4-yl]-4-(4-fluoro-phenyl)-1H-imidazol-2-yl]-5-methyl-[1,3]dioxan-5-ylmethyl}-methanesulfonamide, cis-isomer, (Compound A412);

N-[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-ylmethyl]-methanesulfonamide, cis-isomer, (Compound A413);

N-(2-{4-(4-fluoro-phenyl)-5-[2-(3-morpholin-4-yl-propylamino)-pyrimidin-4-yl]-1H-imidazol-2-yl}-5-methyl-[1,3]dioxan-5-ylmethyl)-methanesulfonamide, cis-isomer, (Compound A414);

N-(2-{4-(4-fluoro-phenyl)-5-[2-(3-hydroxy-propylamino)-pyrimidin-4-yl]-1H-imidazol-2-yl}-5-methyl-[1,3]dioxan-5-ylmethyl)-methanesulfonamide, cis-isomer, (Compound A415);

N-{2-[5-(2-benzylamino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A416);

N-{2-[5-(2-(4-fluorobenzyl)amino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A417);

N-{2-[5-(2-(4-methoxybenzyl)amino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A418);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-methanesulfonamide, R isomer, cis-isomer, (Compound A419);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-methanesulfonamide, S isomer, cis-isomer, (Compound A420);

N-{2-[4-(4-fluoro-phenyl)-5-(2-phenylamino-pyrimidin-4-yl)-1H-imidazol-2-yl]-5-methyl-[1,3]dioxan-5-ylmethyl}-methanesulfonamide, cis-isomer, (Compound A421);

N-{2-[4-(4-fluoro-phenyl)-5-(2-(4-fluorophenyl)amino-pyrimidin-4-yl)-1H-imidazol-2-yl]-5-methyl-[1,3]dioxan-5-ylmethyl}-methanesulfonamide, cis-isomer, (Compound A422);

N-{2-[4-(4-fluoro-phenyl)-5-(2-(3,4-difluorophenyl)amino-pyrimidin-4-yl)-1H-imidazol-2-yl]-5-methyl-[1,3]dioxan-5-ylmethyl}-methanesulfonamide, cis-isomer, (Compound A423);

N-{2-[4-(4-fluoro-phenyl)-5-(2-(3-methoxyphenyl)amino-pyrimidin-4-yl)-1H-imidazol-2-yl]-5methyl-[1,3]dioxan-5-ylmethyl}-methanesulfonamide, cis-isomer, (Compound A424);

N-{2-[4-(4-fluoro-phenyl)-5-(2-piperidin-1-yl-pyrimidin-4-yl)-1H-imidazol-2-yl]-5-methyl-[1,3]dioxan-5-ylmethyl}-methanesulfonamide, cis-isomer, (Compound A425);

N-[2-(4-(4-fluoro-phenyl)-5-{2-[(pyridin-4-ylmethyl)-amino]-pyrimidin-4-yl}-1H-imidazol-2-yl)-5methyl-[1,3]dioxan-5-ylmethyl]-methanesulfonamide, cis-isomer, (Compound A426);

N-[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-ylmethyl]-methanesulfonamide, cis-isomer, (Compound A427);

N-[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-ylmethyl]-methanesulfonamide, cis-isomer, (Compound A428);

N-[2-(4-(4-fluoro-phenyl)-5-{2-[(furan-2-ylmethyl)-amino]-pyrimidin-4-yl}-1H-imidazol-2-yl)-5-methyl-[1,3]dioxan-5-ylmethyl]-methanesulfonamide, cis-isomer, (Compound A429);

N-[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-ylmethyl]-methanesulfonamide, cis-isomer, (Compound A430);

N-[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-ylmethyl]-methanesulfonamide, cis-isomer, (Compound A431);

N-(2-{4-(4-fluoro-phenyl)-5-[2-(4-methyl-piperazin-1-yl)-pyrimidin-4-yl]-1H-imidazol-2-yl}-5-methyl-[1,3]dioxan-5-ylmethyl)-methanesulfonamide, cis-isomer, (Compound A432);

N-{2-[4-(4-fluoro-phenyl)-5-(2-morpholin-4-yl-pyrimidin-4-yl)-1H-imidazol-2-yl]-5-methyl-[1,3]dioxan-5-ylmethyl}-methanesulfonamide, cis-isomer, (Compound A433);

N-(2-{4-(4-fluoro-phenyl)-5-[2-(3-methoxy-propylamino)-pyrimidin-4-yl]-1H-imidazol-2-yl}-methyl-[1,3]dioxan-5-ylmethyl)-methanesulfonamide, cis-isomer, (Compound A434);

N-(2-{4-(4-fluoro-phenyl)-5-[2-(2-methoxy-ethylamino)-pyrimidin-4-yl]-1H-imidazol-2-yl}-methyl-[1,3]dioxan-5-ylmethyl)-methanesulfonamide, cis-isomer, (Compound A435);

N-{2-[5-[2-(3-dimethylamino-propylamino)-pyrimidin-4-yl]-4-(4-fluoro-phenyl)-1H-imidazol-2-yl]-5-methyl-[1,3]dioxan-5-ylmethyl}-methanesulfonamide, cis-isomer, (Compound A436);

N-{2-[5-[2-(2-dimethylamino-ethylamino)-pyrimidin-4-yl]-4-(4-fluoro-phenyl)-1H-imidazol-2-yl]-5-methyl-[1,3]dioxan-5-ylmethyl}-methanesulfonamide, cis-isomer, (Compound A437);

(4-{5-(4-fluoro-phenyl)-2-[5-(methanesulfonylamino-methyl)-5-methyl-[1,3]dioxan-2-yl]-3H-imidazol-4-yl}-pyrimidin-2-ylamino)-acetic acid, cis-isomer, (Compound A438);

3-(4-{5-(4-fluoro-phenyl)-2-[5-(methanesulfonylamino-methyl)-5-methyl-[1,3]dioxan-2-yl]-3H-imidazol-4-yl}-pyrimidin-2-ylamino)-propionic acid, cis-isomer, (Compound A439);

N-{2-[4-(4-fluoro-phenyl)-5-(2-methylsulfanyl-pyrimidin-4-yl)-1H-imidazol-2-yl]-5-methyl-[1,3]-dioxan-5-ylmethyl}-methanesulfonamide, cis-isomer, (Compound A440);

N-{2-[4-(4-fluoro-phenyl)-5-(2-methoxy-pyrimidin-4-yl)-1H-imidazol-2-yl]-5-methyl-[1,3]dioxan-5-ylmethyl}-methanesulfonamide, cis-isomer, (Compound A441);

N-{2-[5-(2-benzyloxy-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A442);

N-{2-[4-(4-fluoro-phenyl)-5-(2-phenoxy-pyrimidin-4-yl)-1H-imidazol-2-yl]-5-methyl-[1,3]dioxan-5-ylmethyl}-methanesulfonamide, cis-isomer, (Compound A443);

N-(2-{4-(4-fluoro-phenyl)-5-[2-(2-methoxy-ethoxy)-pyrimidin-4-yl]-1H-imidazol-2-yl}-5-methyl-[1,3]dioxan-5-ylmethyl)-methanesulfonamide, cis-isomer, (Compound A444);

N-{2-[5-[2-(2-dimethylamino-ethoxy)-pyrimidin-4-y]-4-(4-fluoro-phenyl)-1H-imidazol-2-yl]-5-methyl-[1,3]dioxan-5-ylmethyl}-methanesulfonamide, cis-isomer, (Compound A445);

N-{2-[5-(2-cyclohexyloxy-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A446);

N-{2-[5-(2-Isopropoxy-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A447);

N-{2-[4-(4-fluoro-phenyl)-5-(2-isopropylamino-pyrimidin-4-yl)-1H-imidazol-2-yl]-5-methyl-[1,3]dioxan-5-ylmethyl}-methanesulfonamide, cis-isomer, (Compound A448);

N-{2-[5-(2-allylamino-pyrimidin-4-yl)-4-(4-fluoro-phenyl)-1H-imidazol-2-yl]-5-methyl-[1,3]dioxan-5-ylmethyl}-methanesulfonamide, cis-isomer, (Compound A449);

N-{2-[5-[2-(cyclopropylmethyl-amino)-pyrimidin-4-yl]-4-(4-fluoro-phenyl)-1H-imidazol-2-yl]-5-methyl-[1,3]dioxan-5-ylmethyl}-methanesulfonamide, cis-isomer, (Compound A450);

N-{2-[5-[2-(cyanomethyl-amino)-pyrimidin-4-yl]-4-(4-fluoro-phenyl)-1H-imidazol-2-yl]-5-methyl-[1,3]dioxan-5-ylmethyl}-methanesulfonamide, cis-isomer, (Compound A45 1);

N-{2-[5-[2-(2-cyano-ethylamino)-pyrimidin-4-yl]-4-(4-fluoro-phenyl)-1H-imidazol-2-yl]-5-methyl-[1,3]dioxan-5-ylmethyl}-methanesulfonamide, cis-isomer, (Compound A452);

N-(2-{4-(4-fluoro-phenyl)-5-[2-(pyridin-3-ylamino)-pyrimidin-4-yl]-1H-imidazol-2-yl}-5-methyl-[1,3]dioxan-5-ylmethyl)-methanesulfonamide, cis-isomer, (Compound A453);

N-(2-{4-(4-fluoro-phenyl)-5-[2-(pyridin-4-ylamino)-pyrimidin-4-yl]-1H-imidazol-2-yl}-5-methyl-[1,3]dioxan-5-ylmethyl)-methanesulfonamide, cis-isomer, (Compound A454);

2-(4-{5-(4-fluoro-phenyl)-2-[5-(methanesulfonylamino-methyl)-5-methyl-[1,3]dioxan-2-yl]-3H-imidazol-4-yl}-pyrimidin-2-ylamino)-acetamide, cis-isomer, (Compound A455);

3-(4-{5-(4-fluoro-phenyl)-2-[5-(methanesulfonylamino-methyl)-5-methyl-[1,3]dioxan-2-yl]-3H-imidazol-4-yl}-pyrimidin-2-ylamino)-propionamide, cis-isomer, (Compound A456);

N-{2-[4-(4-fluoro-phenyl)-5-(2-propoxy-pyrimidin-4-yl)-1H-imidazol-2-yl]-5-methyl-[1,3]dioxan-5-ylmethyl}-methanesulfonamide, cis-isomer, (Compound A457);

N-(2-{4-(4-fluoro-phenyl)-5-[2-(2-hydroxy-ethoxy)-pyrimidin-4-yl]-1H-imidazol-2-yl -5-methyl-[1,3]dioxan-5-ylmethyl)-methanesulfonamide, cis-isomer, (Compound A458);

N-(2-{4-(4-fluoro-phenyl)-5-[2-(3-hydroxy-propoxy)-pyrimidin-4-yl]-1H-imidazol-2-yl}-5-methyl-[1,3]dioxan-5-ylmethyl)-methanesulfonamide, cis-isomer, (Compound A459);

N-{2-[4-(4-fluoro-phenyl)-5-(2-propylamino-pyrimidin-4-yl)-1H-imidazol-2-yl]-5-methyl-[1,3]dioxan-5-ylmethyl}-methanesulfonamide, cis-isomer, (Compound A460);

N-{2-[4-(4-fluoro-phenyl)-5-(2-pyrrolidin-1-yl-pyrimidin-4-yl)-1H-imidazol-2-yl]-5-methyl-[1,3]dioxan-5-ylmethyl}-methanesulfonamide, cis-isomer, (Compound A461);

N-{2-[5-(2-amino-pyrimidin-4-yl)-4-(4-fluoro-phenyl)-1H-imidazol-2-yl]-5-methyl-[1,3]dioxan-5-ylmethyl}-benzamide, cis-isomer, (Compound A462);

N-(2-[4-(4-fluoro-phenyl)-5-(2-methylamino-pyrimidin-4-yl)-1H-imidazol-2-yl]-5-methyl-[1,3]dioxan-5-ylmethyl}-benzamide, cis-isomer, (Compound A463);

N-{2-[5-(2-dimethylamino-pyrimidin-4-yl)-4-(4-fluoro-phenyl)-1H-imidazol-2-yl]-5-methyl-[1,3]dioxan-5-ylmethyl}-benzamide, cis-isomer, (Compound A464);

N-{2-[5-(2-cyclopropylamino-pyrimidin-4-yl)-4-(4-fluoro-phenyl)-1H-imidazol-2-yl]-5-methyl-[1,3]dioxan-5-ylmethyl}-benzamide, cis-isomer, (Compound A465);

N-(2-{4-(4-fluoro-phenyl)-5-[2-(piperidin-4-ylamino)-pyrimidin-4-yl]-1H-imidazol-2-yl}-5-methyl-[1,3]dioxan-5-ylmethyl)-benzamide, cis-isomer, (Compound A466);

N-{2-[5-(2-cyclohexylamino-pyrimidin-4-yl)-4-(4-fluoro-phenyl)-1H-imidazol-2-yl]-5-methyl-[1,3]dioxan-5-ylmethyl}-benzamide, cis-isomer, (Compound A467);

N-(2-{4-(4-fluoro-phenyl)-5-[2-(2-hydroxy-ethylamino)-pyrimidin-4-yl]-1H-imidazol-2-yl}-5-methyl-[1,3]dioxan-5-ylmethyl)-benzamide, cis-isomer, (Compound A468);

N-{2-[5-[2-(2-amino-ethylamino)-pyrimidin-4-yl]-4-(4-fluoro-phenyl)-1H-imidazol-2-yl]-5-methyl-[1,3]dioxan-5-ylmethyl}-benzamide, cis-isomer, (Compound A469);

N-[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-ylmethyl]-benzamide, cis-isomer, (Compound A470);

N-(2-{4-(4-fluoro-phenyl)-5-[2-(3-morpholin-4-yl-propylamino)-pyrimidin-4-yl]-1H-imidazol-2-yl}-5-methyl-[1,3]dioxan-5-ylmethyl)-benzamide, cis-isomer, (Compound A471);

N-(2-{4-(4-fluoro-phenyl)-5-[2-(3-hydroxy-propylamino)-pyrimidin-4-yl]-1H-imidazol-2-yl}-5-methyl-[1,3]dioxan-5-ylmethyl)-benzamide, cis-isomer, (Compound A472);

N-{2-[5-(2-benzylamino-pyrimidin-4-yl)-4-(4-fluoro-phenyl)-1H-imidazol-2-yl]-5-methyl-[1,3]dioxan-5-ylmethyl}-benzamide, cis-isomer, (Compound A473);

N-{2-[5-(2-(4-fluorobenzyl)amino-pyrimidin-4-yl)-4-(4-fluoro-phenyl)-1H-imidazol-2-yl]-5-methyl-[1,3]dioxan-5-ylmethyl}-benzamide, cis-isomer, (Compound A474);

N-{2-[5-(2-(4-methoxybenzyl)amino-pyrimidin-4-yl)-4-(4-fluoro-phenyl)-1H-imidazol-2-yl]-5-methyl-[1,3]dioxan-5-ylmethyl}-benzamide, cis-isomer, (Compound A475);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-benzamide, R isomer, cis-isomer, (Compound A476);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-benzamide, S isomer, cis-isomer, (Compound A477);

N-{2-[4-(4-fluoro-phenyl)-5-(2-phenylamino-pyrimidin-4-yl)-1H-imidazol-2-yl]-5-methyl-[1,3]dioxan-5-ylmethyl}-benzamide, cis-isomer, (Compound A478);

N-{2-[4-(4-fluoro-phenyl)-5-(2-(4-fluorophenyl)amino-pyrimidin-4-yl)-1H-imidazol-2-yl]-5-methyl-[1,3]dioxan-5-ylmethyl}-benzamide, cis-isomer, (Compound A479);

N-{2-[4-(4-fluoro-phenyl)-5-(2-(3,4-difluorophenyl)amino-pyrimidin-4-yl)-1H-imidazol-2-yl]-5-methyl-[1,3]dioxan-5-ylmethyl}-benzamide, cis-isomer, (Compound A480);

N-{2-[4-(4-fluoro-phenyl)-5-(2-(3-methoxyphenyl)amino-pyrimidin-4-yl)-1H-imidazol-2-yl]-5-methyl-[1,3]dioxan-5-ylmethyl}-benzamide, cis-isomer, (Compound A481);

N-{2-[4-(4-fluoro-phenyl)-5-(2-piperidin-1-yl-pyrimidin-4-yl)-1H-imidazol-2-yl]-5methyl-[1,3]dioxan-5-ylmethyl}-benzamide, cis-isomer, (Compound A482);

N-[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-ylmethyl]-benzamide, cis-isomer, (Compound A483);

N-[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-ylmethyl]-benzamide, cis-isomer, (Compound A484);

N-[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-ylmethyl]-benzamide, cis-isomer, (Compound A485);

N-[2-(4-(4-fluoro-phenyl)-5-{2-[(furan-2-ylmethyl)-amino]-pyrimidin-4-yl}-1H-imidazol-2-yl)-5-methyl-[1,3]dioxan-5-ylmethyl]-benzamide, cis-isomer, (Compound A486);

N-[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-ylmethyl]-benzamide, cis-isomer, (Compound A487);

N-[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-ylmethyl]-benzamide, cis-isomer, (Compound A488);

N-(2-{4-(4-fluoro-phenyl)-5-[2-(4-methyl-piperazin-1-yl)-pyrimidin-4-yl]-1H-imidazol-2-yl}-5-methyl-[1,3]dioxan-5-ylmethyl)-benzamide, cis-isomer, (Compound A489);

N-{2-[4-(4-fluoro-phenyl)-5-(2-morpholin-4-yl-pyrimidin-4-yl)-1H-imidazol-2-yl]-5-methyl-[1,3]dioxan-5-ylmethyl}-benzamide, cis-isomer, (Compound A490);

N-(2-{4-(4-fluoro-phenyl)-5-[2-(3-methoxy-propylamino)-pyrimidin-4-yl]-1H-imidazol-2-yl}-5-methyl-[1,3]dioxan-5-ylmethyl)-benzamide, cis-isomer, (Compound A491);

N-(2-{4-(4-fluoro-phenyl)-5-[2-(2-methoxy-ethylamino)-pyrimidin-4-yl]-1H-imidazol-2-yl}-5-methyl-[1,3]dioxan-5-ylmethyl)-benzamide, cis-isomer, (Compound A492);

N-{2-[5-[2-(3-dimethylamino-propylamino)-pyrimidin-4-yl]-4-(4-fluoro-phenyl)-1H-imidazol-2-yl]-5-methyl-[1,3]dioxan-5-ylmethyl}-benzamide, cis-isomer, (Compound A493);

N-{2-[5-[2-(2-dimethylamino-ethylamino)-pyrimidin-4-yl]-4-(4-fluoro-phenyl)-1H-imidazol-2-yl]-5-methyl-[1,3]dioxan-5-ylmethyl}-benzamide, cis-isomer, (Compound A494);

{4-[2-[5-(benzoylamino-methyl)-5-methyl-[1,3]dioxan-2-yl]-5-(4-fluoro-phenyl)-3H-imidazol-4-yl]-pyrimidin-2-ylamino}-acetic acid, cis-isomer, (Compound A495);

3-{4-[2-[5-(benzoylamino-methyl)-5-methyl-[1,3]dioxan-2-yl]-5-(4-fluoro-phenyl)-3H-imidazol-4-yl]-pyrimidin-2-ylamino}-propionic acid, cis-isomer, (Compound A496);

N-{2-[4-(4-fluoro-phenyl)-5-(2-methylsulfanyl-pyrimidin-4-yl)-1H-imidazol-2-yl]-5-methyl-[1,3]dioxan-5-ylmethyl}-benzamide, cis-isomer, (Compound A497);

N-{2-[4-(4-fluoro-phenyl)-5-(2-methoxy-pyrimidin-4-yl)-1H-imidazol-2-yl]-5-methyl-[1,3]dioxan-5-ylmethyl}-benzamide, cis-isomer, (Compound A498);

N-{2-[5-(2-benzyloxy-pyrimidin-4-yl)-4-(4-fluoro-phenyl)-1H-imidazol-2-yl]-5-methyl-[1,3]dioxan-5-ylmethyl}-benzamide, cis-isomer, (Compound A499);

N-{2-[4-(4-fluoro-phenyl)-5-(2-phenoxy-pyrimidin-4-yl)-1H-imidazol-2-yl]-5-methyl-[1,3]dioxan-5-ylmethyl}-benzamide, cis-isomer, (Compound A500);

N-(2-{4-(4-fluoro-phenyl)-5-[2-(2-methoxy-ethoxy)-pyrimidin-4-yl]-1H-imidazol-2-yl}-5-methyl-[1,3]dioxan-5-ylmethyl)-benzamide, cis-isomer, (Compound A501);

N-{2-[5-[2-(2-dimethylamino-ethoxy)-pyrimidin-4-yl]-4-(4-fluoro-phenyl)-1H-imidazol-2-yl]-5-methyl-[1,3]dioxan-5-ylmethyl}-benzamide, cis-isomer, (Compound A502);

N-{2-[5-(2-cyclohexyloxy-pyrimidin-4-yl)-4-(4-fluoro-phenyl)-1H-imidazol-2-yl]-5-methyl-[1,3]dioxan-5-ylmethyl}-benzamide, cis-isomer, (Compound A503);

N-{2-[5-(2-Isopropoxy-pyrimidin-4-yl)-4-(4-fluoro-phenyl)-1H-imidazol-2-yl]-5-methyl-[1,3]dioxan-5-ylmethyl}-benzamide, cis-isomer, (Compound A504);

N-{2-[4-(4-fluoro-phenyl)-5-(2-isopropylamino-pyrimidin-4-yl)-1H-imidazol-2-yl]-5-methyl-[1,3]dioxan-5-ylmethyl}-benzamide, cis-isomer, (Compound A505);

N-{2-[5-(2-allylamino-pyrimidin-4-yl)-4-(4-fluoro-phenyl)-1H-imidazol-2-yl]-5-methyl-[1,3]dioxan-5-ylmethyl}-benzamide, cis-isomer, (Compound A506);

N-{2-[5-[2-(cyclopropylmethyl-amino)-pyrimidin-4-yl]-4-(4-fluoro-phenyl)-1H-imidazol-2-yl]-5-methyl-[1,3]dioxan-5-ylmethyl}-benzamide, cis-isomer, (Compound A507);

N-{2-[5-[2-(cyanomethyl-amino)-pyrimidin-4-yl]-4-(4-fluoro-phenyl)-1H-imidazol-2-yl]-5-methyl-[1,3]dioxan-5-ylmethyl}-benzamide, cis-isomer, (Compound A508);

N-{2-[5-[2-(2-cyano-ethylamino)-pyrimidin-4-yl]-4-(4-fluoro-phenyl)-1H-imidazol-2-yl]-5-methyl-[1,3]dioxan-5-ylmethyl}-benzamide, cis-isomer, (Compound A509);

N-(2-{4-(4-fluoro-phenyl)-5-[2-(pyridin-3-ylamino)-pyrimidin-4-yl]-1H-imidazol-2-yl}-5-methyl-[1,3]dioxan-5-ylmethyl)-benzamide, cis-isomer, (Compound A510);

N-(2-{4-(4-fluoro-phenyl)-5-[2-(pyridin-4-ylamino)-pyrimidin-4-yl]-1H-imidazol-2-yl}-5-methyl-[1,3]dioxan-5-ylmethyl)-benzamide, cis-isomer, (Compound A511);

N-{2-[5-[2-(Carbamoylmethyl-amino)-pyrimidin-4-yl]-4-(4-fluoro-phenyl)-1H-imidazol-2-yl]-5-methyl-[1,3]dioxan-5-ylmethyl}-benzamide, cis-isomer, (Compound A512);

N-{2-[5-[2-(2-Carbamoyl-ethylamino)-pyrimidin-4-yl]-4-(4-fluoro-phenyl)-1H-imidazol-2-yl]-5-methyl-[1,3]dioxan-5-ylmethyl}-benzamide, cis-isomer, (Compound A513);

N-{2-[4-(4-fluoro-phenyl)-5-(2-propoxy-pyrimidin-4-yl)-1H-imidazol-2-yl]-5-methyl-[1,3]dioxan-5-ylmethyl}-benzamide, cis-isomer, (Compound A514);

N-(2-{4-(4-fluoro-phenyl)-5-[2-(2-hydroxy-ethoxy)-pyrimidin-4-yl]-1H-imidazol-2-yl}-5-methyl-[1,3]dioxan-5-ylmethyl)-benzamide, cis-isomer, (Compound A515);

N-(2-{4-(4-fluoro-phenyl)-5-[2-(3-hydroxy-propoxy)-pyrimidin-4-yl]-1H-imidazol-2-yl}-5methyl-[1,3]dioxan-5-ylmethyl)-benzamide, cis-isomer, (Compound A516);

N-{2-[4-(4-fluoro-phenyl)-5-(2-propylamino-pyrimidin-4-yl)-1H-imidazol-2-yl]-5-methyl-[1,3]dioxan-5-ylmethyl}-benzamide, cis-isomer, (Compound A517);

N-{2-[4-(4-fluoro-phenyl)-5-(2-pyrrolidin-1-yl-pyrimidin-4-yl)-1H-imidazol-2-yl]-5-methyl-[1,3]dioxan-5-ylmethyl}-benzamide, cis-isomer, (Compound A518);

N-{2-[5-(2-amino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A519);

N-{2-[4-(4-fluoro-phenyl)-5-(2-methylamino-pyrimidin-4-yl)-1H-imidazol-2-yl]-5-methyl-[1,3]dioxan-5-ylmethyl}-2-phenyl-acetamide, cis-isomer, (Compound A520);

N-{2-[5-(2-dimethylamino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A521);

N-{2-[5-(2-cyclopropylamino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A522);

N-(2-{4-(4-fluoro-phenyl)-5-[2-(piperidin-4-ylamino)-pyrimidin-4-yl]-1H-imidazol-2-yl}-methyl-[1,3]dioxan-5-ylmethyl)-2-phenyl-acetamide, cis-isomer, (Compound A523);

N-{2-[5-(2-cyclohexylamino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A524);

N-(2-{4-(4-fluoro-phenyl)-5-[2-(2-hydroxy-ethylamino)-pyrimidin-4-yl]-1H-imidazol-2-yl}-5-methyl-[1,3]dioxan-5-ylmethyl)-2-phenyl-acetamide, cis-isomer, (Compound A525);

N-{2-[5-[2-(2-amino-ethylamino)-pyrimidin-4-yl]-4-(4-fluoro-phenyl)-1H-imidazol-2-yl]-5-methyl-[1,3]dioxan-5-ylmethyl}-2-phenyl-acetamide, cis-isomer, (Compound A526);

N-[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-ylmethyl]-2-phenyl-acetamide, cis-isomer, (Compound A527);

N-(2-{4-(4-fluoro-phenyl)-5-[2-(3-morpholin-4-yl-propylamino)-pyrimidin-4-yl]-1H-imidazol-2-yl}-5-methyl-[1,3]dioxan-5-ylmethyl)-2-phenyl-acetamide, cis-isomer, (Compound A528);

N-(2-{4-(4-fluoro-phenyl)-5-[2-(3-hydroxy-propylamino)-pyrimidin-4-yl]-1H-imidazol-2-yl}-5-methyl-[1,3]dioxan-5-ylmethyl)-2-phenyl-acetamide, cis-isomer, (Compound A529);

N-{2-[5-(2-benzylamino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A530);

N-{2-[5-(2-(4-fluorobenzyl)amino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A531);

N-{2-[5-(2-(4-methoxybenzyl)amino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A532);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-2-phenyl-acetamide, R isomer, cis-isomer, (Compound A533);

N-(2-{4-(4-fluoro-phenyl)-5-[2-(1-phenyl-ethylamino)-pyrimidin-4-yl]-1H-imidazol-2-yl}-5-methyl-[1,3]dioxan-5-ylmethyl)-2-phenyl-acetamide, S isomer, cis-isomer, (Compound A534);

N-{2-[4-(4-fluoro-phenyl)-5-(2-phenylamino-pyrimidin-4-yl)-1H-imidazol-2-yl]-5-methyl-[1,3]dioxan-5-ylmethyl}-2-phenyl-acetamide, cis-isomer, (Compound A535);

N-{2-[4-(4-fluoro-phenyl)-5-(2-(4-fluorophenyl)amino-pyrimidin-4-yl)-1H-imidazol-2-yl]-5-methyl-[1,3]dioxan-5-ylmethyl}-2-phenyl-acetamide, cis-isomer, (Compound A536);

N-{2-[4-(4-fluoro-phenyl)-5-(2-(3,4-difluorophenyl)amino-pyrimidin-4-yl)-1H-imidazol-2-yl]-5-methyl-[1,3]dioxan-5-ylmethyl}-2-phenyl-acetamide, cis-isomer, (Compound A537);

N-{2-[4-(4-fluoro-phenyl)-5-(2-(3-methoxyphenyl)amino-pyrimidin-4-yl)-1H-imidazol-2-yl]-5-methyl-[1,3]dioxan-5-ylmethyl}-2-phenyl-acetamide, cis-isomer, (Compound A538);

N-{2-[4-(4-fluoro-phenyl)-5-(2-piperidin-1-yl-pyrimidin-4-yl)-1H-imidazol-2-yl]-5-methyl-[1,3]dioxan-5-ylmethyl}-2-phenyl-acetamide, cis-isomer, (Compound A539);

N-[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-ylmethyl]-2-phenyl-acetamide, cis-isomer, (Compound A540);

N-[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-ylmethyl]-2-phenyl-acetamide, cis-isomer, (Compound A541);

N-[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-ylmethyl]-2-phenyl-acetamide, cis-isomer, (Compound A542);

N-[2-(4-(4-fluoro-phenyl)-5-{2-[(furan-2-ylmethyl)-amino]-pyrimidin-4-yl}-1H-imidazol-2-yl)-5-methyl-[1,3]dioxan-5-ylmethyl]-2-phenyl-acetamide, cis-isomer, (Compound A543);

N-[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-ylmethyl]-2-phenyl-acetamide, cis-isomer, (Compound A544);

N-[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-ylmethyl]-2-phenyl-acetamide, cis-isomer, (Compound A545);

N-(2-{4-(4-fluoro-phenyl)-5-[2-(4-methyl-piperazin-1-yl)-pyrimidin-4-yl]-1H-imidazol-2-yl}-5-methyl-[1,3]dioxan-5-ylmethyl)-2-phenyl-acetamide, cis-isomer, (Compound A546);

N-{2-[4-(4-fluoro-phenyl)-5-(2-morpholin-4-yl-pyrimidin-4-yl)-1H-imidazol-2-yl]-5-methyl-[1,3]dioxan-5-ylmethyl}-2-phenyl-acetamide, cis-isomer, (Compound A547);

N-(2-{4-(4-fluoro-phenyl)-5-[2-(3-methoxy-propylamino)-pyrimidin-4-yl]-1H-imidazol-2-yl}-5-methyl-[1,3]dioxan-5-ylmethyl)-2-phenyl-acetamide, cis-isomer, (Compound A548);

N-(2-{4-(4-fluoro-phenyl)-5-[2-(2-methoxy-ethylamino)-pyrimidin-4-yl]-1H-imidazol-2-yl}-5-methyl-[1,3]dioxan-5-ylmethyl)-2-phenyl-acetamide, cis-isomer, (Compound A549);

N-{2-[5-[2-(3-dimethylamino-propylamino)-pyrimidin-4-yl]-4-(4-fluoro-phenyl)-1H-imidazol-2-yl]-5-methyl-[1,3]dioxan-5-ylmethyl}-2-phenyl-acetamide, (Compound A550);

N-{2-[5-[2-(2-dimethylamino-ethylamino)-pyrimidin-4-yl]-4-(4-fluoro-phenyl)-1H-imidazol-2-yl]-5-methyl-[1,3]dioxan-5-ylmethyl}-2-phenyl-acetamide, cis-isomer, (Compound A551);

(4-{5-(4-fluoro-phenyl)-2-[5-methyl-5-(phenylacetylamino-methyl)-[1,3]dioxan-2-yl]-3H-imidazol-4-yl}-pyrimidin-2-ylamino)-acetic acid, cis-isomer, (Compound A552);

3-(4-{5-(4-fluoro-phenyl)-2-[5-methyl-5-(phenylacetylamino-methyl)-[1,3]dioxan-2-yl]-3H-imidazol-4-yl}-pyrimidin-2-ylamino)-propionic acid, cis-isomer, (Compound A553);

N-{2-[4-(4-fluoro-phenyl)-5-(2-methylsulfanyl-pyrimidin-4-yl)-1H-imidazol-2-yl]-5-methyl-[1,3]dioxan-5-ylmethyl}-2-phenyl-acetamide, cis-isomer, (Compound A554);

N-{2-[4-(4-fluoro-phenyl)-5-(2-methoxy-pyrimidin-4-yl)-1H-imidazol-2-yl]-5-methyl-[1,3]dioxan-5-ylmethyl}-2-phenyl-acetamide, cis-isomer, (Compound A555);

N-{2-[5-(2-benzyloxy-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A556);

N-{2-[4-(4-fluoro-phenyl)-5-(2-phenoxy-pyrimidin-4-yl)-1H-imidazol-2-yl]-5-methyl-[1,3]dioxan-5-ylmethyl}-2-phenyl-acetamide, cis-isomer, (Compound A557);

N-(2-{4-(4-fluoro-phenyl)-5-[2-(2-methoxy-ethoxy)-pyrimidin-4-yl]-1H-imidazol-2-yl}-5-methyl-[1,3]dioxan-5-ylmethyl)-2-phenyl-acetamide, cis-isomer, (Compound A558);

N-{2-[5-[2-(2-dimethylamino-ethoxy)-pyrimidin-4-yl]-4-(4-fluoro-phenyl)-1H-imidazol-2-yl]-5-methyl-[1,3]dioxan-5-ylmethyl}-2-phenyl-acetamide, cis-isomer, (Compound A559);

N-{2-[5-(2-cyclohexyloxy-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A560);

N-{2-[5-(2-Isopropoxy-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A561);

N-{2-[4-(4-fluoro-phenyl)-5-(2-isopropylamino-pyrimidin-4-yl)-1H-imidazol-2-yl]-5-methyl-[1,3]dioxan-5-ylmethyl}-2-phenyl-acetamide, cis-isomer, (Compound A562);

N-{2-[5-(2-allylamino-pyrimidin-4-yl)-4-(4-fluoro-phenyl)-1H-imidazol-2-yl]-5-methyl-[1,3]dioxan-5-ylmethyl}-2-phenyl-acetamide, cis-isomer, (Compound A563);

N-{2-[5-[2-(cyclopropylmethyl-amino)-pyrimidin-4-yl]-4-(4-fluoro-phenyl)-1H-imidazol-2-yl]5-methyl-[1,3]dioxan-5-ylmethyl}-2-phenyl-acetamide, cis-isomer, (Compound A564);

N-{2-[5-[2-(cyanomethyl-amino)-pyrimidin-4-yl]-4-(4-fluoro-phenyl)-1H-imidazol-2-yl]-5-methyl-[1,3]dioxan-5-ylmethyl}-2-phenyl-acetamide, cis-isomer, (Compound A565);

N-{2-[5-[2-(2-cyano-ethylamino)-pyrimidin-4-yl]-4-(4-fluoro-phenyl)-1H-imidazol-2-yl]-methyl-[1,3]dioxan-5-ylmethyl}-2-phenyl-acetamide, cis-isomer, (Compound A566);

N-(2-{4-(4-fluoro-phenyl)-5-[2-(pyridin-3-ylamino)-pyrimidin-4-yl]-1H-imidazol-2-yl}-5-methyl-[1,3]dioxan-5-ylmethyl)-2-phenyl-acetamide, cis-isomer, (Compound A567);

N-(2-{4-(4-fluoro-phenyl)-5-[2-(pyridin-4-ylamino)-pyrimidin-4-yl]-1H-imidazol-2-yl}-5-methyl-[1,3]dioxan-5-ylmethyl)-2-phenyl-acetamide, cis-isomer, (Compound A568);

2-(4-{5-(4-fluoro-phenyl)-2-[5-methyl-5-(phenylacetylamino-methyl)-[1,3]dioxan-2-yl]-3H-imidazol-4-yl}-pyrimidin-2-ylamino)-acetamide, cis-isomer, (Compound A569);

3-(4-{5-(4-fluoro-phenyl)-2-[5-methyl-5-(phenylacetylamino-methyl)-[1,3]dioxan-2-yl-2-yl]-3H-imidazol-4-yl}-pyrimidin-2-ylamino)-propionamide, cis-isomer, (Compound A570);

N-{2-[4-(4-fluoro-phenyl)-5-(2-propoxy-pyrimidin-4-yl)-1H-imidazol-2-yl]-5-methyl-[1,3]dioxan-5-ylmethyl}-2-phenyl-acetamide, cis-isomer, (Compound A571);

N-(2-{4-(4-fluoro-phenyl)-5-[2-(2-hydroxy-ethoxy)-pyrimidin-4-yl]-1H-imidazol-2-yl}-5-methyl-[1,3]dioxan-5-ylmethyl)-2-phenyl-acetamide, cis-isomer, (Compound A572);

N-(2-{4-(4-fluoro-phenyl)-5-[2-(3-hydroxy-propoxy)-pyrimidin-4-yl]-1H-imidazol-2-yl}-5-methyl-[1,3]dioxan-5-ylmethyl)-2-phenyl-acetamide, cis-isomer, (Compound A573);

N-{2-[4-(4-fluoro-phenyl)-5-(2-propylamino-pyrimidin-4-yl)-1H-imidazol-2-yl]-5-methyl-[1,3]dioxan-5-ylmethyl}-2-phenyl-acetamide, cis-isomer, (Compound A574);

N-{2-[4-(4-fluoro-phenyl)-5-(2-pyrrolidin-1-yl-pyrimidin-4-yl)-1H-imidazol-2-yl]-5-methyl-[1,3]dioxan-5-ylmethyl}-2-phenyl-acetamide, cis-isomer, (Compound A575).

(b) By proceeding in a similar manner to Example 26(a) but using C-{2-[4-(4-fluoro-phenyl)-5-(2-methylsulphanyl-pyrimidin-4-yl)-1H-imidazol-2-yl]-5-methyl-[1,3]dioxan-5-yl}-methylamine, cis-isomer, there are prepared the corresponding trans-isomers of Compounds A348 to A575.

EXAMPLE 27

Compounds KH to KP

A suspension of {2-[4-(4-fluoro-phenyl)-5-(2-methylsulphanylpyrimidin-4-yl)-1H-imidazol-2-yl]-5-methyl-[1,3]dioxan-5-yl}-morpholin-4-yl-methanone, trans isomer, (5.00 g, Compound KQ) in dichloromethane at 0° C. was treated with meta-chloroperbenzoic acid (2equivalents) and the mixture stirred at 0–5° C. for 2 hours and then at room temperature for a further 16 hours. The reaction mixture was treated with aqueous saturated sodium bicarbonate solution. The organic layer was separated then evaporated. The residue was triturated with ether to give {2-[4-(4-fluoro-phenyl)-5-(2-methylsulphonylpyrimidin-4-yl)-1H-imidazol-2-yl]-5-methyl-[1,3]dioxan-5-yl)-morpholin-4-yl-methanone, trans isomer, (4.9 g, Compound KH) as a yellow solid, m.p. 264–266° C. MH$^+$ 532.

By proceeding in a similar manner but using 2-[4-(4-fluoro-phenyl)-5-(2-methylsulphanyl-pyrimidin-4-yl)-1H-imidazol-2-yl]-5,5-dimethyl-[1,3]dioxane (Compound KR) there was prepared 2-[4-(4-fluoro-phenyl)-5-(2-methylsulphonylpyrimidin-4-yl)-1H-imidazol-2-yl]-5,5-dimethyl-[1,3]dioxane (Compound KI) as a cream solid, m.p. 204–206° C. MH$^+$ 433.

By proceeding in a similar manner but using {2-[4-(4-fluoro-phenyl)-5-(2-methylsulphanyl-pyrimidin-4-y)-1H-imidazol-2-yl]-5-methyl-[1,3]dioxan-5-yl}-methanol, trans-isomer (Compound KU) there is prepared {2-[4-(4-fluoro-phenyl)-5-(2-methylsulphonyl-pyrimidin-4-yl) 1H-imidazol-2-yl]-5-methyl-[1,3]dioxan-5-yl}-methanol, trans-isomer (Compound KJ).

By proceeding in a similar manner but using {2-[4-(4-fluoro-phenyl)-5-(2-methylsulphanyl-pyrimidin-4-yl)-1H-imidazol-2-yl]-5-methyl-[1,3]dioxan-5-yl}-methanol, cis-isomer (Compound KT) there is prepared {2-[4-(4-fluoro-phenyl)-5-(2-methylsulphonyl-pyrimidin-4-yl)-1H-imidazol-2-yl]-5-methyl-[1,3]dioxan-5-yl}-methanol, cis-isomer (Compound KK).

By proceeding in a similar manner but using 2-[4-(4-fluoro-phenyl)-5-(2-methylsulphanylpyrimidin-4-yl)-1H-imidazol-2-yl]-5-methylene-[1,3]dioxane (Compound KV) there is prepared 2-[4-(4-fluoro-pheny)-5-(2-methylsulphonylpyrimidin-4-yl)-1H-imidazol-2-yl]-5-methylene-[1,3]dioxane (Compound KL).

By proceeding in a similar manner but using 4-[2-[1,3]dioxan-2-yl-5-(4-fluoro-phenyl)-3H-imidazol-4-yl]-2-methylsulphanyl-pyrimidine (Compound KW) there is prepared 4-[2-[1,3]dioxan-2-yl-5-(4-fluoro-phenyl)-3H-imidazol-4-yl]-2-methylsulphonyl-pyrimidine (Compound KM).

By proceeding in a similar manner but using {2-[4-(4-fluoro-phenyl)-5-(2-methylsulphanyl-pyrimidin-4-yl)-1H-imidazol-2-yl]-[1,3]dioxan-5-yl}-methanol, trans-isomer (Compound KX) there is prepared {2-]4-(4-fluoro-phenyl)-5-(2-methylsulphonyl-pyrimidin-4-yl)-1H-imidazol-2-yl]-[1,3]dioxan-5-yl}-methanol, trans-isomer (Compound KN).

By proceeding in a similar manner but using {2-[4-(4-fluoro-phenyl)-5-(2-methylsulphanyl-pyrimidin-4-yl)-1H-imidazol-2-yl]-[1,3]dioxan-5-yl}-methanol, cis-isomer (Compound KY) there is prepared {2-[4-(4-fluoro-phenyl)-5-(2-methylsulphonyl-pyrimidin-4-yl)-1H-imidazol-2-yl]-[1,3dioxan-5-yl}-methanol, cis-isomer (Compound KO).

By proceeding in a similar manner but using 2,2,2-trifluoro-N-[2-{4-(4-fluoro-phenyl)-5-(2-methylsulphanylpyrimidin-4-yl)-1H-imidazol-2-yl}-5-methyl-[1,3]dioxan-5-yl]acetamide, cis-isomer (Compound KQ) there was prepared 2,2,2-trifluoro-N-[2-{4-(4-fluoro-phenyl)-5-(2-methanesulphonylpyrimidin-4-yl)-1H-imidazol-2-yl}-5-methyl-[1,3]dioxan-5-yl]acetamide, cis-isomer (Compound KP) as a yellow solid, m.p. 236–238° C. MH$^+$ 530.

EXAMPLE 28

Compounds KQ and KY

A solution of 4-[2-dimethoxymethyl-5(4)-(4-fluoro-phenyl)-1H-imidazol-4(5)-yl]-2-methanesulphanyl-pyrimidine (16.0 g, Reference Example 7), p-toluenesulphonic acid (21.13 g), and 3-hydroxy-2-hydroxymethyl-2-methyl-1-morpholino-1-propanone (10.82 g, Reference Example 6) in a mixture of dry tetrahydrofuran and dry dimethylformamide was heated at reflux under a soxhlet apparatus charged with molecular seives (3 Å) for 26 hours. The reaction mixture was evaporated and the residue treated with ethyl acetate and aqueous saturated sodium bicarbonate solution. The organic phase was evaporated and the residue was subjected to flash chromatography on silica eluting with a mixture of ethyl acetate and methanol (9:1, v/v) to give {2-[4-(4-fluoro-phenyl)-5-(2-methylsulphanylpyrimidin-4-yl)-1H-imidazol-2-yl]-5-methyl-[1,31]dioxan-5-yl}-morpholin-4-yl-methanone, trans isomer, (13.8 g, Compound KQ) as a colourless solid, m.p. 160° C. (with decomposition). MH$^+$ 500.

By proceeding in a similar manner but using 2,2-dimethylpropan-1,3-diol there was prepared 2-[4-(4-fluoro-phenyl)-5-(2-methylsulphanylpyrimidin-4-yl)-1H-imidazol-2-yl]-5,5-dimethyl-[1,3]dioxane (Compound KR) as a colourless solid, m.p. 163–165° C. (with decomposition). MH$^+$ 401.

By proceeding in a similar manner but using 2-methyl-2-trifluoroacetamido-1,3-propanediol (Reference Example 4) there was prepared 2,2,2-trifluoro-N-[2-{4-(4-fluoro-phenyl)-5-(2-methylsulphanyl-pyrimidin-4-yl)-1H-imidazol-2-yl}-5-methyl-[1,3]dioxan-5-yl]acetamide, cis-isomer, (Compound KS) as a colourless solid. MH$^+$ 498.R$_F$: 0.55 determined on silica gel plates using a mixture of ethyl acetate and methanol (19:1, v/v).

By proceeding in a similar manner but using 1,1,1-tris(hydroxymethyl)ethane there was prepared {2-[4-(4-fluoro-phenyl)-5-(2-methylsulfanyl-pyrimidin-4-yl)-1H-imidazol-2-yl]-5-methyl-[1,3]dioxan-5-yl}-methanol, cis isomer (Compound KT) as white solid [MH$^+$ 417.R$_F$=0.32 determined on silica gel plates eluting with a mixture of ethyl acetate and methanol (19:1, v/v)]and {2-[4-(4-fluoro-phenyl)-5-(2-methylsulfanyl-pyrimidin-4-yl)-1H-imidazol-2-yl]-5-methyl-[1,3]dioxan-5-yl}-methanol, trans isomer (Compound KU) as a white solid (MH$^+$ 417, R$_F$=0.24, determined on silica gel plates eluting with a mixture of ethyl acetate and methanol (19:1, v/v)].

By proceeding in a similar manner but using 2-methylene-1,3-propanediol there is prepared 4-[5-(4-fluoro-phenyl)-2-(5-methylene-[1,3]dioxan-2-yl)-3H-imidazol-4-yl]-2-methylsulfanyl-pyrimidine (Compound KV).

By proceeding in a similar manner but using 1,3-propanediol there is prepared 4-[2-[1,3]dioxan-2-yl-5-(4- fluoro-phenyl)-3H-imidazol-4-yl]-2-methylsulphanyl-pyrimidine (Compound KW).

By proceeding in a similar manner but using 2-(hydroxymethyl)-1,3-propanediol there is prepared {2-[4-(4-fluoro-phenyl)-5-(2-methylsulphanyl-pyrimidin-4-yl)-1H-imidazol-2-yl]-[1,3]dioxan-5-yl}-methanol, trans-isomer (Compound KX) and {2-[4-(4-fluoro-phenyl)-5-(2-methylsulphanyl-pyrimidin-4-yl)-1H-imidazol-2-yl]-[1,3]dioxan-5-yl}-methanol, cis-isomer (Compound KY).

EXAMPLE 29
Compound KZ

A solution of 2-[4-(4-fluoro-phenyl)-5-(2-methylsulfanyl-pyrimidin-4-yl)-1H-imidazol-2-yl]-5-methyl-[1,3]dioxane-5-carboxylic acid amide, cis isomer (0.5 g, Compound LA) in tetrahydrofuran was treated with lithium aluminium hydride (0.18 g) and the mixture heated at reflux for 0.5 hour. To the cooled solution was added water (0.2 ml), then aqueous sodium hydroxide (15%, 0.2 ml) and then water (0.6 ml). The mixture was then filtered and the filtrate was evaporated. The residue was subjected to flash chromatography on silica, eluting with a mixture of methanol and ethyl acetate (3:7, v/v) to give C-{2-[4-(4-fluoro-phenyl)-5-(2-methylsulfanyl-pyrimidin-4-yl)-1H-imidazol-2-yl]-5-methyl-[1,3]dioxan-5-yl}-methylamine, cis isomer (69 mg, Compound KZ) as a gum. MH$^+$ 416. R$_F$=0.3 determined on silica gel plates using methanol.

EXAMPLE 30
Compound LA

To a solution of 2-[4-(4-fluoro-phenyl)-5-(2-methylsulfanyl-pyrimidin-4-yl)-1H-imidazol-2-yl]-5-methyl-[1,3]dioxane-5-carboxylic acid, cis isomer (1.3 g, Compound LB), diethyl isopropyl amine (0.85 g) and O-(7-azabenzotriazol-1-yl)-1,1,3,3-tetramethyluronium hexafluorophosphate (1.14 g) in dimethylformamide (anhydrous) was added ammonia (1.2 mL, 0.5M solution in 1,4-dioxane). The solution was stirred at room temperature for 3 hours and then evaporated. The residue was stirred with water and the solid filtered to give 2-[4-(4-fluoro-phenyl)-5-(2-methylsulfanyl-pyrimidin-4-yl)-1H-imidazol-2-yl]-5-methyl-[1,3]dioxane-5-carboxylic acid amide, cis isomer (1.2 g, Compound LA) as white solid. MH$^+$ 430. R$_F$=0.27 [determined on silica gel plates using a mixture of ethyl acetate and methanol (8:2 v/v)].

EXAMPLE 31
Compound LB

A solution of 2-[4-(4-fluorophenyl)-5-(2-methylenesulphanylpyrimidin-4-yl)-1H-imidazol-2-yl]-5-methyl-[1,3]dioxan-5-carboxylic acid methyl ester, cis isomer, (5.1 g, Compound LD) and aqueous sodium hydroxide (34.4 ml, 1N) in methanol was heated at reflux for 6 hours. To the cold solution was added aqueous hydrochloric acid (34.4. ml, 1N) and the methanol evaporated. The aqueous was decanted and the residue triturated with acetonitrile to give 2-[4-(4-fluoro-phenyl)-5-(2-methylsulfanyl-pyrimidin-4-yl)-1H-imidazol-2-yl]-5-methyl-[1,3]dioxane-5-carboxylic acid, cis isomer (4.43 g, Compound LB) as a white solid. MH$^+$ 431. TLC R$_F$=0.22(eluting with ethyl Acetate and methanol (8:2, v/v) on silica gel).

EXAMPLE 32
Compound LC and LD

A solution of 2-dimethoxymethyl-4-(4-fluorophenyl)-5-(2-methylylsulphanylpyrimidin-4-yl)-1H-imidazole (4.5 g, Reference Example 7), methyl 2,2-bis(hydroxymethyl) propionate (10 g) and methylorthoformate (11.9 ml) in dimethylformamide was treated with 4-toluenesulphonic acid (20.6 g) and then heated at 80° C. for 4 hours. The reaction mixture was evaporated then partitioned between ethyl acetate and aqueous sodium bicarbonate solution. The organic phase was evaporated and the residue purified using flash chromatography on silica gel eluting with a ethyl acetate to give 2-[4-(4-fluorophenyl)-5-(2-methylsulphanylpyrimidin-4-yl)-1H-imidazol-2-yl]-5-methyl-[1,3]dioxan-5-carboxylic acid methyl ester, trans isomer, (4.95 g, Compound LC), [MH$^+$ 445, m.p. 199–200° C.] and 2-[4-(4-fluorophenyl)-5-(2-methylsulphanylpyrimidin-4-yl)-1H-imidazol-2-yl]-5-methyl-[1,3]dioxan-5-carboxylic acid methyl ester, cis isomer, (7.11 g, Compound LD), MH$^+$ 445, m.p. 161–163° C.).

EXAMPLE 33
Compound LE

To a solution of {2-[4-(4-fluoro-phenyl)-5-pyridin-4-yl-1H-imidazol-2-yl]-5-nitro-[1,3]dioxan-5-yl}-methanol, cis isomer (0.1 g, Compound LG) in ethanol was added palladium on carbon (5%, 0.2 g) and the mixture was hydrogenated at 1 atmosphere of hydrogen, at 50° C., for 6 hours. The solution was filtered through Celite, the solvent evaporated and the residue subjected to flash chromatography on silica gel, eluting with a mixture of methanol and ethyl acetate (1:1, v/v) to give {5-Amino-2-[4-(4-fluoro-phenyl)-5-pyridin-4-yl-1H-imidazol-2-yl]-[1,3]dioxan-5-yl}-methanol, cis isomer, (77 mg, Compound LE) as a gum. MH$^+$ 371. TLC R$_F$=0.27(eluting with methanol on silica gel).

EXAMPLE 34
Compound LF

To a solution of {2-[4-(4-fluoro-phenyl)-5-pyridin-4-yl-1H-imidazol-2-yl]-5-nitro-[1,3]dioxan-5-yl}-methanol, trans isomer (0.1 g, Compound LH) in ethanol was added palladium on carbon (5%, 0.2 g) and the mixture was hydrogenated, at 1 atmosphere of hydrogen, at 50° C. for 8 hours. The solution was filtered through celite and the solvent was evaporated and the residue subjected to flash chromatography on silica gel, eluting with a mixture of methanol and ethyl acetate (1:1, v/v) to give {5-Amino-2-[4-(4-fluoro-phenyl)-5-pyridin-4-yl-1H-imidazol-2-yl]-[1,3]dioxan-5-yl}-methanol, trans isomer, (75mg, Compound LF) as a gum. MH$^+$ 371. TLC R$_F$=0.19 (eluting with a mixture of ethyl acetate:methanol 1:1 on silica gel).

EXAMPLE 35
Compound LG and LH

A solution of of 4-[2-dimethoxymethyl-5(4)-(4-fluorophenyl)-1H-imidazol-4(5)-yl]-pyridine (2.2 g, Reference Example 3), p-toluenesulphonic acid (1.74 g) and tris(hydroxymethyl)-nitromethane (4.24 g) in tetrahydrofuran (anhydrous) and dimethylformamide (anhydrous) was heated at reflux under a soxhlet apparatus charged with molecular sieve (3 Å) for 48 hours. The solvent was evaporated and the residue partitioned between ethyl acetate and aqueous saturated sodium carbonate solution. The organic layer was evaporated and the residue subjected to flash chromatography on silica, eluting with a mixture of methanol and ethyl acetate (1:9, v/v) to give {2-[4-(4-Fluoro-phenyl)-5-pyridin-4-yl-1H-imidazol-2-]-5-nitro-[1,3]dioxan-5-yl}-methanol, cis isomer, (0.61 g, Compound LG) as white solid (MH$^+$401, TLC R$_F$=0.3, eluting with a mixture of Ethyl acetate:Methanol 8:2 on silica gel) and {2-[4-(4-Fluoro-phenyl)-5-pyridin-4-yl-1H-imidazol-2-yl]-5-nitro-[1,3]dioxan-5-yl}-methanol, trans isomer,(0.39 g, Compound LH) as a yellow gum (MH⁺401, TLC $R_F$=0.55, eluting with a mixture of ethyl acetate:methanol 8:2 on silica gel).

EXAMPLE 36
Compound LI

To a solution of 4-[2-(5,5-Dimethyl-4-nitromethyl-[1,3]dioxan-2-yl)-5-(4-fluoro-phenyl)-3H-imidazol-4-yl]-pyridine (115 mg, Compound LJ) in methanol was added to a suspension of nickel boride which had been previously prepared by sonication of nickel chloride and sodium borohydride. The mixture was stirred and sodium borohydride (250 mg) added in portions over 1 hour. The reaction mixture was filtered through a thin pad of silica gel and purified using preparative TLC eluting twice with a mixture of dichloromethane, pentane, methanol and ammonia (55:25:18:2, v/v) to give C-{2-[4-(4-fluoro-phenyl)-5-pyridin-4-yl-1H-imidazol-2-yl]-5,5-dimethyl-[1,3]dioxan-4-yl}-methylamine (57 mg, Compound LI). MH⁺383. $R_F$=0.54, eluting twice with dichloromethane, pentane, methanol and ammonia (55:25:18:2, v/v).

EXAMPLE 37
Compound LJ

To a solution of 4-[2-dimethoxymethyl-5(4)-(4-fluorophenyl)-1H-imidazol-4(5)-yl]-pyridine 115 mg, Reference Example 3) in dry tetrahydrofuran was added 2,2-dimethyl-4-nitrobutane-1,3-diol (150 mg) and p-toluenesulphonic acid. The mixture was heated under reflux for 7 hours before partitioning between water and ethyl acetate and purifying using flash chromatography on silica gel eluting with ethyl acetate:methanol (9:1, v/v) to give 4-[2-(5,5-dimethyl-4-nitromethyl-[1,3]dioxan-2-yl)-5-(4-fluro-phenyl)-3H-imidazol-4-yl]-pyridine (130 mg, Compound LJ). MH⁺413. TLC $R_F$=0.36 (eluting twice with ethyl acetate: on silica gel).

EXAMPLE 38
Compound LK and LL (i) Treatment of C-{2-[4-(4-fluoro-phenyl)-5-(2-methylsulphanyl-pyrimidin-4-yl)-1H-imidazol-2-yl]-5-methyl-[1,3]dioxan-5-yl}-methylamine, cis-isomer (Compound KZ) with trifluoroacetic anhydride (according to method described in Example 12); followed by (ii) treatment of compounds obtained from (i) with meta-chloroperbenzoic acid (according to method described for Example 27) gives 2,2,2-trifluoro-N-{2-[5-(2-methylsulphonyl-pyrimidin-4-yl)-4-(4-fluoro-phenyl)-1H-imidazol-2-yl]-5-methyl-[1,5]dioxan-5-ylmethyl}-acetamide, cis isomer (Compound LK).

By proceeding in a similar manner but using the trans-isomer of Compound KZ there is prepared 2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, trans isomer (Compound LL).

EXAMPLE 39
Compound LM and LN

A solution of 2-[4-(4-fluorophenyl)-5-(2-methylsulphanylpyrimidin-4-yl)-1H-imidazol-2-yl]-5-methyl-[1,3]dioxan-5-carboxylic acid methyl ester, cis isomer, (3.15 g, Compound LC) in a mixture of dichloromethane and methanol (9:1, v/v) was treated with 3-chloroperoxybenzoic acid (2.2 equivalents) and stirred at room temperature for 16 hours. The solution was diluted with ether and shaken with aqueous saturated sodium bicarbonate solution. The organic solution was evaporated and the residue triturated with a mixture of ethyl acetate and ether to give 2-[4-(4-fluorophenyl)-5-(2-methylsulphonylpyrimidin-4-yl)-1H-imidazol-2-yl]-5-methyl-[1,3]dioxan-5-carboxylic acid methyl ester, trans isomer (2.95 g, Compound LM) as a colourless crystalline solid, m.p. 186–187° C. MH⁺477.

By proceeding in a similar manner but using 2-[4-(4-fluorophenyl)-5-(2-methylsulphanylpyrimidin-4-yl)-1H-imidazol-2-yl]-5-methyl-[1,3]dioxan-5-carboxylic acid methyl ester, cis isomer (Compound LD) there is prepared 2-[4-(4-fluorophenyl)-5-(2-methylenesulphonylpyrimidin-4-yl)-1H-imidazol-2-yl]-5-methyl-[1,3]dioxan-5-carboxylic acid methyl ester, cis isomer (Compound LN).

EXAMPLE 40
Compound GT and A557 to A2062

(a)
  Step 1: A suspension of Merrifield resin (20 g, chloromethylpolystyrene resin, Novabiochem) in dimethylformamide (150 ml) was treated with potassium thioacetate (21 g). After stirring at room temperature for 24 hours the mixture was filtered and the modified resin was washed with dimethylformamide, then with tetrahydrofuran, then with water, then with tetrahydrofuran, then with dichloromethane and then dried under high vacuum at 60° C. to give Resin A (20.5 g). IR: 3024s, 2920s, 1691s, 1599m, 1493s, 1453s, 1130m, 758s, 700s.

Step 2: A suspension of Resin A from Step 1 (20.5 g) in tetrahydrofuran (150 ml) was treated with lithium borohydride (5 g). After stirring at room temperature for 24 hours the mixture was filtered and the modified resin was washed with tetrahydrofuran, then with a mixture of hydrochloric acid (1N) and tetrahydrofuran (3:7, v/v), then with water, then with tetrahydrofuran, then with methanol, then with dichloromethane and then dried under high vacuum at 60° C. to give Resin B (20 g). IR: 3026 s, 2924 s, 1599w, 1493 s, 1452 s, 757 s, 700s.

Step 3: A suspension of Resin B from Step 2 (0.1 g) in dimethylformamide (0.5 ml) was treated with sodium hydride (5 mg, 60% dispersion in mineral oil), then stirred at room temperature for 15 minutes, then treated with 2-[4-(4-fluorophenyl)-5-(2-methylylsulphonylpyrimidin-4-yl)-1H-imidazol-2-yl]-5-methyl-[1,3]dioxan-5-carboxylic acid methyl ester, trans isomer, (60 mg, Compound LM) and then heated at 80° for 20 hours. The reaction mixture was filtered and the modified resin was washed with dimethylformamide, then with tetrahydrofuran, then with methanol, then with dichloromethane and then dried under high vacuum at 60° C. to give Resin C (0.11 g). IR:3021m, 2920 m, 1732 m, 1569 m, 1487 s, 1452s, 1091 m, 835 m, 757 s, 699 s.

Step 4: A suspension of Resin C (0.09 g) in tetrahydrofuran was treated with aqueous sodium hydroxide solution (1N, 0.3 ml) and then stirred at 70° C. for 8 hours. The reaction mixture was filtered and the modified resin was washed with tetrahydrofuran, then with a mixture of tetrahydrofuran and hydrochloric acid(1N), then with tetrahydrofuran, then with dimethylformamide, then with tetrahydrofuran, then with methanol then with dichloromethane and then dried under high vacuum at 60° C. to give Resin D (0.09 g). IR: 3060w, 3025 m, 2923m, 2852 w, 1720 w, 1601 m, 1571 s, 1493 s, 1452 s, 1335 s, 1235 m, 1199 m, 1183 m, 1097 s, 838 m, 760 s, 704s.

Step 5: A suspension of Resin D (0.07 g) in dichloromethane was treated with oxalyl chloride solution in dichloromethane (16%), then stirred at room temperature for 10 minutes and then filtered. This procedure was repeated three times. The modified resin was washed with dichloromethane, then treated with a solution of morpholine (0.1 g) in dichloromethane (0.8 ml). After stirring at room temperature for 10 minutes this reaction mixture was filtered and the further modifed resin was washed with dichloromethane, then with tetrahydrofuran, then with methanol, then with dichloromethane and then dried under high vacuum at 60° C. to give Resin E (0.07 g). IR: 3025s, 2922s, 1636w, 1600w, 1570w, 1493s, 1452s, 1329w, 1181w,1115w, 759m, 704s.

Step 6: A suspension of Resin E (0.06 g) in a mixture of dichloromethane (0.8 ml) and methanol (0.1 ml) was treated with m-chloroperoxybenzoic acid (0.24 g). After stirring at room temperature for 96 hours the reaction mixture was filtered and the modified resin was washed with dichloromethane, then with tetrahydrofuran, then with methanol, then with dichloromethane and then dried under high vacuum at 60° C. to give Resin F (0.06 g). IR: 3082 m, 3026 s, 2927 s, 2851 w, 1635 w, 1602 m, 1582 m, 1493 m, 1452 s, 1350 w,1240 m, 1180 m, 1117 m, 1032 m, 761s, 705 s.

Step 7: A suspension of Resin F (0.04 g) in dimethoxyethane (0.4 ml) was treated with benzylamine (0.01 ml) and then heated at 70° C. for 6 hours. The reaction mixture was filtered to remove resin and the filtrate was evaporated. The residue was subjected to high pressure liquid chromatography (gradient elution using water and acetonitrile mixtures as follows: 0–2 minutes 20% acetonitrile, 2–16 minutes ramp up to 80% acetonitrile) to give the {2-[4-(4-fluorophenyl)-5-(2-benzylaminopyrimidin-4-yl)-1H-imidazol-2-yl]-5-methyl-[1,3]dioxan-5-yl}-morpholin-4-yl-methanone, trans isomer (Compound GT). MH$^+$559. High pressure liquid chromatography retention time=11 minutes.

(b) By proceeding in a similar manner but using amines of formula HNY$^4$Y$^5$ in Step 5; and amines of formula HNY$^4$Y$^5$ or sodium salts of appropriately substituted alcohols or phenols in Step 7 there is prepared Compounds A557 to A2062:

[5-(2-amino-pyrimidin-4-yl)-4-(4-fluoro-phenyl)-1H-imidazol-2-yl]-5-methyl-[1,3]dioxane-5-carboxylic acid amide, trans-isomer, (Compound A577);

2-[4-(4-fluoro-phenyl)-5-(2-methylamino-pyrimidin-4-yl)-1H-imidazol-2-yl]-5-methyl-[1,3]dioxane-5-carboxylic acid amide, trans-isomer, (Compound A578);

2-[5-(2-dimethylamino-pyrimidin-4-yl)-4-(4-fluoro-phenyl)-1H-imidazol-2-yl]-5-methyl-[1,3]dioxane-5-carboxylic acid amide, trans-isomer, (Compound A579);

2-[5-(2-cyclopropylamino-pyrimidin-4-yl)-4-(4-fluoro-phenyl)-1H-imidazol-2-yl]-5-methyl-[1,3]dioxane-5-carboxylic acid amide, trans-isomer, (Compound A580);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid amide, trans-isomer, (Compound A581);

2-[5-(2-cyclohexylamino-pyrimidin-4-yl)-4-(4-fluoro-phenyl)-1H-imidazol-2-yl]-5-methyl-[1,3]dioxane-5-carboxylic acid amide, trans-isomer, (Compound A582);

2-{4-(4-fluoro-phenyl)-5-[2-(2-hydroxy-ethylamino)-pyrimidin-4-yl]-1H-imidazol-2}-5-methyl-[1,3]dioxane-5-carboxylic acid amide, trans-isomer, (Compound A583);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid amide, trans-isomer, (Compound A584);

2-(4-(4-fluoro-phenyl)-5-{2-[3-(5H-imidazol-1-yl)-propylamino]-pyrimidin-4-yl}-1H-imidazol-2-yl)5-methyl-[1,3]dioxane-5-carboxylic acid amide, trans-isomer, (Compound A585);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid amide, trans-isomer, (Compound A586);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid amide, trans-isomer, (Compound A587);

2-[5-(2-benzylamino-pyrimidin-4-yl)-4-(4-fluoro-phenyl)-1H-imidazol-2-yl]-5-methyl-[1,3]dioxane-5-carboxylic acid amide, trans-isomer, (Compound A588);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid amide, R-isomer, trans-isomer, (Compound A589);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid amide, S-isomer, trans-isomer, (Compound A590);

2-[4-(4-fluoro-phenyl)-5-(2-phenylamino-pyrimidin-4-yl)-1H-imidazol-2-yl]-5-methyl-[1,3]dioxane-5-carboxylic acid amide, trans-isomer, (Compound A591);

2-[4-(4-fluoro-phenyl)-5-(2-piperidin-1-yl-pyrimidin-4-yl)-1H-imidazol-2-yl]-5-methyl-[1,3]dioxane-5-carboxylic acid amide, trans-isomer, (Compound A592);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid amide, trans-isomer, (Compound A593);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid amide, trans-isomer, (Compound A594);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid amide, trans-isomer, (Compound A595);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid amide, trans-isomer, (Compound A596);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid amide, trans-isomer, (Compound A597);

2-(4-(4-fluoro-phenyl)-5-{2-[(tetrahydro-furan-2-ylmethyl)-amino]-pyrimidin-4-yl}-1H-imidazol-2yl)-5-methyl-[1,3]dioxane-5-carboxylic acid amide, trans-isomer, (Compound A598);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid amide, trans-isomer, (Compound A599);

2-[4-(4-fluoro-phenyl)-5-(2-morpholin-4-yl-pyrimidin-4-yl)-1H-imidazol-2-yl]-5-methyl-[1,3]dioxane-5-carboxylic acid amide, trans-isomer, (Compound A600);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid amide, trans-isomer, (Compound A601);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid amide, trans-isomer, (Compound A602);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid amide, trans-isomer, (Compound A603);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid amide, trans-isomer, (Compound A604);

{4-[2-(5-Carbamoyl-5-methyl-[1,3]dioxan-2-yl)-5-(4-fluoro-phenyl)-3H-imidazol-4-yl]-pyrimidin-2-ylamino}-acetic acid, trans-isomer, (Compound A605);

3-{4-[2-(5-Carbamoyl-5-methyl-[1,3]dioxan-2-yl)-5-(4-fluoro-phenyl)-3H-imidazol-4-yl]-pyrimidin-2-ylamino}-propionic acid, trans-isomer, (Compound A606);

2-[4-(4-fluoro-phenyl)-5-(2-isopropylamino-pyrimidin-4-yl)-1H-imidazol-2-yl]-5-methyl-[1,3]dioxane-5-carboxylic acid amide, trans-isomer, (Compound A607);

2-[5-(2-allylamino-pyrimidin-4-yl)-4-(4-fluoro-phenyl)-1H-imidazol-2-yl]-5-methyl-[1,3]dioxane-5-carboxylic acid amide, trans-isomer, (Compound A608);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid amide, trans-isomer, (Compound A609);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid amide, trans-isomer, (Compound A610);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid amide, trans-isomer, (Compound A611);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid amide, trans-isomer, (Compound A612);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid amide, trans-isomer, (Compound A613);

2-[4-(4-fluoro-phenyl)-5-(2-propylamino-pyrimidin-4-yl)-1H-imidazol-2-yl]-5-methyl-[1,3]dioxane-5-carboxylic acid amide, trans-isomer, (Compound A614);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid amide, trans-isomer, (Compound A615);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid amide, trans-isomer, (Compound A616);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid amide, trans-isomer, (Compound A617);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid amide, trans-isomer, (Compound A618);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid amide, trans-isomer, (Compound A619);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid amide, trans-isomer, (Compound A620);

2-[4-(4-fluoro-phenyl)-5-(2-methoxy-pyrimidin-4-yl)-1H-imidazol-2-yl]-5-methyl-[1,3]dioxane-5-carboxylic acid amide, trans-isomer, (Compound A621);

2-[5-(2-benzyloxy-pyrimidin-4-yl)-4-(4-fluoro-phenyl)-1H-imidazol-2-yl]-5-methyl-[1,3]dioxane-5-carboxylic acid amide, trans-isomer, (Compound A622);

2-[4-(4-fluoro-phenyl)-5-(2-phenoxy-pyrimidin-4-yl)-1H-imidazol-2-yl]-5-methyl-[1,3]dioxane-5-carboxylic acid amide, trans-isomer, (Compound A623);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid amide, trans-isomer, (Compound A624);

2-[5-[2-(2-dimethylamino-ethoxy)-pyrimidin-4-yl]-4-(4-fluoro-phenyl)-1H-imidazol-2-yl]-5methyl-[1,3]dioxane-5-carboxylic acid amide, trans-isomer, (Compound A625);

2-[5-(2-cyclohexyloxy-pyrimidin-4-yl)-4-(4-fluoro-phenyl)-1H-imidazol-2-yl]-5-methyl-[1,3]dioxane-5-carboxylic acid amide, trans-isomer, (Compound A626);

2-[5-(2-Isopropoxy-pyrimidin-4-yl)-4-(4-fluoro-phenyl)-1H-imidazol-2-yl]-5-methyl-[1,3]dioxane-5-carboxylic acid amide, trans-isomer, (Compound A627);

2-[4-(4-fluoro-phenyl)-5-(2-propoxy-pyrimidin-4-yl)-1H-imidazol-2-yl]-5-methyl-[1,3]dioxane-5-carboxylic acid amide, trans-isomer, (Compound A628);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid amide, trans-isomer, (Compound A629);

2-{4-(4-fluoro-phenyl)-5-[2-(3-hydroxy-propoxy)-pyrimidin-4-yl]-1H-imidazol-2-yl}-methyl-[1,3]dioxane-5-carboxylic acid amide, trans-isomer, (Compound A630);

2-[4-(4-fluoro-phenyl)-5-(2-methylsulfanyl-pyrimidin-4-yl)-1H-imidazol-2-yl]-5-methyl-[1,3]dioxane-5-carboxylic acid amide, trans-isomer, (Compound A631);

2-[5-(2-amino-pyrimidin-4-yl)-4-(4-fluoro-phenyl)-1H-imidazol-2-yl]-5-methyl-[1,3]dioxane-5-carboxylic acid methylamide, trans-isomer, (Compound A632);

2-[4-(4-fluoro-phenyl)-5-(2-methylamino-pyrimidin-4-yl)-1H-imidazol-2-yl]-5-methyl-[1,3]dioxane-5-carboxylic acid methylamide, trans-isomer, (Compound A633);

2-[5-(2-dimethylamino-pyrimidin-4-yl)-4-(4-fluoro-phenyl)-1H-imidazol-2-yl]-5-methyl-[1,3]dioxane-5-carboxylic acid methylamide, trans-isomer, (Compound A634);

2-[5-(2-cyclopropylamino-pyrimidin-4-yl)-4-(4-fluoro-phenyl)-1H-imidazol-2-yl]-5-methyl-[1,3]dioxane-5-carboxylic acid methylamide, trans-isomer, (Compound A635), 2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid methylamide, trans-isomer, (Compound A636);

2-[5-(2-cyclohexylamino-pyrimidin-4-yl)-4-(4-fluoro-phenyl)-1H-imidazol-2-yl]-5-methyl-[1,3]dioxane-5-carboxylic acid methylamide, trans-isomer, (Compound A637);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid methylamide, trans-isomer, (Compound A638);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid methylamide, trans-isomer, (Compound A639);

2-(4-(4-fluoro-phenyl)-5-{2-[3-(5 H-imidazol-1-yl)-propylamino]-pyrimidin-4-yl}-1H-imidazol-2-yl)-5-methyl-[1,3]dioxane-5-carboxylic acid methylamide, trans-isomer, (Compound A640);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid methylamide, trans-isomer, (Compound A641);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid methylamide, trans-isomer, (Compound A642);

2-[5-(2-benzylamino-pyrimidin-4-yl)-4-(4-fluoro-phenyl)-1H-imidazol-2-yl]-5-methyl-[1,3]dioxane-5-carboxylic acid methylamide, trans-isomer, (Compound A643);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid methylamide, R-isomer, trans-isomer, (Compound A644);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid methylamide, S-isomer, trans-isomer, (Compound A645);

2-[4-(4-fluoro-phenyl)-5-(2-phenylamino-pyrimidin-4-yl)-1H-imidazol-2-yl]-5-methyl-[1,3]dioxane-5-carboxylic acid methylamide, trans-isomer, (Compound A646);

2-[4-(4-fluoro-phenyl)-5-(2-piperidin-1-yl-pyrimidin-4-yl)-1H-imidazol-2-yl]-5-methyl-[1,3]dioxane-5-carboxylic acid methylamide, trans-isomer, (Compound A647);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid methylamide, trans-isomer, (Compound A648);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid methylamide, trans-isomer, (Compound A649);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid methylamide, trans-isomer, (Compound A650);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid methylamide, trans-isomer, (Compound A651);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid methylamide, trans-isomer, (Compound A652);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid methylamide, trans-isomer, (Compound A653);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid methylamide, trans-isomer, (Compound A654);

2-[4-(4-fluoro-phenyl)-5-(2-morpholin-4-yl-pyrimidin-4-yl)-1H-imidazol-2-yl]-5-methyl-[1,3]dioxane-5-carboxylic acid methylamide, trans-isomer, (Compound A655);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid methylamide, trans-isomer, (Compound A656);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid methylamide, trans-isomer, (Compound A657);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid methylamide, trans-isomer, (Compound A658);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid methylamide, trans-isomer, (Compound A659);

{4-[5-(4-fluoro-phenyl)-2-(5-methyl-5-methylcarbamoyl-[1,3]dioxan-2-yl)-3H-imidazol-4-yl]-pyrimidin-2-ylamino}-acetic acid, trans-isomer, (Compound A660);

3-{4-[5-(4-fluoro-phenyl)-2-(5-methyl-5-methylcarbamoyl-[1,3]dioxan-2-yl)-3H-imidazol-4-yl]-pyrimidin-2-ylamino}-propionic acid, trans-isomer, (Compound A661);

2-[4-(4-fluoro-phenyl)-5-(2-isopropylamino-pyrimidin-4-yl)-1H-imidazol-2-yl]-5-methyl-[1,3]dioxane-5-carboxylic acid methylamide, trans-isomer, (Compound A662);

2-[5-(2-allylamino-pyrimidin-4-yl)-4-(4-fluoro-phenyl)-1H-imidazol-2-yl]-5-methyl-[1,3]dioxane-5-carboxylic acid methylamide, trans-isomer, (Compound A663);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid methylamide, trans-isomer, (Compound A664);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid methylamide, trans-isomer, (Compound A665);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid methylamide, trans-isomer, (Compound A666);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid methylamide, trans-isomer, (Compound A667);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid methylamide, trans-isomer, (Compound A668);

2-[4-(4-fluoro-phenyl)-5-(2-propylamino-pyrimidin-4-yl)-1H-imidazol-2-yl]-5-methyl-[1,3]dioxane-5-carboxylic acid methylamide, trans-isomer, (Compound A669);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid methylamide, trans-isomer, (Compound A670);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid methylamide, trans-isomer, (Compound A671);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid methylamide, trans-isomer, (Compound A672);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid methylamide, trans-isomer, (Compound A673);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid methylamide, trans-isomer, (Compound A674);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid methylamide, trans-isomer, (Compound A675);

2-[4-(4-fluoro-phenyl)-5-(2-methoxy-pyrimidin-4-yl)-1H-imidazol-2-yl]-5-methyl-[1,3]dioxane-5-carboxylic acid methylamide, trans-isomer, (Compound A676);

2-[5-(2-benzyloxy-pyrimidin-4-yl)-4-(4-fluoro-phenyl)-1H-imidazol-2-yl]-5-methyl-[1,3]dioxane-5-carboxylic acid methylamide, trans-isomer, (Compound A677);

2-[4-(4-fluoro-phenyl)-5-(2-phenoxy-pyrimidin-4-yl)-1-imidazol-2-yl]-5-methyl-[1,3]dioxane-5-carboxylic acid methylamide, trans-isomer, (Compound A678);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid methylamide, trans-isomer, (Compound A679);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid methylamide, trans-isomer, (Compound A680);

2-[5-(2-cyclohexyloxy-pyrimidin-4-yl)-4-(4-fluoro-phenyl)-1H-imidazol-2-yl]-5-methyl-[1,3]dioxane-5-carboxylic acid methylamide, trans-isomer, (Compound A681);

2-[5-(2-Isopropoxy-pyrimidin-4-yl)-4-(4-fluoro-phenyl)-1H-imidazol-2-yl]-5-methyl-[1,3]dioxane-5-carboxylic acid methylamide, trans-isomer, (Compound A682);

2-[4-(4-fluoro-phenyl)-5-(2-propoxy-pyrimidin-4-yl)-1H-imidazol-2-yl]-5-methyl-[1,3]dioxane-5-carboxylic acid methylamide, trans-isomer, (Compound A683);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid methylamide, trans-isomer, (Compound A684);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid methylamide, trans-isomer, (Compound A685);

2-[4-(4-fluoro-phenyl)-5-(2-methylsulfanyl-pyrimidin-4-yl)-1H-imidazol-2-yl]-5-methyl-[1,3]dioxane-5-carboxylic acid methylamide, trans-isomer, (Compound A686);

2-[5-(2-amino-pyrimidin-4-yl)-4-(4-fluoro-phenyl)-1H-imidazol-2-yl]-5-methyl-[1,3]dioxane-5-carboxylic acid dimethylamide, trans-isomer, (Compound A687);

2-[4-(4-fluoro-phenyl)-5-(2-methylamino-pyrimidin-4-yl)-1H-imidazol-2-yl]-5-methyl-[1,3]dioxane-5-carboxylic acid dimethylamide, trans-isomer, (Compound A688);

2-[5-(2-dimethylamino-pyrimidin-4-yl)-4-(4-fluoro-phenyl)-1H-imidazol-2-yl]-5-methyl-[1,3]dioxane-5-carboxylic acid dimethylamide, trans-isomer, (Compound A689);

2-[5-(2-cyclopropylamino-pyrimidin-4-yl)-4-(4-fluoro-phenyl)-1H-imidazol-2-yl]-5-methyl-[1,3]dioxane-5-carboxylic acid dimethylamide, trans-isomer, (Compound A690);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid dimethylamide, trans-isomer, (Compound A691);

2-[5-(2-cyclohexylamino-pyrimidin-4-yl)-4-(4-fluoro-phenyl)-1H-imidazol-2-yl]-5-methyl-[1,3]dioxane-5-carboxylic acid dimethylamide, trans-isomer, (Compound A692);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid dimethylamide, trans-isomer, (Compound A693);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A694);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid dimethylamide, trans-isomer, (Compound A695);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid dimethylamide, trans-isomer, (Compound A696);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid dimethylamide, trans-isomer, (Compound A697);

2-[5-(2-benzylamino-pyrimidin-4-yl)-4-(4-fluoro-phenyl)-1H-imidazol-2-yl]-5-methyl-[1,3]dioxane-5-carboxylic acid dimethylamide, trans-isomer, (Compound A698);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid dimethylamide, R-isomer, trans-isomer, (Compound A699);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid dimethylamide, S-isomer, trans-isomer, (Compound A700);

2-[4-(4-fluoro-phenyl)-5-(2-phenylamino-pyrimidin-4-yl)-1H-imidazol-2-yl]-5-methyl-[1,3]dioxane-5-carboxylic acid dimethylamide, trans-isomer, (Compound A701);

2-[4-(4-fluoro-phenyl)-5-(2-piperidin-1-yl-pyrimidin-4-yl)-1H-imidazol-2-yl]-5-methyl-[1,3]dioxane-5-carboxylic acid dimethylamide, trans-isomer, (Compound A702);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid dimethylamide, trans-isomer, (Compound A703);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid dimethylamide, trans-isomer, (Compound A704);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid dimethylamide, trans-isomer, (Compound A705);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid dimethylamide, trans-isomer, (Compound A706);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid dimethylamide, trans-isomer, (Compound A707);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid dimethylamide, trans-isomer, (Compound A708);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid dimethylamide, trans-isomer, (Compound A709);

2-[4-(4-fluoro-phenyl)-5-(2-morpholin-4-yl-pyrimidin-4-yl)-1H-imidazol-2-yl]-5-methyl-[1,3]dioxane-5-carboxylic acid dimethylamide, trans-isomer, (Compound A710);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid dimethylamide, trans-isomer, (Compound A711);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid dimethylamide, trans-isomer, (Compound A712);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A713);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A714);

{4-[2-(5-dimethylcarbamoyl-5-methyl-[1,3]dioxan-2-yl)-5-(4-fluoro-phenyl)-3H-imidazol-4-yl]-pyrimidin-2-ylamino}-acetic acid, trans-isomer, (Compound A715);

3-{4-[2-(5-dimethylcarbamoyl-5-methyl-[1,3]dioxan-2-yl)-5-(4-fluoro-phenyl)-3H-imidazol-4-yl]-pyrimidin-2-ylamino}-propionic acid, trans-isomer, (Compound A716);

2-[4-(4-fluoro-phenyl)-5-(2-isopropylamino-pyrimidin-4-yl)-1H-imidazol-2-yl]-5-methyl-[1,3]dioxane-5-carboxylic acid dimethylamide, trans-isomer, (Compound A717);

2-[5-(2-allylamino-pyrimidin-4-yl)-4-(4-fluoro-phenyl)-1H-imidazol-2-yl]-5-methyl-[1,3]dioxane-5-carboxylic acid dimethylamide, trans-isomer, (Compound A718);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A719);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A720);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A721);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid dimethylamide, trans-isomer, (Compound A722);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid dimethylamide, trans-isomer, (Compound A723);

2-[4-(4-fluoro-phenyl)-5-(2-propylamino-pyrimidin-4-yl)-1H-imidazol-2-yl]-5-methyl-[1,3]dioxane-5-carboxylic acid dimethylamide, trans-isomer, (Compound A724);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid dimethylamide, trans-isomer, (Compound A725);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid dimethylamide, trans-isomer, (Compound A726);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A727);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid dimethylamide, trans-isomer, (Compound A728);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid dimethylamide, trans-isomer, (Compound A729);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid dimethylamide, trans-isomer, (Compound A730);

2-[4-(4-fluoro-phenyl)-5-(2-methoxy-pyrimidin-4-yl)-1H-imidazol-2-yl]-5-methyl-[1,3]dioxane-5-carboxylic acid dimethylamide, trans-isomer, (Compound A73 1);

2-[5-(2-benzyloxy-pyrimidin-4-yl)-4-(4-fluoro-phenyl)-1H-imidazol-2-yl]-5-methyl-[1,3]dioxane-5-carboxylic acid dimethylamide, trans-isomer, (Compound A732);

2-[4-(4-fluoro-phenyl)-5-(2-phenoxy-pyrimidin-4-yl)-1H-imidazol-2-yl]-5-methyl-[1,3]dioxane-5-carboxylic acid dimethylamide, trans-isomer, (Compound A733);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid dimethylamide, trans-isomer, (Compound A734);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid dimethylamide, trans-isomer, (Compound A735);

2-[5-(2-cyclohexyloxy-pyrimidin-4-yl)-4-(4-fluoro-phenyl)-1H-imidazol-2-yl]-5-methyl-[1,3]-dioxane-5-carboxylic acid dimethylamide, trans-isomer, (Compound A736);

2-[5-(2-Isopropoxy-pyrimidin-4-yl)-4-(4-fluoro-phenyl)-1H-imidazol-2-yl]-5-methyl-[1,3]dioxane-5-carboxylic acid dimethylamide, trans-isomer, (Compound A737);

2-[4-(4-fluoro-phenyl)-5-(2-propoxy-pyrimidin-4-yl)-1H-imidazol-2-yl]-5-methyl-[1,3]dioxane-5-acid dimethylamide, trans-isomer, (Compound A738);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid dimethylamide, trans-isomer, (Compound A739);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid dimethylamide, trans-isomer, (Compound A740);

b 2-[4-(4-fluoro-phenyl)-5-(2-methylsulfanyl-pyrimidin-4-yl)-1H-imidazol-2-yl]-5-methyl-[1,3]dioxane-5-carboxylic acid dimethylamide, trans-isomer, (Compound A741);

2-[5-(2-amino-pyrimidin-4-yl)-4-(4-fluoro-phenyl)-1H-imidazol-2-yl]-5-methyl-[1,3]dioxane-5-methyl-acid cyclopropylamide, trans-isomer, (Compound A742);

2-[4-(4-fluoro-phenyl)-5-(2-methylamino-pyrimidin-4-yl)-1H-imidazol-2-yl]-5-methyl-[1,3]dioxane-5-carboxylic acid cyclopropylamide, trans-isomer, (Compound A743);

2-[5-(2-dimethylamino-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A744);

2-[5-(2-cyclopropylamino-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A745);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid cyclopropylamide, trans-isomer, (Compound A746);

2-[5-(2-cyclohexylamino-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A747);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid cyclopropylamide, trans-isomer, (Compound A748);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A749);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid cyclopropylamide, trans-isomer, (Compound A750);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid cyclopropylamide, trans-isomer, (Compound A751);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid cyclopropylamide, trans-isomer, (Compound A752);

2-[5-(2-benzylamino-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A753);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyclopropylamide, R-isomer, trans-isomer, (Compound A754);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyclopropylamide, S-isomer, trans-isomer, (Compound A755);

2-[4-(4-fluoro-phenyl)-5-(2-phenylamino-pyrimidin-4-yl)-1H-imidazol-2-yl]-5-methyl-[1,3]dioxane-5-carboxylic acid cyclopropylamide, trans-isomer, (Compound A756);

2-[4-(4-fluoro-phenyl)-5-(2-piperidin-1-yl-pyrimidin-4-yl)-1H-imidazol-2-yl]-5-methyl-[1,3]dioxane-5-carboxylic acid cyclopropylamide, trans-isomer, (Compound A757);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid cyclopropylamide, trans-isomer, (Compound A758);

2-(4-(4-fluoro-phenyl)-5-{2-[(pyridin-3-ylmethyl)-amino]-pyrimidin-4-yl}-1H-imazol-2-yl)-5-methyl-[1,3]dioxane-5-carboxylic acid cyclopropylamide, trans-isomer, (Compound A759);

2-(4-(4-fluoro-phenyl)-5-{2-[(pyridin-2-ylmethyl)-amino]-pyrimidin-4-yl}-1H-imiazol-2-yl)-5-methyl-[1,3]dioxane-5-carboxylic acid cyclopropylamide, trans-isomer, (Compound A760);

2-(4-(4-fluoro-phenyl)-5-{2-[(furan-2-ylmethyl)-amino]-pyrimidin-4-yl}-1H-imazol-2-yl)-5-methyl-[1,3]dioxane-5-carboxylic acid cyclopropylamide, trans-isomer, (Compound A761);

2-(4-(4-fluoro-phenyl)-5-{2-[(thiophen-2-ylmethyl)-amino]-pyrimidin-4-yl}-1H-imidadozal-2-yl)-5-methyl-[1,3]dioxane-5-carboxylic acid cyclopropylamide, trans-isomer, (Compound A762);

2-(4-(4-fluoro-phenyl)-5-{2-[(tetrahydro-furan-2-ylmethyl)-amino]-pyrimidin-4-yl}1H-imidazol-2-yl)-5-methyl-[1,3]dioxane-5-carboxylic acid cyclopropylamide, trans-isomer, (Compound A763);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid cyclopropylamide, trans-isomer, (Compound A764);

2-[4-(4-fluoro-phenyl)-5-(2-morpholin-4-yl-pyrimidin-4-yl)-1H-imidazol-2-yl]-5-methyl-[1,3]dioxane-5-carboxylic acid cyclopropylamide, trans-isomer, (Compound A765);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid cyclopropylamide, trans-isomer, (Compound A766);

2-{4-(4-fluoro-phenyl)-5-[2-(2-methoxy-ethylamino)-pyrimidin-4-yl]-1H-imidazol-2-y }-5-methyl-[1,3]dioxane-5-carboxylic acid cyclopropylamide, trans-isomer, (Compound A767);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A768);

2-[5-[2-(2-dimethylamino-ethylamino)-pyrimidin-4-yl]-4-(4-fluoro-phenyl)-1H-imidazol-2-yl]-5-methyl-5-[1,3]dioxane-5-carboxylic acid cyclopropylamide, trans-isomer, (Compound A769);

{4-[2-(5-cyclopropylcarbamoyl-5-methyl-[1,3]dioxan-2-yl)-5-(4-fluoro-phenyl)-3H-imidazo;-4-yl]-pyrimidin-2-ylamino}-acetic acid, trans-isomer, (Compound A770);

3-{4-[2-(5-cyclopropylcarbamoyl-5-methyl-[1,3]dioxan-2-yl)-5-(4-fluoro-phenyl-3H-imidazol-4-yl]-pyrimidin-2-ylamino}-propionic acid, trans-isomer, (Compound A771);

2-[4-(4-fluoro-phenyl)-5-(2-isopropylamino-pyrimidin-4-yl)-1H-imidazol-2-yl]-5-methyl-[1,3]dioxane-5-carboxylic acid cyclopropylamide, trans-isomer, (Compound A772);

2-[5-(2-allylamino-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A773);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A774);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A775);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A776);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A777);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid cyclopropylamide, trans-isomer, (Compound A778);

2-{4-(4-flouro-phenyl)-5-[2-(pyridin-4-ylamino)-pyrimidin-4-yl]-1H-imidazol-2-yl}-5-methyl-[1,3]dioxane-5-carboxylic acid cyclopropylamide, trans-isomer, (Compound A779);

2-[4-(4-fluoro-phenyl)-5-(2-propylamino-pyrimidin-4-yl)-1H-imidazol-2-yl]-5-methyl-[1,3]dioxane-5-carboxylic acid cyclopropylamide, trans-isomer, (Compound A780);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid cyclopropylamide, trans-isomer, (Compound A781);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid cyclopropylamide, trans-isomer, (Compound A782);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A783);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid cyclopropylamide, trans-isomer, (Compound A784);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A785);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid cyclopropylamide, trans-isomer, (Compound A786);

2-[4-(4-fluoro-phenyl)-5-(2-methoxy-pyrimidin-4-yl)-1H-imidazol-2-yl]-5-methyl-[1,3]dioxane-5-carboxylic acid cyclopropylamide, trans-isomer, (Compound A787);

2-[5-(2-benzyloxy-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A788);

2-[4-(4-fluoro-phenyl)-5-(2-phenoxy-pyrimidin-4-yl)-1H-imidazol-2-yl]-5-methyl-[1,3]dioxane-5-carboxylic acid cyclopropylamide, trans-isomer, (Compound A789);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid cyclopropylamide, trans-isomer, (Compound A790);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid cyclopropylamide, trans-isomer, (Compound A791);

2-[5-(2-cyclohexyloxy-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A792);

2-[5-(2-Isopropoxy-pyrimidin-4-yl)-4-(4-fluoro-phenyl)-1H-imidazol-2-yl]-5-methyl-[1,3]dioxane-5-carboxylic acid cyclopropylamide, trans-isomer, (Compound A793);

2-[4-(4-fluoro-phenyl)-5-(2-propoxy-pyrimidin-4-yl)-1H-imidazol-2-yl]-5-methyl-[1,3]dioxane-5-carboxylic acid cyclopropylamide, trans-isomer, (Compound A794);

2-{4-(4-fluoro-phenyl)-5-[2-(2-hydroxy-ethoxy)-pyrimidin-4-yl]-1H-imidazol-2-yl}-5-methyl-[1,3]dioxane 5-carboxylic acid cyclopropylamide, trans-isomer, (Compound A795);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid cyclopropylamide, trans-isomer, (Compound A796);

2-[4-(4-fluoro-phenyl)-5-(2-methylsulfanyl-pyrimidin-4-yl)-1H-imidazol-2-yl]-5-methyl-[1,3]dioxane-5-carboxylic acid cyclopropylamide, trans-isomer, (Compound A797);

2-[5-(2-amino-pyrimidin-4-yl)-4-(4-fluoro-phenyl)-1H-imidazol-2-yl]-5-methyl-[1,3]dioxane-5-acid propylamide, trans-isomer, (Compound A798);

2-[4-(4-fluoro-phenyl)-5-(2-methylamino-pyrimidin-4-yl)-1H-imidazol-2-yl]-5-methyl-[1,3]dioxane-5-carboxylic acid propylamide, trans-isomer, (Compound A799);

2-[5-(2-dimethylamino-pyrimidin-4-yl)-4-(4-fluoro-phenyl)-1H-imidazol-2-yl]-5-methyl-[1,3]dioxane-5-carboxylic acid propylamide, trans-isomer, (Compound A800);

2-[5-(2-cyclopropylamino-pyrimidin-4-yl)-4-(4-fluoro-phenyl)-1H-imidazol-2-yl]-5-methyl-[1,3]dioxane-5-carboxylic acid propylamide, trans-isomer, (Compound A801);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid propylamide, trans-isomer, (Compound A802);

2-[5-(2-cyclohexylamino-pyrimidin-4-yl)-4-(4-fluoro-phenyl)-1H-imidazol-2-yl]-5-methyl-[1,3]dioxane-5-carboxylic acid propylamide, trans-isomer, (Compound A803);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid propylamide, trans-isomer, (Compound A804);

2-[5-[2-(2-amino-ethylamino)-pyrimidin-4-yl]-4-(4-fluoro-phenyl)-1H-imidazol-3-yl]-5-methyl-[1,3]dioxane-5-carboxylic acid propylamide, trans-isomer, (Compound A805);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid propylamide, trans-isomer, (Compound A806);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid propylamide, trans-isomer, (Compound A807);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid propylamide, trans-isomer, (Compound A808);

2-[5-(2-benzylamino-pyrimidin-4-yl)-4-(4-fluoro-phenyl)-1H-imidazol-2-yl]-5-methyl-[1,3]dioxane-5-carboxylic acid propylamide, trans-isomer, (Compound A809);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid propylamide, R-isomer, trans-isomer, (Compound A810);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid propylamide, S-isomer, trans-isomer, (Compound A811);

2-[4-(4-fluoro-phenyl)-5-(2-phenylamino-pyrimidin-4-yl)-1H-imidazol-2-yl]-5-methyl-[1,3]dioxane-5-carboxylic acid propylamide, trans-isomer, (Compound A812);

2-[4-(4-fluoro-phenyl)-5-(2-piperidin-1-yl-pyrimidin-4-yl)-1H-imidazol-2-yl]-5-methyl-[1,3]dioxane-5-carboxylic acid propylamide, trans-isomer, (Compound A813);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid propylamide, trans-isomer, (Compound A814);

2-(4-(4-fluoro-phenyl)-5-{2-[(pyridin-3-ylmethyl)-amino]-pyrimidin-4-yl}-1H -imidazol-2-yl)-5-methyl-[1,3]dioxane-5-carboxylic acid propylamide, trans-isomer, (Compound A815);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid propylamide, trans-isomer, (Compound A816);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid propylamide, trans-isomer, (Compound A817);

2-(4-(4-fluoro-phenyl)-5-{2-[(thiophen-2-ylmethyl)-amino]-pyrimidin-4-yl}-1H-imidazol-2-5-methyl-[1,3]

dioxane-5-carboxylic acid propylamide, trans-isomer, (Compound A818);

2-(4-(4-fluoro-phenyl)-5-{2-[(tetrahydro-furan-2-ylmethyl)-amino]-pyrimidin-4-yl}-1H-imidazo-2-yl)-5-methyl-[1,3]dioxane-5-carboxylic acid propylamide, trans-isomer, (Compound A819);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid propylamide, trans-isomer, (Compound A820);

2-[4-(4-fluoro-phenyl)-5-(2-morpholin-4-yl-pyrimidin-4-yl)-1H-imidazol-2-yl]-5-methyl-[1,3]dioxane-5-carboxylic acid propylamide, trans-isomer, (Compound A821);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid propylamide, trans-isomer, (Compound A822);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid propylamide, trans-isomer, (Compound A823);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid propylamide, trans-isomer, (Compound A824);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid propylamide, trans-isomer, (Compound A825);

{4-[5-(4-fluoro-phenyl)-2-(5-methyl-5-propylcarbamoyl-[1,3]dioxan-2-yl)-3H-imidazol-4]-pyrimadin-2-ylamino}-acetic acid, trans-isomer, (Compound A826);

3-{4-[5-(4-fluoro-phenyl)-2-(5-methyl-5-propylcarbamoyl-[1,3]dioxan-2-yl)-3H-imidazol-4-yl]-pyrimidin-2-ylamino}-propionic acid, trans-isomer, (Compound A827);

2-[4-(4-fluoro-phenyl)-5-(2-isopropylamino-pyrimidin-4-yl)-1H-imidazol-2-yl]-5-methyl-[1,3]dioxane-5-carboxylic acid propylamide, trans-isomer, (Compound A828);

2-[5-(2-allylamino-pyrimidin-4-yl)-4-(4-fluoro-phenyl)-1H-imidazol-2-yl]-5-methyl-[1,3]dioxane-5-carboxylic acid propylamide, trans-isomer, (Compound A829);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid propylamide, trans-isomer, (Compound A830);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid propylamide, trans-isomer, (Compound A831);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid propylamide, trans-isomer, (Compound A832);

2-{4-(4-fluoro-phenyl)-5-[2-(pyridin-3-ylamino)-pyrimidin-4-yl]-1H-imidazol-2yl}-5-methyl-[1,3]dioxane-5-carboxylic acid propylamide, trans-isomer, (Compound A833);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid propylamide, trans-isomer, (Compound A834);

2-[4-(4-fluoro-phenyl)-5-(2-propylamino-pyrimidin-4-yl)-1H-imidazol-2-yl]-5-methyl-[1,3]dioxane-5-carboxylic acid propylamide, trans-isomer, (Compound A835);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid propylamide, trans-isomer, (Compound A836);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid propylamide, trans-isomer, (Compound A837);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid propylamide, trans-isomer, (Compound A838);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid propylamide, trans-isomer, (Compound A839);

2-[5-[2-(4-fluoro-benzylamino)-pyrimidin-4-yl]-4-(4-fluoro-phenyl)-1H-imidazol2-yl]-5-methyl-[1,3]dioxane-5-carboxylic acid propylamide, trans-isomer, (Compound A840);

2-{4-(4-fluoro-phenyl)-5-[2-(4-methoxy-benzylamino)-pyrimidin-4-yl]-1-H -imidazol-2-yl}-5-methyl-[1,3]dioxane-5-carboxylic acid propylamide, trans-isomer, (Compound A841);

2-[4-(4-fluoro-phenyl)-5-(2-methoxy-pyrimidin-4-yl)-1H-imidazol-2-yl]-5-methyl-[1,3]dioxane-5-carboxylic acid propylamide, trans-isomer, (Compound A842);

2-[5-(2-benzyloxy-pyrimidin-4-yl)-4-(4-fluoro-phenyl)-1H-imidazol-2-yl]-5-methyl-[1,3]dioxane-5-carboxylic acid propylamide, trans-isomer, (Compound A843);

2-[4-(4-fluoro-phenyl)-5-(2-phenoxy-pyrimidin-4-yl)-1H-imidazol-2-yl]-5-methyl-[1,3]dioxane-5-carboxylic acid propylamide, trans-isomer, (Compound A844);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid propylamide, trans-isomer, (Compound A845);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid propylamide, trans-isomer, (Compound A846);

2-[5-(2-cyclohexyloxy-pyrimidin-4-yl)-4-(4-fluoro-phenyl)-1H-imidazol-2-yl]-5-methyl-[1,3]dioxane-5-carboxylic acid propylamide, trans-isomer, (Compound A847);

2-[5-(2-Isopropoxy-pyrimidin-4-yl)-4-(4-fluoro-phenyl)-1H-imidazol-2-yl]-5-methyl-[1,3]dioxane-5-carboxylic acid propylamide, trans-isomer, (Compound A848);

2-[4-(4-fluoro-phenyl)-5-(2-propoxy-pyrimidin-4-yl)-1H-imidazol-2-yl]-5-methyl-[1,3]dioxane-5-carboxylic acid propylamide, trans-isomer, (Compound A849);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid propylamide, trans-isomer, (Compound A850);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid propylamide, trans-isomer, (Compound A851);

2-[4-(4-fluoro-phenyl)-5-(2-methylsulfanyl-pyrimidin-4-yl)-1H-imidazol-2-yl]-5-methyl-[1,3]dioxane-5-carboxylic acid propylamide, trans-isomer, (Compound A852);

2-[5-(2-amino-pyrimidin-4-yl)-4-(4-fluoro-phenyl)-1H-imidazol-2-yl]-5-methyl-[1,3]dioxane-5-carbolic acid cyclohexylamide, trans-isomer, (Compound A853);

2-[4-(4-fluoro-phenyl)-5-(2-methylamino-pyrimidin-4-yl)-1H-imidazol-2-yl]-5-methyl-[1,3]dioxane-5-carboxylic acid cyclohexylamide, trans-isomer, (Compound A854);

2-[5-(2-dimethylamino-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A855);

b 2-[5-(2-cyclopropylamino-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A856);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid cyclohexylamide, trans-isomer, (Compound A857);

2-[5-(2-cyclohexylamino-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A858);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid cyclohexylamide, trans-isomer, (Compound A859);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A860);

2-(4-(4-fluoro-phenyl)-5-{2-[3-(5H-imidazol-4-yl)-propylamino]-pyrimidin-4-yl}-1H-imidazol-2-yl)-5-methyl-[1,3]dioxane-5-carboxylic acid cyclohexylamide, trans-isomer, (Compound A861);

2-{4-(4-fluoro-phenyl)-5-[2-(3-morpholin-4-yl-propylamino)-pyrimidin-4-yl]-1H-imidazol-2}-5-methyl-[1,3]dioxane-5-carboxylic acid cyclohexylamide, trans-isomer, (Compound A862);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid cyclohexylamide, trans-isomer, (Compound A863);

2-[5-(2-benzylamino-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A864);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyclohexylamide, R-isomer, trans-isomer, (Compound A865);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyclohexylamide, S-isomer, trans-isomer, (Compound A866);

2-[4-(4-fluoro-phenyl)-5-(2-phenylamino-pyrimidin-4-yl)-1H-imidazol-2-yl]-5-methyl-[1,3]dioxane-5-carboxylic acid cyclohexylamide, trans-isomer, (Compound A867);

2-[4-(4-fluoro-phenyl)-5-(2-piperidin-1-yl-pyrimidin-4-yl)-1H-imidazol-2-yl]-5-methyl-[1,3]dioxane-5-carboxylic acid cyclohexylamide, trans-isomer, (Compound A868);

2-(4-(4-fluoro-phenyl)-5-{2-[(pyridin-4-ylmethyl)-amino]-pyrimidin-4-yl}-1H-imidazo-2-yl)-5-methyl-[1,3]dioxane-5-carboxylic acid cyclohexylamide, trans-isomer, (Compound A869);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid cyclohexylamide, trans-isomer, (Compound A870);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid cyclohexylamide, trans-isomer, (Compound A871);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid cyclohexylamide, trans-isomer, (Compound A872);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid cyclohexylamide, trans-isomer, (Compound A873);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid cyclohexylamide, trans-isomer, (Compound A874);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid cyclohexylamide, trans-isomer, (Compound A875);

2-[4-(4-fluoro-phenyl)-5-(2-morpholin-4-yl-pyrimidin-4-yl)-1H-imidazol-2-yl]-5-methyl-[1,3]dioxane-5-carboxylic acid cyclohexylamide, trans-isomer, (Compound A876);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid cyclohexylamide, trans-isomer, (Compound A877);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid cyclohexylamide, trans-isomer, (Compound A878);

2-[5-[2-(3-dimethylamino-propylamino)-pyrimidin4-yl]-4-(4-fluoro-phenyl)-1H-imidazol-2-yl]-5-methyl-[1,3]dioxane-5-carboxylic acid cyclohexylamide, trans-isomer, (Compound A879);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A880);

{4-[2-(5-cyclohexylcarbamoyl-5-methyl-[1,3]dioxan-2-yl)-5-(4-fluoro-phenyl)-3H-imidazol-4-yl]-pyrimidin-2-ylamino}-acetic acid, trans-isomer, (Compound A881);

3-{4-[2-(5-cyclohexylcarbamoyl-5-methyl-[1,3]dioxan-2-yl)-5-(4-fluoro-phenyl)-3H-imidazol-4-yl]-pyrimidin-2-ylamino}-propionic acid, trans-isomer, (Compound A882);

2-[4-(4-fluoro-phenyl)-5-(2-isopropylamino-pyrimidin-4-yl)-1H-imidazol-2-yl]-5-methyl-[1,3]dioxane-5-carboxylic acid cyclohexylamide, trans-isomer, (Compound A883);

2-[5-(2-allylamino-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A884);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A885);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A886);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A887);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid cyclohexylamide, trans-isomer, (Compound A888);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid cyclohexylamide, trans-isomer, (Compound A889);

2-[4-(4-fluoro-phenyl)-5-(2-propylamino-pyrimidin-4-yl)-1H-imidazol-2-yl]-5-methyl-[1,3]dioxane-5carboxylic acid cyclohexylamide, trans-isomer, (Compound A890);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid cyclohexylamide, trans-isomer, (Compound A891);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid cyclohexylamide, trans-isomer, (Compound A892);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A893);

2-(4-(4-fluoro-phenyl)-5-[2-(3-methoxy-phenylamino)-pyrimidin-4-yl]-1H-imidazol-2-yl}-5-methyl-[1,3]dioxane-5-carboxylic acid cyclohexylamide, trans-isomer, (Compound A894);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A895);

2-{4-(4-fluoro-phenyl)-5-[2-(4-methoxy-benzylamino)-pyrimidin-4-yl]-1H-imidazol-2}-5-methyl-[1,3]dioxane-5-carboxylic acid cyclohexylamide, trans-isomer, (Compound A896);

2-[4-(4-fluoro-phenyl)-5-(2-methoxy-pyrimidin-4-yl)-1H-imidazol-2-yl]-5-methyl-[1,3]dioxane-5-carboxylic acid cyclohexylamide, trans-isomer, (Compound A897);

2-[5-(2-benzyloxy-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A898);

2-[4-(4-fluoro-phenyl)-5-(2-phenoxy-pyrimidin-4-yl)-1H-imidazol-2-yl]-5-methyl-[1,3]dioxane-5-carboxylic acid cyclohexylamide, trans-isomer, (Compound A899);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid cyclohexylamide, trans-isomer, (Compound A900);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid cyclohexylamide, trans-isomer, (Compound A901);

2-[5-(2-cyclohexyloxy-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A902);

2-[5-(2-Isopropoxy-pyrimidin-4-yl)-4-(4-fluoro-phenyl)-1H-imidazol-2-yl]-5-methyl-[1,3]dioxane-5-carboxylic acid cyclohexylamide, trans-isomer, (Compound A903);

2-[4-(4-fluoro-phenyl)-5-(2-propoxy-pyrimidin-4-yl)-1H-imidazol-2-yl]-5-methyl-[1,3]dioxane-5-acid cyclohexylamide, trans-isomer, (Compound A904);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid cyclohexylamide, trans-isomer, (Compound A905);

2-{4-(4-fluoro-phenyl)-5-[2-(3-hydroxy-propoxy)-pyrimidin-4-yl]-1H-imidazol-2-yl}-5methyl-[1,3]dioxane-5-carboxylic acid cyclohexylamide, trans-isomer, (Compound A906);

2-[4-(4-fluoro-phenyl)-5-(2-methylsulfanyl-pyrimidin-4-yl)-1H-imidazol-2-yl]-5-methyl-[1,3]dioxane-5-carboxylic acid cyclohexylamide, trans-isomer, (Compound A907);

2-[5-(2-amino-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A908);

2-[4-(4-fluoro-phenyl)-5-(2-methylamino-pyrimidin-4-yl)-1H-imidazol-2-yl]-5-methyl-[1,3]dioxane-5-carboxylic acid (2-hydroxy-ethyl)-amide, trans-isomer, (Compound A909);

2-[5-(2-dimethylamino-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A910);

2-[5-(2-cyclopropylamino-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A911);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (2-hydroxy-ethyl)-amide, trans-isomer, (Compound A912);

2-[5-(2-cyclohexylamino-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A913);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid (2-hydroxy-ethyl)-amide, trans-isomer, (Compound A914);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A915);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid (2-hydroxy-ethyl)-amide, trans-isomer, (Commpound A916);

2-{4-(4-fluoro-phenyl)-5-[2-(3-morpholin-4-yl-propylamino)-pyrimidin-4-yl]-1-H-imidazol-2-yl}-5-methyl-[1,3]dioxane-5-carboxylic acid (2-hydroxy-ethyl)-amide, trans-isomer, (Compound A917);

2-{4-(4-fluoro-phenyl)-5-[2-(3-hydroxy-propylamino)-pyrimidin-4-yl]-1-H-imidazol-2-yl}-5-methyl-[1,3]dioxane-5-carboxylic acid (2-hydroxy-ethyl)-amide, trans-isomer, (Compound A918);

2-[5-(2-benzylamino-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A919);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-hydroxy-ethyl)-amide, R-isomer, trans-isomer, (Compound A920);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-hydroxy-ethyl)-amide, S-isomer, trans-isomer, (Compound A921);

2-[4-(4-fluoro-phenyl)-5-(2-phenylamino-pyrimidin-4-yl)-1H-imidazol-2-yl]-5-methyl-[1,3]dioxane-5-carboxylic acid (2-hydroxy-ethyl)-amide, trans-isomer, (Compound A922);

2-[4-(4-fluoro-phenyl)-5-(2-piperidin-1-yl-pyrimidin-4-yl)-1H-imidazol-2-yl]-5-methyl-[1,3]dioxane-5-carboxylic acid (2-hydroxy-ethyl)-amide, trans-isomer, (Compound A923);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid (2-hydroxy-ethyl)-amide, trans-isomer, (Compound A924);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (2-hydroxy-ethyl)-amide, trans-isomer, (Compound A925);

2-(4-(4-fluoro-phenyl)-5-{2-[(pyridin-2-ylmethyl)-amino]-pyrimidin-4-yl}-1H-imidazol-2-yl)-5-[1,3]dioxane-5-carboxylic acid (2-hydroxy-ethyl)-amide, trans-isomer, (Compound A926);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (2-hydroxy-ethyl)-amide, trans-isomer, (Compound A927);

2-(4-(4-fluoro-phenyl)-5-{2-[(thiophen-2-ylmethyl)-amino]-pyrimidin-4-yl}-1-H-imidazol-2-yl)-5-methyl-[1,3]dioxane-5-carboxylic acid (2-hydroxy-ethyl)-amide, trans-isomer, (Compound A928);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (2-hydroxy-ethyl)-amide, trans-isomer, (Compound A929);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (2-hydroxy-ethyl)-amide, trans-isomer, (Compound A930);

2-[4-(4-fluoro-phenyl)-5-(2-morpholin-4-yl-pyrimidin-4-yl)-1H-imidazol-2-yl]-5-methyl-[1,3]dioxane-5-carboxylic acid (2-hydroxy-ethyl)-amide, trans-isomer, (Compound A931);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (2-hydroxy-ethyl)-amide, trans-isomer, (Compound A932);

2-{4-(4-fluoro-phenyl)-5-[2-(2-methoxy-ethylamino)-pyrimidin-4-yl]-1H-imidazol-2-yl}-5methyl-[1,3]dioxane-5-carboxylic acid (2-hydroxy-ethyl)-amide, trans-isomer, (Compound A933);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A934);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A935);

(4-{5-(4-fluoro-phenyl)-2-[5-(2-hydroxy-ethylcarbamoyl)-5-methyl-[1,3]dioxan-2-yl]3H-imidazol-4-yl}-pyrimidin-2-ylamino)-acetic acid, trans-isomer, (Compound A936);

3-(4-{5-(4-fluoro-phenyl)-2-[5-(2-hydroxy-ethylcarbamoyl)-5-methyl-[1,3]dioxan-2-yl]-3H-imidaxol-4-yl}-pyrimidin-2-ylamino)-propionic acid, trans-isomer, (Compound A937);

2-[4-(4-fluoro-phenyl)-5-(2-isopropylamino-pyrimidin-4-yl)-1H-imidazol-2-yl]-5-methyl-[1,3]dioxane-5-carboxylic acid (2-hydroxy-ethyl)-amide, trans-isomer, (Compound A938);

2-[5-(2-allylamino-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A939);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A940);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A941);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A942);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid (2-hydroxy-ethyl)-amide, trans-isomer, (Compound A943);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (2-hydroxy-ethyl)-amide, trans-isomer, (Compound A944);

2-[4-(4-fluoro-phenyl)-5-(2-propylamino-pyrimidin-4-yl)-1H-imidazol-2-yl]-5-methyl-[1,3]dioxane-5-carboxylic acid (2-hydroxy-ethyl)-amide, trans-isomer, (Compound A945);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (2-hydroxy-ethyl)-amide, trans-isomer, (Compound A946);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (2-hydroxy-ethyl)-amide, trans-isomer, (Compound A947);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A948);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (2-hydroxy-ethyl)-amide, trans-isomer, (Compound A949);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A950);

2-{4-(4-fluoro-phenyl)-5-[2-(4-methoxy-benzylamino)-pyrimidin-4-yl]-1H-imidazol-2-yl}-5methyl-[1,3]dioxane-5-carboxylic acid (2-hydroxy-ethyl)-amide, trans-isomer, (Compound A951);

2-[4-(4-fluoro-phenyl)-5-(2-methoxy-pyrimidin-4-yl)-1H-imidazol-2-yl]-5-methyl-[1,3]dioxane-5-carboxylic acid (2-hydroxy-ethyl)-amide, trans-isomer, (Compound A952);

2-[5-(2-benzyloxy-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A953);

2-[4-(4-fluoro-phenyl)-5-(2-phenoxy-pyrimidin-4-yl)-1H-imidazol-2-yl]-5-methyl-[1,3]dioxane-5-carboxylic acid (2-hydroxy-ethyl)-amide, trans-isomer, (Compound A954);

2-{4-(4-fluoro-phenyl)-5-[2-(2-methoxy-ethoxy)-pyrimidin-4-yl]-1H-imidazol-2-yl}-5methyl-[1,3]dioxane-5-carboxylic acid (2-hydroxy-ethyl)-amide, trans-isomer, (Compound A955);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid (2-hydroxy-ethyl)-amide, trans-isomer, (Compound A956);

2-[5-(2-cyclohexyloxy-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A957);

2-[5-(2-Isopropoxy-pyrimidin-4-yl)-4-(4-fluoro-phenyl)-1H-imidazol-2-yl]-5-methyl-[1,3]dioxane-5-carboxylic acid (2-hydroxy-ethyl)-amide, trans-isomer, (Compound A958);

2-[4-(4-fluoro-phenyl)-5-(2-propoxy-pyrimidin-4-yl)-1H-imidazol-2-yl]-5-methyl-[1,3]dioxane-5-carboxylic acid (2-hydroxy-ethyl)-amide, trans-isomer, (Compound A959);

2-{4-(4-fluoro-phenyl)-5-[2-(2-hydroxy-ethoxy)-pyrimidin-4-yl]-1H-imidazol-2-yl}-5-methyl-[1,3]dioxne-5-carboxylic acid (2-hydroxy-ethyl)-amide, trans-isomer, (Compound A960);

2-{4-(4-fluoro-phenyl)-5-[2-(3-hydroxy-propoxy)-pyrimidin-4-yl]-1H-imidazol-2-yl}-5methyl-[1,3]dioxane-5-carboxylic acid (2-hydroxy-ethyl)-amide, trans-isomer, (Compound A961);

2-[4-(4-fluoro-phenyl)-5-(2-methylsulfanyl-pyrimidin-4-yl)-1H-imidazol-2-yl]-5-methyl-[1,3]dioxane-5-carboxylic acid (2-hydroxy-ethyl)-amide, trans-isomer, (Compound A962);

2-[5-(2-amino-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A963);

2-[4-(4-fluoro-phenyl)-5-(2-methylamino-pyrimidin-4-yl)-1H-imidazol-2-yl]-5-methyl-[1,3]dioxane-5-carboxylic acid (2-amino-ethyl)-amide, trans-isomer, (Compound A964);

2-[5-(2-dimethylamino-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A965);

2-[5-(2-cyclopropylamino-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A966);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (2-amino-ethyl)-amide, trans-isomer (Compound A967);

2-[5-(2-cyclohexylamino-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A968);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid (2-amino-ethyl)-amide, trans-isomer, (Compound A969);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A970);

2-(4-(4-fluoro-phenyl)-5-{2-[3-(5H-imidazol-1-yl)-propylamino]-pyrimidin-4-yl}1H-imidazol-2-yl)-5-methyl-[1,3]dioxane-5-carboxylic acid (2-amino-ethyl)-amide, trans-isomer, (Compound A971);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid (2-amino-ethyl)-amide, trans-isomer, (Compound A972);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (2-amino-ethyl)-amide, trans-isomer, (Compound A973);

2-[5-(2-benzylamino-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A974);

2-{4-(4-fluoro-phenyl)-5-[2-(1-phenyl-ethylamino)-pyrimidin-4-yl]-1H-imidazol-2-yl}-5methyl-[1,3]dioxane-5-carboxylic acid (2-amino-ethyl)-amide, R-isomer, trans-isomer, (Compound A975);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-amino-ethyl)-amide, S-isomer, trans-isomer, (Compound A976);

2-[4-(4-fluoro-phenyl)-5-(2-phenylamino-pyrimidin-4-yl)-1H-imidazol-2-yl]-5-methyl-[1,3]dioxane-5-carboxylic acid (2-amino-ethyl)-amide, trans-isomer, (Compound A977);

2-[4-(4-fluoro-phenyl)-5-(2-piperidin-1-yl-pyrimidin-4-yl)-1H-imidazol-2-yl]-5-methyl-[1,3]dioxane-5-carboxylic acid (2-amino-ethyl)-amide, trans-isomer, (Compound A978);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid (2-amino-ethyl)-amide, trans-isomer, (Compound A979);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (2-amino-ethyl)-amide, trans-isomer, (Compound A980);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (2-amino-ethyl)-amide, trans-isomer, (Compound A981);

-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (2-amino-ethyl)-amide, trans-isomer, (Compound A982);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (2-amino-ethyl)-amide, trans-isomer, (Compound A983);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (2-amino-ethyl)-amide, trans-isomer, (Compound A984);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (2-amino-ethyl)-amide, trans-isomer, (Compound A985);

2-[4-(4-fluoro-phenyl)-5-(2-morpholin-4-yl-pyrimidin-4-yl)-1H-imidazol-2-yl]-5-methyl-[1,3]dioxane-5-carboxylic acid (2-amino-ethyl)-amide, trans-isomer, (Compound A986);

2-{4-(4-fluoro-phenyl)-5-[2-(3-methoxy-propylamino)-pyrimidin-4-yl]-1H-imidazol-2-yl}-5methyl-[1,3]dioxane-5-carboxylic acid (2-amino-ethyl)-amide, trans-isomer, (Compound A987);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (2-amino-ethyl)-amide, trans-isomer, (Compound A988);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A989);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A990);

{4-[2-[5-(2-amino-ethylcarbamoyl)-5-methyl-[1,3]dioxan-2-yl]-5-(4-fluoro-phenyl)-3H-imidiazol-4-yl]-pyrimidin-2-ylamino}-acetic acid, trans-isomer, (Compound A991);

3-{4-[2-[5-(2-amino-ethylcarbamoyl)-5-methyl-[1,3]dioxan-2-yl]-5-(4-flouro-phenyl)-3H-imidazol-4-yl]-pyrimidin-2-ylamino}-propionic acid, trans-isomer, (Compound A992);

2-[4-(4-fluoro-phenyl)-5-(2-isopropylamino-pyrimidin-4-yl)-1H-imidazol-2-yl]-5-methyl-[1,3]dioxane-5-carboxylic acid (2-amino-ethyl)-amide, trans-isomer, (Compound A993);

2-[5-(2-allylamino-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A994);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A995);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A996);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A997);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid (2-amino-ethyl)-amide, trans-isomer, (Compound A998);

2-{4-(4-fluoro-phenyl)-5-[2-(pyridin-4-ylamino)-pyrimidin-4-yl]-1H-imidazol-2-yl}-5-methyl-[1,3]-dioxane-5-carboxylic acid (2-amino-ethyl)-amide, trans-isomer, (Compound A999);

2-[4-(4-fluoro-phenyl)-5-(2-propylamino-pyrimidin-4-yl)-1H-imidazol-2-yl]-5-methyl-[1,3]dioxane-5-carboxylic acid (2-amino-ethyl)-amide, trans-isomer, (Compound A1000);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (2-amino-ethyl)-amide, trans-isomer, (Compound A1001);

2-{4-(4-fluoro-phenyl)-5-[2-(4-fluoro-phenylamino)-pyrimidin-4-yl]-1H-imidazol-2-yl}-5methyl-[1,3]dioxane-5-carboxylic acid (2-amino-ethyl)-amide, trans-isomer, (Compound A1002);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A1003);

2-{4-(4-fluoro-phenyl)-5-[2-(3-methoxy-phenylamino)-pyrimidin-4-yl]-1H-imidazol-2-yl}-5methyl-[1,3]dioxane-5-carboxylic acid (2-amino-ethyl)-amide, trans-isomer, (Compound A1004);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A1005);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid (2-amino-ethyl)-amide, trans-isomer, (Compound A1006);

2-[4-(4-fluoro-phenyl)-5-(2-methoxy-pyrimidin-4-yl)-1H-imidazol-2-yl]-5-methyl-[1,3]dioxane-5-carboxylic acid (2-amino-ethyl)-amide, trans-isomer, (Compound A1007);

2-[5-(2-benzyloxy-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A1008);

2-[4-(4-fluoro-phenyl)-5-(2-phenoxy-pyrimidin-4-yl)-1H-imidazol-2-yl]-5-methyl-[1,3]dioxane-5-carboxylic acid (2-amino-ethyl)-amide, trans-isomer, (Compound A1009);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (2-amino-ethyl)-amide, trans-isomer, (Compound A1010);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid (2-amino-ethyl)-amide, trans-isomer, (Compound A1011);

2-[5-(2-cyclohexyloxy-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A1012);

2-[5-(2-Isopropoxy-pyrimidin-4-yl)-4-(4-fluoro-phenyl)-1H-imidazol-2-yl]-5-methyl-[1,3]dioxane-5-carboxylic acid (2-amino-ethyl)-amide, trans-isomer, (Compound A1013);

2-[4-(4-fluoro-phenyl)-5-(2-propoxy-pyrimidin-4-yl)-1H-imidazol-2-yl]-5-methyl-[1,3]dioxane-5-carboxylic acid (2-amino-ethyl)-amide, trans-isomer, (Compound A1014);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (2-amino-ethyl)-amide, trans-isomer, (Compound A1015);

2-{4-(4-fluoro-phenyl)-5-[2-(3-hydroxy-propoxy)-pyrimidin-4-yl]-1H-imidazol-2-yl}-5methyl-[1,3]dioxane-5-carboxylic acid (2-amino-ethyl)-amide, trans-isomer, (Compound A1016);

2-[4-(4-fluoro-phenyl)-5-(2-methylsulfanyl-pyrimidin-4-yl)-1H-imidazol-2-yl]-5-methyl-[1,3]dioxane-5-carboxylic acid (2-amino-ethyl)-amide, trans-isomer, (Compound A1017);

2-[5-(2-amino-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1018);

2-[4-(4-fluoro-phenyl)-5-(2-methylamino-pyrimidin-4-yl)-1H-imidazol-2-yl]-5-methyl-[1,3]dioxane-5-carboxylic acid (3-hydroxy-propyl)-amide, trans-isomer, (Compound A1019);

2-[5-(2-dimethylamino-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1020);

2-[5-(2-cyclopropylamino-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1021);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (3-hydroxy-propyl)-amide, trans-isomer, (Compound A1022);

2-[5-(2-cyclohexylamino-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1023);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid (3-hydroxy-propyl)-amide, trans-isomer, (Compound A1024);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1025);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid (3-hydroxy-propyl)-amide, trans-isomer, (Compound A1026);

2-{4-(4-fluoro-pheny)-5-[2-(3-morpholin-4-yl-propylamino)-pyrimidin-4-yl]-1H-imidazol-2-yl}-5-methyl-[1,3]dioxane-5-carboxylic acid (3-hydroxy-propyl)-amide, trans-isomer, (Compound A1027);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (3-hydroxy-propyl)-amide, trans-isomer, (Compound A1028);

2-[5-(2-benzylamino-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1029);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (3-hydroxy-propyl)-amide, R-isomer, trans-isomer; (Compound A1030);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (3-hydroxy-propyl)-amide, S-isomer, trans-isomer, (Compound A1031);

2-[4-(4-fluoro-phenyl)-5-(2-phenylamino-pyrimidin-4-yl)-1H-imidazol-2-yl]-5-methyl-[1,3]dioxane-5-carboxylic acid (3-hydroxy-propyl)-amide, trans-isomer, (Compound A1032);

2-[4-(4-fluoro-phenyl)-5-(2-piperidin-1-yl-pyrimidin-4-yl)-1H-imidazol-2-yl]-5-methyl-[1,3]dioxane-5-carboxylic acid (3-hydroxy-propyl)-amide, trans-isomer, (Compound A1033);

2-(4-(4-fluoro-phenyl)-5-{2-[(pyridin-4-ylmethyl)-amino]-pyrimidin-4-yl}-1H-imidazol-2-yl)-5methyl-[1,3]dioxane-5-carboxylic acid (3-hydroxy-propyl)-amide, trans-isomer, (Compound A1034);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (3-hydroxy-propyl)-amide, trans-isomer, (Compound A1035);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (3-hydroxy-propyl)-amide, trans-isomer, (Compound A1036);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (3-hydroxy-propyl)-amide, trans-isomer, (Compound A1037);

2-(4-(4-fluoro-phenyl)-5-{2-[(thiophen-2-ylmethyl)-amino]-pyrimidin-4-yl}-1H-imidazol-2-yl)-5methyl-[1,3]dioxane-5-carboxylic acid (3-hydroxy-propyl)-amide, trans-isomer, (Compound A1038);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (3-hydroxy-propyl)-amide, trans-isomer, (Compound A1039);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (3-hydroxy-propyl)-amide, trans-isomer, (Compound A1040);

2-[4-(4-fluoro-phenyl)-5-(2-morpholin-4-yl-pyrimidin-4-yl)-1H-imidazol-2-yl]-5-methyl-[1,3]dioxane-5-carboxylic acid (3-hydroxy-propyl)-amide, trans-isomer, (Compound A1041);

2-{4-(4-fluoro-phenyl)-5-[2-(3-methoxy-propylamino)-pyrimidin-4-yl]-1H-imidazol-2-yl}-5methyl-[1,3]dioxane-5-carboxylic acid (3-hydroxy-propyl)-amide, trans-isomer, (Compound A1042);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (3-hydroxy-propyl)-amide, trans-isomer, (Compound A1043);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1044);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1045);

(4-{5-(4-fluoro-phenyl)-2-[5-(3-hydroxy-propylcarbamoyl)-5-methyl-[1,3]dioxan-2-yl]-3H-imidazol-4-yl}-pyrimidin-2-ylamino)-acetic acid, trans-isomer, (Compound A1046);

3-(4-{5-(4-fluoro-phenyl)-2-[5-(3-hydroxy-propylcarbamoyl)-5-methyl-[1,3]dioxan-2-yl]-3H-imidazol-4-yl}-pyrimidin-2-ylamino)-propionic acid, trans-isomer, (Compound A1047);

2-[4-(4-fluoro-phenyl)-5-(2-isopropylamino-pyrimidin-4-yl)-1H-imidazol-2-yl]-5-methyl-[1,3]dioxane-5-carboxylic acid (3-hydroxy-propyl)-amide, trans-isomer, (Compound A1048);

2-[5-(2-allylamino-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1049);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1050);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1051);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1052);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid (3-hydroxy-propyl)-amide, trans-isomer, (Compound A1053);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (3-hydroxy-propyl)-amide, trans-isomer, (Compound A1054);

2-[4-(4-fluoro-phenyl)-5-(2-propylamino-pyrimidin-4-yl)-1H-imidazol-2-yl]-5-methyl-[1,3]dioxane-5-carboxylic acid (3-hydroxy-propyl)-amide, trans-isomer, (Compound A1055);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (3-hydroxy-propyl)-amide, trans-isomer, (Compound A1056);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (3-hydroxy-propyl)-amide, trans-isomer, (Compound A1057);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1058);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (3-hydroxy-propyl)-amide, trans-isomer, (Compound A1059);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1060);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid (3-hydroxy-propyl)-amide, trans-isomer, (Compound A1061);

2-[4-(4-fluoro-phenyl)-5-(2-methoxy-pyrimidin-4-yl)-1H-imidazol-2-yl]-5-methyl-[1,3]dioxane-5-carboxylic acid (3-hydroxy-propyl)-amide, trans-isomer, (Compound A1062);

2-[5-(2-benzyloxy-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1063);

2-[4-(4-fluoro-phenyl)-5-(2-phenoxy-pyrimidin-4-yl)-1H-imidazol-2-yl]-5-methyl-[1,3]dioxane-5-carboxylic acid (3-hydroxy-propyl)-amide, trans-isomer, (Compound A1064);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (3-hydroxy-propyl)-amide, trans-isomer, (Compound A1065);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid (3-hydroxy-propyl)-amide, trans-isomer, (Compound A1066);

2-[5-(2-cyclohexyloxy-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1067);

2-[5-(2-Isopropoxy-pyrimidin-4-yl)-4-(4-fluoro-phenyl)-1H-imidazol-2-yl]-5-methyl-[1,3]dioxane-5-carboxylic acid (3-hydroxy-propyl)-amide, trans-isomer, (Compound A1068);

2-[4-(4-fluoro-phenyl)-5-(2-propoxy-pyrimidin-4-yl)-1H-imidazol-2-yl]-5-methyl-[1,3]dioxane-5-carboxylic acid (3-hydroxy-propyl)-amide, trans-isomer, (Compound A1069);

{4-(4-flouro-phenyl)-5-[2-(2-hydroxy-ethoxy)-pryrimidin-4-yl]-1H-imidazol-2-yl}-5-methyl-[1,3]dioxane-5-carboxylic acid (3-hydroxy-propyl)-amide, trans-isomer, (Compound A1070);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (3-hydroxy-propyl)-amide, trans-isomer, (Compound A1071);

2-[4-(4-fluoro-phenyl)-5-(2-methylsulfany-pyrimidin-4-yl)-1H-imidazol-2-yl]-5-methyl-[1,3]dioxane-5-carboxylic acid (3-hydroxy-propyl)-amide, trans-isomer, (Compound A1072);

2-[5-(2-amino-pyrimidin-4-yl)-4-(4-fluoro-phenyl)-1H-imidazol-2-yl]-5-methyl-[1,3]dioxane-5-carboxylic acid benzylamide, trans-isomer, (Compound A1073);

2-[4-(4-fluoro-phenyl)-5-(2-methylamino-pyrimidin-4-yl)-1H-imidazol-2-yl]-5-methyl-[1,3]dioxane-5-carboxylic acid benzylamide, trans-isomer, (Compound A1074);

2-[5-(2-dimethylamino-pyrimidin-4-yl)-4-(4-fluoro-phenyl)-1H-imidazol-2-yl]-5-methyl-[1,3]dioxane-5-carboxylic acid benzylamide, trans-isomer, (Compound A1075);

2-[5-(2-cyclopropylamino-pyrimidin-4-yl)-4-(4-fluoro-phenyl)-1H-imidazol-2-yl]-5-methyl-[1,3]dioxane-5-carboxylic acid benzylamide, trans-isomer, (Compound A1076);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid benzylamide, trans-isomer, (Compound A1077);

2-[5-(2-cyclohexylamino-pyrimidin-4-yl)-4-(4-fluoro-phenyl)-1H-imidazol-2-yl]-5-methyl-[1,3]dioxane-5-carboxylic acid benzylamide, trans-isomer, (Compound A1078);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid benzylamide, trans-isomer, (Compound A1079);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid benzylamide, trans-isomer, (Compound A1080);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid benzylamide, trans-isomer, (Compound A1081), 2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid benzylamide, trans-isomer, (Compound A1082);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid benzylamide, trans-isomer, (Compound A1083);

2-[5-(2-benzylamino-pyrimidin-4-yl)-4-(4-fluoro-phenyl)-1H-imidazol-2-yl]-5-methyl-[1,3]dioxane-5-carboxylic acid benzylamide, trans-isomer, (Compound A1084);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid benzylamide, R-isomer, trans-isomer, (Compound A1085);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid benzylamide, S-isomer, trans-isomer, (Compound A1086);

2-[4-(4-fluoro-phenyl)-5-(2-phenylamino-pyrimidin-4-yl)-1H-imidazol-2-yl]-5-methyl-[1,3]dioxane-5-carboxylic acid benzylamide, trans-isomer, (Compound A1087);

2-[4-(4-fluoro-phenyl)-5-(2-piperidin-1-yl-pyrimidin-4-yl)-1H-imidazol-2-yl]-5-methyl-[1,3]dioxane-5-carboxylic acid benzylamide, trans-isomer, (Compound A1088);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid benzylamide, trans-isomer, (Compound A1089);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid benzylamide, trans-isomer, (Compound A1090);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid benzylamide, trans-isomer, (Compound A1091);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid benzylamide, trans-isomer, (Compound A1092);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid benzylamide, trans-isomer, (Compound A1093);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid benzylamide, trans-isomer, (Compound A1094);

2-{4-(4-fluoro-phenyl)-5-[2-(4-methyl-piperazin-1-yl)-pyrimidin-4-yl]-1H-imidazol-2-yl}-5methyl-[1,3]dioxane-5-carboxylic acid benzylamide, trans-isomer, (Compound A1095);

2-[4-(4-fluoro-phenyl)-5-(2-morpholin-4-yl-pyrimidin-4-yl)-1H-imidazol-2-yl]-5-methyl-[1,3]dioxane-5-carboxylic acid benzylamide, trans-isomer, (Compound A1096);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid benzylamide, trans-isomer, (Compound A1097);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid benzylamide, trans-isomer, (Compound A1098);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid benzylamide, trans-isomer, (Compound A1099);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid benzylamide, trans-isomer, (Compound A1100);

{4-[2-(5-benzylcarbamoyl-5-methyl-[1,3]dioxan-2-yl)-5-(4-fluoro-phenyl)-3H-imidazol-4-yl]-pyrimidin-2-ylamino}-acetic acid, trans-isomer, (Compound A1101);

3-{4-[2-(5-benzylcarbamoyl-5-methyl-[1,3]dioxan-2-yl)-5-(4-fluoro-phenyl)-3H-imidazol-4-yl]-pyrimidin-2-ylamino}-propionic acid, trans-isomer, (Compound A1102);

2-[4-(4-fluoro-phenyl)-5-(2-isopropylamino-pyrimidin-4-yl)-1H-imidazol-2-yl]-5-methyl-[1,3]dioxane-5-carboxylic acid benzylamide, trans-isomer, (Compound A1103);

2-[5-(2-allylamino-pyrimidin-4-yl)-4-(4-fluoro-phenyl)-1H-imidazol-2-yl]-5-methyl-[1,3]dioxane-5-carboxylic acid benzylamide, trans-isomer, (Compound A1104);

2-[5-[2-(cyclopropylmethyl-amino)-pyrimidin-4-yl-4-(4-fluoro-phenyl)-1H-imidazol-2-yl]-5-methyl-[1,3]dioxane-5-carboxylic acid benzylamide, trans-isomer, (Compound A1105);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid benzylamide, trans-isomer, (Compound A1106);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid benzylamide, trans-isomer, (Compound A1107);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid benzylamide, trans-isomer, (Compound A1108);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid benzylamide, trans-isomer, (Compound A1109);

2-[4-(4-fluoro-phenyl)-5-(2-propylamino-pyrimidin-4-yl)-1H-imidazol-2-yl]-5-methyl-[1,3]dioxane-5-carboxylic acid benzylamide, trans-isomer, (Compound A1110);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid benzylamide, trans-isomer, (Compound A1111);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid benzylamide, trans-isomer, (Compound A1112);

2-[5-[2-(3,4-difluoro-phenylamino)-pyrimidin-4-yl]-4-(4-fluoro-phenyl)-1H-imidazol-2-yl]5-methyl-[1,3]dioxane-5-carboxylic acid benzylamide, trans-isomer, (Compound A1113);

2-[4-(4-fluoro-phenyl)-5-[2-(3-methoxy-phenylamino)-pyrimidin-4-yl]-1H-imidazol-2-yl]-5-methyl-[1,3]dioxane-5-carboxylic acid benzylamide, trans-isomer, (Compound A1114);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid benzylamide, trans-isomer, (Compound A1115);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid benzylamide, trans-isomer, (Compound A1116);

2-[4-(4-fluoro-phenyl)-5-(2-methoxy-pyrimidin-4-yl)-1H-imidazol-2-yl]-5-methyl-[1,3]-5-dioxane-5-carboxylic acid benzylamide, trans-isomer, (Compound A1117);

2-[5-(2-benzyloxy-pyrimidin-4-yl)-4-(4-fluoro-phenyl)-1H-imidazol-2-yl]-5-methyl-[1,3]dioxane-5-carboxylic acid benzylamide, trans-isomer, (Compound A1118);

2-[4-(4-fluoro-phenyl)-5-(2-phenoxy-pyrimidin-4-yl)-1H-imidazol-2-yl]-5-methyl-[1,3]dioxane-5-carboxylic acid benzylamide, trans-isomer, (Compound A1119);

2-{4-(4-fluoro-phenyl)-5-[2-(2-methoxy-ethoxy)-pyrimidin-4-yl]-1H-imidazol-2-yl}5-methyl-[1,3]dioxane-5-carboxylic acid benzylamide, trans-isomer, (Compound A1120);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid benzylamide, trans-isomer, (Compound A1121);

2-[5-(2-cyclohexyloxy-pyrimidin-4-yl)-4-(4-fluoro-phenyl)-1H-imidazol-2-yl]-5-methyl-[1,3]dioxane-5-carboxylic acid benzylamide, trans-isomer, (Compound A1122);

2-[5-(2-Isopropoxy-pyrimidin-4-yl)-4-(4-fluoro-phenyl)-1H-imidazol-2-yl]-5-methyl-[1,3]dioxane-5-carboxylic acid benzylamide, trans-isomer, (Compound A1123);

2-[4-(4-fluoro-phenyl)-5-(2-propoxy-pyrimidin-4-yl)-1H-imidazol-2-yl]-5-methyl-[1,3]-5-carboxylic acid benzylamide, trans-isomer, (Compound A1124);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid benzylamide, trans-isomer, (Compound A1125);

2-{4-(4-fluoro-phenyl)-5-[2-(3-hydroxy-propoxy)-pyrimidin-4-yl]-1H-imidazol-2-yl}-5methyl-[1,3]dioxane-5-carboxylic acid benzylamide, trans-isomer, (Compound A1126);

2-[4-(4-fluoro-phenyl)-5-(2-methylsulfanyl-pyrimidin-4-yl)-1H-imidazol-2-yl]-5-methyl-[1,3]dioxane-5-carboxylic acid benzylamide, trans-isomer, (Compound A1127);

2-[5-(2-amino-pyrimidin-4-yl)-4-(4-fluoro-phenyl)-1H-imidazol-2-yl]-5-methyl-[1,3]dioxane-5-carboxylic acid phenylamide, trans-isomer, (Compound A1128);

2-[4-(4-fluoro-phenyl)-5-(2-methylamino-pyrimidin-4-yl)-1H-imidazol-2-yl]-5-methyl-[1,3]dioxane-5-carboxylic acid phenylamide, trans-isomer, (Compound A1129);

2-[5-(2-dimethylamino-pyrimidin-4-yl)-4-(4-fluoro-phenyl)-1H-imidazol-2-yl]-5-methyl-[1,3]dioxane-5-carboxylic acid phenylamide, trans-isomer, (Compound A1130);

2-[5-(2-cyclopropylamino-pyrimidin-4-yl)-4-(4-fluoro-phenyl)-1H-imidazol-2-yl]-5-methyl-[1,3]dioxane-5-carboxylic acid phenylamide, trans-isomer, (Compound A1131);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid phenylamide, trans-isomer, (Compound A1132);

2-[5-(2-cyclohexylamino-pyrimidin-4-yl)-4-(4-fluoro-phenyl)-1H-imidazol-2-yl]-5-methyl-[1,3]dioxane-5-carboxylic acid phenylamide, trans-isomer, (Compound A1133);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid phenylamide, trans-isomer, (Compound A1134);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid phenylamide, trans-isomer, (Compound A1135);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid phenylamide, trans-isomer, (Compound A1136);

2-{4-(4-fluoro-phenyl)-5-[2-(3-morpholin-4-yl-propylamino)-pyrimidin-4-yl]-1H-imidazol-2-yl}-5methyl-[1,3]dioxane-5-carboxylic acid phenylamide, trans-isomer, (Compound A1137);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid phenylamide, trans-isomer, (Compound A1138);

2-[5-(2-benzylamino-pyrimidin-4-yl)-4-(4-fluoro-phenyl)-1H-imidazol-2-yl]-5-methyl-[1,3]dioxane-5-carboxylic acid phenylamide, trans-isomer, (Compound A1139);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid phenylamide, R-isomer, trans-isomer, (Compound A1140);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid phenylamide, S-isomer, trans-isomer, (Compound A1141);

2-[4-(4-fluoro-phenyl)-5-(2-phenylamino-pyrimidin-4-yl)-1H-imidazol-2-yl]-5-methyl-[1,3]dioxane-5-carboxylic acid phenylamide, trans-isomer, (Compound A1142);

2-[4-(4-fluoro-phenyl)-5-(2-piperidin-1-yl-pyrimidin-4-yl)-1H-imidazol-2-yl]-5-[1,3]dioxane-5-carboxylic acid phenylamide, trans-isomer, (Compound A1143);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid phenylamide, trans-isomer, (Compound A1144);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid phenylamide, trans-isomer, (Compound A1145);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid phenylamide, trans-isomer, (Compound A1146);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid phenylamide, trans-isomer, (Compound A1147);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid phenylamide, trans-isomer, (Compound A1148);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid phenylamide, trans-isomer, (Compound A1149)

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid phenylamide, trans-isomer, (Compound A1150);

2-[4-(4-fluoro-phenyl)-5-(2-morpholin-4-yl-pyrimidin-4-yl]-1H-imidazol-2-yl]-5-methyl-[1,3]dioxane-5-carboxylic acid phenylamide, trans-isomer, (Compound A1151);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid phenylamide, trans-isomer, (Compound A1152);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid phenylamide, trans-isomer, (Compound A1153);

2-[5-[2-(3-dimethylamino-propylamino)-pyrimidin-4-yl]-4-(4-fluoro-phenyl)-1H-imidazol-2-yl-]-5-methyl-[1,3]dioxane-5-carboxylic acid phenylamide, trans-isomer, (Compound A1154);

2-[5-[2-(2-dimethylamino-ethylamino)-pyrimidin-4-yl]-4-(4-fluoro-phenyl)-1H-imidazol-2-yl]5-methyl-[1,3]dioxane-5-carboxylic acid phenylamide, trans-isomer, (Compound A1155);

{4-[5-(4-fluoro-phenyl)-2-(5-methyl-5-phenylcarbamoyl-[1,3]dioxan-2-yl)-3H-imidazol-4-yl]-pyrimidin-2-ylamino}-acetic acid, trans-isomer, (Compound A1156);

3-{4-[5-(4-fluoro-phenyl)-2-(5-methyl-5-phenylcarbamoyl-[1,3]dioxan-2-yl)-3H-imidazol-4-yl]-pyrimidin-2-ylamino}-propionic acid, trans-isomer, (Compound A1157);

2-[4-(4-fluoro-phenyl)-5-(2-isopropylamino-pyrimidin-4-yl)-1H-imidazol-2-yl]-5-methyl-[1,3]dioxane-5-carboxylic acid phenylamide, trans-isomer, (Compound A1158);

2-[5-(2-allylamino-pyrimidin-4-yl)-4-(4-fluoro-phenyl)-1H-imidazol-2-yl]-5-methyl-[1,3]dioxane-5-carboxylic acid phenylamide, trans-isomer, (Compound A1159);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid phenylamide, trans-isomer, (Compound A1160);

2-[5-[2-(cyanomethyl-amino)-pyrimidin-4-yl]-4-(4-fluoro-phenyl)-1H-imidazol-2-yl]-5-methyl-5-[1,3]dioxane-5-carboxylic acid phenylamide, trans-isomer, (Compound A1161);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid phenylamide, trans-isomer, (Compound A1162);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid phenylamide, trans-isomer, (Compound A1163);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid phenylamide, trans-isomer, (Compound A1164);

2-[4-(4-fluoro-phenyl)-5-(2-propylamino-pyrimidin-4-yl)-1H-imidazol-2-yl]-5-methyl-[1,3]dioxane-5-carboxylic acid phenylamide, trans-isomer, (Compound A1165);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid phenylamide, trans-isomer, (Compound A1166);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid phenylamide, trans-isomer, (Compound A1167);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid phenylamide, trans-isomer, (Compound A1168);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid phenylamide, trans-isomer, (Compound A1169);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid phenylamide, trans-isomer, (Compound A1170);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid phenylamide, trans-isomer, (Compound A1171);

2-[4-(4-fluoro-phenyl)-5-(2-methoxy-pyrimidin-4-yl)-1H-imidazol-2-yl]-5-methyl-[1,3]dioxane-5-carboxylic acid phenylamide, trans-isomer, (Compound A1172);

2-[5-(2-benzyloxy-pyrimidin-4-yl)-4-(4-fluoro-phenyl)-1H-imidazol-2-yl]-5-methyl-[1,3]dioxane-5-carboxylic acid phenylamide, trans-isomer, (Compound A1173);

2-[4-(4-fluoro-phenyl)-5-(2-phenoxy-pyrimidin-4-yl)-1H-imidazol-2-yl]-5-methyl-[1,3]dioxane-5-carboxylic acid phenylamide, trans-isomer, (Compound A1174);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid phenylamide, trans-isomer, (Compound A1175);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid phenylamide, trans-isomer, (Compound A1176);

2-[5-(2-cyclohexyloxy-pyrimidin-4-yl)-4-(4-fluoro-phenyl)-1H-imidazol-2-yl]-5-methyl-[1,3]dioxane-5-carboxylic acid phenylamide, trans-isomer, (Compound A1177);

2-[5-(2-Isopropoxy-pyrimidin-4-yl)-4-(4-fluoro-phenyl)-1H-imidazol-2-yl]-5-methyl-[1,3]dioxane-5-carboxylic acid phenylamide, trans-isomer, (Compound A1178);

2-[4-(4-fluoro-phenyl)-5-(2-propoxy-pyrimidin-4-yl)-1H-imidazol-2-yl]-5-methyl-[1,3]dioxane-5-acid phenylamide, trans-isomer, (Compound A1179);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid phenylamide, trans-isomer, (Compound A1180);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid phenylamide, trans-isomer, (Compound A1181);

2-[4-(4-fluoro-phenyl)-5-(2-methylsulfanyl-pyrimidin-4-yl)-1H-imidazol-2-yl]-5-methyl-[1,3]dioxane-5-carboxylic acid phenylamide, trans-isomer, (Compound A1182);

{2-[5-(2-amino-pyrimidin-4-yl)-4-(4-fluoro-phenyl)-1H-imidazol-2-yl]-5-methyl-[1,3]dioxan-5-yl}-piperidin-1-yl-methanone, trans-isomer, (Compound A1183);

{2-[4-(4-fluoro-phenyl)-5-(2-methylamino-pyrimidin-4-yl)-1H-imidazol-2-yl]-5-methyl-[1,3]dioxan-5-yl}-piperidin-1-yl-methanone, trans-isomer, (Compound A1184);

{2-[5-(2-dimethylamino-pyrimidin-4-yl)-4-(4-fluoro-phenyl)-1H-imidazol-2-yl]-5-methyl-[1,3]dioxan-5-yl}-piperidin-1-yl-methanone, trans-isomer, (Compound A1185);

{2-[5-(2-cyclopropylamino-pyrimidin-4-yl)-4-(4-fluoro-phenyl)-1H-imidazol-2-yl]-5-methyl-[1,3]dioxan-5-yl}-piperidin-1-yl-methanone, trans-isomer, (Compound A1186);

(2-{4-(4-fluoro-phenyl)-5-[2-(piperidin-4-ylamino)-pyrimidin-4-yl]-1H-imidazol-2-yl}-5-methyl-[1,3]dioxan-5-yl)-piperidin-1-yl-methanone, trans-isomer, (Compound A1187);

{2-[5-(2-cyclohexylamino-pyrimidin-4-yl)-4-(4-fluoro-phenyl)-1H-imidazol-2-yl]-5-methyl-[1,3]dioxan-5-yl}-piperidin-1-yl-methanone, trans-isomer, (Compound A1188);

(2-{4-(4-fluoro-phenyl)-5-[2-(2-hydroxy-ethylamino)-pyrimidin-4-yl]-1H-imidazol-2-yl}-5-methyl-[1,3]dioxan-5-yl)-piperidin-1-yl-methanone, trans-isomer, (Compound A1189);

{2-[5-[2-(2-amino-ethylamino)-pyrimidin-4-yl]-4-(4-fluoro-phenyl)-1H-imidazol-2-yl]-5-methyl-[1,3]dioxan-5-yl}-piperidin-1-yl-methanone, trans-isomer, (Compound A1190);

[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-yl]-piperidin-1-yl-methanone, trans-isomer, (Compound A1191);

(2-{4-(4-fluoro-phenyl)-5-[2-(3-morpholin-4-yl-propylamino)-pyrimidin-4-yl]-1H-imidazol-2-imidazol-2-yl}-5-methyl-[1,3]dioxan-5-yl)-piperidin-1-yl-methanone, trans-isomer, (Compound A1192);

(2-{4-(4-fluoro-phenyl)-5-[2-(3-hydroxy-propylamino)-pyrimidin-4-yl]-1H-imidazol-2-yl}-5-methyl-[1,3]dioxan-5-yl)-piperidin-1-yl-methanone, trans-isomer, (Compound A1193);

{2-[5-(2-benzylamino-pyrimidin-4-yl)-4-(4-fluoro-phenyl)-1H-imidazol-2-yl]-5-methyl-[1,3]dioxan-5-yl}-piperidin-1-yl-methanone, trans-isomer, (Compound A1194);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-piperidin-1-yl-methanone, R-isomer, trans-isomer, (Compound A1195);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-piperidin-1-yl-methanone, S-isomer, trans-isomer, (Compound A1196);

{2-[4-(4-fluoro-phenyl)-5-(2-phenylamino-pyrimidin-4-yl)-1H-imidazol-2-yl]-5-methyl-[1,3]dioxan-5-yl}-piperidin-1-yl-methanone, trans-isomer, (Compound A1197);

{2-[4-(4-fluoro-phenyl)-5-(2-piperidin-1-yl-pyrimidin-4-yl)-1H-imidazol-2-yl]-5-methyl-[1,3]dioxan-5-yl}-piperidin-1-yl-methanone, trans-isomier, (Compound A1198);

[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-yl]-piperidin-1-yl-methanone, trans-isomer, (Compound A1199);

[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-yl]-piperidin-1-yl-methanone, trans-isomer, (Compound A1200);

[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-yl]-piperidin-1-yl-methanone, trans-isomer, (Compound A1201);

[2-(4-(4-fluoro-phenyl)-5-{2-[(furan-2-ylmethyl)-amino]-pyrimidin-4-yl}-1H-imidazol-2-yl)-5-methyl-[1,3]dioxan-5-yl]-piperidin-1-yl-methanone, trans-isomer, (Compound A1202);

[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-yl]-piperidin-1-yl-methanone, trans-isomer, (Compound A1203);

[2-(4-(4-fluoro-phenyl)-5-{2-[(tetrahydro-furan-2-ylmethyl)-amino]-pyrimidin-4-yl}-1H-imidazol-2-yl)-5- methyl-[1,3]dioxan-5-yl)-piperidin-1-yl-methanone, trans-isomer, (Compound A1204);

(2-{4-(4-fluoro-phenyl)-5-[2-(4-methyl-piperazin-1-yl)-pyrimidin-4-yl]-1H-imidazol-2-yl}-5-methyl-[1,3]dioxan-5-yl)-piperidin-1-yl-methanone, trans-isomer, (Compound A1205);

{2-[4-(4-fluoro-phenyl)-5-(2-morpholin-4-yl-pyrimidin-4-yl)-1H-imidazol-2-yl]-5-methyl-[1,3]dioxane-5-yl}-piperidin-1-yl-methanone, trans-isomer, (Compound A1206);

(2-{4-(4-fluoro-phenyl)-5-[2-(3-methoxy-propylamino)-pyrimidin-4-yl]-1H-imidazol-2-yl}-5-methyl-[1,3]dioxan-5-yl)-piperidin-1-yl-methanone, trans-isomer, (Compound A1207);

(2-{4-(4-fluoro-phenyl)-5-[2-(2-methoxy-ethylamino)-pyrimidin-4-yl]-1H-imidazol-2-yl}-5-methyl-[1,3]dioxan-5-yl)-piperidin-1-yl-methanone, trans-isomer, (Compound A1208);

{2-[5-[2-(3-dimethylamino-propylamino)-pyrimidin-4-yl]-4-(4-fluoro-phenyl)-1H-imidazol-2-yl]-5-methyl-[1,3]dioxan-5-yl}-piperidin-1-yl-methanone, trans-isomer, (Compound A1209);

{2-[5-[2-(2-dimethylamino-ethylamino)-pyrimidin-4-yl]-4-(4-fluoro-phenyl)-1H-imidazol-2-yl]-5-methyl-[1,3]dioxan-5-yl}-piperidin-1-yl-methanone, trans-isomer, (Compound A1210);

(4-{5-(4-fluoro-phenyl)-2-[5-methyl-5-(piperidine-1-carbonyl)-[1,3]dioxan-2-yl]-3H-imidazol-4-yl}-pyrimidin-2-ylamino)-acetic acid, trans-isomer, (Compound A1211);

3-(4-{5-(4-fluoro-phenyl)-2-[5-methyl-5-(piperidine-1-carbonyl)-[1,3]-3H-imidazol-4-yl}-pyrimidin-2-ylamino)-propionic acid, trans-isomer, (Compound A1212);

{2-[4-(4-fluoro-phenyl)-5-(2-isopropylamino-pyrimidin-4-yl)-1H-imidazol-2-yl]-5-methyl-[1,3]dioxane-5-yl}-piperidin-1-yl-methanone, trans-isomer, (Compound A1213);

{2-[5-(2-allylamino-pyrimidin-4-yl)-4-(4-fluoro-phenyl)-1H-imidazol-2-yl]-5-methyl-[1,3]dioxane-5-yl-piperidin-1-yl-methanone, trans-isomer, (Compound A1214);

{2-[5-[2-(cyclopropylmethyl-amino)-pyrimidin-4-yl]-4-(4-fluoro-phenyl)-1H-imidazol-2-yl]-5-methyl-[1,3]dioxane-5-yl}-piperidin-1-yl-methanone, trans-isomer, (Compound A1215);

(4-{5-(4-fluoro-phenyl)-2-[5-methyl-5-(piperidine-1-carbonyl)-[1,3]dioxan-2-yl]-3H-imidazol-4-yl}-pyrimidin-2-ylamino)-acetonitrile, trans-isomer, (Compound A1216);

3-(4-{5-(4-fluoro-phenyl)-2-[5-methyl-5-(piperidine-1-carbonyl)-[1,3]dioxan-2-yl]-3H-imidazol-4-yl}-pyrimidin-2-ylamino)-propionitrile, trans-isomer, (Compound A1217);

(2-{4-(4-fluoro-phenyl)-5-[2-(pyridin-3-ylamino)-pyrimidin-4-yl]-1H-imidazol-2-yl}-5-methyl-[1,3]dioxan-5-yl)-piperidin-1-yl-methanone, trans-isomer, (Compound A1218);

(2-{4-(4-fluoro-phenyl)-5-[2-(pyridin-4-ylamino)-pyrimidin-4-yl]-1H-imidazol-2-yl}-5-methyl-[1,3]dioxan-5-yl)-piperidin-1-yl-methanone, trans-isomer, (Compound A1219);

{2-[4-(4-fluoro-phenyl)-5-(2-propylamino-pyrimidin-4-yl)-1H-imidazol-2-yl]-5-methyl-[1,3]dioxan-5-yl}-piperidin-1-yl-methanone, trans-isomer, (Compound A1220);

{2-[4-(4-fluoro-phenyl)-5-(2-pyrrolidin-1-yl-pyrimidin-4-yl)-1H-imidazol-2-yl]-5-methyl-[1,3]dioxan-5-yl}-piperidin-1-yl-methanone, trans-isomer, (Compound A1221);

(2-{4-(4-fluoro-phenyl)-5-[2-(4-fluoro-phenylamino)-pyrimidin-4-yl]-1H-imidazol-2-yl}-5-methyl-[1,3]dioxan-5-yl)-piperidin-1-yl-methanone, trans-isomer, (Compound A1222);

{2-[5-[2-(3,4-difluoro-phenylamino)-pyrimidin-4-yl]-4-(4-fluoro-phenyl)-1H-imidazol-2-yl]-5-methyl-[1,3]dioxan-5-yl}-piperidin-1-yl-methanone, trans-isomer, (Compound A1223);

(2-{4-(4-fluoro-phenyl)-5-[2-(3-methoxy-phenylamino)-pyrimidin-4-yl]-1H-imidazol-2-yl}-5-methyl-[1,3]dioxan-5-yl)-piperidin-1-yl-methanone, trans-isomer, (Compound A1224);

{2-[5-[2-(4-fluoro-benzylamino)-pyrimidin-4-yl]-4-(4-fluoro-phenyl)-1H-imidazol-2-yl]-5-methyl-[1,3]dioxan-5-yl}-piperidin-1-yl-methanone, trans-isomer, (Compound A1225);

(2-{4-(4-fluoro-phenyl)-5-[2-(4-methoxy-benzylamino)-pyrimidin-4-yl]-1H-imidazol-2-yl}-5-methyl-[1,3]dioxan-5-yl)-piperidin-1-yl-methanone, trans-isomer, (Compound A1226);

{2-[4-(4-fluoro-phenyl)-5-(2-methoxy-pyrimidin-4-yl)-1H-imidazol-2-yl]-5-methyl-[1,3]dioxan-5-yl}-piperidin-1-yl-methanone, trans-isomer, (Compound A1227);

{2-[5-(2-benzyloxy-pyrimidin-4-yl)-4-(4-fluoro-phenyl)-1H-imidazol-2-yl]-5-methyl-[1,3]dioxan-5-yl}-methyl-piperidin-1-yl-methanone, trans-isomer, (Compound A1228);

{2-[4-(4-fluoro-phenyl)-5-(2-phenoxy-pyrimidin-4-yl)-1H-imidazol-2-yl]-5-methyl-[1,3]dioxan-5-yl}-piperidin-1-yl-methanone, trans-isomer, (Compound A1229);

(2-{4-(4-fluoro-phenyl)-5-[2-(2-methoxy-ethoxy)-pyrimidin-4-yl]-1H-imidazol-2-yl}-5-methyl -[1,3]dioxan-5-yl)-piperidin-1-yl-methanone, trans-isomer, (Compound A1230);

{2-[5-[2-(2-dimethylamino-ethoxy)-pyrimidin-4-yl]-4-(4-fluoro-phenyl)-1H-imidazol-2-yl]-5-methyl-[1,3]dioxan-5-yl}-piperidin-1-yl-methanone, trans-isomer, (Compound A1231);

{2-[5-(2-cyclohexyloxy-pyrimidin-4-yl)-4-(4-fluoro-phenyl)-1H-imidazol-2-yl]-5-methyl-[1,3]dioxan-5-yl}-piperidin-1-yl-methanone, trans-isomer, (Compound A1232);

{2-[5-(2-Isopropoxy-pyrimidin-4-yl)-4-(4-fluoro-phenyl)-1-imidazol-2-yl]-5-methyl-[1,3]dioxan-5-yl}-piperidin-1-yl-methanone, trans-isomer, (Compound A1233);

{2-[4-(4-fluoro-phenyl)-5-(2-propoxy-pyrimidin-4-yl)-1H-imidazol-2-yl]-5-methyl-[1,3]dioxan-5-yl}-piperidin-1-yl-methanone, trans-isomer, (Compound A1234);

(2-{4-(4-fluoro-phenyl)-5-[2-(2-hydroxy-ethoxy)-pyrimidin-4-yl]-1H-imidazol-2-yl}-5-methyl-[1,3]dioxan-5-yl)-piperidin-1-yl-methanone, trans-isomer, (Compound A1235);

(2-{4-(4-fluoro-phenyl)-5-[2-(3-hydroxy-propoxy)-pyrimidin-4-yl]-1H-imidazol-2-yl}-5-methyl-[1,3]dioxan-5-yl)-piperidin-1-yl-methanone, trans-isomer, (Compound A1236);

{2-[4-(4-fluoro-phenyl)-5-(2-methylsulfanyl-pyrimidin-4-yl)-1H-imidazol-2-yl]-5-methyl-[1,3]dioxan-5-yl}-piperidin-1-yl-methanone, trans-isomer, (Compound A1237);

2-[5-(2-amino-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1238);

2-[4-(4-fluoro-phenyl)-5-(2-methylamino-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1239);

2-[5-(2-dimethylamino-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1240);

2-[5-(2-cyclopropylamino-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1241);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (tetrahydro-furan-2-ylmethyl)-amide, trans-isomer A1242);

2-[5-(2-cyclohexylamino-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1243);

2-{4-(4-fluoro-phenyl)-5-[2-(2-hydroxy-ethylamino)-pyrimidin-4-yl]-1H-imidazol-2-yl]-5-mehtyl-[1,3]dioxane-5-[1,3]dioxane-carboxylic acid (tetrahydro-furan-2-ylmethyl)-amide, trans-isomer, (Compound A1244);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1245);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid (tetrahydro-furan-2-ylmethyl)-amide, trans-isomer, (Compound A1246);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1247);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1248);

2-[5-(2-benzylamino-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1249);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (tetrahydro-furan-2-ylmethyl)-amide, R-isomer, trans-isomer, (Compound A1250);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (tetrahydro-furan-2-ylmethyl)-amide, S-isomer, trans-isomer, (Compound A1251);

2-[4-(4-fluoro-phenyl)-5-(2-phenylamino-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1252);

2-[4-(4-fluoro-phenyl)-5-(2-piperidin-1-yl-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1253);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid (tetrahydro-furan-2-ylmethyl)-amide, trans-isomer, (Compound A1254);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (tetrahydro-furan-2-ylmethyl)-amide, trans-isomer, (Compound A1255);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (tetrahydro-furan-2-ylmethyl)-amide, trans-isomer, (Compound A1256);

2-(4-(4-fluoro-phenyl)-5-{2-[(puran-2-ylmethyl)-amino]-pyrimidin-4-yl}-1H-imidazol-2-yl)-5methyl-[1,3]dioxane-5-carboxylic acid (tetrahydro-furan-2-ylmethyl)-amide, trans-isomer, (Compound A1257);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (tetrahydro-furan-2-ylmethyl)-amide, trans-isomer, (Compound A1258);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (tetrahydro-furan-2-ylmethyl)-amide, trans-isomer, (Compound A1259);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1260);

2-[4-(4-fluoro-phenyl)-5-(2-morpholin-4-yl-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1261);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1262);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1263);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1264);

2-[5-[2-(2-dimethylamino-ethyamino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1265);

[4-(5-(4-fluoro-phenyl)-2-{5-methyl-5-[(tetrahydro-furan-2-ylmethyl)-carbamoyl]-[1,3]dioxan-2-yl}-3H-imidazol-4-yl)-pyrimidin-2-ylamino]-acetic acid, trans-isomer, (Compound A1266);

3-[4-(5-(4-fluoro-phenyl)-2-{5-methyl-5-[(tetrahydro-furan-2-ylmethyl)-carbamoyl]-[1,3]dioxan-2-yl}-3H-imidazol-4-yl)-pyrimidin-2-ylamino]-propionic acid, trans-isomer, (Compound A1267);

2-[4-(4-fluoro-phenyl)-5-(2-isopropylamino-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1268);

2-[5-(2-allylamino-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1269);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1270);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1271);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1272);

2-{4-(4-fluoro-phenyl)-5-[2-(pyridin-3-ylamino)-pyrimidin-4-yl]-1H-imidazol-2-yl}-5-methyl-[1,3]

dioxane-5-carboxylic acid (tetrahydro-furan-2-ylmethyl)-amide, trans-isomer, (Compound A1273);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (tetrahydro-furan-2-ylmethyl)-amide, trans-isomer (Compound A1274);

2-[4-(4-fluoro-phenyl)-5-(2-propylamino-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1275);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1276);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1277);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1278);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1279);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1280);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1281);

2-[4-(4-fluoro-phenyl)-5-(2-methoxy-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1282);

2-[5-(2-benzyloxy-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1283);

2-[4-(4-fluoro-phenyl)-5-(2-phenoxy-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1284);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1285);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid (tetrahydro-furan-2-ylmethyl) amide, trans-isomer, (Compound 1286);

2-[5-(2-cyclohexyloxy-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1287);

2-[5-(2-Isopropoxy-pyrimidin-4-yl)-4-(4-fluoro-phenyl)-1H-imidazol-2-yl]-5-methyl-[1,3]dioxane-5-carboxylic acid (tetrahydro-furan-2-ylmethyl)-amide, trans-isomer, (Compound A1288);

2-[4-(4-fluoro-phenyl)-5-(2-propoxy-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1289);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1290);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (tetrahydro-furan-2-ylmethyl)-amide, trans-isomer, (Compound A1291);

2-[4-(4-fluoro-phenyl)-5-(2-methylsulfanyl-pyrimidin-4-yl)-1H-imidazol-2-yl]-5-methyl-[1,3]dioxane-5-carboxylic acid (tetrahydro-furan-2-ylmethyl)-amide, trans-isomer, (Compound A1292);

{2-[5-(2-amino-pyrimidin-4-yl)-4-(4-fluoro-phenyl)-1H-imidazol-2-yl]-5-methyl-[1,3]dioxane-5-yl}-(4-methyl-piperazin-1-yl)-methanone, trans-isomer, (Compound A1293);

{2-[4-(4-fluoro-phenyl)-5-(2-methylamino-pyrimidin-4-yl)-1H-imidazol-2-yl]-5-methyl-[1,3]dioxan-5-yl}-(4-methyl-piperazin-1-yl)-methanone, trans-isomer, (Compound A1294);

{2-[5-(2-dimethylamino-pyrimidin-4-yl)-4-(4-fluoro-phenyl)-1H-imidazol-2-yl]-5-methyl-[1,3]dioxan-5-yl}-(4-methyl-piperazin-1-yl)-methanone, trans-isomer, (Compound A1295);

{2-[5-(2-cyclopropylamino-pyrimidin-4-yl)-4-(4-fluoro-phenyl)-1H-imidazol-2-yl]-5-methyl-[1,3]dioxan-5-yl}-(4-methyl-piperazin-1-yl)-methanone, trans-isomer, (Compound A1296);

(2-{4-(4-fluoro-phenyl)-5-[2-(piperidin-4-ylamino)-pyrimidin-4-yl]-1H-imidazol-2-yl}-5-methyl-[1,3]dioxan-5-yl)-(4-methyl-piperazin-1-yl)-methanone, trans-isomer, (Compound A1297);

{2-[5-(2-cyclohexylamino-pyrimidin-4-yl)-4-(4-fluoro-phenyl)-1H-imidazol-2-yl]-5-methyl-[1,3]dioxan-5-yl}-(4-methyl-piperazin-1-yl)-methanone, trans-isomer, (Compound A1298);

(2-{4-(4-fluoro-phenyl)-5-[2-(2-hydroxy-ethylamino)-pyrimidin-4-yl]-1H-imidazol-2-yl}-5-methyl-[1,3]dioxan-5-yl)-(4-methyl-piperazin-1-yl)-methanone, trans-isomer, (Compound A1299);

{2-[5-[2-(2-amino-ethylamino)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1300);

[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-yl]-(4-methyl-piperazin-1-yl)-methanone, trans-isomer, (Compound A1301);

(2-{4-(4-fluoro-phenyl)-5-[2-(3-morpholin-4-yl-propylamino)-pyrimidin-4-yl]-1H-imidazol-2-yl}-5-methyl-[1,3]dioxan-5-yl)-(4-methyl-piperazin-1-yl)-methanone, trans-isomer, (Compound A1302);

(2-{4-(4-fluoro-phenyl)-5-[2-(3-hydroxy-propylamino)-pyrimidin-4-yl]-1H-imidazol-2-yl}-5-methyl-[1,3]dioxan-5-yl)-(4-methyl-piperazin-1-yl)-methanone, trans-isomer, (Compound A1303);

{2-[5-(2-benzylamino-pyrimidin-4-yl)-4-(4-fluoro-phenyl)-1H-imidazol-2-yl]-5-methyl-[1,3]dioxan-5-yl}-(4-methyl-piperazin-1-yl)-methanone, trans-isomer, (Compound A1304);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-(4-methyl-piperazin-1-yl)-methanone, R-isomer, trans-isomer, (Compound A1305);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-(4-methyl-piperazin-1-yl)-methanone, S-isomer, trans-isomer, (Compound A1306);

{2-[4-(4-fluoro-phenyl)-5-(2-phenylamino-pyrimidin-4-yl)-1H-imidazoi-2-yl]-5-methyl-[1,3]dioxan-5-yl}-(4- methyl-piperazin-1-yl)-methanone, trans-isomer, (Compound A1307);

{2-[4-(4-fluoro-phenyl)-5-(2-piperidin-1-yl-pyrimidin-4-yl)-1H-imidazol-2-yl]-5-methyl-[1,3]dioxan-5-yl}-(4-methyl-piperazin-1-yl)-methanone, trans-isomer, (Compound A1308);

[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-yl]-(4-methyl-piperazin-1-yl)-methanone, trans-isomer, (Compound A1309);

[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-yl]-(4-methyl-piperazin-1-yl)-methanone, trans-isomer, (Compound A1310);

[2-(4-(4-fluoro-phenyl)-5-{2-[(pyridin-2-ylmethyl)-amino]-pyrimidin-4-yl}-1H-imidazol-[1,3]dioxan-5-yl]-(4-methyl-piperazin-1-yl)-methanone, trans-isomer, (Compound A1311);

[2-(4-(4-fluoro-phenyl)-5-{2-[(furan-2-ylmethyl)-amino]-pyrimidin-4-yl}-1H-imidazol-2-yl)-5-methyl-[1,3]dioxan-5-yl]-(4-methyl-piperazin-1-yl)-methanone, trans-isomer, (Compound A1312);

[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-yl]-(4-methyl-piperazin-1-yl)-methanone, trans-isomer, (Compound A1313);

[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-yl]-(4-methyl-piperazin-1-yl)-methanone, trans-isomer, (Compound A1314);

(2-{4-(4-fluoro-phenyl)-5-[2-(4-methyl-piperazin-1-yl)-pyrimidin-4-yl]-1H-imidazol-2-yl}-5-methyl-[1,3]dioxan-5-yl)-(4-methyl-piperazin-1-yl)-methanone, trans-isomer, (Compound A1315);

{2-[4-(4-fluoro-phenyl)-5-(2-morpholin-4-yl-pyrimidin-4-yl)-1H-imidazol-2-yl]-5-methyl-[1,3]dioxan-5-yl}-(4-methyl-piperazin-1-yl)-methanone, trans-isomer, (Compound A1316);

(2-{4-(4-fluoro-phenyl)-5-[2-(3-methoxy-propylamino)-pyrimidin-4-yl]-1H-imidazol-2-yl}-5-methyl-[1,3]dioxan-5-yl)-(4-methyl-piperazin-1-yl)-methanone, trans-isomer, (Compound A1317);

(2-{4-(4-fluoro-phenyl)-5-[2-(2-methoxy-ethylamino)-pyrimidin-4-yl]-1H-imidazol-2-yl}-5-methyl-[1,3]dioxan-5-yl)-(4-methyl-piperazin-1-yl)-methanone, trans-isomer, (Compound A1318);

{2-[5-[2-(3-dimethylamino-propylamino)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1319);

{2-[5-[2-(2-dimethylamino-ethylamino)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1320);

(4-{5-(4-fluoro-phenyl)-2-[5-methyl-5-(4-methyl-piperazine-1-carbonyl)-[1,3]dioxan-2-yl]-3H-imidazol-4-yl}-pyrimidin-2-ylamino)-acetic acid, trans-isomer, (Compound A1321);

3-(4-{5-(4-fluoro-phenyl)-2-[5-methyl-5-(4-methyl-piperazine-1-carbonyl)-[1,3]dioxan-2-yl]-3H-imidazol-4-yl}-pyrimidin-2-ylamino)-propionic acid, trans-isomer, (Compound A1322);

{2-[4-(4-fluoro-phenyl)-5-(2-isopropylamino-pyrimidin-4-yl)-1H-imidazol-2-yl]-5-methyl-[1,3]dioxan-5-yl}-(4-methyl-piperazin-1-yl)-methanone, trans-isomer, (Compound A1323);

{2-[5-(2-allylamino-pyrimidin-4-yl)-4-(4-fluoro-phenyl)-1H-imidazol-2-yl]-5-methyl-[1,3]dioxan-5-yl}-4-methyl-piperazin-1-yl)-methanone, trans-isomer, (Compound A1324);

{2-[5-[2-(cyclopropylmethyl-amino)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1325);

(4-{5-(4-fluoro-phenyl)-2-[5-methyl-5-(4-methyl-piperazine-1-carbonyl)-[1,3]dioxan-2-yl]-3H-imidazol-4-yl}-pyrimidin-2-ylamino)-acetonitrile, trans-isomer, (Compound A1326);

3-(4-{5-(4-fluoro-phenyl)-2-[5-methyl-5-(4-methyl-piperazine-1-carbonyl)-[1,3]dioxan-2-yl]-3H-imidazol-4-yl}-pyrimidin-2-ylamino)-propionitrile, trans-isomer, (Compound A1327);

(2-{4-(4-fluoro-phenyl)-5-[2-(pyridin-3-ylamino)-pyrimidin-4-yl]-1H-imidazol-2-yl}-5-methyl-[1,3]dioxan-5-yl)-(4-methyl-piperazin-1-yl)-methanone, trans-isomer, (Compound A1328);

(2-{4-(4-fluoro-phenyl)-5-[2-(pyridin-4-ylamino)-pyrimidin-4-yl]-1H-imidazol-2-yl}-5-methyl-[1,3]dioxan-5-yl)-(4-methyl-piperazin-1-yl)-methanone, trans-isomer, (Compound A1329);

{2-[4-(4-fluoro-phenyl)-5-(2-propylamino-pyrimidin-4-yl)-1H-imidazol-2-yl]-5-methyl-[1,3]dioxan-5-yl}-(4-methyl-piperazin-1-yl)-methanone, trans-isomer, (Compound A1330);

{2-[4-(4-fluoro-phenyl)-5-(2-pyrrolidin-1-yl-pyrimidin-4-yl)-1H-imidazol-2-yl]-5-methyl-[1,3]dioxan-5-yl}-(4-methyl-piperazin-1-yl)-methanone, trans-isomer, (Compound A1331);

(2-{4-(4-fluoro-phenyl)-5-[2-(4-fluoro-phenylamino)-pyrimidin-4-yl]-1H-imidazol-2-yl}-5-methyl-[1,3]dioxan-5-yl)-(4-methyl-piperazin-1-yl]-methanone, trans-isomer, (Compound A1332);

{b 2-[5-[2-(3,4-difluoro-phenylamino)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1333);

(2-{4-(4-fluoro-phenyl)-5-[2-(3-methoxy-phenylamino)-pyrimidin-4-yl]-1H-imidazol-2-yl}-5-methyl-[1,3]dioxan-5-yl)-(4-methyl-piperazin-1-yl)-methanone, trans-isomer, (Compound A1334);

2-[5-[2-(4-fluoro-benzylamino)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1335);

(2-{4-(4-fluoro-phenyl)-5-[2-(4-methoxy-benzylamino)-pyrimidin-4-yl]-1H-imidazol-2-yl}-5-methyl-[1,3]dioxan-5-yl)-(4-methyl-piperazin-1-yl)-methanone, trans-isomer, (Compound A1336);

{2-[4-(4-fluoro-phenyl)-5-(2-methoxy-pyrimidin-4-yl)-1H-imidazol-2-yl]-5-methyl-[1,3]dioxan-5-yl}-(4-methyl-piperazin-1-yl)-methanone, trans-isomer, (Compound A1337);

{2-[5-(2-benzyloxy-pyrimidin-4-yl)-4-(4-fluoro-phenyl)-1H-imidazol-2-yl]-5-methyl-[1,3]dioxan-5-yl}-4-methyl-piperazin-1-yl)-methanone, trans-isomer, (Compound A1338);

{2-[4-(4-fluoro-phenyl)-5-(2-phenoxy-pyrimidin-4-yl)-1H-imidazol-2-yl]-5-methyl-[1,3]dioxan-5-yl}-4-methyl-piperazin-1-yl)-methanone, trans-isomer, (Compound A1339);

(2-{4-(4-fluoro-phenyl)-5-[2-(2-methoxy-ethoxy)-pyrimidin-4-yl]-1H-imidazol-2-yl}-5-methyl-[1,3]dioxan-5-yl)-(4-methyl-piperazin-1-yl)-methanone, trans-isomer, (Compound A1340);

{2-[5-[2-(2-dimethylamino-ethoxy)-pyrimidin-4-yl]-4-(4-fluoro-phenyl)-1H-imidazol-2-yl]-5-methyl-[1,3]dioxan-5-yl}-(4-methyl-piperazin-1-yl)-methanone, trans-isomer, (Compound A1341);

{2-[5-(2-cyclohexyloxy-pyrimidin-4-yl)-4-(4-fluoro-phenyl)-1H-imidazol-2-yl]-5-methyl-[1,3]dioxan-5-yl}-(4-methyl-piperazin-1-yl)-methanone, trans-isomer, (Compound A1342);

{2-[5-(2-Isopropoxy-pyrimidin-4-yl)-4-(4-fluoro-phenyl)-1H-imidazol-2-yl]-5-methyl-[1,3]dioxan-5-yl}-(4-methyl-piperazin-1-yl)-methanone, trans-isomer, (Compound A1343);

{2-[4-(4-fluoro-phenyl)-5-(2-propoxy-pyrimidin-4-yl)-1H-imidazol-2-yl]-5-methyl-[1,3]dioxan-5-yl}-(4-methyl-piperazin-1-yl)-methanone, trans-isomer, (Compound A1344);

(2-{4-(4-fluoro-phenyl)-5-[2-(2-hydroxy-ethoxy)-pyrimidin-4-yl]-1H-imidazol-2-yl}-5-methyl-[1,3]dioxan-5-yl)-(4-methyl-piperazin-1-yl)-methanone, trans-isomer, (Compound A1345);

(2-{4-(4-fluoro-phenyl)-5-[2-(3-hydroxy-propoxy)-pyrimidin-4-yl]-1H-imidazol-2-yl}-5-methyl-[1,3]dioxan-5-yl)-(4-methyl-piperazin-1-yl)-methanone, trans-isomer, (Compound A1346);

{2-[4-(4-fluoro-phenyl)-5-(2-methylsulfanyl-pyrimidin-4-yl)-1H-imidazol-2-yl]-5-methyl[1,3]dioxan-5-yl}-(4-methyl-piperazin-1-yl)-methanone, trans-isomer, (Compound A1347);

{2-[5-(2-amino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1348);

{2-[4-(4-fluoro-phenyl)-5-(2-methylamino-pyrimidin-4-yl)-1H-imidazol-2-yl]-5-methyl-[1,3]dioxan-5-yl}-morpholin-4-yl-methanone, trans-isomer, (Compound A1349);

{2-[5-(2-dimethylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1350);

{2-[5-(2-cyclopropylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1351);

(2-{4-(4-fluoro-phenyl)-5-[2-(piperidin-4-ylamino)-pyrimidin-4-yl]-1H-imidazol-2-yl}-5-methyl-[1,3]dioxan-5-yl)-morpholin-4-yl-methanone, trans-isomer, (Compound A1352);

{2-[5-(2-cyclohexylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1353);

(2-{4-(4-fluoro-phenyl)-5-[2-(2-hydroxy-ethylamino)-pyrimidin-4-yl]-1H-imidazol-2-yl}-5-methyl-[1,3]dioxan-5-yl)-morpholin-4-yl-methanone, trans-isomer, (Compound A1354);

{2-[5-[2-(2-amino-ethylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1355);

[2-(4-(4-fluoro-phenyl)-5-{2-[3-(5H-imidazol-1-yl)-propylamino]-pyrimidin-4-yl}-1H-imidazol-2-yl)-5-methyl-[1,3]dioxan-5-yl]-morpholin-4-yl-methanone, trans-isomer, (Compound A1356);

(2-{4-(4-fluoro-phenyl)-5-[2-(3-morpholin-4-yl-propylamino)-pyrimidin-4-yl]-1H-imidazol-2-yl}-5-methyl-[1,3]dioxan-5-yl)-morpholin-4-yl-methanone, trans-isomer, (Compound A1357);

(2-{4-(4-fluoro-phenyl)-5-[2-(3-hydroxy-propylamino)-pyrimidin-4-yl]-1H-imidazol-2-yl}-5-methyl-[1,3]dioxan-5-yl)-morpholin-4-yl-methanone, trans-isomer, (Compound A1358);

{2-[5-(2-benzylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1359);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-morpholin-4-yl-methanone, R-isomer, trans-isomer, (Compound A1360);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-morpholin-4-yl-methanone, S-isomer, trans-isomer, (Compound A1361);

{2-[4-(4-fluoro-phenyl)-5-(2-phenylamino-pyrimidin-4-yl)-1H-imidazol-2-yl]-5-methyl-[1,3]dioxan-5-yl}-morpholin-4-yl-methanone, trans-isomer, (Compound A1362);

{2-[4-(4-fluoro-phenyl)-5-(2-piperidin-1-yl-pyrimidin-4-yl)-1H-imidazol-2-yl]-5-methyl-[1,3]dioxan-5-yl}-morpholin-4-yl-methanone, trans-isomer, (Compound A1363);

[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-yl]-morpholin-4-yl-methanone, trans-isomer, (Compound A1364);

[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-yl]-morpholin-4-yl-methanone, trans-isomer, (Compound A1365);

[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-yl]-morpholin-4-yl-methanone, trans-isomer, (Compound A1366);

[2-(4-(4-fluoro-phenyl)-5-{2-[(furan-2-ylmethyl)-amino]-pyrimidin-4-yl}-1H-imidazol-2-yl)-5-methyl-[1,3]dioxan-5-yl]-morpholin-4-yl-methanone, trans-isomer, (Compound A1367);

[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-yl]-morpholin-4-yl-methanone, trans-isomer, (Compound A1368);

[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-yl]-morpholin-4-yl-methanone, trans-isomer, (Compound A1369);

(2-{4-(4-fluoro-phenyl)-5-[2-(4-methyl-piperazin-1-yl)-pyrimidin-4-yl]-1H-imidazol-2-yl}-5-methyl-[1,3]dioxan-5-yl)-morpholin-4-yl-methanone, trans-isomer, (Compound A1370);

{2-[4-(4-fluoro-phenyl)-5-(2-morpholin-4-yl-pyrimidin-4-yl)-1H-imidazol-2-yl]-5-methyl-[1,3]dioxan-5-yl}-morpholin-4-yl-methanone, trans-isomer, (Compound A1371);

(2-{4-(4-fluoro-phenyl)-5-[2-(3-methoxy-propylamino)-pyrimidin-4-yl]-1H-imidazol-2-yl}-5-methyl-[1,3]dioxan-5-yl)-morpholin-4-yl-methanone, trans-isomer, (Compound A1372);

(2-{4-(4-fluoro-phenyl)-5-[2-(2-methoxy-ethylamino)-pyrimidin-4-yl]-1H-imidazol-2-yl}-5-methyl-[1,3]dioxan-5-yl)-morpholin-4-yl-methanone, trans-isomer, (Compound A1373);

{2-[5-[2-(3-dimethylamino-propylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1374);

{2-[5-[2-(2-dimethylamino-ethylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1375);

(4-{5-(4-fluoro-phenyl)-2-[5-methyl-5-(morpholine-4-carbonyl)-[1,3]dioxan-2-yl]-3H-imidazol-4-yl}-pyrimidin-2-ylamino)-acetic acid, trans-isomer, (Compound A1376);

3-(4-{5-(4-fluoro-phenyl)-2-[5-methyl-5-(morpholine-4-carbonyl)-[1,3]dioxan-2-yl]-3H-imidazol-4-yl}-pyrimidin-2-ylamino)-propionic acid, trans-isomer, (Compound A1377);

{2-[4-(4-fluoro-phenyl)-5-(2-isopropylamino-pyrimidin-4-yl)-1H-imidazol-2-yl]-5-methyl-[1,3]dioxan-5-yl}-morpholin-4-yl-methanone, trans-isomer, (Compound A1378);

{2-[5-(2-allylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1379);

{2-[5-[2-(cyclopropylmethyl-amino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1380);

(4-{5-(4-fluoro-phenyl)-2-[5-methyl-5-(morpholine-4-carbonyl)-[1,3]dioxan-2-yl]-3H-imidazol-4-yl}-pyrimidin-2-ylamino)-acetonitrile, trans-isomer, (Compound A1381);

3-(4-{5-(4-fluoro-phenyl)-2-[5-methyl-5-(morpholine-4-carbonyl)-[1,3]dioxan-2-yl]-3H-imidazol-4-yl}-pyrimidin-2-ylamino)-propionitrile, trans-isomer, (Compound A1382);

(2-{4-(4-fluoro-phenyl)-5-[2-(pyridin-3-ylamino)-pyrimidin-4-yl]-1H-imidazol-2-yl}-5-methyl-[1,3]dioxan-5-yl)-morpholin-4-yl-methanone, trans-isomer, (Compound A1383);

(2-{4-(4-fluoro-phenyl)-5-[2-(pyridin-4-ylamino)-pyrimidin-4-yl]-1H-imidazol-2-yl}-5-methyl-[1,3]dioxan-5-yl)-morpholin-4-yl-methanone, trans-isomer, (Compound A1384);

{2-[4-(4-fluoro-phenyl)-5-(2-propylamino-pyrimidin-4-yl)-1H-imidazol-2-yl]-5-methyl-morpholin-4-yl-methanone, trans-isomer, (Compound A1385);

{2-[4-(4-fluoro-phenyl)-5-(2-pyrrolidin-1-yl-pyrimidin-4-yl)-1H-imidazol-2-yl]-5-methyl-[1,3]dioxan-5-yl}-morpholin-4-yl-methanone, trans-isomer, (Compound A1386);

(2-{4-(4-fluoro-phenyl)-5-[2-(4-fluoro-phenylamino)-pyrimidin-4-yl]-1H-imidazol-2-yl}-5-methyl-[1,3]dioxan-5-yl)-morpholin-4-yl-methanone, trans-isomer, (Compound A1387);

{2-[5-[2-(3,4-difluoro-phenylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1388);

(2-{4-(4-fluoro-phenyl)-5-[2-(3-methoxy-phenylamino)-pyrimidin-4-yl]-1H-imidazol-2-yl}-5-methyl-[1,3]dioxan-5-yl)-morpholin-4-yl-methanone, trans-isomer, (Compound A1389);

{2-[5-[2-(4-fluoro-benzylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1390);

(2-{4-(4-fluoro-phenyl)-5-[2-(4-methoxy-benzylamino)-pyrimidin-4-yl]-1H-imidazol-2-yl}-5-methyl-[1,3]dioxan-5-yl)-morpholin-4-yl-methanone, trans-isomer, (Compound A1391);

{2-[4-(4-fluoro-phenyl)-5-(2-methoxy-pyrimidin-4-yl)-1H-imidazol-2-yl]-5-methyl-[1,3]dioxan-5-yl}-morpholin-4-yl-methanone, trans-isomer, (Compound A1392);

{2-[5-(2-benzyloxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1393);

{2-[4-(4-fluoro-phenyl)-5-(2-phenoxy-pyrimidin-4-yl)-1H-imidazol-2-yl]-5-methyl-[1,3]dioxan-5-yl}-morpholin-4-yl-methanone, trans-isomer, (Compound A1394);

(2-{4-(4-fluoro-phenyl)-5-[2-(2-methoxy-ethoxy)-pyrimidin-4-yl]-1H-imidazol-2-yl}-5-metnyl-[1,3]dioxan-5-yl)-morpholin-4-yl-methanone, trans-isomer, (Compound A1395);

{2-[5-[2-(2-dimethylamino-ethoxy)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound A1396);

{2-[5-(2-cyclohexyloxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1397);

{2-[5-(2-Isopropoxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound A1398);

{2-[4-(4-fluoro-phenyl)-5-(2-propoxy-pyrimidin-4-yl)-1H-imidazol-2-yl]-5-methyl-[1,3]dioxan-5-yl}-morpholin-4-yl-methanone, trans-isomer, (Compound A1399);

(2-{4-(4-fluoro-phenyl)-5-[2-(2-hydroxy-ethoxy)-pyrimidin-4-yl]-1H-imidazol-2-yl}-5-methyl-[1,3]dioxan-5-yl)-morpholin-4-yl-methanone, trans-isomer, (Compound A1400);

(2-{4-(4-fluoro-phenyl)-5-[2-(3-hydroxy-propoxy)-pyrimidin-4-yl]-1H-imidazol-2-yl}-5-methyl-[1,3]dioxan-5-yl)-morpholin-4-yl-methanone, trans-isomer, (Compound A1401);

{2-[4-(4-fluoro-phenyl)-5-(2-methylsulfanyl-pyrimidin-4-yl)-1H-imidazol-2-yl]-5-methyl-[1,3]dioxan-5-yl}-morpholin-4-yl-methanone, trans-isomer, (Compound A1402);

2-[5-(2-amino-pyrimidin-4-yl)-4-(4-fluoro-phenyl)-1H-imidazol-2-yl]-5-methyl-[1,3]dioxan-5-carboxylic acid (3-methoxy-propyl)-amide, trans-isomer, (Compound A1403);

2-[4-(4-fluoro-phenyl)-5-(2-methylamino-pyrimidin-4-yl)-1H-imidazol-2-yl]-5-methyl-[1,3]dioxane-5-carboxylic acid (3-methoxy-propyl)-amide, trans-isomer, (Compound A1404);

2-[5-(2-dimethylamino-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1405);

2-[5-(2-cyclopropylamino-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1406);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (3-methoxy-propyl)-amide, trans-isomer, (Compound A1407);

2-[5-(2-cyclohexylamino-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1408);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid (3-methoxy-propyl)-amide, trans-isomer, (Compound A1409);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1410);

2-(4-(4-fluoro-phenyl)-5-{2-[3-(5H-imidazol-1-yl)-propylamino]-pyrimidin-4-yl}-1H-imidazol-2-yl)-5- methyl-[1,3]dioxane-5-carboxylic acid (3-methoxy-propyl)-amide, trans-isomer, (Compound A1411);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid (3-methoxy-propyl)-amide, trans-isomer, (Compound A1412);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (3-methoxy-propyl)-amide, trans-isomer, (Compound A1413);

2-[5-(2-benzylamino-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1414);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (3-methoxy-propyl)-amide, R-isomer, trans-isomer, (Compound A1415);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (3-methoxy-propyl)-amide, S-isomer, trans-isomer, (Compound A1416);

2-[4-(4-fluoro-phenyl)-5-(2-phenylamino-pyrimidin-4-yl)-1H-imidazol-2-yl]-5-methyl-[1,3]dioxane-5-carboxylic acid (3-methoxy-propyl)-amide, trans-isomer, (Compound A1417);

2-[4-(4-fluoro-phenyl)-5-(2-piperidin-1-yl-pyrimidin-4-yl)-1H-imidazol-2-yl]-5-methyl-[1,3]dioxane-5-carboxylic acid (3-methoxy-propyl)-amide, trans-isomer, (Compound A1418);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid (3-methoxy-propyl)-amide, trans-isomer, (Compound A1419);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (3-methoxy-propyl)-amide, trans-isomer, (Compound A1420);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (3-methoxy-propyl)-amide, trans-isomer, (Compound A1421);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (3-methoxy-propyl)-amide, trans-isomer, (Compound A1422);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (3-methoxy-propyl)-amide, trans-isomer, (Compound A1423);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (3-methoxy-propyl)-amide, trans-isomer, (Compound A1424);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (3-methoxy-propyl)-amide, trans-isomer, (Compound A1425);

2-[4-(4-fluoro-phenyl)-5-(2-morpholin-4-yl-pyrimidin-4-yl)-1H-imidazol-2-yl]-5-methyl-[1,3]dioxane-5-carboxylic acid (3-methoxy-propyl)-amide, trans-isomer, (Compound A1426);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (3-methoxy-propyl)-amide, trans-isomer, (Compound A1427);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (3-methoxy-propyl)-amide, trans-isomer, (Compound A1428);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1429);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1430);

(4-{5-(4-fluoro-phenyl)-2-[5-(3-methoxy-propylcarbamoyl)-5-methyl-[1,3]dioxan-2-yl]-3H-imidazol-4-yl}-pyrimidin-2-ylamino)-acetic acid, trans-isomer, (Compound A1431);

3-(4-{5-(4-fluoro-phenyl)-2-[5-(3-methoxy-propylcarbamoyl)-5-methyl-[1,3]dixan-2-yl]-3H-imidazol-4-yl}-pyrimidin-2-ylamino)-propionic acid, trans-isomer, (Compound A1432);

2-[4-(4-fluoro-phenyl)-5-(2-isopropylamino-pyrimidin-4-yl)-1H-imidazol-2-yl]-5-methyl-[1,3]dioxane-5-carboxylic acid (3-methoxy-propyl)-amide, trans-isomer, (Compound A1433);

2-[5-(2-allylamino-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1434);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1435);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1436);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1437);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid (3-methoxy-propyl)-amide, trans-isomer, (Compound A1438);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (3-methoxy-propyl)-amide, trans-isomer, (Compound A1439);

2-[4-(4-fluoro-phenyl)-5-(2-propylamino-pyrimidin-4-yl)-1H-imidazol-2-yl]-5-methyl-[1,3]dioxane-5-carboxylic acid (3-methoxy-propyl)-amide, trans-isomer, (Compound A1440);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (3-methoxy-propyl)-amide, trans-isomer, (Compound A1441);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (3-methoxy-propyl)-amide, trans-isomer, (Compound A1442);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (3-methoxy-propyl)-amide, trans-isomer, (Compound A1443);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (3-methoxy-propyl)-amide, trans-isomer, (Compound A1444);

2-[5-[2-(4-fluoro-benzylamino)-pyrimidin-4-yl]-4-(4-fluoro-phenyl)-1H-imidazol-2-yl]-5-methyl-[1,3]

dioxane-5-carboxylic acid (3-methoxy-propyl)-amide, trans-isomer, (Compound A1445);

2-{4-(4-fluoro-phenyl)-5-[2-(4-methoxy-benzylamino)-pyrimidin-4-yl]-1H-imidazol-2-yl}-5-methyl-[1,3] dioxane-5-carboxylic acid (3-methoxy-propyl)-amide, trans-isomer, (Compound A1446);

2-[4-(4-fluoro-phenyl)-5-(2-methoxy-pyrimidin-4-yl)-1H-imidazol-2-yl]-5-methyl-[1,3]dioxane-5-carboxylic acid (3-methoxy-propyl)-amide, trans-isomer, (Compound A1447);

2-[5-(2-benzyloxy-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1448);

2-[4-(4-fluoro-phenyl)-5-(2-phenoxy-pyrimidin-4-yl)-1H-imidazol-2-yl]-5-methyl-[1,3]dioxane-5-carboxylic acid (3-methoxy-propyl)-amide, trans-isomer, (Compound A1449);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (3-methoxy-propyl)-amide, trans-isomer, (Compound A1450);

2-[5-[2-(2-dimethylamino-ethoxy)-pyrimidin-4-yl]-4-(4-fluoro-phenyl)-1H-imidazol-2-yl]-5-methyl-[1,3] dioxane-5-carboxylic acid (3-methoxy-propyl)-amide, trans-isomer, (Compound A1451);

2-[5-(2-cyclohexyloxy-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1452);

2-[5-(2-Isopropoxy-pyrimidin-4-yl)-4-(4-fluoro-phenyl)-1H-imidazol-2-yl]-5-methyl-[1,3]dioxane-5-carboxylic acid (3-methoxy-propyl)-amide, trans-isomer, (Compound A1453);

2-[4-(4-fluoro-phenyl)-5-(2-propoxy-pyrimidin-4-yl)-1H-imidazol-2-yl]-5-methyl-[1,3]dioxane-5-carboxylic acid (3-methoxy-propyl)-amide, trans-isomer, (Compound A1454);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (3-methoxy-propyl)-amide, trans-isomer, (Compound A1455);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (3-methoxy-propyl)-amide, trans-isomer, (Compound A1456);

2-[4-(4-fluoro-phenyl)-5-(2-methylsulfanyl-pyrimidin-4-yl)-1H-imidazol-2-yl]-5-methyl-[1,3]dioxane-5-carboxylic acid (3-methoxy-propyl)-amide, trans-isomer, (Compound A1457);

2-[5-(2-amino-pyrimidin-4-yl)-4-(4-fluoro-phenyl)-1H-imidazol-2-yl]-5-methyl-[(1,3]dioxane-5-carboxylic acid (2-methoxy-ethyl)-amide, trans-isomer, (Compound A1458);

2-[4-(4-fluoro-phenyl)-5-(2-methylamino-pyrimidin-4-yl)-1H-imidazol-2-yl]-5-methyl-[1,3]dioxane-5-carboxylic acid (2-methoxy-ethyl)-amide, trans-isomer, (Compound A1459);

2-[5-(2-dimethylamino-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1460);

2-[5-(2-cyclopropylamino-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1461);

2-{4-(4-fluoro-phenyl)-5-[2-(piperidin-4-ylamino)-pyrimidin-4-yl]-1H-imidazol-2-yl}-5-methyl-[1,3] dioxane-5-carboxylic acid (2-methoxy-ethyl)-amide, trans-isomer, (Compound A1462);

2-[5-(2-cyclohexylamino-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1463);

2-{4-(4-fluoro-phenyl)-5-[2-(2-hydroxy-ethylamino)-pyrimidin-4-yl]-1H-imidazol-2-yl}-5-methyl-[1,3] dioxane-5-carboxylic acid (2-methoxy-ethyl)-amide, trans-isomer, (Compound A1464);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1465);

2-(4-(4-fluoro-phenyl)-5-{2-[3-(5H-imidazol-1-yl)-propylamino]-pyrimidin-4-yl}-1H-imidzol-2-yl)-5-methyl-[1,3]dioxane-5-carboxylic acid (2-methoxy-ethyl)-amide, trans-isomer, (Compound A1466);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid (2-methoxy-ethyl)-amide, trans-isomer, (Compound A1467);

2-{4-(4-fluoro-phenyl)-5-[2-(3-hydroxy-propylamino)-pyrimidin-4-yl]-1H-imidazol-2-yl}-5-methyl-[1,3] dioxane-5-carboxylic acid (2-methoxy-ethyl)-amide, trans-isomer, (Compound A1468);

2-[5-(2-benzylamino-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1469);

2-{4-(4-fluoro-phenyl)-5-[2-(1-phenyl-ethylamino)-pyrimidin-4-yl]-1H-imidazol-2-yl}-5-methyl-[1,3] dioxane-5-carboxylic acid (2-methoxy-ethyl)-amide, R-isomer, trans-isomer, (Compound A1470);

2-{4-(4-fluoro-phenyl)-5-[2-(1-phenyl-ethylamino)-pyrimidin-4-yl]-1H-imidazol-2-yl}-5-methyl-[1,3] dioxane-5-carboxylic acid (2-methoxy-ethyl)-amide, S-isomer, trans-isomer, (Compound A1471);

2-[4-(4-fluoro-phenyl)-5-(2-phenylamino-pyrimidin-4-yl)-1H-imidazol-2-yl]-5-methyl-[1,3]dioxane-5-carboxylic acid (2-methoxy-ethyl)-amide, trans-isomer, (Compound A1472);

2-[4-(4-fluoro-phenyl)-5-(2-piperidin-1-yl-pyrimidin-4-yl)-1H-imidazol-2-yl]-5-methyl-[1,3]dioxane-5-carboxylic acid (2-methoxy-ethyl)-amide, trans-isomer, (Compound A1473);

2-(4-(4-fluoro-phenyl)-5-{2-[(pyridin-4-ylmethyl)-amino]-pyrimidin-4-yl}-1H-imidazol-2-yl)-5-methyl-[1,3] dioxane-5-carboxylic acid (2-methoxy-ethyl)-amide, trans-isomer, (Compound A1474);

2-(4-(4-fluoro-phenyl)-5-{2-[(pyridin-3-ylmethyl)-amino]-pyrimidin-4-yl}-1H-imidazol-2-yl)-5-methyl-[1,3] dioxane-5-carboxylic acid (2-methoxy-ethyl)-amide, trans-isomer, (Compound A1475);

2-(4-(4-fluoro-phenyl)-5-{2-[(pyridin-2-ylmethyl)-amino]-pyrimidin-4-yl}-1H-imidazol-2-yl)-5-methyl-[1,3] dioxane-5-carboxylic acid (2-methoxy-ethyl)-amide, trans-isomer, (Compound A1476);

2-(4-(4-fluoro-phenyl)-5-{2-[(furan-2-ylmethyl)-amino]-pyrimidin-4-yl}-1H-imidazol-2-yl)-5-methyl-[1,3] dioxane-5-carboxylic acid (2-methoxy-ethyl)-amide, trans-isomer, (Compound A1477);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (2-methoxy-ethyl)-amide, trans-isomer, (Compound A1478);

2-(4-(4-fluoro-phenyl)-5-{2-[(tetrahydro-furan-2-ylmethyl)-amino]-pyrimidin-4-yl}-1H-imidazol-2-yl)-5- methyl-[1,3]dioxane-5-carboxylic acid (2-methoxy-ethyl)-amide, trans-isomer, (Compound A1479);
2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (2-methoxy-ethyl)-amide, trans-isomer, (Compound A1480);
2-[4-(4-fluoro-phenyl)-5-(2-morpholin-4-yl-pyrimidin-4-yl)-1H-imidazol-2-yl]-5-methyl-[1,3]dioxane-5-carboxylic acid (2-methoxy-ethyl)-amide, trans-isomer, (Compound A1481);
2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (2-methoxy-ethyl)-amide, trans-isomer, (Compound A1482);
2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (2-methoxy-ethyl)-amide, trans-isomer, (Compound A1483);
2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1484);
2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1485);
(4-{5-(4-fluoro-phenyl)-2-[5-(2-methoxy-ethylcarbamoyl)-5-methyl-[1,3]dioxan-2-yl]-3H-imidazol-4-yl}-pyrimidin-2-ylamino)-acetic acid, trans-isomer, (Compound A1486);
3-(4-{5-(4-fluoro-phenyl)-2-[5-(2-methoxy-ethylcarbamoyl)-5-methyl-[1,3]dioxan-2-yl]-3H-imidazol-4-yl}-pyrimidin-2-ylamino)-propionic acid, trans-isomer, (Compound A1487);
2-[4-(4-fluoro-phenyl)-5-(2-isopropylamino-pyrimidin-4-yl)-1H-imidazol-2-yl]-5-methyl-[1,3]dioxane-5-carboxylic acid (2-methoxy-ethyl)-amide, trans-isomer, (Compound A1488);
2-[5-(2-allylamino-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1489);
2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1490);
2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1491);
2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1492);
2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid (2-methoxy-ethyl)-amide, trans-isomer, (Compound A1493);
2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (2-methoxy-ethyl)-amide, trans-isomer, (Compound A1494);
2-[4-(4-fluoro-phenyl)-5-(2-propylamino-pyrimidin-4-yl)-1H-imidazol-2-yl]-5-methyl-[1,3]dioxane-5-carboxylic acid (2-methoxy-ethyl)-amide, trans-isomer, (Compound A1495);
2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (2-methoxy-ethyl)-amide, trans-isomer, (Compound A1496);
2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (2-methoxy-ethyl)-amide, trans-isomer, (Compound A1497);
2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1498);
2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (2-methoxy-ethyl)-amide, trans-isomer, (Compound A1499);
2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1500);
2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid (2-methoxy-ethyl)-amide, trans-isomer, (Compound A1501);
2-[4-(4-fluoro-phenyl)-5-(2-methoxy-pyrimidin-4-yl)-1H-imidazol-2-yl]-5-methyl-[1,3]dioxane-5-carboxylic acid (2-methoxy-ethyl)-amide, trans-isomer, (Compound A1502);
2-[5-(2-benzyloxy-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1503);
2-[4-(4-fluoro-phenyl)-5-(2-phenoxy-pyrimidin-4-yl)-1H-imidazol-2-yl]-5-methyl-[1,3]dioxane-5-carboxylic acid (2-methoxy-ethyl)-amide, trans-isomer, (Compound A1504);
2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (2-methoxy-ethyl)-amide, trans-isomer, (Compound A1505);
2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid (2-methoxy-ethyl)-amide, trans-isomer, (Compound A1506);
2-[5-(2-cyclohexyloxy-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1507);
2-[5-(2-Isopropoxy-pyrimidin-4-yl)-4-(4-fluoro-phenyl)-1H-imidazol-2-yl]-5-methyl-[1,3]dioxane-5-carboxylic acid (2-methoxy-ethyl)-amide, trans-isomer, (Compound A1508);
2-[4-(4-fluoro-phenyl)-5-(2-propoxy-pyrimidin-4-yl)-1H-imidazol-2-yl]-5-methyl-[1,3]dioxane-5-carboxylic acid (2-methoxy-ethyl)-amide, trans-isomer, (Compound A1509);
2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (2-methoxy-ethyl)-amide, trans-isomer, (Compound A1510);
2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (2-methoxy-ethyl)-amide, trans-isomer, (Compound A1511);
2-[4-(4-fluoro-phenyl)-5-(2-methylsulfanyl-pyrimidin-4-yl)-1H-imidazol-2-yl]-5-methyl-[1,3]dioxane-5-carboxylic acid (2-methoxy-ethyl)-amide, trans-isomer, (Compound A1512);
2-[5-(2-amino-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1513);

2-[4-(4-fluoro-phenyl)-5-(2-methylamino-pyrimidin-4-yl)-1H-imidazol-2-yl]-5-methyl-[1,3]dioxane-5-carboxylic acid (3-dimethylamino-propyl)-amide, trans-isomer, (Compound A1514);

2-[5-(2-dimethylamino-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1515);

2-[5-(2-cyclopropylamino-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1516);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (3-dimethylamino-propyl)-amide, trans-isomer, (Compound A1517);

2-[5-(2-cyclohexylamino-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1518);

2-{4-(4-fluoro-phenyl)-5-[2-(2-hydroxy-ethylamino)-pyrimidin-4-yl]-1H-imidazol-2-yl}5-methyl-[1,3]dioxane-5-carboxylic acid (3-dimethylamino-propyl)-amide, trans-isomer, (Compound A1519);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1520);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid (3-dimethylamino-propyl)-amide, trans-isomer, (Compound A1521);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid (3-dimethylamino-propyl)-amide, trans-isomer, (Compound A1522);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (3-dimethylamino-propyl)-amide, trans-isomer, (Compound A1523);

2-[5-(2-benzylamino-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1524);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (3-dimethylamino-propyl)-amide, R-isomer, trans-isomer, (Compound A1525);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (3-dimethylamino-propyl)-amide, S-isomer, trans-isomer, (Compound A1526);

2-[4-(4-fluoro-phenyl)-5-(2-phenylamino-pyrimidin-4-yl)-1H-imidazol-2-yl]-5-methyl-[1,3]dioxane-5-carboxylic acid (3-dimethylamino-propyl)-amide, trans-isomer, (Compound A1527);

2-[4-(4-fluoro-phenyl)-5-(2-piperidin-1-yl-pyrimidin-4-yl)-1H-imidazol-2-yl]-5-methyl-[1,3]dioxane-5-carboxylic acid (3-dimethylamino-propyl)-amide, trans-isomer, (Compound A1528);

2-(4-(4-fluoro-phenyl)-5-{2-[(pyridin-4-ylmethyl)-amino]-pyrimidin-4-yl-}-1H-imidazol-2-yl)-5-methyl-[1,3]dioxane-5-carboxylic acid (3-dimethylamino-propyl)-amide, trans-isomer, (Compound A1529);

2-(4-(4-fluoro-phenyl)-5-2-[(pyridin-3-ylmethyl)-amino]-pyrimidin-4-yl-1H-imidazol-2-yl)-5-methyl-[1,3]dioxane-5-carboxylic acid (3-dimethylamino-propyl)-amide, trans-isomer, (Compound A1530);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (3-dimethylamino-propyl)-amide, trans-isomer, (Compound A1531);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (3-dimethylamino-propyl)-amide, trans-isomer, (Compound A1532);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (3-dimethylamino-propyl)-amide, trans-isomer, (Compound A1533);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (3-dimethylamino-propyl)-amide, trans-isomer, (Compound A1534);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (3-dimethylamino-propyl)-amide, trans-isomer, (Compound A1535);

2-[4-(4-fluoro-phenyl)-5-(2-morpholin-4-yl-pyrimidin-4-yl)-1H-imidazol-2-yl]-5-methyl-[1,3]dioxane-5-carboxylic acid (3-dimethylamino-propyl)-amide, trans-isomer, (Compound A1536);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (3-dimethylamino-propyl)-amide, trans-isomer, (Compound A1537);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (3-dimethylamino-propyl)-amide, trans-isomer, (Compound A1538);

2-[-5-[2-(3-dimethylamino-propylamino)-pyrimidin-4-yl]-4-(4-fluoro-phenyl)-1H-imidazol-2-yl]-5-methyl-([1,3]dioxane-5-carboxylic acid (3-dimethylamino-propyl)-amide, trans-isomer, (Compound A1539);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1540);

{4-[2-[5-(3-dimethylamino-propylcarbamoyl)-5-methyl-[1,3]dioxan-2-yl]-5-(4-fluoro-phenyl)-3H-imidazol-4-yl]-pyrimidin-2-ylamino}-acetic acid, trans-isomer, (Compound A1541);

3-{4-[2-[5-(3-dimethylamino-propylcarbamoyl)-5-methyl-[1,3]dioxan-2-yl]-5-(4-fluoro-phenyl)-3H-imidazol-4-yl]-pyrimidin-2-ylamino}-propionic acid, trans-isomer, (Compound A1542);

2-[4-(4-fluoro-phenyl)-5-(2-isopropylamino-pyrimidin-4-yl)-1H-imidazol-2-yl]-5-methyl-[1,3]dioxane-5-carboxylic acid (3-dimethylamino-propyl)-amide, trans-isomer, (Compound A1543);

2-[5-(2-allylamino-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1544);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1545);

2-[5-[2-(cyanomethyl-amino)-pyrimidin-4-yl]-4-(4-fluoro-phenyl)-1H-imidazol-2-yl]-5-methyl-[1,3]dioxane-5- carboxylic acid (3-dimethylamino-propyl)-amide, trans-isomer, (Compound A1546);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1547);

2-{4-(4-fluoro-phenyl)-5-[2-(pyridin-3-ylamino)-pyrimidin-4-yl]-1H-imidazol-2-yl}-5-mentyl-[1,3]dioxane-5-carboxylic acid (3-dimethylamino-propyl)-amide, trans-isomer, (Compound A1548);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (3-dimethylamino-propyl)-amide, trans-isomer, (Compound A1549);

2-[4-(4-fluoro-phenyl)-5-(2-propylamino-pyrimidin-4-yl)-1H-imidazol-2-yl]-5-methyl-[1,3]dioxane-5-carboxylic acid (3-dimethylamino-propyl)-amide, trans-isomer, (Compound A1550);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (3-dimethylamino-propyl)-amide, trans-isomer, (Compound A1551);

2-{4-(4-fluoro-phenyl)-5-[2-(4-fluoro-phenylamino)-pyrimidin-4-yl]-1-imidazol-2-yl}-5-methyl-[1,3]dioxane-5-carboxylic acid (3-dimethylamino-propyl)-amide, trans-isomer, (Compound A1552);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1553);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (3-dimethylamino-propyl)-amide, trans-isomer, (Compound A1554);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1555);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid (3-dimethylamino-propyl)-amide, trans-isomer, (Compound A1556);

2-[4-(4-fluoro-phenyl)-5-(2-methoxy-pyrimidin-4-yl)-1H-imidazol-2-yl]-5-methyl-[1,3]dioxane-5-carboxylic acid (3-dimethylamino-propyl)-amide, trans-isomer, (Compound A1557);

2-[5-(2-benzyloxy-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1558);

2-[4-(4-fluoro-phenyl)-5-(2-phenoxy-pyrimidin-4-yl)-1H-imidazol-2-yl]-5-methyl-[1,3]dioxane-5-carboxylic acid (3-dimethylamino-propyl)-amide, trans-isomer, (Compound A1559);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (3-dimethylamino-propyl)-amide, trans-isomer, (Compound A1560);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid (3-dimethylamino-propyl)-amide, trans-isomer, (Compound A1561);

2-[5-(2-cyclohexyloxy-pyrimidin-4-yl)4-(4-fluoro-phenyl)-1H-imidazol-2-yl]-5-methyl-[1,3]dioxane-5-carboxylic acid (3-dimethylamino-propyl)-amide, trans-isomer, (Compound A1562);

2-[5-(2-Isopropoxy-pyrimidin-4-yl)-4-(4-fluoro-phenyl)-1H-imidazol-2-yl]-5-methyl-[1,3]dioxane-5-carboxylic acid (3-dimethylamino-propyl)-amide, trans-isomer, (Compound A1563);

2-[4-(4-fluoro-phenyl)-5-(2-propoxy-pyrimidin-4-yl)-1H-imidazol-2-yl]-5-methyl-[1,3]dioxane-5-carboxylic acid (3-dimethylamino-propyl)-amide, trans-isomer, (Compound A1564);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (3-dimethylamino-propyl)-amide, trans-isomer, (Compound A1565);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (3-dimethylamino-propyl)-amide, trans-isomer, (Compound A1566);

2-[4-(4-fluoro-phenyl)-5-(2-methylsulfanyl-pyrimidin-4-yl)-1H-imidazol-2-yl]-5-methyl-[1,3]dioxane-5-carboxylic acid (3-dimethylamino-propyl)-amide, trans-isomer, (Compound A1567);

2-[5-(2-amino-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1568);

2-[4-(4-fluoro-phenyl)-5-(2-methylamino-pyrimidin-4-yl)-1H-imidazol-2-yl]-5-methyl-[1,3]dioxane-5-carboxylic acid (2-dimethylamino-ethyl)-amide, trans-isomer, (Compound A1569);

2-[5-(2-dimethylamino-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1570);

2-[5-(2-cyclopropylamino-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1571);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (2-dimethylamino-ethyl)-amide, trans-isomer, (Compound A1572);

2-[5-(2-cyclohexylamino-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1573);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid (2-dimethylamino-ethyl)-amide, trans-isomer, (Compound A1574);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1575);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid (2-dimethylamino-ethyl)-amide, trans-isomer, (Compound A1576);

2-{4-(4-fluoro-phenyl)-5-[2-(3-morpholin-4-yl-propylamino)-pyrimidin-4-y]-1H-imidazol-2-yl}-5-methyl-[1,3]dioxane-5-carboxylic acid (2-dimethylamino-ethyl)-amide, trans-isomer, (Compound A1577);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (2-dimethylamino-ethyl)-amide, trans-isomer, (Compound A1578);

2-[5-(2-benzylamino-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1579);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-dimethylamino-ethyl)-amide, R-isomer, trans-isomer, (Compound A1580);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-dimethylamino-ethyl)-amide, S-isomer, trans-isomer, (Compound A1581);

2-[4-(4-fluoro-phenyl)-5-(2-phenylamino-pyrimidin-4-yl)-1H-imidazol-2-yl]-5-methyl-[1,3]dioxane-5-carboxylic acid (2-dimethylamino-ethyl)-amide, trans-isomer, (Compound A1582);

2-[4-(4-fluoro-phenyl)-5-(2-piperidin-1-yl-pyrimidin-4-yl)-1H-imidazol-2-yl]-5-methyl-[1,3]dioxane-5-carboxylic acid (2-dimethylamino-ethyl)-amide, trans-isomer, (Compound A1583);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid (2-dimethylamino-ethyl)-amide, trans-isomer, (Compound A1584);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (2-dimethylamino-ethyl)-amide, trans-isomer, (Compound A1585);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (2-dimethylamino-ethyl)-amide, trans-isomer, (Compound A1586);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (2-dimethylamino-ethyl)-amide, trans-isomer, (Compound A1587);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (2-dimethylamino-ethyl)-amide, trans-isomer, (Compound A1588);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (2-dimethylamino-ethyl)-amide, trans-isomer, (Compound A1589);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (2-dimethylamino-ethyl)-amide, trans-isomer, (Compound A1590);

2-[4-(4-fluoro-phenyl)-5-(2-morpholin-4-yl-pyrimidin-4-yl)-1H-imidazol-2-yl]-5-methyl-[1,3]dioxane-5-carboxylic acid (2-dimethylamino-ethyl)-amide, trans-isomer, (Compound A1591);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (2-dimethylamino-ethyl)-amide, trans-isomer, (Compound A1592);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid (2-dimethylamino-ethyl)-amide, trans-isomer, (Compound A1593);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1594);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1595);

{4-[2-[5-(2-dimethylamino-ethylcarbamoyl)-5-methyl-[1,3]dioxan-2-yl]-5-(4-flouro-phenyl)-3H-imidazol-4-yl]-pyrimidin-2-ylamino}-acetic acid, trans-isomer, (Compound A1596);

3-{4-[2-[5-(2-dimethylamino-ethylcarbamoyl)-5-methyl-[1,3]dioxan-2-yl]-5-(4-fluoro-phenyl)-3H-imidazol-4-yl]-pyrimidin-2-ylamino}-propionic acid, trans-isomer, (Compound A1597);

2-[4-(4-fluoro-phenyl)-5-(2-isopropylamino-pyrimidin-4-yl)-1H-imidazol-2-yl]-5-methyl-[1,3]dioxane-5-carboxylic acid (2-dimethylamino-ethyl)-amide, trans-isomer, (Compound A1598);

2-[5-(2-allylamino-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1599);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1600);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1601);

2-[5-[2-(2-cyano-ethylamino)-pyrimidin-4-yl]-4-(4-fluoro-phenyl)-1H-imidazol-2-yl-]5-methyl-[1,3]dioxane-5-carboxylic acid (2-dimethylamino-ethyl)-amide, trans-isomer, (Compound A1602);

2-{4-(4-fluoro-phenyl)-5-[2-(pyridin-3-ylamino)-pyrimidin-4-yl]-1H-imidazol-(2-yl}-5-methyl-[1,3]dioxane-5-carboxylic acid (2-dimethylamino-ethyl)-amide, trans-isomer, (Compound A1603);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid (2-dimethylamino-ethyl)-amide, trans-isomer, (Compound A1604);

2-[4-(4-fluoro-phenyl)-5-(2-propylamino-pyrimidin-4-yl)-1H-imidazol-2-yl]-5-methyl-[1,3]dioxane-5-carboxylic acid (2-dimethylamino-ethyl)-amide, trans-isomer, (Compound A1605);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (2-dimethylamino-ethyl)-amide, trans-isomer, (Compound A1606);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (2-dimethylamino-ethyl)-amide, trans-isomer, (Compound A1607);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1608);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (2-dimethylamino-ethyl)-amide, trans-isomer, (Compound A1609);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (2-dimethylamino-ethyl)-amide, trans-isomer, (Compound A1610);

2-{4-(4-fluoro-phenyl)-5-[2-(4-methoxy-benzylamino)-pyrimidin-4-yl]-1H-imidazol-2-yl}-5-methyl-[1,3]dioxande-5-carboxylic acid (2-dimethylamino-ethyl)-amide, trans-isomer, (Compound A1611);

2-[4-(4-fluoro-phenyl)-5-(2-methoxy-pyrimidin-4-yl)-1H-imidazol-2-yl]-5-methyl-[1,3]dioxane-5-carboxylic acid (2-dimethylamino-ethyl)-amide, trans-isomer, (Compound A1612);

2-[5-(2-benzyloxy-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1613);

2-[4-(4-fluoro-phenyl)-5-(2-phenoxy-pyrimidin-4-yl)-1H-imidazol-2-yl]-5-methyl-[1,3]dioxane-5-carboxylic acid (2-dimethylamino-ethyl)-amide, trans-isomer, (Compound A1614);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (2-dimethylamino-ethyl)-amide, trans-isomer, (Compound A1615);

2-[5-[2-(2-dimethylamino-ethoxy)-pyrimidin-4-yl]-4-(4-fluoro-phenyl)-1H-imidazol-2-yl]-5-methyl-[1,3]dioxane-5-[1,3]dioxane-5-carboxylic acid (2-dimethylamino-ethyl)-amide, trans-isomer, (Compound A1616);

2-[5-(2-cyclohexyloxy-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1617);

2-[5-(2-Isopropoxy-pyrimidin-4-yl)-4-(4-fluoro-phenyl)-1H-imidazol-2-yl]-5-methyl-[1,3]dioxane-5-carboxylic acid (2-dimethylamino-ethyl)-amide, trans-isomer, (Compound A1618);

2-[4-(4-fluoro-phenyl)-5-(2-propoxy-pyrimidin-4-yl)-1H-imidazol-2-yl]-5-methyl-[1,3]dioxane-5-carboxylic acid (2-dimethylamino-ethyl)-amide, trans-isomer, (Compound A1619);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (2-dimethylamino-ethyl)-amide, trans-isomer, (Compound A1620);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (2-dimethylamino-ethyl)-amide, trans-isomer, (Compound A1621);

2-[4-(4-fluoro-phenyl)-5-(2-methylsulfanyl-pyrimidin-4-yl)-1H-imidazol-2-yl]-5-methyl-[1,3]dioxane-5-carboxylic acid (2-dimethylamino-ethyl)-amide, trans-isomer, (Compound A1622);

{2-[5-(2-amino-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1623);

{2-[4-(4-fluoro-phenyl)-5-(2-methylamino-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1624);

{2-[5-(2-dimethylamino-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1625);

{2-[5-(2-cyclopropylamino-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1626);

(2-{4-(4-fluoro-phenyl)-5-[2-(piperidin-4-ylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1627);

{2-[5-(2-cyclohexylamino-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1628);

(2-{4-(4-fluoro-phenyl)-5-[2-(2-hydroxy-ethylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1629);

{2-[5-[2-(2-amino-ethylamino)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1630);

[2-(4-(4-fluoro-phenyl)-5-{2-[3-(5H-iqmidazol-1-yl)-propylamino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1631);

(2-{4-(4-fluoro-phenyl)-5-[2-(3-morpholin-4-yl-propylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1632);

(2-{4-(4-fluoro-phenyl)-5-[2-(3-hydroxy-propylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1633);

{2-[5-(2-benzylamino-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1634);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-(3-hydroxy-pyrrolidin-1-yl)-methanone, R-isomer, trans-isomer, (Compound A1635);

(2-{4-(4-fluoro-phenyl)-5-[2-(1-phenyl-ethylamino)-pyrimidin-4-yl]-1H-imidazol-2-yl}-5-methyl-[1,3]dioxan-5-yl)-(3-hydroxy-pyrrolidin-1-yl)-methanone, S-isomer, trans-isomer, (Compound A1636);

{2-[4-(4-fluoro-phenyl)-5-(2-phenylamino-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1637);

{2-[4-(4-fluoro-phenyl)-5-(2-piperidin-1-yl-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1638);

[2-(4-(4-fluoro-phenyl)-5-{2-[(pyridin-4-ylmethyl)-amino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1639);

[2-(4-(4-fluoro-phenyl)-5-{2-[(pyridin-3-ylmethyl)-amino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1640);

[2-(4-(4-fluoro-phenyl)-5-{2-[(pyridin-2-ylmethyl)-amino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1641);

[2-(4-(4-fluoro-phenyl)-5-{2-[(furan-2-ylmethyl)-amino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1642);

[2-(4-(4-fluoro-phenyl)-5-{2-[(thiophen-2-ylmethyl)-amino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1643);

[2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxan-5-yl]-(3-hydroxy-pyrrolidin-1-yl)-methanone, trans-isomer, (Compound A1644);

(2-{4-(4-fluoro-phenyl)-5-[2-(4-methyl-piperazin-1-yl)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1645);

{2-[4-(4-fluoro-phenyl)-5-(2-morpholin-4-yl-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1646);

(2-{4-(4-fluoro-phenyl)-5-[2-(3-methoxy-propylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1647);

(2-{4-(4-fluoro-phenyl)-5-[2-(2-methoxy-ethylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1648);

{2-[5-[2-(3-dimethylamino-propylamino)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1649);

{2-[5-[2-(2-dimethylamino-ethylamino)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1650);

(4-{5-(4-fluoro-phenyl)-2-[5-(3-hydroxy-pyrrolidine-1-carbonyl)-5-methyl-[1,3]dioxan-2-yl]-3H-imidazol-4-yl}-pyrimidin-2-ylamino)-acetic acid, trans-isomer, (Compound A1651);

3-(4-{5-(4-fluoro-phenyl)-2-[5-(3-hydroxy-pyrrolidine-1-carbonyl)-5-methyl-[1,3]dioxan-2-yl]-3H-imidazol-4-yl}-pyrimidin-2-ylamino)propionic acid, trans-isomer, (Compound A1652);

{2-[4-(4-fluoro-phenyl)-5-(2-isopropylamino-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1653);

{2-[5-(2-allylamino-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1654);

{2-[5-[2-(cyclopropylmethyl-amino)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1655);

(4-{5-(4-fluoro-phenyl)-2-[5-(3-hydroxy-pyrrolidine-1-carbonyl)-5-methyl-[1,3]dioxan-2-yl]-3H-imidazol-4-yl}-pyrimidin-2-ylamino)-acetonitrile, trans-isomer, (Compound A1656);

3-(4-{5-(4-fluoro-phenyl)-2-[5-(3-hydroxy-pyrrolidine-1-carbonyl)-5-methyl-[1,3]dioxan-2-yl]-3H-imidazol-4-yl}-pyrimidin-2-ylamino)-propionitrile, trans-isomer, (Compound A1657);

(2-{4-(4-fluoro-phenyl)-5-[2-(pyridin-3-ylamino)-pyrimidin-4-yl]-1H-imidazol-2-yl}-5-methyl-[1,3]dioxan5-yl)-(3-hydroxy-pyrrolidin-1-yl)-methanone, trans-isomer, (Compound A1658);

(2-{4-(4-fluoro-phenyl)-5-[2-(pyridin-4-ylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1659);

{2-[4-(4-fluoro-phenyl)-5-(2-propylamino-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1660);

{2-[4-(4-fluoro-phenyl)-5-(2-pyrrolidin-1-yl-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1661);

(2-{4-(4-fluoro-phenyl)-5-[2-(4-fluoro-phenylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1662);

{2-[5-[2-(3,4-difluoro-phenylamino)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1663);

(2-{4-(4-fluoro-phenyl)-5-[2-(3-methoxy-phenylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1664);

{2-[5-[2-(4-fluoro-benzylamino)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1665);

(2-{4-(4-fluoro-phenyl)-5-[2-(4-methoxy-benzylamino)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1666);

{2-[4-(4-fluoro-phenyl)-5-(2-methoxy-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1667);

{2-[5-(2-benzyloxy-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1668);

{2-[4-(4-fluoro-phenyl)-5-(2-phenoxy-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1669);

(2-{4-(4-fluoro-phenyl)-5-[2-(2-methoxy-ethoxy)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1670);

{2-[5-[2-(2-dimethylamino-ethoxy)-pyrimidin-4-yl]-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1671);

{2-[5-(2-cyclohexyloxy-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1672);

{2-[5-(2-Isopropoxy-pyrimidin-4-yl)-4-(4-fluoro-phenyl)-1H-imidazol-2-yl]-5-methyl-[1,3]dioxan-5-yl}-(3-hydroxy-pyrrolidin-1-yl)-methanone, trans-isomer, (Compound A1673);

{2-[4-(4-fluoro-phenyl)-5-(2-propoxy-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1674);

(2-{4-(4-fluoro-phenyl)-5-[2-(2-hydroxy-ethoxy)-pyrimidin-4-yl]-1H-imidazol-2-yl}-5-methyl-[1,3]dioxan-5-yl)-(3-hydroxy-pyrrolidin-1-yl)-methanone, trans-isomer, (Compound A1675);

(2-{4-(4-fluoro-phenyl)-5-[2-(3-hydroxy-propoxy)-pyrimidin-4-yl]-H1H-imidazol-2-yl}-5-methyl-[1,3]dioxan-5-yl)-(3-hydroxy-pyrrolidin-1-yl)-methanone, trans-isomer, (Compound A1676);

{2-[4-(4-fluoro-phenyl)-5-(2-methylsulfanyl-pyrimidin-4-yl)-1H-imidazol-2-yl]-5-methyl-[1,3]dioxan-5-yl}-(3-hydroxy-pyrrolidin-1-yl)-methanone, trans-isomer, (Compound A1677);

2-[5-(2-amino-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1678);

2-[4-(4-fluoro-phenyl)-5-(2-methylamino-pyrimidin-4-yl)-1H-imidazol-2-yl]-5-methyl-[1,3]dioxane-5-carboxylic acid isopropyl-amide, trans-isomer, (Compound A1679);

2-[5-(2-dimethylamino-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1680);

2-[5-(2-cyclopropylamino-pyrimidin-4-yl)-4-(4-fluoro-phenyl)-1H-imidazol-2-yl]-5-methyl-[1,3]dioxane-5- carboxylic acid isopropyl-amide, trans-isomer, (Compound A1681);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid isopropyl-amide, trans-isomer, (Compound A1682);

2-[5-(2-cyclohexylamino-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1683);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid isopropyl-amide, trans-isomer, (Compound A1684);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1685);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid isopropyl-amide, trans-isomer, (Compound A1686);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid isopropyl-amide, trans-isomer, (Compound A1687);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid isopropyl-amide, trans-isomer, (Compound A1688);

2-[5-(2-benzylamino-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1689);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid isopropyl-amide, R-isomer, trans-isomer, (Compound A1690);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid isopropyl-amide, S-isomer, trans-isomer, (Compound A1691);

2-[4-(4-fluoro-phenyl)-5-(2-phenylamino-pyrimidin-4-yl)-1H-imidazol-2-yl]-5-methyl-[1,3]dioxane-5-carboxylic acid isopropyl-amide, trans-isomer, (Compound A1692);

2-[4-(4-fluoro-phenyl)-5-(2-piperidin-1-yl-pyrimidin-4-yl)-1H-imidazol-2-yl]-5-methyl-[1,3]dioxane-5-carboxylic acid isopropyl-amide, trans-isomer, (Compound A1693);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid isopropyl-amide, trans-isomer, (Compound A1694);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid isopropyl-amide, trans-isomer, (Compound A1695);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid isopropyl-amide, trans-isomer, (Compound A1696);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid isopropyl-amide, trans-isomer, (Compound A1697);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid isopropyl-amide, trans-isomer, (Compound A1698);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid isopropyl-amide, trans-isomer, (Compound A1699);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid isopropyl-amide, trans-isomer, (Compound A1700);

2-[4-(4-fluoro-phenyl)-5-(2-morpholin-4-yl-pyrimidin-4-yl)-1H-imidazol-2-yl]-5-methyl-[1,3]dioxane-5-carboxylic acid isopropyl-amide, trans-isomer, (Compound A1701);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid isopropyl-amide, trans-isomer, (Compound A1702);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid isopropyl-amide, trans-isomer, (Compound A1703);

2-[5-[2-(3-dimethylamino-propylamino)-pyrimidin-4-y]-4-(4-fluoro-phenyl)-1H-imidazol-2-yl]-5-methyl-[1,3]dioxane-5-carboxylic acid isopropyl-amide, trans-isomer, (Compound A1704);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1705);

{4-[5-(4-fluoro-phenyl)-2-(5-isopropylcarbamoyl-5-methyl-[1,3]dioxan-2-yl)-3H-imidazol-4-yl]-pyrimidin-2-ylamino}-acetic acid, trans-isomer, (Compound A1706);

3-{4-[5-(4-fluoro-phenyl)-2-(5-isopropylcarbamoyl-5-methyl-[1,3]dioxan-2-yl)-3H-imidazol-4-yl]-pyrimidin-2-ylamino}-propionic acid, trans-isomer, (Compound A1707);

2-[4-(4-fluoro-phenyl)-5-(2-isopropylamino-pyrimidin-4-yl)-1H-imidazol-2-yl]-5-methyl-[1,3]dioxane-5-carboxylic acid isopropyl-amide, trans-isomer, (Compound A1708);

2-[5-(2-allylamino-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1709);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1710);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1711);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1712);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid isopropyl-amide, trans-isomer, (Compound A1713);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid isopropyl-amide, trans-isomer, (Compound A1714);

2-[4-(4-fluoro-phenyl)-5-(2-propylamino-pyrimidin-4-yl)-1H-imidazol-2-yl]-5-methyl-[1,3]dioxane-5-carboxylic acid isopropyl-amide, trans-isomer, (Compound A1715);

2-[4-(4-fluoro-phenyl)-5-(2-pyrrolidin-1-yl-pyrimidin-4-yl)-1H-imidazol-2-yl]-5-methyl-[1,3]dioxane-5- carboxylic acid isopropyl-amide, trans-isomer, (Compound A1716);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid isopropyl-amide, trans-isomer, (Compound A1717);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1718);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid isopropyl-amide, trans-isomer, (Compound A1719);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1720);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid isopropyl-amide, trans-isomer, (Compound A1721);

2-[4-(4-fluoro-phenyl)-5-(2-methoxy-pyrimidin-4-yl)-1H-imidazol-2-yl]-5-methyl-[1,3]dioxane-5-carboxylic acid isopropyl-amide, trans-isomer, (Compound A1722);

2-[5-(2-benzyloxy-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1723);

2-[4-(4-fluoro-phenyl)-5-(2-phenoxy-pyrimidin-4-yl)-1H-imidazol-2-yl]-5-methyl-[1,3]dioxane-5-carboxylic acid isopropyl-amide, trans-isomer, (Compound A1724);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid isopropyl-amide, trans-isomer, (Compound A1725);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid isopropyl-amide, trans-isomer, (Compound A1726);

2-[5-(2-cyclohexyloxy-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1727);

2-[5-(2-Isopropoxy-pyrimidin-4-yl)-4-(4-fluoro-phenyl)-1H-imidazol-2-yl]-5-methyl-[1,3]dioxane-5-carboxylic acid isopropyl-amide, trans-isomer, (Compound A1728);

2-[4-(4-fluoro-phenyl)-5-(2-propoxy-pyrimidin-4-yl)-1H-imidazol-2-yl]-5-methyl-[1,3]dioxane-5-carboxylic acid isopropyl-amide, trans-isomer, (Compound A1729);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid isopropyl-amide, trans-isomer, (Compound A1730);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid isopropyl-amide, trans-isomer, (Compound A1731);

2-[4-(4-fluoro-phenyl)-5-(2-methylsulfanyl-pyrimidin-4-yl)-1H-imidazol-2-yl]-5-methyl-[1,3]dioxane-5-carboxylic acid isopropyl-amide, trans-isomer, (Compound A1732);

2-[5-(2-amino-pyrimidin-4-yl)-4-(4-fluoro-phenyl)-1H-imidazol-2-yl]-5-methyl-[1,3]dioxane-5-carboxylic acid allylamide, trans-isomer, (Compound A1733);

2-[4-(4-fluoro-phenyl)-5-(2-methylamino-pyrimidin-4-yl)-1H-imidazol-2-yl]-5-methyl-[1,3]dioxane-5-carboxylic acid allylamide, trans-isomer, (Compound A1734);

2-[5-(2-dimethylamino-pyrimidin-4-yl)-4-(4-fluoro-phenyl)-1H-imidazol-2-yl]-5-methyl-[1,3]dioxane-5-carboxylic acid allylamide, trans-isomer, (Compound A1735);

2-[5-(2-cyclopropylamino-pyrimidin-4-yl)-4-(4-fluoro-phenyl)-1H-imidazol-2-yl]-5-methyl-[1,3]dioxane-5-carboxylic acid allylamide, trans-isomer, (Compound A1736);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid allylamide, trans-isomer, (Compound A1737);

2-[5-(2-cyclohexylamino-pyrimidin-4-yl)-4-(4-fluoro-phenyl)-1H-imidazol-2-yl]-5-methyl-[1,3]dioxane-5-carboxylic acid allylamide, trans-isomer, (Compound A1738);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid allylamide, trans-isomer, (Compound A1739);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid allylamide, trans-isomer, (Compound A1740);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid allylamide, trans-isomer, (Compound A1741);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid allylamide, trans-isomer, (Compound A1742);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid allylamide, trans-isomer, (Compound A1743);

2-[5-(2-benzylamino-pyrimidin-4-yl)-4-(4-fluoro-phenyl)-1H-imidazol-2-yl]-5-methyl-[1,3]dioxane-5-carboxylic acid allylamide, trans-isomer, (Compound A1744);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid allylamide, R-isomer, trans-isomer, (Compound A1745);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid allylamide, S-isomer, trans-isomer, (Compound A1746);

2-[4-(4-fluoro-phenyl)-5-(2-phenylamino-pyrimidin-4-yl)-1H-imidazol-2-yl]-5-methyl-[1,3]dioxane-5-carboxylic acid allylamide, trans-isomer, (Compound A1747);

2-[4-(4-fluoro-phenyl)-5-(2-piperidin-1-yl-pyrimidin-4-yl)-1H-imidazol-2-yl]-5-methyl-[1,3]dioxane-5-carboxylic acid allylamide, trans-isomer, (Compound A1748);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid allylamide, trans-isomer, (Compound A1749);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid allylamide, trans-isomer, (Compound A1750);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid allylamide, trans-isomer, (Compound A1751);

2-(4-(4-fluoro-phenyl)-5-{2-[(furan-2-ylmethyl)-amino]-pyrimidin-4-yl}-H1H-imidazol-2-yl)-5-methyl-[1,3]

dioxane-5-carboxylic acid allylamide, trans-isomer, (Compound A1752);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid allylamide, trans-isomer, (Compound A1753);

2-(4-(4-fluoro-phenyl)-5-{2-[(tetrahydro-furan-2-ylmethyl)-amino]-pyrimidin-4-yl}-1H-imidazol-2-yl)-5methyl-[1,3]dioxane-5-carboxylic acid allylamide, trans-isomer, (Compound A1754);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid allylamide, trans-isomer, (Compound A1755);

2-[4-(4-fluoro-phenyl)-5-(2-morpholin-4-yl-pyrimidin-4-yl)-1H-imidazol-2-yl]-5-methyl-[1,3]dioxane-5-carboxylic acid allylamide, trans-isomer, (Compound A1756);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid allylamide, trans-isomer, (Compound A1757);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid allylamide, trans-isomer, (Compound A1758);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid allylamide, trans-isomer, (Compound A1759);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid allylamide, trans-isomer, (Compound A1760);

{4-[2-(5-allylcarbamoyl-5-methyl-[1,3]dioxan-2-yl)-5-(4-fluoro-phenyl)-3H-imidazol-4-yl]pyrimidin-2-ylamino}-acetic acid, trans-isomer, (Compound A1761);

3-{4-[2-(5-allylcarbamoyl-5-methyl-[1,3]dioxan-2-yl)-5-(4-fluoro-phenyl)-3H-imidazol-4-yl]pyrimidin-2-ylamino}-propionic acid, trans-isomer, (Compound A1762);

2-[4-(4-fluoro-phenyl)-5-(2-isopropylamino-pyrimidin-4-yl)-1H-imidazol-2-yl]-5-methyl-[1,3]dioxane-5-carboxylic acid allylamide, trans-isomer, (Compound A1763);

2-[5-(2-allylamino-pyrimidin-4-yl)-4-(4-fluoro-phenyl)-1H-imidazol-2-yl]-5-methyl-[1,3]dioxane-5-carboxylic acid allylamide, trans-isomer, (Compound A1764);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid allylamide, trans-isomer, (Compound A1765);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid allylamide, trans-isomer, (Compound A1766);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid allylamide, trans-isomer, (Compound A1767);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid allylamide, trans-isomer, (Compound A1768);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid allylamide, trans-isomer, (Compound A1769);

2-[4-(4-fluoro-phenyl)-5-(2-propylamino-pyrimidin-4-yl)-1H-imidazol-2-yl]-5-methyl-[1,3]dioxane-5-carboxylic acid allylamide, trans-isomer, (Compound A1770);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid allylamide, trans-isomer, (Compound A1771);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid allylamide, trans-isomer, (Compound A1772);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid allylamide, trans-isomer, (Compound A1773);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid allylamide, trans-isomer, (Compound A1774);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid allylamide, trans-isomer, (Compound A1775);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid allylamide, trans-isomer, (Compound A1776);

2-[4-(4-fluoro-phenyl)-5-(2-methoxy-pyrimidin-4-yl)-1H-imidazol-2-yl]-5-methyl-[1,3]dioxane-5-carboxylic acid allylamide, trans-isomer, (Compound A1777);

2-[5-(2-benzyloxy-pyrimidin-4-yl)-4-(4-fluoro-phenyl)-1H-imidazol-2-yl]-5-methyl-[1,3]dioxane-5-carboxylic acid allylamide, trans-isomer, (Compound A1778);

2-[4-(4-fluoro-phenyl)-5-(2-phenoxy-pyrimidin-4-yl)-1H-imidazol-2-yl]-5-methyl-[1,3]dioxane-5-carboxylic acid allylamide, trans-isomer, (Compound A1779);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid allylamide, trans-isomer, (Compound A1780);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid allylamide, trans-isomer, (Compound A1781);

2-[5-(2-cyclohexyloxy-pyrimidin-4-yl)-4-(4-fluoro-phenyl)-1H-imidazol-2-yl]-5-methyl-[1,3]dioxane-5-carboxylic acid allylamide, trans-isomer, (Compound A1782);

2-[5-(2-Isopropoxy-pyrimidin-4-yl)-4-(4-fluoro-phenyl)-1H-imidazol-2-yl]-5-methyl-[1,3]dioxane-5-carboxylic acid allylamide, trans-isomer, (Compound A1783);

2-[4-(4-fluoro-phenyl)-5-(2-propoxy-pyrimidin-4-yl)-1H-imidazol-2-yl]-5-methyl-[1,3]dioxane-5-carboxylic acid allylamide, trans-isomer, (Compound A1784);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid allylamide, trans-isomer, (Compound A1785);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid allylamide, trans-isomer, (Compound A1786);

2-[4-(4-fluoro-phenyl)-5-(2-methylsulfanyl-pyrimidin-4-yl)-1H-imidazol-2-yl]-5-methyl-[1,3]dioxane-5-carboxylic acid allylamide, trans-isomer, (Compound A1787);

2-[5-(2-amino-pyrimidin-4-yl)-4-(4-fluoro-phenyl)-1H-imidazol-2-yl]-5-methyl-[1,3dioxane-5-carboxylic acid cyclopropylmethyl-amide, trans-isomer, (Compound A1788);

2-[4-(4-fluoro-phenyl)-5-(2-methylamino-pyrimidin-4-yl)-1H-imidazol-2-yl]-5-methyl-[1,3]dioxane-5-carboxylic acid cyclopropylmethyl-amide, trans-isomer, (Compound A1789);

2-[5-(2-dimethylamino-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1790);

2-[5-(2-cyclopropylamino-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1791);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid cyclopropylmethyl-amide, trans-isomer, (Compound A1792);

2-[5-(2-cyclohexylamino-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1793);

2-{4-(4-fluoro-phenyl)-5-[2-(2-hydroxy-ethylamino)-pyrimidin-4-yl]-1H-imidazol-2-yl}-5-methyl-1,3]dioxane-5-carboxylic acid cyclopropylmethyl-amide, trans-isomer, (Compound A1794);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1795);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid cyclopropylmethyl-amide, trans-isomer, (Compound A1796);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid cyclopropylmethyl-amide, trans-isomer, (Compound A1797);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid cyclopropylmethyl-amide, trans-isomer, (Compound A1798);

2-[5-(2-benzylamino-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1799);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyclopropylmethyl-amide, R-isomer, trans-isomer, (Compound A1800);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyclopropylmethyl-amide, S-isomer, trans-isomer, (Compound A1801);

2-[4-(4-fluoro-phenyl)-5-(2-phenylamino-pyrimidin-4-yl)-1H-imidazol-2-yl]-5-methyl-[1,3]dioxane-5-carboxylic acid cyclopropylmethyl-amide, trans-isomer, (Compound A1802);

2-[4-(4-fluoro-phenyl)-5-(2-piperidin-1-yl-pyrimidin-4-yl)-1H-imidazol-2-yl]-5-methyl-[1,3]dioxane-5-carboxylic acid cyclopropylmethyl-amide, trans-isomer, (Compound A1803);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid cyclopropylmethyl-amide, trans-isomer, (Compound A1804);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid cyclopropylmethyl-amide, trans-isomer, (Compound A1805);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid cyclopropylmethyl-amide, trans-isomer, (Compound A1806);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid cyclopropylmethyl-amide, trans-isomer, (Compound A1807);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid cyclopropylmethyl-amide, trans-isomer, (Compound A1808);

2-(4-(4-fluoro-phenyl)-5-{2-[(tetrahydro-furan-2-ylmethyl)-amino]-pyrimidin-4-yl}-1H-imidazol-2-yl)-5-methyl-methyl-[1,3]dioxane-5-carboxylic acid cyclopropylmethyl-amide, trans-isomer, (Compound A1809);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid cyclopropylmethyl-amide, trans-isomer, (Compound A1810);

2-[4-(4-fluoro-phenyl)-5-(2-morpholin-4-yl-pyrimidin-4-yl)-1H-imidazol-2-yl]-5-methyl-[1,3]dioxane-5-carboxylic acid cyclopropylmethyl-amide, trans-isomer, (Compound A1811);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid cyclopropylmethyl-amide, trans-isomer, (Compound A1812);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid cyclopropylmethyl-amide, trans-isomer, (Compound A1813);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1814);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1815);

{4-[2-[5-(cyclopropylmethyl-carbamoyl)-5-methyl-[1,3]dioxan-2-yl]-5-(4-fluoro-phenyl)-3H-imidazol-4-yl]-pyrimidin-2-ylamino}-acetic acid, trans-isomer, (Compound A1816);

3-{4-[2-[5-(cyclopropylmethyl-carbamoyl)-5-methyl-[1,3]dioxan-2-yl]-5-(4-fluoro-phenyl)-3H-imidazol-4-yl]-pyrimidin-2-ylamino}-propionic acid, trans-isomer, (Compound A1817);

2-[4-(4-fluoro-phenyl)-5-(2-isopropylamino-pyrimidin-4-yl)-1H-imidazol-2-yl]-5-methyl-[1,3]dioxane-5-carboxylic acid cyclopropylmethyl-amide, trans-isomer, (Compound A1818);

2-[5-(2-allylamino-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1819);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1820);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1821);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1822);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid cyclopropylmethyl-amide, trans-isomer, (Compound A1823);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid cyclopropylmethyl-amide, trans-isomer, (Compound A1824);

2-[4-(4-fluoro-phenyl)-5-(2-propylamino-pyrimidin-4-yl)-1H-imidazol-2-yl]-5-methyl-[1,3]dioxane-5-carboxylic acid cyclopropylmethyl-amide, trans-isomer, (Compound A1825);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid cyclopropylmethyl-amide, trans-isomer, (Compound A1826);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid cyclopropylmethyl-amide, trans-isomer, (Compound A1827);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1828);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid cyclopropylmethyl-amide, trans-isomer, (Compound A1829);

2-[5-[2-(4-fluoro-benzylamino)pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1830);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid cyclopropylmethyl-amide, trans-isomer, (Compound A1831);

2-[4-(4-fluoro-phenyl)-5-(2-methoxy-pyrimidin-4-yl)-1H-imidazol-2-yl]-5-methyl-[1,3]dioxane-5-carboxylic acid cyclopropylmethyl-amide, trans-isomer, (Compound A1832);

2-[5-(2-benzyloxy-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1833);

2-[4-(4-fluoro-phenyl)-5-(2-phenoxy-pyrimidin-4-yl)-1H-imidazol-2-yl]-5-methyl-[1,3]dioxane-5-carboxylic acid cyclopropylmethyl-amide, trans-isomer, (Compound A1834);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid cyclopropylmethyl-amide, trans-isomer, (Compound A1835);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid cyclopropylmethyl-amide, trans-isomer, (Compound A1836);

2-[5-(2-cyclohexyloxy-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1837);

2-[5-(2-Isopropoxy-pyrimidin-4-yl)-4-(4-fluoro-phenyl)-1H-imidazol-2-yl]-5-methyl-[1,3]dioxane-5-carboxylic acid cyclopropylmethyl-amide, trans-isomer, (Compound A1838);

2-[4-(4-fluoro-phenyl)-5-(2-propoxy-pyrimidin-4-yl)-1H-imidazol-2-yl]-5-methyl-[1,3]dioxane-5-carboxylic acid cyclopropylmethyl-amide, trans-isomer, (Compound A1839);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid cyclopropylmethyl-amide, trans-isomer, (Compound A1840);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid cyclopropylmethyl-amide, trans-isomer, (Compound A1841);

2-[4-(4-fluoro-phenyl)-5-(2-methylsulfanyl-pyrimidin-4-yl)-1H-imidazol-2-yl]-5-methyl-[1,3]dioxane-5-carboxylic acid cyclopropylmethyl-amide, trans-isomer, (Compound A1842);

2-[5-(2-amino-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1843);

2-[4-(4-fluoro-phenyl)-5-(2-methylamino-pyrimidin-4-yl)-1H-imidazol-2-yl]-5-methyl-[1,3]dioxane-5-carboxylic acid cyanomethyl-amide, trans-isomer, (Compound A1844);

2-[5-(2-dimethylamino-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1845);

2-[5-(2-cyclopropylamino-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1846);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid cyanomethyl-amide, trans-isomer, (Compound A1847);

2-[5-(2-cyclohexylamino-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1848);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid cyanomethyl-amide, trans-isomer, (Compound A1849);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1850);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid cyanomethyl-amide, trans-isomer, (Compound A1851);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid cyanomethyl-amide, trans-isomer, (Compound A1852);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid cyanomethyl-amide, trans-isomer, (Compound A1853);

2-[5-(2-benzylamino-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1854);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyanomethyl-amide, R-isomer, trans-isomer, (Compound A1855);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid cyanomethyl-amide, S-isomer, trans-isomer, (Compound A1856);

2-[4-(4-fluoro-phenyl)-5-(2-phenylamino-pyrimidin-4-yl)-1H-imidazol-2-yl]-5-methyl-[1,3]dioxane-5-carboxylic acid cyanomethyl-amide, trans-isomer, (Compound A1857);

2-[4-(4-fluoro-phenyl)-5-(2-piperidin-1-yl-pyrimidin-4-yl)-1H-imidazol-2-yl]-5-methyl-[1,3]dioxane-5-carboxylic acid cyanomethyl-amide, trans-isomer, (Compound A1858);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid cyanomethyl-amide, trans-isomer, (Compound A1859);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid cyanomethyl-amide, trans-isomer, (Compound A1860);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid cyanomethyl-amide, trans-isomer, (Compound A1861);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid cyanomethyl-amide, trans-isomer, (Compound A1862);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid cyanomethyl-amide, trans-isomer, (Compound A1863);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid cyanomethyl-amide, trans-isomer, (Compound A1864);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid cyanomethyl-amide, trans-isomer, (Compound A1865);

2-[4-(4-fluoro-phenyl)-5-(2-morpholin-4-yl-pyrimidin-4-yl)-1H-imidazol-2-yl]-5-methyl-[1,3]dioxane-5-carboxylic acid cyanomethyl-amide, trans-isomer, (Compound A1866);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid cyanomethyl-amide, trans-isomer, (Compound A1867);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid cyanomethyl-amide, trans-isomer, (Compound A1868);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1869);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1870);

{4-[2-[5-(cyanomethyl-carbamoyl)-5-methyl-[1,3]dioxan-2-yl]-5-(4-fluoro-phenyl)-3H-imidazol-4-yl]-pyrimidin-2-ylamino}-acetic acid, trans-isomer, (Compound A1871);

3-{4-[2-[5-(cyanomethyl-carbamoyl)-5-methyl-[1,3]dioxan-2-yl]-5-(4-fluoro-phenyl)-3H-imidazol-4-yl]-pyrimidin-2-ylamino}-propionic acid, trans-isomer, (Compound A1872);

2-[4-(4-fluoro-phenyl)-5-(2-isopropylamino-pyrimidin-4-yl)-1H-imidazol-2-yl]-5-methyl-[1,3]dioxane-5-carboxylic acid cyanomethyl-amide, trans-isomer, (Compound A1873);

2-[5-(2-allylamino-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1874);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1875);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1876);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1877);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid cyanomethyl-amide, trans-isomer, (Compound A1878);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid cyanomethyl-amide, trans-isomer, (Compound A1879);

2-[4-(4-fluoro-phenyl)-5-(2-propylamino-pyrimidin-4-yl)-1H-imidazol-2-yl]-5-methyl-[1,3]dioxane-5-carboxylic acid cyanomethyl-amide, trans-isomer, (Compound A1880);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid cyanomethyl-amide, trans-isomer, (Compound A1881);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid cyanomethyl-amide, trans-isomer, (Compound A1882);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1883);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid cyanomethyl-amide, trans-isomer, (Compound A1884);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1885);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid cyanomethyl-amide, trans-isomer, (Compound A1886);

2-[4-(4-fluoro-phenyl)-5-(2-methoxy-pyrimidin-4-yl)-1H-imidazol-2-yl]-5-methyl-[1,3]dioxane-5-carboxylic acid cyanomethyl-amide, trans-isomer, (Compound A1887);

2-[5-(2-benzyloxy-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1888);

2-[4-(4-fluoro-phenyl)-5-(2-phenoxy-pyrimidin-4-yl)-1H-imidazol-2-yl]-5-methyl-[1,3]dioxane-5-carboxylic acid cyanomethyl-amide, trans-isomer, (Compound A1889);

2-{4-(4-fluoro-phenyl)-5-[2-(2-methoxy-ethoxy)-pyrimidin-4-yl]-1H-imidazol-2-yl}-5-methyl-[1,3]

dioxane-5-carboxylic acid cyanomethyl-amide, trans-isomer, (Compound A1890);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid cyanomethyl-amide, trans-isomer, (Compound A1891);

2-[5-(2-cyclohexyloxy-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1892);

2-[5-(2-Isopropoxy-pyrimidin-4-yl)-4-(4-fluoro-phenyl)-1H-imidazol-2-yl]-5-methyl-[1,3]dioxane-5-carboxylic acid cyanomethyl-amide, trans-isomer, (Compound A1893);

2-[4-(4-fluoro-phenyl)-5-(2-propoxy-pyrimidin-4-yl)-1H-imidazol-2-yl]-5-methyl-[1,3]dioxane-5-carboxylic acid cyanomethyl-amide, trans-isomer, (Compound A1894);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid cyanomethyl-amide, trans-isomer, (Compound A1895);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid cyanomethyl-amide, trans-isomer, (Compound A1896);

2-[4-(4-fluoro-phenyl)-5-(2-methylsulfanyl-pyrimidin-4-yl)-1H-imidazol-2-yl]-5-methyl-[1,3]dioxane-5-carboxylic acid cyanomethyl-amide, trans-isomer, (Compound A1897);

2-[5-(2-amino-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1898);

2-[4-(4-fluoro-phenyl)-5-(2-methylamino-pyrimidin-4-yl)-1H-imidazol-2-yl]-5-methyl-[1,3]dioxane-5-carboxylic acid (2-cyano-ethyl)-amide, trans-isomer, (Compound A1899);

2-[5-(2-dimethylamino-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1900);

2-[5-(2-cyclopropylamino-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1901);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid (2-cyano-ethyl)-amide, trans-isomer, (Compound A1902);

2-[5-(2-cyclohexylamino-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1903);

2-{4-(4-fluoro-phenyl)-5-[2-(2-hydroxy-ethylamino)-pyrimidin-4-yl]-1H-imidazol-2-yl}-methyl-[1,3]dioxane-5-carboxylic acid (2-cyano-ethyl)-amide, trans-isomer, (Compound A1904);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1905);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid (2-cyano-ethyl)-amide, trans-isomer, (Compound A1906);

2-{4-(4-fluoro-phenyl)-5-[2-(3-morpholin-4-yl-propylamino)-pyrimidin-4-yl-]-1H-imidazol-2-yl}-5-methyl-[1,3]dioxane-5-carboxylic acid (2-cyano-ethyl)-amide, trans-isomer, (Compound A1907);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid (2-cyano-ethyl)-amide, trans-isomer, (Compound A1908);

2-[5-(2-benzylamino-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1909);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-cyano-ethyl)-amide, R-isomer, trans-isomer, (Compound A1910);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid (2-cyano-ethyl)-amide, S-isomer, trans-isomer, (Compound A1911);

2-[4-(4-fluoro-phenyl)-5-(2-phenylamino-pyrimidin-4-yl)-1H-imidazol-2-yl]-5-methyl-[1,3]dioxane-5-carboxylic acid (2-cyano-ethyl)-amide, trans-isomer, (Compound A1912);

2-[4-(4-fluoro-phenyl)-5-(2-piperidin-1-yl-pyrimidin-4-yl)-1H-imidazol-2-yl]-5-methyl-[1,3]dioxane-5-carboxylic acid (2-cyano-ethyl)-amide, trans-isomer, (Compound A1913);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid (2-cyano-ethyl)-amide, trans-isomer, (Compound A1914);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid (2-cyano-ethyl)-amide, trans-isomer, (Compound A1915);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid (2-cyano-ethyl)-amide, trans-isomer, (Compound A1916);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid (2-cyano-ethyl)-amide, trans-isomer, (Compound A1917);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid (2-cyano-ethyl)-amide, trans-isomer, (Compound A1918);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid (2-cyano-ethyl)-amide, trans-isomer, (Compound A1919);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid (2-cyano-ethyl)-amide, trans-isomer, (Compound A1920);

2-[4-(4-fluoro-phenyl)-5-(2-morpholin-4-yl-pyrimidin-4-yl)-1H-imidazol-2-yl]-5-methyl-[1,3]dioxane-5-carboxylic acid (2-cyano-ethyl)-amide, trans-isomer, (Compound A1921);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid (2-cyano-ethyl)-amide, trans-isomer, (Compound A1922);

2-{4-(4-fluoro-phenyl)-5-[2-(2-methoxy-ethylamino)-pyrimidin-4-yl]1H-imidazol-2-yl}-5-methyl-[1,3]dioxane-5-carboxylic acid (2-cyano-ethyl)-amide, trans-isomer, (Compound A1923);

2-[5-[2-(3-dimethylamino-propylamino)-pyrimidin-4-yl]-4-(4-fluoro-phenyl)-1H-imidazol-2-yl]-5-methyl-[1,3]

dioxane-5-carboxylic acid (2-cyano-ethyl)-amide, trans-isomer, (Compound A1924);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1925);

{4-[2-[5-(2-cyano-ethylcarbamoyl)-5-methyl-[1,3]dioxan-2-yl]-5-(4-fluoro-phenyl)-3H-imidazol-4-yl]-pyrimidin-2-ylamino}-acetic acid, trans-isomer, (Compound A1926);

3-{4-[2-[5-(2-cyano-ethylcarbamoyl)-5-methyl-[1,3]dioxan-2-yl]-5-(4-fluoro-phenyl)-3H-imidazol-4-yl]-pyrimidin-2-ylamino}-propionic acid, trans-isomer, (Compound A1927);

2-[4-(4-fluoro-phenyl)-5-(2-isopropylamino-pyrimidin-4-yl)-1H-imidazol-2-yl]-5-methyl-[1,3]dioxane-5-carboxylic acid (2-cyano-ethyl)-amide, trans-isomer, (Compound A1928);

2-[5-(2-allylamino-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1929);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1930);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1931);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1932);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid (2-cyano-ethyl)-amide, trans-isomer, (Compound A1933);

2-{4-(4-fluoro-phenyl)-5-[2-(pyridin-4-ylamino)-pyrimidin-4-yl]-1H-imidazol-2-yl }-5-methyl-[1,3]dioxane-5-carboxylic acid (2-cyano-ethyl)-amide, trans-isomer, (Compound A1934);

2-[4-(4-fluoro-phenyl)-5-(2-propylamino-pyrimidin-4-yl)-1H-imidazol-2-yl]-5-methyl-[1,3]dioxane-5-carboxylic acid (2-cyano-ethyl)-amide, trans-isomer, (Compound A1935);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid (2-cyano-ethyl)-amide, trans-isomer, (Compound A1936);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid (2-cyano-ethyl)-amide, trans-isomer, (Compound A1937);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1938);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid (2-cyano-ethyl)-amide, trans-isomer, (Compound A1939);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid (2-cyano-ethyl)-amide, trans-isomer, (Compound A1940);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid (2-cyano-ethyl)-amide, trans-isomer, (Compound A1941);

2-[4-(4-fluoro-phenyl)-5-(2-methoxy-pyrimidin-4-yl)-1H-imidazol-2-yl]-5-methyl-[1,3]dioxane-5-carboxylic acid (2-cyano-ethyl)-amide, trans-isomer, (Compound A1942);

2-[5-(2-benzyloxy-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1943);

2-[4-(4-fluoro-phenyl)-5-(2-phenoxy-pyrimidin-4-yl)-1H-imidazol-2-yl]-5-methyl-[1,3]dioxane-5-carboxylic acid (2-cyano-ethyl)-amide, trans-isomer, (Compound A1944);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid (2-cyano-ethyl)-amide, trans-isomer, (Compound A1945);

2-[5-[2-(2-dimethylamino-ethoxy)-pyrimidin-4-yl]-4-(4-fluoro-phenyl)-1H-imidazol-2-yl]-5-methyl-[1,3]dioxane-[1,3]dioxane-5-carboxylic acid (2-cyano-ethyl)-amide, trans-isomer, (Compound A1946);

2-[5-(2-cyclohexyloxy-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1947);

2-[5-(2-Isopropoxy-pyrimidin-4-yl)-4-(4-fluoro-phenyl)-1H-imidazol-2-yl]-5-methyl-[1,3]dioxane-5-carboxylic acid (2-cyano-ethyl)-amide, trans-isomer, (Compound A1948);

2-[4-(4-fluoro-phenyl)-5-(2-propoxy-pyrimidin-4-yl)-1H-imidazol-2-yl]-5-methyl-[1,3]dioxane-5-carboxylic acid (2-cyano-ethyl)-amide, trans-isomer, (Compound A1949);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid (2-cyano-ethyl)-amide, trans-isomer, (Compound A1950);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid (2-cyano-ethyl)-amide, trans-isomer, (Compound A1951);

2-[4-(4-fluoro-phenyl)-5-(2-methylsulfanyl-pyrimidin-4-yl)-1H-imidazol-2-yl]-5-methyl-[1,3]dioxane-5-carboxylic acid (2-cyano-ethyl)-amide, trans isomer, (Compound A1952);

2-[5-(2-amino-pyrimidin-4-yl)-4-(4-fluoro-phenyl)-1H-imidazol-2-yl]-5-methyl-[1,3]dioxane-5-carboxylic acid pyridin-3-ylamide, trans-isomer, (Compound A1953);

2-[4-(4-fluoro-phenyl)-5-(2-methylamino-pyrimidin-4-yl)-1H-imidazol-2-yl]-5-methyl-[1,3]dioxane-5-carboxylic acid pyridin-3-ylamide, trans-isomer, (Compound A1954);

2-[5-(2-dimethylamino-pyrimidin-4-yl)-4-(4-fluoro-phenyl)-1H-imidazol-2-yl]-5-methyl-[1,3]dioxane-5-carboxylic acid pyridin-3-ylamide, trans-isomer, (Compound A1955);

2-[5-(2-cyclopropylamino-pyrimidin-4-yl)-4-(4-fluoro-phenyl)-1H-imidazol-2-yl]-5-methyl-[1,3]dioxane-5-carboxylic acid pyridin-3-ylamide, trans-isomer, (Compound A1956);

2-{4-(4-fluoro-phenyl)-5-[2-(piperidin-4-ylamino)-pyrimidin-4-yl]-1H-imidazol-2-yl }-5-methyl-[1,3]dioxane-5-carboxylic acid pyridin-3-ylamide, trans-isomer, (Compound A1957);

2-[5-(2-cyclohexylamino-pyrimidin-4-yl)-4-(4-fluoro-phenyl)-1H-imidazol-2-yl]-5-methyl-[1,3]dioxane-5- carboxylic acid pyridin-3-ylamide, trans-isomer, (Compound A1958);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid pyridin-3-ylamide, trans-isomer, (Compound A1959);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1960);

2-(4-(4-fluoro-phenyl)-5-{2-[3-(5H-imidazol-1-yl)-propylamino]-pyrimidin-4-yl}-1H-imidazol-2-yl)-5methyl-[1,3]dioxane-5-carboxylic acid pyridin-3-ylamide, trans-isomer, (Compound A1961);

2-{4-(4-fluoro-phenyl)-5-[2-(3-morpholin-4-yl-propylamino)-pyrimidin-4-yl]-1H-imidazol-2-yl}-5-methyl-[1,3]dioxane-5-carboxylic acid pyridin-3-ylamide, trans-isomer, (Compound A1962);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid pyridin-3-ylamide, trans-isomer, (Compound A1963);

2-[5-(2-benzylamino-pyrimidin-4-yl)-4-(4-fluoro-phenyl)-1H-imidazol-2-yl]-5-methyl-[1,3]dioxane-5-carboxylic acid pyridin-3-ylamide, trans-isomer, (Compound A1964);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid pyridin-3-ylamide, R-isomer, trans-isomer, (Compound A1965);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid pyridin-3-ylamide, S-isomer, trans-isomer, (Compound A1966);

2-[4-(4-fluoro-phenyl)-5-(2-phenylamino-pyrimidin-4-yl)-1H-imidazol-2-yl]-5-methyl-[1,3]dioxane-5-carboxylic acid pyridin-3-ylamide, trans-isomer, (Compound A1967);

2-[4-(4-fluoro-phenyl)-5-(2-piperidin-1-yl-pyrimidin-4-yl)-1H-imidazol-2-yl]-5-methyl-[1,3]dioxane-5-carboxylic acid pyridin-3-ylamide, trans-isomer, (Compound A1968);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid pyridin-3-ylamide, trans-isomer, (Compound A1969);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid pyridin-3-ylamide, trans-isomer, (Compound A1970);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid pyridin-3-ylamide, trans-isomer, (Compound A1971);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid pyridin-3-ylamide, trans-isomer, (Compound A1972);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid pyridin-3-ylamide, trans-isomer, (Compound A1973);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid pyridin-3-ylamide, trans-isomer, (Compound A1974);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid pyridin-3-ylamide, trans-isomer, (Compound A1975);

2-[4-(4-fluoro-phenyl)-5-(2-morpholin-4-yl-pyrimidin-4-yl)-1H-imidazol-2-yl]-5-methyl-[1,3]dioxane-5-carboxylic acid pyridin-3-ylamide, trans-isomer, (Compound A1976);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid pyridin-3-ylamide, trans-isomer, (Compound A1977);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid pyridin-3-ylamide, trans-isomer, (Compound A1978);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1979);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1980);

(4-{5-(4-fluoro-phenyl)-2-[5-methyl-5-(pyridin-3-ylcarbamoyl)-[1,3]dioxan-2-yl]-3H-imidazol-4-yl}-pyrimidin-2-ylamino)-acetic acid, trans-isomer, (Compound A1981);

3-(4-{5-(4-fluoro-phenyl)-2-[5-methyl-5-(pyridin-3-ylcarbamoyl)-[1,3]dioxan-2-yl]-3H-imidazol-4-yl}-pyrimidin-2-ylamino)-propionic acid, trans-isomer, (Compound A1982);

2-[4-(4-fluoro-phenyl)-5-(2-isopropylamino-pyrimidin-4-yl)-1H-imidazol-2-yl]-5-methyl-[1,3]dioxane-5-carboxylic acid pyridin-3-ylamide, trans-isomer, (Compound A1983);

2-[5-(2-allylamino-pyrimidin-4-yl)-4-(4-fluoro-phenyl)-1H-imidazol-2-yl]-5-methyl-[1,3]dioxane-5-carboxylic acid pyridin-3-ylamide, trans-isomer, (Compound A1984);

2-[5-[2-(cyclopropylmethyl-amino)-pyrimidin-4-yl]4-(4-fluoro-phenyl)-1H-imidazol-2-yl]-5-methyl-[1,3]dioxane-5-carboxylic acid pyridin-3-ylamide, trans-isomer, (Compound A1985);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1986);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1987);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid pyridin-3-ylamide, trans-isomer, (Compound A1988);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid pyridin-3-ylamide, trans-isomer, (Compound A1989);

2-[4-(4-fluoro-phenyl)-5-(2-propylamino-pyrimidin-4-yl-1H-imidazol-2-yl]-5-methyl-[1,3]dioxane-5-carboxylic acid pyridin-3-ylamide, trans-isomer, (Compound A1990);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid pyridin-3-ylamide, trans-isomer, (Compound A1991);

2-{4-(4-fluoro-phenyl)-5-[2-(4-fluoro-phenylamino)-pyrimidin-4-yl]-1H-imidazol-2-yl}-5-methyl-[1,3]

dioxane-5-carboxylic acid pyridin-3-ylamide, trans-isomer, (Compound A1992);

2-[5-[2-(3,4-difluoro-phenylamino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1993);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid pyridin-3-ylamide, trans-isomer, (Compound A1994);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A1995);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid pyridin-3-ylamide, trans-isomer, (Compound A1996);

2-[4-(4-fluoro-phenyl)-5-(2-methoxy-pyrimidin-4-yl)-1H-imidazol-2-yl]-5-methyl-[1,3]dioxane-5-methyl-carboxylic acid pyridin-3-ylamide, trans-isomer, (Compound A1997);

2-[5-(2-benzyloxy-pyrimidin-4-yl)-4-(4-fluoro-phenyl)-1H-imidazol-2-yl]-5-methyl-[1,3]dioxane-5-methyl-carboxylic acid pyridin-3-ylamide, trans-isomer, (Compound A1998);

2-[4-(4-fluoro-phenyl)-5-(2-phenoxy-pyrimidin-4-yl)-1H-imidazol-2-yl]-5-methyl-[1,3]dioxane-5-carboxylic acid pyridin-3-ylamide, trans-isomer, (Compound A1999);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid pyridin-3-ylamide, trans-isomer, (Compound A2000);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid pyridin-3-ylamide, trans-isomer, (Compound A2001);

2-[5-(2-cyclohexyloxy-pyrimidin-4-yl)-4-(4-fluoro-phenyl)-1H-imidazol-2-yl]-5-methyl-[1,3]dioxane-5-carboxylic acid pyridin-3-ylamide, trans-isomer, (Compound A2002);

2-[5-(2-Isopropoxy-pyrimidin-4-yl)-4-(4-fluoro-phenyl)-1H-imidazol-2-yl]-5-methyl-[1,3]dioxane-5carboxylic acid pyridin-3-ylamide, trans-isomer, (Compound A2003);

2-[4-(4-fluoro-phenyl)-5-(2-propoxy-pyrimidin-4-yl)-1H-imidazol-2-yl]-5-methyl-[1,3]dioxane-5-carboxylic acid pyridin-3-ylamide, trans-isomer, (Compound A2004);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid pyridin-3-ylamide, trans-isomer, (Compound A2005);

2-{4-(4-fluoro-phenyl)-5-[2-(3-hydroxy-propoxy)-pyrimidin-4-yl]-1H-imidazol-2}-5-methyl-[1,3]dioxane-5-carboxylic acid pyridin-3-ylamide, trans-isomer, (Compound A2006);

2-[4-(4-fluoro-phenyl)-5-(2-methylsulfanyl-pyrimidin-4-yl)-1H-imidazol-2-yl]-5-methyl-[1,3]dioxane-5-carboxylic acid pyridin-3-ylamide, trans-isomer, (Compound A2007);

2-[5-(2-amino-pyrimidin-4-yl)-4-(4-fluoro-phenyl)-1H-imidazol-2-yl]-5-methyl-[1,3]dioxane-5-carboxylic-acid pyridin-4-ylamide, trans-isomer, (Compound A2008);

2-[4-(4-fluoro-phenyl)-5-(2-methylamino-pyrimidin-4-yl)-1H-imidazol-2-yl]-5-methyl-[1,3]dioxane-5-carboxylic acid pyridin-4-ylamide, trans-isomer, (Compound A2009);

2-[5-(2-dimethylamino-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2010);

2-[5-(2-cyclopropylamino-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2011);

2-{4-(4-fluoro-phenyl)-5-[2-(piperidin-4-ylamino)-pyrimidin-4-yl]-1H-imidazol-2-yl}-5-methyl-[1,3]dioxane-5-carboxylic acid pyridin-4-ylamide, trans-isomer, (Compound A2012);

2-[5-(2-cyclohexylamino-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2013);

2-{4-(4-fluoro-phenyl)-5-[2-(2-hydroxy-ethylamino)-pyrimidin-4-yl]-1H-imidazol-2-yl}-5-methyl-[1,3]dioxane-5-carboxylic acid pyridin-4-ylamide, trans-isomer, (Compound A2014);

2-[5-[2-(2-amino-ethylamino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2015);

2-(4-(4-fluoro-phenyl)-5-{2-[3-(5H-imidazol-1-yl)-propylamino]-pyrimidin-4-yl}-1H-imidazol-2-yl)-5-methyl-[1,3]dioxane-5-carboxylic acid pyridin-4-ylamide, trans-isomer, (Compound A2016);

2-{4-(4-fluoro-phenyl)-5-[2-(3-morpholin in-4-yl-propylamino)-pyrimidin-4-yl]-1H-imidazol-2-yl}-5-methyl-[1,3]dioxane-5-carboxylic acid pyridin-4-ylamide, trans-isomer, (Compound A2017);

2-{4-(4-fluoro-phenyl)-5-[2-(3-hydroxy-propylamino)-pyrimidin-4-yl]-1H-imidazol-2-yl}-5-methyl-[1,3]dioxane-5-carboxylic acid pyridin-4-ylamide, trans-isomer, (Compound A2018);

2-[5-(2-benzylamino-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2019);

2-{4-(4-fluoro-phenyl)-5-[2-(1-phenyl-ethylamino)-pyrimidin-4-yl]1H-imidazol-2-yl}-5-methyl-[1,3]dioxane-5-carboxylic acid pyridin-4-ylamide, R-isomer, trans-isomer, (Compound A2020);

2-{4-(4-fluoro-phenyl)-5-[2-(1-phenyl-ethylamino)-pyrimidin-4-yl]-1H-imidazol-2-yl}-5-methyl-[1,3]dioxane-5-carboxylic acid pyridin-4-ylamide, S-isomer, trans-isomer, (Compound A2021);

2-[4-(4-fluoro-phenyl)-5-(2-phenylamino-pyrimidin-4-yl)-1H-imidazol-2-yl]-5-methyl-[1,3]dioxane-5-carboxylic acid pyridin-4-ylamide, R-isomer, trans-isomer, (Compound A2022);

2-[4-(4-fluoro-phenyl)-5-(2-piperidin-1-yl-pyrimidin-4-yl)-1H-imidazol-2-yl]-5-methyl-[1,3]dioxane-5-carboxylic acid pyridin-4-ylamide, S-isomer, trans-isomer, (Compound A2023);

2-(4-(4-fluoro-phenyl)-5-{2-[(pyridin-4-ylmethyl)-amino]-pyrimidin-4-yl}-1H-imidazol-2-yl)-5-methyl-[1,3]dioxane-5-carboxylic acid pyridin-4-ylamide, trans-isomer, (Compound A2024);

2-(4-(4-fluoro-phenyl)-5-{2-[(pyridin-3-ylmethyl)-amino]-pyrimidin-4-yl}-1H-imidazol-2-yl)-5-methyl-[1,3]dioxane-5-carboxylic acid pyridin-4-ylamide, trans-isomer, (Compound A2025);

2-(4-(4-fluoro-phenyl)-5-{2-[(pyridin-2-ylmethyl)-amino]-pyrimidin-4-yl}-1H-imidazol-2-yl)-5-methyl-[1,3]dioxane-5-carboxylic acid pyridin-4-ylamide, trans-isomer, (Compound A2026);

2-(4-(4-fluoro-phenyl)-5-{2-[(furan-2-ylmethyl)-amino]-pyrimidin-4-yl}-1H-imidazol-2-yl)-5-methyl-[1,3]dioxane-5-carboxylic acid pyridin-4-ylamide 2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid pyridin-4-ylamide, trans-isomer, (Compound A2027);

2-(4-(4-fluoro-phenyl)-5-{2-[(thiophen-2-ylmethyl)-amino]-pyrimidin-4-yl}-1H-imidazol-2-yl)-5-methyl-[1,3]dioxane-5-carboxylic acid pyridin-4-ylamide, trans-isomer, (Compound A2028);

2-(4-(4-fluoro-phenyl)-5-{2-[(tetrahydro-furan-2-ylmethyl)-amino]-pyrimidin-4-yl}-1H-imidazol-2-yl)-5-methyl-[1,3]dioxane-5-carboxylic acid pyridin-4-ylamide, trans-isomer, (Compound A2029);

2-{4-(4-fluoro-phenyl)-5-[2-(4-methyl-piperazin-1-yl)-pyrimidin-4-yl]-1H-imidazol-2-yl}-5-methyl-[1,3]dioxane-5-carboxylic acid pyridin-4-ylamide, trans-isomer, (Compound A2030);

2-[4-(4-fluoro-phenyl)-5-(2-morpholin-4-yl-pyrimidin-4-yl)-1H-imidazol-2-yl]-5-methyl-[1,3]dioxane-5-carboxylic acid pyridin-4-ylamide, trans-isomer, (Compound A2031);

2-{4-(4-fluoro-phenyl)-5-[2-(3-methoxy-propylamino)-pyrimidin-4-yl]-1H-imidazol-2-yl}-5-methyl-[1,3]dioxane-5-carboxylic acid pyridin-4-ylamide, trans-isomer, (Compound A2032);

2-{4-(4-fluoro-phenyl)-5-[2-(2-methoxy-ethylamino)-pyrimidin-4-yl]-1H-imidazol-2-yl}-5-methyl-[1,3]dioxane-5-carboxylic acid pyridin-4-ylamide, trans-isomer, (Compound A2033);

2-[5-[2-(3-dimethylamino-propylamino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2034);

2-[5-[2-(2-dimethylamino-ethylamino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2035);

(4-{5-(4-fluoro-phenyl)-2-[5-methyl-5-(pyridin-4-ylcarbamoyl)-[1,3]dioxan-2-yl]-3H-imidazol-4-yl}-pyrimidin-2-ylamino)-acetic acid, trans-isomer, (Compound A2036);

3-(4-{5-(4-fluoro-phenyl)-2-[5-methyl-5-(pyridin-4-ylcarbamoyl)-[1,3]dioxan-2-yl]-3H-imidazol-4-yl}-pyrimidin-2-ylamino)-propionic acid, trans-isomer, (Compound A2037);

2-[4-(4-fluoro-phenyl)-5-(2-isopropylamino-pyrimidin-4-yl)-1H-imidazol-2-yl]-5-methyl-[1,3]dioxane-5-carboxylic acid pyridin-4-ylamide, trans-isomer, (Compound A2038);

2-[5-(2-allylamino-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2039);

2-[5-[2-(cyclopropylmethyl-amino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2040);

2-[5-[2-(cyanomethyl-amino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2041);

2-[5-[2-(2-cyano-ethylamino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2042);

2-{4-(4-fluoro-phenyl)-5-[2-(pyridin-3-ylamino)-pyrimidin-4-yl]-1H-imidazol-2-yl}-5-methyl-[1,3]dioxane-5-carboxylic acid pyridin-4-ylamide, trans-isomer, (Compound A2043);

2-{4-(4-fluoro-phenyl)-5-[2-(pyridin-4-ylamino)-pyrimidin-4-yl]-1H-imidazol-2-yl}-5-methyl-[1,3]dioxane-5-carboxylic acid pyridin-4-ylamide, trans-isomer, (Compound A2044);

2-[4-(4-fluoro-phenyl)-5-(2-propylamino-pyrimidin-4-yl)-1H-imidazol-2-yl]-5-methyl-[1,3]dioxane-5-carboxylic acid pyridin-4-ylamide, trans-isomer, (Compound A2045);

2-[4-(4-fluoro-phenyl)-5-(2-pyrrolidin-1-yl-pyrimidin-4-yl)-1H-imidazol-2-yl]-5-methyl-[1,3]dioxane-5-carboxylic acid pyridin-4-ylamide, trans-isomer, (Compound A2046);

2-{4-(4-fluoro-phenyl)-5-[2-(4-fluoro-phenylamino)-pyrimidin-4-yl]-1H-imidazol-2-yl}-5-methyl-[1,3]dioxane-5-carboxylic acid pyridin-4-ylamide, trans-isomer, (Compound A2047);

2-[5-[2-(3,4-difluoro-phenylamino)-pyrimidin-4-y]-4-(4-fluoro-phenyl)-1H-imidazol-2-yl]-5-methyl-[1,3]dioxane-5-carboxylic acid pyridin-4-ylamide, trans-isomer, (Compound A2048);

2-{4-(4-fluoro-phenyl)-5-[2-(3-methoxy-phenylamino)-pyrimidin-4-yl]-1H-imidazol-2-yl}-5-methyl-[1,3]dioxane-5-carboxylic acid pyridin-4-ylamide, trans-isomer, (Compound A2049);

2-[5-[2-(4-fluoro-benzylamino)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2050);

2-{4-(4-fluoro-phenyl)-5-[2-(4-methoxy-benzylamino)-pyrimidin-4-yl]-1H-imidazol-2-yl}-5-methyl-[1,3]dioxane-5-carboxylic acid pyridin-4-ylamide, trans-isomer, (Compound A2051);

2-[4-(4-fluoro-phenyl)-5-(2-methoxy-pyrimidin-4-yl)-1H-imidazol-2-yl]-5-methyl-[1,3]dioxane-5-carboxylic acid pyridin-4-ylamide, trans-isomer, (Compound A2052);

2-[5-(2-benzyloxy-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2053);

2-[4-(4-fluoro-phenyl)-5-(2-phenoxy-pyrimidin-4-yl)-1H-imidazol-2-yl]-5-methyl-[1,3]dioxane-5-carboxylic acid pyridin-4-ylamide, trans-isomer, (Compound A2054);

2-{4-(4-fluoro-phenyl)-5-[2-(2-methoxy-ethoxy)-pyrimidin-4-yl]-1H-imidazol-2-yl}-5-methyl-[1,3]dioxane-5-carboxylic acid pyridin-4-ylamide, trans-isomer, (Compound A2055);

2-[5-[2-(2-dimethylamino-ethoxy)-pyrimidin-4-yl]-4-(4-fluoro-phenyl)-1H-imidazol-2-yl]-5-methyl-[1,3]dioxane-5-carboxylic acid pyridin-4-ylamide, trans-isomer, (Compound A2056);

2-[5-(2-cyclohexyloxy-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2057);

2-[5-(2-Isopropoxy-pyrimidin-4-yl)-4-(4-fluoro-phenyl)-1H-imidazol-2-yl]-5-methyl-[1,3]dioxane-5-carboxylic acid pyridin-4-ylamide, trans-isomer, (Compound A2058);

2-[4-(4-fluoro-phenyl)-5-(2-propoxy-pyrimidin-4-yl)-1H-imidazol-2-yl]-5-methyl-[1,3]dioxane-5-carboxylic acid pyridin-4-ylamide, trans-isomer, (Compound A2059);

2-{4-(4-fluoro-phenyl)-5-[2-(2-hydroxy-ethoxy)-pyrimidin-4-yl]-1H-imidazol-2-yl}-5-methyl-[1,3]dioxane-5-carboxylic acid pyridin-4-ylamide, trans-isomer, (Compound A2060);

2-{4-(4-fluoro-phenyl)-5-[2-(3-hydroxy-propoxy)-pyrimidin-4-yl]-1H-imidazol-2-yl}-5-methyl-[1,3]dioxane-5-carboxylic acid pyridin-4-ylamide, trans-isomer, (Compound A2061);

2-[4-(4-fluoro-phenyl)-5-(2-methylsulfanyl-pyrimidin-4-yl)-1H-imidazol-2-yl]-5-methyl-[1,3]dioxane-5-carboxylic acid pyridin-4-ylamide, trans-isomer, (Compound A2062);

(c) By proceeding in a similar manner to Example 40 (b) but using 2-[4-(4-fluorophenyl)-5-(2-methylylsulphonylpyrimidin-4-yl)-1H-imidazol-2-yl]-5-methyl-[1,3]dioxan-5-carboxylic acid methyl ester, cis isomer (Compound LN) there is prepared the corresponding cis-isomers of Compound GT and Compounds A557 to A2062.

Reference Example 1

4-[5-(4-Fluoro-phenyl)-2-formyl-1-[(2-(trimethylsilyl)ethoxy)methyl]-1H-imidazol-4-yl]-pyridine A solution of 4-[5-(4-fluoro-phenyl)-1-[(2-(trimethylsilyl)ethoxy)methyl]-1H-imidazol-4-yl]-pyridine (8.15 g, reference Example 2) in tetrahydrofuran (100 ml) was treated with a solution of n-butyllithium in hexane (10.6 ml, 2.1M) to give a dark green solution. The solution was stirred at −78° C. for 15 minutes then treated with a solution of N-formylmorpholine (2.45 ml) in tetrahydrofuran (10 ml). After stirring for 15 minutes at −78° C., the mixture was allowed to warm to room temperature then stirred at this temperature for a further 1 hour. The reaction mixture was quenched with water (50 ml) and then extracted four times with ethyl acetate (50 ml). The combined extracts were dried over magnesium sulphate and evaporated. The residual oil was subjected to flash chromatography on silica, eluting with ethyl acetate, to give the title compound (7.86 g) as a yellow oil.

Reference Example 2

4-[5-(4-Fluoro-phenyl)-1-[(2-(trimethylsilyl)ethoxy)methyl]-1H-imidazol-4-yl]-pyridine A stirred solution of 5-(4-fluoro-phenyl)-4-(4-pyridyl)-imidazole [BOEHM ET AL.,] (12.86 g, prepared according to the procedure of Boehm et. al., J.Med.Chem., 1996, 39, page 3829–3937) in dry dimethylformamide (150 ml) was treated portionwise with sodium hydride (2.58 g, 60% dispersion in mineral oil). The mixture was stirred at room temperature until the evolution of hydrogen stopped, then treated dropwise with 2-(trimethylsilyl)ethoxymethyl chloride (10.66 ml). After stirring at room temperature for 1.5 hours, the reaction mixture was treated with water (10 ml) then evaporated. The residual oil was then partitioned between ethyl acetate and water (100 ml). The aqueous phase was extracted three times with ethyl acetate (100 ml). The combined organic phases were washed with brine (50 ml), then dried over magnesium sulphate, then evaporated. The residual yellow oil was subjected to flash chromatography on silica eluting with a mixture of methanol and dichloromethane (98:2, v/v) to give the title compound.

Reference Example 3

4-[2-Dimethoxymethyl-5-(4-fluoro-phenyl)-1H-imidazol-4-yl]-pyridine

Method A: A solution of 4-[2-formyl-5-(4-fluoro-phenyl)-1-{(2-(trimethylsilyl)ethoxy)-methyl}-1H-imidazol-4-yl]-pyridine (0.525 g, Reference Example 1) in methanol (10 ml) was treated with trimethylorthoformate (5 ml) then with 4-toluenesulphonic acid (0.39 g). The reaction mixture was refluxed for 5 hours, then cooled to room temperature, then evaporated. The residue was partitioned between ethyl acetate and saturated aqueous sodium bicarbonate solution (30 ml). The aqueous phase was extracted four times with ethyl acetate (20 ml). The combined organic phases were washed with water (15 ml), then with brine (15 ml), then dried over magnesium sulphate and then evaporated. The residual oil was subjected to flash chromatography on silica eluting with a mixture of dichloromethane and methanol (8:1, v/v) to give the title compound (0.344 g) as a white solid, m.p. 186–189° C.

Method B: A stirred suspension of 1-(4-fluorophenyl)-2-(4-pyridyl)-1,2-ethandione (162.74 g, Reference Example 10) in tert-butylmethyl ether (735 ml), at 20–25° C., was treated with a solution of glyoxal 1,1-dimethylacetal in tert-butylmethyl ether (244.4 ml, 45%) followed by a solution of ammonium acetate (140.75 g) in methanol (260 ml) over a period of 30 minutes, during which time the suspension dissolved to form an orange solution. After stirring for 1 hour at 20–25° C., the resulting suspension was cooled to 5–10° C., then stirred for a further 1 hour, then filtered. The damp filter cake was slurry washed three times with water (350 ml) and then the pressed cake washed twice with tert-butylmethyl ether (350 ml). The air-dry cake was then dried in vacuo at 60–65° C. for 16 hours, to afford the title compound, as a cream coloured, free-flowing solid, m.p. 204–206° C. $^1$H NMR [δ, (CD$_3$)$_2$SO]: 8.35 (d, 2H); 7.43 (dt, 2H); 7.36 (d, 2H); 7.19 (dt, 2H); 5.39 (s, 1H); 3.34 (s, 6H).

Reference Example 4

2-methyl-2-trifluoroacetamido-1,3-propanediol

A stirred solution of 2-amino-2-methyl-1,3-propanediol (1.05 g) in dry dimethylformamide (20 ml), at room temperature, was treated with potassium carbonate (1.52 g). After stirring at room temperature for 15 minutes the mixture was treated dropwise with trifluoroacetic anhydride (1.55 ml) and stirring was then continued for a further 18 hours. The reaction mixture was evaporated and the residue was subjected to flash chromatography on silica eluting with a mixture of dichloromethane and methanol (95:5, v/v) to give the title compound (1 g) as a white solid.

Reference Example 5

2-azidomethyl-2-methyl-1,3-propanediol

A mixture of 5-azidomethyl-2-dimethyl-5-methyl-1,3-dioxane [1.48 g, prepared according to the procedure in J.Org.Chem., 1992, page 6080] concentrated hydrochloric acid (0.3 ml), water (0.8 ml) and tetrahydrofuran (10 ml) was heated at reflux for 1 hour. After cooling to room temperature the reaction mixture was evaporated. The residue was dried under vacuum to give the title compound (1.3 g) as a colourless oil.

Reference Example 6

3-hydroxy-2-hydroxymethyl-2-methyl-1-morpholino-1-propanone

A stirred mixture of diisopropylethylamine (339.67 ml) and morpholine (141.71 ml) in acetonitrile (500 ml), at 20–25° C., was treated with 2,2-bis(hydroxymethyl)propionic acid (87.18 g) and 1-hydroxybenzotriazole (43.92 g). The resulting suspension was warmed to 55–60° C. then treated dropwise with a solution of 1,3-dicyclohexylcarbodiimide (147.62 g) in acetonitrile (232.2 ml) over 30 minutes. The resulting solution was then stirred at 55–60° C. for a further 2 hours then filtered to remove the dicyclohexylurea (131.88 g) by-product. The filter cake was washed twice with acetonitrile (250 ml). The filtrate was evaporated and the residue was treated with warm ethyl acetate (500 ml). The resultant solution was allowed to cool for 16 hours then the 1-hydroxybenzotriazole (42.04 g) which crystallised was removed by filtration. Further cooling of the filtrate over 5 hours and filtration gave the title compound (44.82 g), m.p. 95–97° C. $^1$H NMR (d, CDCl$_3$): 4.02 (d, 2H); 3.70 (m, 10H); 3.30 (bs, 2H); 1.08(s, 3H). A further quantity of the title compound (41.33 g) was obtained following evaporation of the filtrate from the first crop of product, then treating the residue with ethyl acetate (1000 ml), then passing the solution through a silica gel pad (4 cm high×11 cm diameter), then evaporating the filtrate and then crystallising the residue from n-butyl acetate (1000 ml) over 16 hours.

Reference Example 7

4-[2-Dimethoxymethyl-5(4)-(4-fluoro-phenyl)-1H-imidazol-4(5)-yl]-2-methanesulphanyl-pyrimidine A solution of 1-(4-fluorophenyl)-2-(2-methylsulphanylpyrimidin-4-yl)-1,2-ethandione (18.7 g, Reference Example 8) in t-butyl methyl ether (75 ml) and glyoxal dimethylacetal in t-butylmethyl ether (36 ml, 40%), at room temperature, was treated dropwise over 30 minutes with a solution of ammonium acetate (21.7 g) in methanol (40 ml) to give an orange solution. After stirring for 2 hours at room temperature the resulting suspension was filtered to give the title compound (15.6 g) as a colourless solid, m.p. 180–182° C. MH$^+$ 361.

Reference Example 8

1-(4-fluorophenyl)-2-(2-methylsulphanylpyrimidin-4-yl)-1,2-ethandione

A solution of 1-(4-fluorophenyl)-2-(2-methylsulphanylpyrimidin-4-yl)-1-ethanone(65.5 g, Reference Example 9) in dimethylsulphoxide, at 55–70° C., was treated dropwise with an aqueous solution of hydrogen bromide (48%). After stirring at 60° C. for 3 hours, the reaction mixture was cooled to room temperature, then poured into water and the pH of the mixture adjusted to pH8 by addition of sodium bicarbonate. The reaction mixture was extracted with ethyl acetate and the extracts were evaporated to give the title compound (40.87 g), m.p. 74–76° C. MH$^+$ 277.

Reference Example 9

1-(4-fluorophenyl)-2-(2-methylsulphanylpyrimidin-4-yl)-1-ethanone

A solution of lithium hexamethyldisilazane in tetrahydrofuran (1.221, 1M), at −40° C., was treated with a solution of 4-methyl-2-methylsulphanylpyrimidine (76.03 g) in tetrahydrofuran (100 ml). The solution was warmed to 0° C., then stirred for 15 minutes, then cooled to −40° C., then treated with a solution of ethyl 4-fluorobenzoate (91.32 g) in tetrahydrofuran (200 ml). After stirring at −40° C. for 15 minutes the reaction mixture was allowed to warm to room temperature over 2 hours, then treated with ammonium chloride solution. The organic phase was separated and the aqueous phase was extracted with ethyl acetate. The combined organic phases were evaporated to give the title compound (136.19 g), m.p. 212–214° C. MH$^+$ 263.

Reference Example 10

1-(4-fluorophenyl)-2-(4-pyridyl)-1,2-ethandione

A mixture of 1-(4-fluorophenyl)-2-(4-pyridyl)-1-ethanone (247.69 g, Reference Example 11) was mixed with dimethylsulfoxide (500 ml) then warmed on a rotary evaporator (no vacuum). The resulting solution was transferred to a reaction vessel with two rinses of dimethylsulfoxide (500 ml and 240 ml) incorporated to ensure complete transfer. The resulting solution was then warmed to 55–65° C. and hydrogen bromide (581.47 g) was added at such a rate so as to maintain the solution temperature in the range 55–65° C., without the need for any external heating. The solution was stirred at 55–65° C. for a further 2 hours, when thin layer chromatography on silica indicated the reaction to be complete. The reaction mixture was added to water (4000 ml) a separate vessel, with external cooling to maintain a solution temperature in the range 15–25° C. The residual contents of the reaction vessel were transferred using a further aliquot of water (2000 ml). The aqueous solution was then treated with a solution of sodium acetate (600 g) in water (2000 ml), over 15 minutes, and the resulting suspension was stirred for 2 hours at ambient temperature, then filtered. The filter cake was washed three times with water (500 ml), then air-dried for 1 hour, then dried in vacuo for 16 hours at 15–25° C. to give the title compound (296.93 g) as a free-flowing yellow-orange powder, m.p. 84–86° C. $^1$H NMR (CDCl$_3$): δ8.81 (d, 2H); 7.98 (dd, 2H); 7.74 (d, 2H); 7.18 (t, 2H).

Reference Example 11

1-(4-fluorophenyl)-2-(4-pyridyl)-1-ethanone

A stirred solution of sodium bis(trimethylsilyl)amide in tetrahydrofuran (720 ml, 2M), under nitrogen, was treated with 4-picoline (64.7 ml). After 5 minutes a solution of ethyl 4-fluorobenzoate (111.7 g) was added over 30 minutes whilst maintaining the temperature at 18–20° C. by occasional cooling. After stirring at 20–21° C. for 30 minutes, the resultant slurry was cooled in an ice-bath then treated with toluene (500 ml). When the temperature reached 15° C. a solution of acetic acid (82 ml) in water (300 ml) was added over 15 minutes maintaining the temperature below 25° C. After a further 30 minutes stirring at 20–25° C., the organic phase was separated and then evaporated. The oily residue was triturated with heptane to give the title compound (133 g) as a yellow solid, m.p. 80–84° C. $^1$H NMR (δ, CDCl$_3$): 8.42 (d, 2H); 7.88 (dd, 2H); 7.06 (d, 2H,); 7.01 (t, 2H); 4.12 (s, 2H).

In vitro and in vivo Test Procedures
1. In vitro Inhibitory Effects on TNF-alpha Release by Human Monocytes The effects of compounds on TNF-alpha production by human peripheral blood monocytes (PBMs) are examined as follows.

1.1. Preparation of Human Peripheral Blood Monocytes

Freshly drawn blood from normal healthy donors was mixed (4:1, v/v) with sodium citrate (3.8%, w/v). Mononuclear cells were prepared by centrifugation of the blood on Histopaque-1077 (Sigma Diagnostics) according to manufacturers instructions. The fraction enriched with mononuclear cells was washed and resuspended in Hank's balanced salts solution (HBSS) supplemented with deoxyribonuclease (37.5 U/ml) and human serum albumin (0.3%). Differential (cytospin) cell counts revealed that the mononuclear cell fraction routinely comprised 70–80% monocytes.

Cells from the mononuclear leukocyte fraction were centrifuged (200 g, 10 min, 20° C.), resuspended, at a density of $10^6$ cells/ml, in RPMI 1640 containing foetal calf serum (FCS) (1%), penicillin (50 U/ml) and streptomycin (50 µg/ml) and allowed to adhere in 96 well plates. Following incubation (5% $CO_2$, 37° C.) for 90 min, medium containing non-adherent cells was removed, the cells were washed once with fresh medium and fresh medium was added.

1.2. Measurement of Monocyte TNF-alpha Release

Adherent cells in culture medium were incubated for 1 h (5% $CO_2$, 37° C.) with fresh medium containing compounds or vehicle (0.1% dimethylsulphoxide). Compounds were tested within the concentration range of $3\times10^{-9}$M to $3\times10^{-6}$M. LPS (10 ng/ml) was then added to the cells and the incubation continued for a further 18 hours. Cell supernatants were removed into 96 well, 0.22 µm filtration plates for storage at −20° C.

TNF-alpha concentrations in cell supernatants were quantified by sandwich ELISA. Briefly, ELISA plates were coated overnight with 2 µg/ml of mouse anti-human TNF-alpha antibody in bicarbonate buffer (pH 9.9). After washing the wells with wash buffer (0.05% (v/v) Tween in PBS),and blocking unoccupied sites (1% BSA in PBS), monocyte supernatant samples or human recombinant TNF-alpha standards were vacuum filtered into the corresponding wells of the ELISA plate. Biotinylated rabbit polyclonal anti-human TNF-alpha antibody (3 µg/ml) was used as the second antibody and streptavidin-horseradish peroxidase was used as the detection antibody. The peroxidase substrate was 3,3',5,5'-tetramethylbenzidine (TMB), in the presence of hydrogen peroxide.

TNFα concentrations in supernatants from control and LPS-stimulated monocyte incubations were calculated by interpolation from a standard (log/log) curve (0.125–16 ng/ml) fitted by linear regression using a Multicalc software program (Wallac U.K., Ltd).

1.3. Results

Compounds within the scope of the invention produce 50% inhibition of LPS induced TNF-alpha release from human monocytes at concentrations within the range of $10^{-9}$ M to $10^{-4}$ M, preferably within the range of $10^{-9}$ M to $10^{-7}$ M.

2. Inhibitory Effects of Compounds on Serum TNF-alpha Levels in LPS-challenged Mice 2.1. Treatment of Animals and Measurement of Murine TNF-alpha Female Balb/c mice (age 6–8 weeks, weight 20–22 g from Charles River, U.K.) in groups of five or more animals were dosed p.o. with compounds (1 to 100 mg/kg) suspended in 1.5% (w/v) carboxymethyl cellulose then challenged after a minimum period of 30 minutes with 30 mg of LPS i.p. After 90 minutes, the animals were killed by carbon dioxide asphyxiation and bled by cardiac puncture. Blood was allowed to clot at 4° C., centrifuged (12,000 g for 5 minutes) and serum taken for TNF-alpha analysis. TNF-alpha levels are measured using a commercially available murine TNF-alpha ELISA kit, purchased from Genzyme (Cat. no. 1509.00), as recommended by the manufacturer. Values for TNF-alpha were calculated from a recombinant murine TNF-alpha standard curve as above.

2.2. Results

Compounds within the scope of the invention inhibit TNF-alpha release in LPS challenged mice up to 50% at doses of 0.1 mg/kg to 100 mg/kg.

What is claimed is:

1. A compound of formula (I):

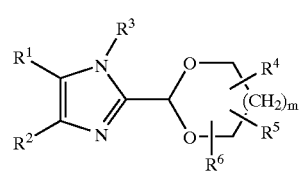

wherein:
$R^1$ is optionally substituted 4-pyrimidinyl;
$R^2$ is optionally substituted aryl or optionally substituted heteroaryl;
$R^3$ represents a group —$L^1$—$R^7$ or —$L^2$—$R^8$
where $L^1$ represents a straight- or branched-chain alkylene linkage consisting of 1 to 6 carbon atoms optionally substituted by halogen or oxo; $R^7$ is hydrogen, aryl, cyano, cycloalkyl, heteroaryl, heterocycloalkyl, nitro, —S(O)$_n$R$^9$, (where $R^9$ is alkyl, aryl, arylalkyl, cycloalkyl, heteroaryl, heteroarylalkyl, or heterocycloalkyl and n is zero or an integer 1 or 2), —NHSO$_2$R$^9$, —C(=Z)OR$^{10}$ (where Z is an oxygen or sulphur atom and $R^{10}$ is hydrogen or $R^9$), —C(=Z)R$^{10}$, —OR$^{10}$—N(R$^{11}$)—C(=Z)R$^9$ (where $R^{11}$ is hydrogen or alkyl), —NY$^1$Y$^2$ {where $Y^1$ and $Y^2$ are independently hydrogen, alkenyl, alkyl, alkynyl, aryl, arylalkyl, cycloalkenyl, cycloalkyl, heteroaryl or heteroarylalkyl, or the group —NY$^1$Y$^2$ may form a 5–7 membered cyclic amine which may optionally contain a further heteroatom selected from O, S, or NY$^3$ (where $Y^3$ is hydrogen, alkyl, aryl, arylalkyl, —CHO, —C(=Z)R$^9$ or —SO$_2$R$^9$), or which may also be fused to additional aryl, heteroaryl, heterocycloalkyl or cycloalkyl rings to form a bicyclic or tricyclic ring system}, —SO$_2$—NY$^1$Y$^2$, —C(=Z)—NY$^1$Y$^2$, —N(R$^{11}$)—C(=Z)—NY$^1$Y$^2$, —N(OR$^{10}$)—C(=Z)—NY$^1$Y$^2$, —N(OR$^{10}$)—C(=Z)R$^{10}$, —C(=NOR$^{10}$)R$^{10}$, —C(=Z)NR$^{10}$OR$^{12}$ (where $R^{12}$ is hydrogen, alkyl, aryl or arylalkyl), —N(R$^{11}$)—C(=NR$^{13}$)—NY$^1$Y$^2$ (where $R^{13}$ is hydrogen, cyano, alkyl, cycloalkyl or aryl), or —N(R$^{11}$)—C(=Z)OR$^{11}$; $L^2$ represents a direct bond or a straight- or branched-carbon chain consisting of 2 to 6 carbon atoms and containing a double or triple carbon-carbon bond; and $R^8$ is hydrogen, aryl, cycloalkenyl, cycloalkyl, heteroaryl or heterocycloalkyl;

$R^4$ represents a group —$L^3$—$R^{14}$
where $L^3$ represents a direct bond or a straight- or branched-chain alkylene linkage consisting of 1 to 6 carbon atoms (optionally substituted by halogen, hydroxy, alkoxy or oxo); and $R^{14}$ is hydrogen, alkyl, azido, hydroxy, alkoxy, aryl, arylalkyloxy, aryloxy, carboxy (or an acid bioisostere), cycloalkyloxy, heteroaryl, heteroarylalkyloxy, heteroaryloxy, heterocycloalkyl, heterocycloalkyloxy, nitro, —NY$^4$Y$^5$, {where $Y^4$ and $Y^5$ are independently hydrogen, aryl, cycloalkyl, heterocycloalkyl, heteroaryl or alkyl optionally substituted by alkoxy, aryl, cyano, cycloalkyl, heteroaryl, heterocycloalkyl, hydroxy, oxo, —CO$_2$R$^{10}$, —CONY$^1$Y$^2$ or —NY$^1$Y$^2$, or the group —NY$^4$Y$^5$ may form a 5–7 membered cyclic amine which (i) may be optionally substituted with one or more substituents selected from alkoxy, carboxamido, carboxy, hydroxy, oxo (or a 5, 6,or 7 membered cyclic acetal derivative thereof), $R^9$ or alkyl substituted by carboxy, carboxamido or hydroxy (ii) may also contain a further heteroatom selected from O, S, $SO_2$ or $NY^6$ (where $Y^6$ is hydrogen, alkyl, aryl, arylalkyl, —C(=Z)$R^9$, —C(=Z)O$R^9$ or —$SO_2R^9$) and (iii) may also be fused to additional aryl, heteroaryl, heterocycloalkyl or cycloalkyl rings to form a bicyclic or tricyclic ring system}, —N($R^{10}$)—C(=Z)—$R^{15}$ (where $R^{15}$ is alkyl, alkoxy, aryl, arylalkyloxy, cycloalkyl, heteroaryl, heteroarylalkoxy or heterocycloalkyl); —N($R^{10}$)—C(=Z)—$L^4$—$R^{16}$ (where $R^{16}$ is alkoxy, aryl, arylalkyloxy, arylalkyloxycarbonylamino, carboxy (or an acid bioisostere), cycloalkyl, cyano, halo, heteroaryl, heteroarylalkoxy, heterocycloalkyl, hydroxy or —$NY^1Y^2$, and $L^4$ is a straight- or branched-chain alkylene linkage consisting of 1 to 6 carbon atoms), —NH—C(=Z)—NH—$R^{15}$, —NH—C(=Z)—NH—$L^4$—$R^{16}$, —N($R^{10}$)—$SO_2$—$R^{15}$, —N($R^{10}$)—$SO_2$—$L^4$—$R^{16}$, —S(O)$_n$$R^9$, —C(=Z)—$NY^4Y^5$ or —C(=Z)—O$R^9$;

$R^5$ represents hydrogen, alkyl or hydroxyalkyl; or $R^4$ and $R^5$, when attached to the same carbon atom, may form with the said carbon atom a cycloalkyl, cycloalkenyl or heterocycloalkyl ring or a group C=$CH_2$;

$R^6$ represents hydrogen or alkyl; and m is zero or an integer 1 or 2;

or N-oxides thereof; or pharmaceutically acceptable salts or solvates thereof.

2. A compound according to claim 1 in which $R^1$ is 2-substituted 4-pyrimidinyl.

3. A compound according to claim 2 in which the 2-substituent is a group selected from $R^{17}Z^3$—where $R^{17}$ is alkyl, aryl, cycloalkyl, heteroaryl, heterocycloalkyl, or alkyl substituted by alkoxy, aryl, cyano, cycloalkyl, heteroaryl, heterocycloalkyl, hydroxy, oxo, —$CO_2R^{10}$, —$CONY^1Y^2$ or —$NY^4Y^5$ and $Z^3$ is O or S(O)$_n$ and $Y^4Y^5$N—.

4. A compound according to claim 3 in which the 2-substituent is —$NY^4Y^5$ (where one of $Y^4$ and $Y^5$ is hydrogen and the other is hydrogen, aryl, cycloalkyl, heterocycloalkyl, heteroaryl or alkyl optionally substituted by alkoxy, aryl, cyano, cycloalkyl, heteroaryl, heterocycloalkyl, hydroxy, oxo, —$CO_2R^{10}$, —$CONY^1Y^2$ or —$NY^1Y^2$) or —$OR^{17}$.

5. A compound according to claim 4 in which $R^2$ is optionally substituted phenyl.

6. A compound according claim 5 in which $R^2$ is phenyl substituted by halogen.

7. A compound according to claim 2 in which $R^2$ is 4-fluorophenyl.

8. A compound according to claim 1 in which $R^2$ is hydrogen or $C_{1-4}$alkyl.

9. A compound according to claim 8 in which $R^3$ is hydrogen.

10. A compound according to claim 1 in which $R^6$ is hydrogen or $C_{1-4}$alkyl.

11. A compound according to claim 10 in which $R^6$ is hydrogen.

12. A compound according to claim 1 in which m is the integer 1.

13. A compound of formula (Ib):

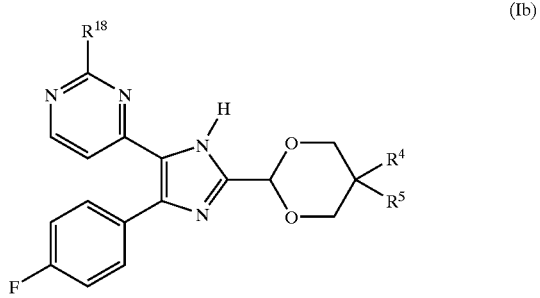

(Ib)

in which
$R^4$ represents a group —$L^3$—$R^{14}$
where $L^3$ represents a direct bond or a straight- or branched-chain alkylene linkage consisting of 1 to 6 carbon atoms (optionally substituted by halogen, hydroxy, alkoxy or oxo); and $R^{14}$ is hydrogen, alkyl, azido, hydroxy, alkoxy, aryl, arylalkyloxy, aryloxy, carboxy (or an acid bioisostere), cycloalkyloxy, heteroaryl, heteroarylalkyloxy, heteroaryloxy, heterocycloalkyl, heterocycloalkyloxy, nitro, —$NY^4Y^5$, {where $Y^4$ and $Y^5$ are independently hydrogen, aryl, cycloalkyl, heterocycloalkyl, heteroaryl or alkyl optionally substituted by alkoxy, aryl, cyano, cycloalkyl, heteroaryl, heterocycloalkyl, hydroxy, oxo, —$CO_2R^{10}$, —$CONY^1Y^2$ or —$NY^1Y^2$, or the group —$NY^4Y^5$ may form a 5–7 membered cyclic amine which (i) may be optionally substituted with one or more substituents selected from alkoxy, carboxamido, carboxy, hydroxy, oxo (or a 5, 6,or 7 membered cyclic acetal derivative thereof), $R^9$ or alkyl substituted by carboxy, carboxamido or hydroxy (ii) may also contain a further heteroatom selected from O, S, $SO_2$ or $NY^6$ (where $Y^6$ is hydrogen, alkyl, aryl, arylalkyl, —C(=Z)$R^9$, —C(=Z)O$R^9$ or —$SO_2R^9$) and (iii) may also be fused to additional aryl, heteroaryl, heterocycloalkyl or cycloalkyl rings to form a bicyclic or tricyclic ring system}, —N($R^{10}$)—C(=Z)—$R^{15}$ (where $R^{15}$ is alkyl, alkoxy, aryl, arylalkyloxy, cycloalkyl, heteroaryl, heteroarylalkoxy or heterocycloalkyl); —N($R^{10}$)—C(=Z)—$L^4$—$R^{16}$ (where $R^{16}$ is alkoxy, aryl, arylalkyloxy, arylalkyloxycarbonylamino, carboxy (or an acid bioisostere), cycloalkyl, cyano, halo, heteroaryl, heteroarylalkoxy, heterocycloalkyl, hydroxy or —$NY^1Y^2$, and $L^4$ is a straight- or branched-chain alkylene linkage consisting of 1 to 6 carbon atoms), —NH—C(=Z)—NH—$R^{15}$, —NH—C(=Z)—NH—$L^4$—$R^{16}$, —N($R^{10}$)—$SO_2$—$R^{15}$, —N($R^{10}$)—$SO_2$—$L^4$—$R^{16}$, —S(O)$_n$$R^9$, —C(=Z)—$NY^4Y^5$ or —C(=Z)—O$R^9$;

$R^5$ represents hydrogen, alkyl or hydroxyalkyl; or $R^4$ and $R^5$, when attached to the same carbon atom, may form with the said carbon atom a cycloalkyl, cycloalkenyl or heterocycloalkyl ring or a group C=$CH_2$;

where $R^9$ is alkyl, aryl, arylalkyl, cycloalkyl, heteroaryl, heteroarylalkyl, or heterocycloalkyl and n is zero or an integer 1 or 2;

$R^{10}$ is hydrogen or $R^9$; and $Y^1$ and $Y^2$ are independently hydrogen, alkenyl, alkyl, alkynyl, aryl, arylalkyl, cycloalkenyl, cycloalkyl, heteroaryl or heteroarylalkyl, or the group —$NY^1Y^2$ may form a 5–7 membered cyclic amine which may optionally contain a further heteroatom selected from O, S, or $NY^3$ (where $Y^3$ is hydrogen, alkyl, aryl, arylalkyl, —CHO, —C(=Z)$R^9$ or —SO$_2R^9$), or which may also be fused to additional aryl, heteroaryl, heterocycloalkyl or cycloalkyl rings to form a bicyclic or tricyclic ring system;

$R^{18}$ is $R^{17}Z^3$— or $Y^4Y^5N$—, where $R^{17}$ is alkyl, aryl, cycloalkyl, heteroaryl, heterocycloalkyl, or alkyl substituted by alkoxy, aryl, cyano, cycloalkyl, heteroaryl, heterocycloalkyl, hydroxy, oxo, —CO$_2R^{10}$, —CONY$^1Y^2$ or —NY$^4Y^5$ and $Z^3$ is O or S(O)$_n$ and $Y^4Y^5N$—;

or N-oxides thereof; or pharmaceutically acceptable salts or solvates thereof.

14. A compound according to claim 1 in which $R^4$ is a group —$L^3$—$R^{14}$ where $L^3$ is a direct bond and $R^{14}$ is selected from alkyl, —NY$^4Y^5$, —N($R^{10}$)—C(=Z)—$R^{15}$, —N($R^{10}$)—C(=Z)—$L^4$—$R^{16}$, —C(=Z)—NY$^4Y^5$ and —C(=Z)O$R^9$.

15. A compound according to claim 1 in which $R^4$ is a group —$L^3$—$R^{14}$, where $L^3$ is a methylene linkage and $R^{14}$ is selected from aryl, heteroaryl, hydroxy, —N($R^{10}$)—C(=Z)—$R^{15}$, —N($R^{10}$)—C(=Z)—$L^4$—$R^{16}$, —NH—C(=Z)—NH—$R^{15}$, —NH—C(=Z)—NH—$L^4$—$R^{16}$, —NY$^4Y^5$ and —N($R^{10}$)—SO$_2$—$R^{15}$.

16. A compound according to claim 1 in which $R^5$ is hydrogen, $C_{1-4}$alkyl or hydroxyalkyl.

17. A compound according to claim 16 in which $R^5$ is methyl.

18. A compound according to claim 16 in which $R^5$ is hydroxymethyl.

19. A compound according to of claim 1 in which $R^4$ and $R^5$ together with the carbon atom to which they are attached represent the group C=CH$_2$ or a 5–7 membered cyclic ether.

20. A compound according to claim 13 in which $R^{18}$ is —NY$^4Y^5$ where $Y^4$ is hydrogen and $Y^5$ is selected from aryl, arylalkyl, cycloalkyl, heteroarylalkyl, and $C_{2-6}$alkyl substituted by hydroxy, alkoxy or —NY$^1Y^2$.

21. A compound according to claim 13 in which $R^{18}$ is —O$R^{17}$, where $R^{17}$ is alkyl, aryl or cycloalkyl.

22. A compound according to claim 1 selected from:

{2-[5-(2-cyclopropylamino-pyrimidin-4-yl)-4-(4-fluoro-phenyl)-1H-imidazol-2-yl]-5-methyl-[1,3]dioxan-5-yl}-morpholin-4-yl-methanone, trans isomer, (Compound GE);

2-[5-(2-Amino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GI);

{2-[5-(2-Dimethylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GJ);

(2-{4-(4-Fluoro-phenyl)-5-[2-(3-hydroxy-propylamino)-pyrimidin-4-yl]-1H-imidazol-2-yl}-5-methyl-[1,3]dioxan-5-yl)-morpholin-4-yl-methanone, trans-isomer, (Compound GK);

(2-{4-(4-Fluoro-phenyl)-5-[2-(2-methoxy-ethylamino)-pyrimidin-4-yl]-1H-imidazol-2-yl}-5-methyl-[1,3]dioxan-5-yl)-morpholin-4-yl-methanone, trans-isomer, (Compound GL);

{2-[4-(4-Fluoro-phenyl)-5-(2-methylamino-pyrimidin-4-yl)-1H-imidazol-2-yl]-5-methyl-[1,3]dioxan-5-yl}-morpholin-4-yl-methanone, trans-isomer, (Compound GM);

(2-{4-(4-Fluoro-phenyl)-5-[2-(1-ethoxycarbonylpiperidin-4-ylamino)-pyrimidin-4-yl]-1H-imidazol-2-yl}-5-methyl-[1,3]dioxan-5-yl)-morpholin-4-yl-methanone, trans-isomer, (Compound GN);

{2-[5-(2-Cyclohexylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GO);

(2-{4-(4-Fluoro-phenyl)-5-[2-(2-hydroxy-ethylamino)-pyrimidin-4-yl]-1H-imidazol-2-}-5-methyl-[1,3]dioxan-5-yl)-morpholin-4-yl-methanone, trans-isomer, (Compound GP);

{2-[5-[2-(2-Amino-ethylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound GQ);

[2-(4-(4-Fluoro-phenyl)-5-{2-[3-(5H-imidazol-1-yl)-propylamino]-pyrimidin-4-yl}-1H-imidazol-2-yl)-5-methyl-[1,3]dioxan-5-yl]-morpholin-4-yl-methanone, trans-isomer, (Compound GR);

(2-{4-(4-Fluoro-phenyl)-5-[2-(3-morpholin-4-yl-propylamino)-pyrimidin-4-yl]-1H-imidazaol-2-yl}-5-methyl-[1,3]dioxan-5-yl)-morpholin-4-yl-methanone, trans-isomer, (Compound GS);

2-[5-(2-Benzylamino-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound GT);

(2-{4-(4-Fluoro-phenyl)-5-[2-(1-phenyl-ethylamino)-pyrimidin-4-yl]-1H-imidazol-2-yl}-5methyl-[1,3]dioxan-5-yl)-morpholin-4-yl-methanone, R isomer, trans-isomer, (Compound GU);

(2-{4-(4-Fluoro-phenyl)-5-[2-(1-phenyl-ethylamino)-pyrimidin-4-yl]-1H-imidazol-2-yl}-5-methyl-[1,3]dioxan-5-yl)-morpholin-4-yl-methanone, S isomer, trans-isomer, (Compound GV);

{2-[4-(4-Fluoro-phenyl)-5-(2-phenylamino-pyrimidin-4-yl)-1H-imidazol-2-yl]-5-methyl-[1,3]dioxan-5-yl}-morpholin-4-yl-methanone, trans-isomer, (Compound GW);

{2-[4-(4-Fluoro-phenyl)-5-(2-piperidin-1-yl-pyrimidin-4-yl)-1H-imidazol-2-yl]-5-methyl-[1,3]dioxan-5-yl}-morpholin-4-yl-methanone, trans-isomer, (Compound GX);

[2-(4-(4-Fluoro-phenyl)-5-{2-[(pyridin-4-ylmethyl)-amino]-pyrimidin-4-yl}-1-imidazol-2-yl)-5-methyl-[1,3]dioxan-5-yl]-morpholin-4-yl-methanone, trans-isomer, (Compound GY);

[2-(4-(4-Fluoro-phenyl)-5-{2-[(pyridin-2-ylmethyl)-amino]-pyrimidin-4-yl}-1H-imidazol-2-yl)-5-methyl-[1,3]dioxan-5-yl]-morpholin-4-yl-methanone, trans-isomer, (Compound GZ);

[2-(4-(4-Fluoro-phenyl)-5-{2-[(pyridin-3-ylmethyl)-amino]-pyrimidin-4-yl}-1H-imidazol-2-yl)-5-methyl-[1,3]dioxan-5-yl]-morpholin-4-yl-methanone, trans-isomer, (Compound HA);

[2-(4-(4-Fluoro-phenyl)-5-{2-[(furan-2-ylmethyl)-amino]-pyrimidin-4-yl}-1H-imidazol-2-yl)-5-methyl-[1,3]dioxan-5-yl]-morpholin-4-yl-methanone, trans-isomer, (Compound HB);

[2-(4-(4-Fluoro-phenyl)-5-{2-[(thiophen-2-ylmethyl)-amino]-pyrimidin-4-yl}-1H-imidazol-2-yl)-5-methyl-[1,3]dioxan-5-yl]-morpholin-4-yl-methanone, trans-isomer, (Compound HC);

[2-(4-(4-Fluoro-phenyl)-5-{2-[(tetrahydro-furan-2-ylmethyl)-amino]-pyrimidin-4-yl}-1H-imidazol-2-yl)-5-methyl-[1,3]dioxan-5-yl]-morpholin-4-yl-methanone, trans-isomer, (Compound HD);

(2-{4-(4-Fluoro-phenyl)-5-[2-(4-methyl-piperazin-1-yl)-pyrimidin-4-yl]-1H-imidazol-2-yl}-5-methyl-[1,3]dioxan-5-yl)-morpholin-4-yl-methanone, trans-isomer, (Compound HE);

{2-[4-(4-Fluoro-phenyl)-5-(2-morpholin-4-yl-pyrimidin-4-yl)-1H-imidazol-2-yl]-5-methyl-[1,3]dioxan-5-yl}-morpholin-4-yl-methanone, trans-isomer, (Compound HF);

(2-{4-(4-Fluoro-phenyl)-5-[2-(3-methoxy-propylamino)-pyrimidin-4-yl]-1H-imidazol-2yl-}-5-methyl-[1,3]dioxan-5-yl)-morpholin-4-yl-methanone, trans-isomer, (Compound FG);

{2-[5-[2-(3-Dimethylamino-propylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound HH);

{2-[5-[2-(2-Dimethylamino-ethylamino)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound HI);

(4-{5-(4-Fluoro-phenyl)-2-[5-methyl-5-(morpholine-4-carbonyl)-[1,3]dioxan-2-yl]-3H-imidazol-4-yl}-pyrimidin-2-ylamino)-acetic acid, trans-isomer, (Compound HJ); and 3-(4-{5-(4-Fluoro-phenyl)-2-[5-methyl-5-(morpholine-4-carbonyl)-[1,3]dioxan-2-yl]-3H-imidazol-4-yl}-pyrimidin-2-ylamino)-propionic acid, trans-isomer, (Compound HK);

or the corresponding N-oxides; or pharmaceutically acceptable salts or solvates thereof.

23. A compound according to claim 1 selected from:

4-[2-(5,5-dimethyl-[1,3]dioxan-2-yl)-5-(4-fluoro-phenyl)-3H-imidazol-4-yl]-pyrimidin-2-ylamine, (Compound HL);

{4-[2-(5,5-dimethyl-[1,3]dioxan-2-yl)-5-(4-fluoro-phenyl)-3H-imidazol-4-yl]-pyrimidin-2-yl}-methyl-amine, (Compound HM);

{4-[2-(5,5-dimethyl-[1,3]dioxan-2-yl)-5-(4-fluoro-phenyl)-3H-imidazol-4-yl]-pyrimidin-2-yl}-dimethyl-amine, (Compound HN);

cyclopropyl-{4-[2-(5,5-dimethyl-[1,3]dioxan-2-yl)-5-(4-fluoro-phenyl)-3H-imidazol-4-yl]-pyrimidin-2-yl}-amine, (Compound HO);

cyclohexyl-{4-[2-(5,5-dimethyl-[1,3]dioxan-2-yl)-5-(4-fluoro-phenyl)-3H-imidazol-4-yl]-pyrimidin-2-yl}-amine, (Compound HQ);

2-{4-[2-(5,5-dimethyl-[1,3]dioxan-2-yl)-5-(4-fluoro-phenyl)-3H-imidazol-4-yl]-pyrimidin-2-ylamino}-ethanol, (Compound HR);

N1-{4-[2-(5,5-dimethyl-[1,3]dioxan-2-yl)-5-(4-fluoro-phenyl)-3H-imidazol-4-yl]-pyrimidin-2-yl}-ethane-1,2-diamine, (Compound HS);

{4-[2-(5,5-dimethyl-[1,3]dioxan-2-yl)-5-(4-fluoro-phenyl)-3H-imidazol-4-yl]-pyrimidin-2-yl}-[3-(5H-imidazol-1-yl)-propyl]-amine, (Compound HT);

{4-[2-(5,5-dimethyl-[1,3]dioxan-2-yl)-5-(4-fluoro-phenyl)-3H-imidazol-4-yl]-pyrimidin-2-yl}-2-morpholin-4-yl-propyl)-amine, (Compound HU);

3-{4-[2-(5,5-dimethyl-[1,3]dioxan-2-yl)-5-(4-fluoro-phenyl)-3H-imidazol-4-yl]-pyrimidin-2-ylamino}-propan-1-ol, (Compound HV);

benzyl-{4-[2-(5,5-dimethyl-[1,3]dioxan-2-yl)-5-(4-fluoro-phenyl)-3H-imidazol-4-yl]-pyrimidin-2-yl}-amine, (Compound HW);

{4-[2-(5,5-dimethyl-[1,3]dioxan-2-yl)-5-(4-fluoro-phenyl)-3H-imidazol-4-yl]-pyrimidin-2-yl}-(1-phenyl-ethyl)-amine, R-isomer, (Compound HX);

{4-[2-(5,5-dimethyl-[1,3]dioxan-2-yl)-5-(4-fluoro-phenyl)-3H-imidazol-4-yl]-pyrimidin-2-yl}-(1-phenyl-ethyl)-amine, S-isomer, (Compound HY);

{4-[2-(5,5-dimethyl-[1,3]dioxan-2-yl)-5-(4-fluoro-phenyl)-3H-imidazol-4-yl]-pyrimidin-2-yl}-phenyl-amine, (Compound HZ);

4-[2-(5,5-dimethyl-[1,3]dioxan-2-yl)-5-(4-fluoro-phenyl)-3H-imidazol-4-yl]-2-piperdin-1-yl-pyrimidine, (Compound IA);

{4-[2-(5,5-dimethyl-[1,3]dioxan-2-yl)-5-(4-fluoro-phenyl)-3H-imidazol-4-yl]-pyrimidin-2-yl}-pyridin-4-ylmethyl-amine, (Compound IB);

{4-[2-(5,5-dimethyl-[1,3]dioxan-2-yl)-5-(4-fluoro-phenyl)-3H-imidazol-4-yl]-pyrimidin-2-yl}-pyridin-2-ylmethyl-amine, (Compound IC);

{4-[2-(5,5-dimethyl-[1,3]dioxan-2-yl)-5-(4-fluoro-phenyl)-3H-imidazol-4-yl]-pyrimidin-2-yl}-pyridin-3-ylmethyl-amine, (Compound ID);

{4-[2-(5,5-dimethyl-[1,3]dioxan-2-yl)-5-(4-fluoro-phenyl)-3H-imidazol-4-yl]-pyrimidin-2-yl}-(furan-2-ylmethyl)-amine, (Compound IE);

{4-[2-(5,5-dimethyl-[1,3]dioxan-2-yl)-5-(4-fluoro-phenyl)-3H-imidazol-4-yl]-pyrimidin-2-yl}-(thiophen-2-ylmethyl)-amine, (Compound IF);

{4-[2-(5,5-dimethyl-[1,3]dioxan-2-yl)-5-(4-fluoro-phenyl)-3H-imidazol-4-yl]-pyrimidin-2-yl}-(tetrahydro-furan-2-ylmethyl)-amine, (Compound IG);

4-[2-(5,5-dimethyl-[1,3]dioxan-2-yl)-5-(4-fluoro-phenyl)-3H-imidazol-4-yl]-2-(4-methyl-piperazin-1-yl)-pyrimidine, (Compound IH);

4-{4-[2-(5,5-dimethyl-[1,3]dioxan-2-yl)-5-(4-fluoro-phenyl)-3H-imidazol-4-yl]-pyrimidin-2-yl}-morpholine, (Compound IJ);

{4-[2-(5,5-dimethyl-[1,3]dioxan-2-yl)-5-(4-fluoro-phenyl)-3H-imidazol-4-yl]-pyrimidin-2-yl}-3-methoxy-propyl)-amine, (Compound IK);

{4-[2-(5,5-dimethyl-[1,3]dioxan-2-yl)-5-(4-fluoro-phenyl)-3H-imidazol-4-yl]-pyrimidin-2-yl}-2-methoxy-ethyl)-amine, (Compound IL);

N-{4-[2-(5,5-dimethyl-[1,3]dioxan-2-yl)-5-(4-fluoro-phenyl)-3H-imidazol-4-yl]-pyrimidin-2-yl}-N',N'-dimethyl-propane-1,3-diamine, (Compound IM); and N-{4-[2-(5,5-dimethyl-[1,3]dioxan-2-yl)-5-(4-fluoro-phenyl)-3H-imidazol-4-yl]-pyrimidin-2-yl}-N',N'-dimethyl-ethane-1,2-diamine, (Compound IN);

or the corresponding N-oxides; or pharmaceutically acceptable salts or solvates thereof.

24. A compound according to claim 1 selected from:

{2-[5-(2-amino-pyrimidin-4-yl)-4-(4-fluoro-phenyl)-1H-imidazol-2-yl]-5-methyl-[1,3]dioxan-5-yl}-methanol, trans-isomer, (Compound IO); or the corresponding N-oxides; or pharnaceutically acceptable salts or solvates thereof.

25. A compound according to claim 1 selected from:

{2-[4-(4-Fluoro-phenyl)-5-(2-methoxy-pyrimidin-4-yl)-1H-imidazol-2-yl]-5-methyl-[1,3]dioxan-5-yl}-morpholin-4-yl-methanone, trans-isomer, (Compound IP);

{2-[5-(2-Benzyloxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound IQ);

{2-[4-(4-Fluoro-phenyl)-5-(2-phenoxy-pyrimidin-4-yl)-1H-imidazol-2-yl]-5-methyl-[1,3]dioxan-5-yl}-morpholin-4-yl-methanone, trans-isomer, (Compound IR);

(2-{4-(4-Fluoro-phenyl)-5-[2-(2-methoxy-ethoxy)-pyrimidin-4-yl]-1H-imidazol-2-yl}-5-methyl-[1,3]

dioxan-5-yl)-morpholin-4-yl-methanone, trans-isomer, (Compound IS);
{2-[5-[2-(2-Dimethylamino-ethoxy)-pyrimidin-4-yl]-4-(4-fluoro-phenyl)-1H-imidazol-2-yl]-5-methyl-[1,3]dioxan-5-yl}-morpholin-4-yl-methanone, trans-isomer, (Compound IT);
{2-[5-(2-Cyclohexyloxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound IU); and
{2-[5-(2-Isopropoxy-pyrimidin-4-yl)-4-(4-fluoro-phenyl)-1H-imidazol-2-yl]-5-methyl-[1,3]dioxan-5-yl}-morpholin-4-yl-methanone, trans-isomer, (Compound IW);

or the corresponding N-oxides; or pharmaceutically acceptable salts or solvates thereof.

26. A compound according to claim 1 selected from:

4-[2-(5,5-dimethyl-[1,3]dioxan-2-yl)-5-(4-fluoro-phenyl)-3H-imidazol-4-yl]-2-methoxy-pyrimidine, (Compound IY);
2-benzyloxy-4-[2-(5,5-dimethyl-[1,3]dioxan-2-yl)-5-(4-fluoro-phenyl)-3H-imidazol-4-yl-]-pyrimidine, (Compound IZ);
4-[2-(5,5-dimethyl-[1,3]dioxan-2-yl)-5-(4-fluoro-phenyl)-3H-imidazol-4-yl]-2-phenoxy-pyrimidine, (Compound JA);
4-[2-(5,5-dimethyl-[1,3]dioxan-2-yl)-5-(4-fluoro-phenyl)-3H-imidazol-4-yl]-2-(2-methoxy-ethoxy)-pyrimidine, (Compound JB);
(2-{4-[2-(5,5-dimethyl-[1,3]dioxan-2-yl)-5-(4-fluoro-phenyl)-3H-imidazol-4-yl]-pyrimidin-2-yloxy}-ethyl)-dimethyl-amine, (Compound JC);
2-cyclohexyloxy-4-[2-(5,5-dimethyl-[1,3]dioxan-2-yl)-5-(4-fluoro-phenyl)-3H-imidazol-4-yl]-pyrimidine, (Compound JD);
2-isopropoxy-4-[2-(5,5-dimethyl-[1,3]dioxan-2-yl)-5-(4-fluoro-phenyl)-3H-imidazol-4-yl]-pyrimidine, (Compound JE);

or the corresponding N-oxides; or pharmaceutically acceptable salts or solvates thereof.

27. A compound according to claim 1 selected from:

4-[2-(5-amino-5-methyl-[1,3]dioxan-2-yl)-5-(4-fluoro-phenyl)-3H-imidazol-4yl]-pyrimidin-2ylamine, cis-isomer, (Compound JF);
{4-[2-(5-amino-5-methyl-[1,3]dioxan-2-yl)-5-(4-fluoro-phenyl)-3H-imidazol-4-yl]-pyrimidin-2yl}-methyl-amine, cis-isomer, (Compound JG);
{4-[2-(5-amino-5-methyl-[1,3]dioxan-2-yl)-5-(4-fluoro-phenyl)-3H-imidazol-4-yl]-pyrimidin-2-yl}-dimethyl-amine, cis-isomer, (Compound JH);
{4-[2-(5-amino-5-methyl-[1,3]dioxan-2-yl)-5-(4-fluoro-phenyl)-3H-imidazol-4-yl]-pyrimidin-2-yl}-cyclopropyl-amine, cis-isomer, (Compound JI);
{4-[2-(5-amino-5-methyl-[1,3]dioxan-2-yl)-5-(4-fluoro-phenyl)-3H-imidazol-4-yl]-pyrimidin-2-yl}-piperidin-4-yl-amine, cis-isomer, (Compound JJ);
{4-[2-(5-amino-5-methyl-[1,3]dioxan-2-yl)-5-(4-fluoro-phenyl)-3H-imidazol-4-yl]-pyrimidin-2-yl}-cyclohexyl-amine, cis-isomer, (Compound JK);
2-{4-[2-(5-amino-5-methyl-[1,3]dioxan-2-yl)-5-(4-fluoro-phenyl)-3H-imidazol-4-yl]-pyrimidin-2-ylamino}-ethanol, cis-isomer, (Compound JL);
N1-{4-[2-(5-amino-5-methyl-[1,3]dioxan-2-yl)-5-(4-fluoro-phenyl)-3H-imidazol-4-yl]-pyrimidin-2-yl}-ethane-1,2-diamine, cis-isomer, (Compound JM);
{4-[2-(5-amino-5-methyl-[1,3]dioxan-2-yl)-5-(4-fluoro-phenyl)-3H-imidazol-4-yl]-pyrimidin-2-yl}-[3-(5H-imidazol-1-yl)-propyl]-amine, cis-isomer, (Compound JN);
{4-[2-(5-amino-5-methyl-[1,3]dioxan-2-yl)-5-(4-fluoro-phenyl)-3H-imidazol-4-yl]-pyrimidin-2-yl}-(3-morpholin-4-yl-propyl)-amine, cis-isomer, (Compound JO);
3-{4-[2-(5-amino-5-methyl-[1,3]dioxan-2-yl)-5-(4-fluoro-phenyl)-3H-imidazol-4-yl]-pyrimidin-2-ylamino}-propan-1-ol, cis-isomer, (Compound JP);
{4-[2-(5-amino-5-methyl-[1,3]dioxan-2-yl)-5-(4-fluoro-phenyl)-3H-imidazol-4-yl]-pyrimidin-2-yl}-benzyl-amine, cis-isomer, (Compound JQ);
{4-[2-(5-amino-5-methyl-[1,3]dioxan-2-yl)-5-(4-fluoro-phenyl)-3H-imidazol-4-yl]-pyrimidin-2-yl}-(1-phenyl-ethyl)-amine, R isomer, cis-isomer, (Compound JR);
{4-[2-(5-amino-5-methyl-[1,3]dioxan-2-yl)-5-(4-fluoro-phenyl)-3H-imidazol-4-yl]-pyrimidin-2-yl}-(1-phenyl-ethyl)-amine, S isomer, cis-isomer, (Compound JS);
{4-[2-(5-amino-5-methyl-[1,3]dioxan-2-yl)-5-(4-fluoro-phenyl)-3H-imidazol-4-yl]-pyrimidin-2-yl}-phenyl-amine, cis-isomer, (Compound JT);
2-[4-(4-fluoro-phenyl)-5-(2-piperidin-1-yl-pyrimidin-4-yl)-1H-imidazol-2-yl]-5-methyl-[1,3]dioxan-5-ylamine, cis-isomer, (Compound JU);
{4-[2-(5-amino-5-methyl-[1,3]dioxan-2-yl)-5-(4-fluoro-phenyl)-3H-imidazol-4-yl]-pyrimidin-2-yl}-pyridin-4-ylmethyl-amine, cis-isomer, (Compound JV);
{4-[2-(5-amino-5-methyl-[1,3]dioxan-2-yl)-5-(4-fluoro-phenyl)-3H-imidazol-4-yl]-pyrimidin-2-yl}-pyridin-2-ylmethyl-amine, cis-isomer, (Compound JW);
{4-[2-(5-amino-5-methyl-[1,3]dioxan-2-yl)-5-(4-fluoro-phenyl)-3H-imidazol-4-yl]-pyrimidin-2-yl}-pyridin-3-ylmethyl-amine, cis-isomer, (Compound JX);
{4-[2-(5-amino-5-methyl-[1,3]dioxan-2-yl)-5-(4-fluoro-phenyl)-3H-imidazol-4-yl]-pyrimidin-2-yl}-(furan-2-ylmethyl)-amine , cis-isomer, (Compound JY);
{4-[2-(5-amino-5-methyl-[1,3]dioxan-2-yl)-5-(4-fluoro-phenyl)-3H-imidazol-4-yl]-pyrimidin-2-yl}-(thiophen-2-ylmethyl)-amine, cis-isomer, (Compound JZ);
{4-[2-(5-amino-5-methyl-[1,3]dioxan-2-yl)-5-(4-fluoro-phenyl)-3H-imidazol-4-yl]-pyrimidin-2-yl}-(tetrahydro-furan-2-ylmethyl)-amine, cis-isomer, (Compound KA);
2-{4-(4-fluoro-phenyl)-5-[2-(4-methyl-piperazin-1-yl)-pyrimidin-4-yl]-1H-imidazol-2-yl}-5-methyl-[1,3]dioxan-5-ylamine, cis-isomer, (Compound KB);
2-[4-(4-fluoro-phenyl)-5-(2-morpholin-4-yl-pyrimidin-4-yl)-1H-imidazol-2-yl]-5-methyl-[1,3]dioxan-5-ylamine, cis-isomer, (Compound KC);
{4-[2-(5-amino-5-methyl-[1,3]dioxan-2-yl)-5-(4-fluoro-phenyl)-3H-imidazol-4-yl]-pyrimidin-2-yl}-(3-methoxy-propyl)-amine, cis-isomer, (Compound KD);
{4-[2-(5-amino-5-methyl-[1,3]dioxan-2-yl)-5-(4-fluoro-phenyl)-3H-imidazol-4-yl]-pyrimidin-2-yl}-(2-methoxy-ethyl)-amine, cis-isomer, (Compound KE);
N-{4-[2-(5-amino-5-methyl-[1,3]dioxan-2-yl)-5-(4-fluoro-phenyl)-3H-imidazol-4-yl]-pyrimidin-2-yl}-N',N'-dimethyl-propane-1,3-diamine, cis-isomer, (Compound KF); and
N-{4-[2-(5-amino-5-methyl-[1,3]dioxan-2-yl)-5-(4-fluoro-phenyl)-3H-imidazol-4-yl]-pyrimidin-2-yl)-N',N'-dimethyl-ethane-1,2-diamine, cis-isomer, (Compound KG);

or the corresponding N-oxides; or pharmaceutically acceptable salts or solvates thereof.

28. A compound according to claim 1 selected from:

{2-[4-(4-fluoro-phenyl)-5-(2-methylsulphonylpyrimidin-4-yl)-1H-imidazol-2-yl]-5-methyl-[1,3]dioxan-5-yl}-morpholin-4-yl-methanone, trans isomer, (Compound KH);

2-[4-(4-fluoro-phenyl)-5-(2-methylsulphonylpyrimidin-4-yl)-1H-imidazol-2-yl]-5,5-dimethyl-[1,3]dioxane (Compound KI);

{2-[4-(4-fluoro-phenyl)-5-(2-methylsulphonyl-pyrimidin-4-yl)-1H-imidazol-2-yl]-5-methyl-[1,3]dioxan-5-yl}-methanol, trans-isomer (Compound KJ);

{2-[4-(4-fluoro-phenyl)-5-(2-methylsulphonyl-pyrimidin-4-yl)-1H-imidazol-2-yl]-5-methyl-[1,3]dioxan-5-yl}-methanol, cis-isomer (Compound KK);

2-[4-(4-fluoro-phenyl)-5-(2-methylsulphonylpyrimidin-4-yl)-1H-imidazol-2-yl]-5-methylene-[1,3]dioxane (Compound KL);

4-[2-[1,3]dioxan-2-yl-5-(4-fluoro-phenyl)-3H-imidazol-4-yl]-2-methylsulphonyl-pyrimidine (Compound KM);

{2-[4-(4-fluoro-phenyl)-5-(2-methylsulphonyl-pyrimidin-4-yl)-1H-imidazol-2-yl]-[1,3]dioxan-5-yl}-methanol, trans-isomer (Compound KN);

{2-[4-(4-fluoro-phenyl)-5-(2-methylsulphonyl-pyrimidin-4-yl)-1H-imidazol-2-yl]-[1,3]dioxan-5yl}-methanol, cis-isomer (Compound KO); and 2,2,2-trifluoro-N-[2-{4-(4-fluoro-phenyl)-5-(2-methanesulphonylpyrimidin-4-yl)-1H-imidazol-2-yl}-5-methyl-[1,3]dioxan-5-yl]acetamide, cis-somer (Compound KP);

or the corresponding N-oxides; or pharmaceutically acceptable salts or solvates thereof.

29. A compound according to claim 1 selected from:

{2-[4-(4-fluoro-phenyl)-5-(2-methylsulphanylpyrimidin-4-yl)-1H-imidazol-2-yl]-5-methyl-[1,3]dioxan-5-yl}-morpholin-4-yl-methanone, trans isomer, (Compound KQ);

2-[4-(4-fluoro-phenyl)-5-(2-methylsulphanylpyrimidin-4-yl)-1H-imidazol-2-yl]-5,5-dimethyl-[1,3]dioxane (Compound KR);

2,2,2-trifluoro-N-[2-{4-(4-fluoro-phenyl)-5-(2-methylsulphanyl-pyrimidin-4-yl)-1H-imidazol-2yl}-5-methyl-[1,3]dioxan-5-yl]acetamide, cis-isomer, (Compound KS);

{2-[4-(4-fluoro-phenyl)-5-(2-methylsulfanyl-pyrimidin-4-yl)-1H-imidazol-2-yl]-5-methyl-[1,3]dioxan-5-yl}-methanol, cis isomer (Compound KT);

{2-[4-(4-fluoro-phenyl)-5-(2-methylsulfanyl-pyrimidin-4-yl)-1H-imidazol-2-yl]-5-methyl-[1,3]dioxan-5-yl}-methanol, trans isomer (Compound KU);

4-[5-(4-fluoro-phenyl)-2-(5-methylene-[1,3]dioxan-2-yl)-3H-imidazol-4-yl]-2-methylsulfanyl-pyrimidine (Compound KV);

4-[2-[1,3]dioxan-2-yl-5-(4-fluoro-phenyl)-3H-imidazol-4-yl]-2-methylsulphanyl-pyrimidine (Compound KW);

{2-[4-(4-fluoro-phenyl)-5-(2-methylsulphanyl-pyrimidin-4-yl)-1H-imidazol-2-yl]-[1,3]dioxan-5-yl}-methanol, trans-isomer (Compound KX); and {2-[4-(4-fluoro-phenyl)-5-(2-methylsulphanyl-pyrimidin-4-yl)-1H-imidazol-2-yl]-[1,3]dioxan-5-yl}-methanol, cis-isomer (Compound KY);

or the corresponding N-oxides; or pharmaceutically acceptable salts or solvates thereof.

30. A compound according to claim 1 selected from:

C-{2-[4-(4-fluoro-phenyl)-5-(2-methylsulfanyl-pyrimidin-4-yl)-1H-imidazol-2-yl]-5-methyl-[1,3]dioxan-5-yl}-methylamine, cis isomer (Compound KZ);

2-[4-(4-fluoro-phenyl)-5-(2-methylsulfanyl-pyrimidin-4-yl)-1H-imidazol-2-yl]-5-methyl-[1,3]dioxane-5-carboxylic acid amide, cis isomer Compound LA);

2-[4-(4-fluoro-phenyl)-5-(2-methylsulfanyl-pyrimidin-4-yl)-1H-imidazol-2-yl]-5-methyl-[1,3]dioxane-5-carboxylic acid, cis isomer (Compound LB);

2-[4-(4-fluorophenyl)-5-(2-methylsulphanylpyrimidin-4-yl)-1H-imidazol-2-yl]-5-methyl-[1,3]dioxan-5-carboxylic acid methyl ester, trans isomer, (Compound LC);

2-[4-(4-fluorophenyl)-5-(2-methylsulphanylpyrimidin-4-yl)-1H-imidazol-2-yl]-5-methyl-[1,3]dioxan-5-carboxylic acid methyl ester, cis isomer, (Compound LD);

2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, cis isomer, (Compound LK);

2,2,2-trifluoro-N-{2-[5-(2-methylsulphonyl-pyrimidin-4-yl)-4-(4-fluoro-phenyl)-1H-imidazol-2-yl]-5-methyl-[1,3]dioxan-5-ylmethyl}-acetamide, trans isomer, (Compound LL);

2-[4-(4-fluorophenyl)-5-(2-methylsulphonylpyrimidin-4-yl)-1H-imidazol-2-yl]-5-methyl-[1,3]dioxan-5-carboxylic acid methyl ester, trans isomer, (Compound LM); and 2-[4-(4-fluorophenyl)-5-(2-methylenesulphonylpyrimidin-4-yl)-1H-imidazol-2-yl]-5-methyl-[1,3]dioxan-5-carboxylic acid methyl ester, cis isomer (Compound LN);

or the corresponding N-oxides; or pharmaceutically acceptable salts or solvates thereof.

31. A compound according to claim 1 which is (2-{4-(4-Fluoro-phenyl)-5-[2-(1-phenyl-ethylamino)-pyrimidin-4-yl]-1H-imidazol-2-yl}-5-methyl-[1,3]dioxan-5-yl)-morpholin-4-yl-methanone, S isomer, trans-isomer, (Compound GV); or the corresponding N-oxide; or pharmaceutically acceptable salts or solvates thereof.

32. A pharmaceutical composition comprising a compound according to claim 1 together with a pharmaceutically acceptable carrier or excipient.

33. A method of treating asthma in a patient in need thereof, comprising administering to said patient, a pharmaceutically effective amount of a compound according to claim 1.

34. A method of treating joint inflammation in a patient in need thereof, comprising administering to said patient, a pharmaceutically effective amount of a compound according to claim 1.

35. A compound according to claim 1 which is 2-[4-(4-fluorophenyl)-5-(2-propylamino-pyrimidin-4-yl)-1H-imidazol-2-yl]-5-methyl-[1,3]dioxane-5-carboxylic acid cyclopropyl amide, trans-isomer or the corresponding N-oxides; or pharmaceutically acceptable salts or solvates thereof.

36. A compound according to claim 1 which is 2-{4-(4-fluoro-phenyl)-5-[2-(2-methoxyethylamino)pyrimidin-4-yl]-1H-imidazol-2-yl}-5-methyl-[1,3]dioxane-5-carboxy acid propylamide, trans-isomer or the corresponding N-oxides; or pharmaceutically acceptable salts or solvates thereof.

* * * * *